(12) United States Patent
de la Monte et al.

(10) Patent No.: US 7,833,513 B2
(45) Date of Patent: Nov. 16, 2010

(54) TREATMENT OF ALZHEIMER'S DISEASE

(75) Inventors: Suzanne Marie de la Monte, East Greenwich, RI (US); Jack Raymond Wands, East Greenwich, RI (US)

(73) Assignee: Rhode Island Hospital, Providence, RI (US)

(*) Notice: Subject to any disclaimer, the term of this patent is extended or adjusted under 35 U.S.C. 154(b) by 0 days.

(21) Appl. No.: 11/394,179

(22) Filed: Mar. 31, 2006

(65) Prior Publication Data
US 2007/0042437 A1 Feb. 22, 2007

Related U.S. Application Data

(63) Continuation-in-part of application No. PCT/US2005/043856, filed on Dec. 5, 2005.

(60) Provisional application No. 60/632,619, filed on Dec. 3, 2004, provisional application No. 60/654,080, filed on Feb. 18, 2005, provisional application No. 60/731,862, filed on Nov. 1, 2005.

(51) Int. Cl.
A61K 49/00 (2006.01)
A01N 61/00 (2006.01)

(52) U.S. Cl. ............................ 424/9.1; 514/1
(58) Field of Classification Search ........................ None
See application file for complete search history.

(56) References Cited

U.S. PATENT DOCUMENTS

| | | | | |
|---|---|---|---|---|
| 5,817,623 A * | 10/1998 | Ishii | | 514/3 |
| 6,787,552 B2 * | 9/2004 | Sakuma et al. | | 514/256 |
| 7,119,104 B2 * | 10/2006 | Sakuma et al. | | 514/311 |
| 7,402,597 B2 * | 7/2008 | Sakuma et al. | | 514/311 |
| 2004/0058873 A1 | 3/2004 | Esmond et al. | | |
| 2004/0060077 A1 | 3/2004 | Esmond et al. | | |
| 2005/0043242 A1 | 2/2005 | Esmond et al. | | |
| 2005/0137122 A1 * | 6/2005 | Sharif | | 514/2 |

FOREIGN PATENT DOCUMENTS

| | | |
|---|---|---|
| WO | WO 03/062405 A2 | 7/2003 |
| WO | WO 03/077940 A1 | 9/2003 |
| WO | WO 2004/060871 A1 | 7/2004 |
| WO | WO/2004/093910 | * 11/2004 |

OTHER PUBLICATIONS

Lackey et al. Growth Hormone and IGF Research, 10: 1-13, Feb. 2000.*
Stewart and Liolitsa, Diabetic Medicine, 16: 93-112, Feb. 1999.*
Merriam-Webster's Online Dictionary (2003) Retrieved from: http://www.m-w.com Retrieved on Nov. 5, 2007.*
Vickers JC. Drugs Aginig 19(7):487-494, 2002.*
Kojo et al., J Pharmacol Sci, 93:347-355, Nov. 2003.*
Dokmeci D., Folia Medica, 46(2): 5-10 (2004).*
de la Monte et al., J Alzheimer's Res., 10(1):89-109, 2006.*

Abraham, R., et al., "Substantial linkage disequilibrium across the insulin-degrading enzyme locus but no association with late-onset Alzheimer's disease," *Hum. Genet.* 109:646-652, Springer-Verlag Berlin (2001).
"Activation of Receptor Boosts Development of Precancerous Intestinal Polyps," *ASBMB Today*:17, American Society for Biochemistry and Molecular Biology (Mar. 2004).
Adelman, A.M. and Daly, M.P., "Initial Evaluation of the Patient with Suspected Dementia," *Am. Fam. Physician* 71:1745-1750, American Academy of Family Physicians (May 2005).
Ait-Ghezala, G., et al., "Confirmation of association between D10S583 and Alzheimer's disease in a case-control sample," *Neurosci. Lett.* 325:87-90, Elsevier Science Ltd. (2002).
Alessi, D.R. and Downes, C.P., "The role of PI 3-kinase in insulin action," *Biochim. Biophys. Acta 1436*:151-164, Elsevier Science B.V. (1998).
Balasubramanian, A.S., "Amyloid Beta Peptide Processing, Insulin Degrading Enzyme, and Butyrylcholinesterase," *Neurochem. Res.* 26:453-456, Kluwer Academic/Plenum Publishers (2001).
Bassaganya-Riera, J., et al., "Peroxisome Proliferator-Activated Receptors: The Nutritionally Controlled Molecular Networks that Integrate Inflammation, Immunity and Metabolism," *Curr. Nutr. Food Sci.* 1:179-187, Bentham Science Publishers Ltd. (Jun. 2005).
Bedu, E., et al., "Peroxisome proliferator-activated receptor β/δ as a therapeutic target for metabolic diseases," *Expert Opin. Ther. Targets* 9:861-873, Ashley Publications Ltd. (Aug. 2005).
Berger, J. and Wagner, J.A., "Physiological and Therapeutic Roles of Peroxisome Proliferator-Activated Receptors," *Diabetes Technol. Ther.* 4:163-174, Mary Ann Liebert, Inc. (2002).
Bernstein, H.-G., et al., "Insulin-degrading enzyme in the Alzheimer's disease brain: prominent localization in neurons and senile plaques," *Neurosci. Lett.* 263:161-164, Elsevier Science Ireland Ltd. (1999).
Bertram, L., et al., Evidence for Genetic Linkage of Alzheimer's Disease to Chromosome 10q, *Science* 290:2302-2303, American Association for the Advancement of Science (2000).
Blass, J.P., et al., "The role of the metabolic lesion in Alzheimer's disease," *J. Alzheimers Dis.* 4:225-232, IOS Press (2002).
Blum-Degen, D., et al., "Altered regulation of brain glucose metabolism as a cause of neurodegenerative disorders?," *J. Neural Transm.* 46:139-147, Springer-Verlag (1995).
Boussaha, M., et al., "Polymorphisms of insulin degrading enzyme gene are not associated with Alzheimer's disease," *Neurosci. Lett.* 329:121-123, Elsevier Science Ireland Ltd. (2002).
Braak, H. and Braak, E., "Neuropathological stageing of Alzheimer-related changes," *Acta Neuropathol.* 82:239-259, Springer-Verlag (1991).

(Continued)

*Primary Examiner*—Daniel E. Kolker
*Assistant Examiner*—Stacey MacFarlane
(74) *Attorney, Agent, or Firm*—Mintz Levin Cohn Ferris Glovsky and Popeo, P.C.; Ingrid A. Beattie

(57) ABSTRACT

This invention relates to methods for diagnosing Alzheimer's Disease (AD) by determining the level or function of insulin, insulin-like growth factors, their receptors and/or their downstream signaling molecules. The invention further relates to methods for the treatment of AD by administering an insulin agonist and an insulin-like growth factor agonist. The invention additionally provides an animal model of AD and methods of screening for agents useful in the treatment, amelioration, or prevention of AD.

11 Claims, 54 Drawing Sheets

OTHER PUBLICATIONS

Figure 1A:
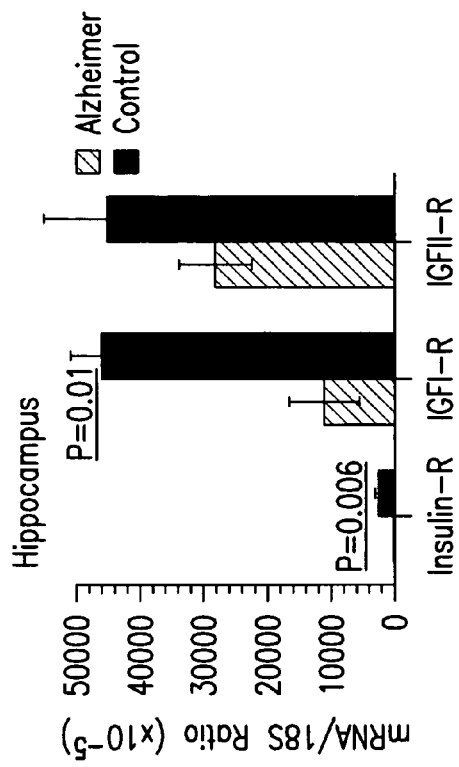
Figure 1B:
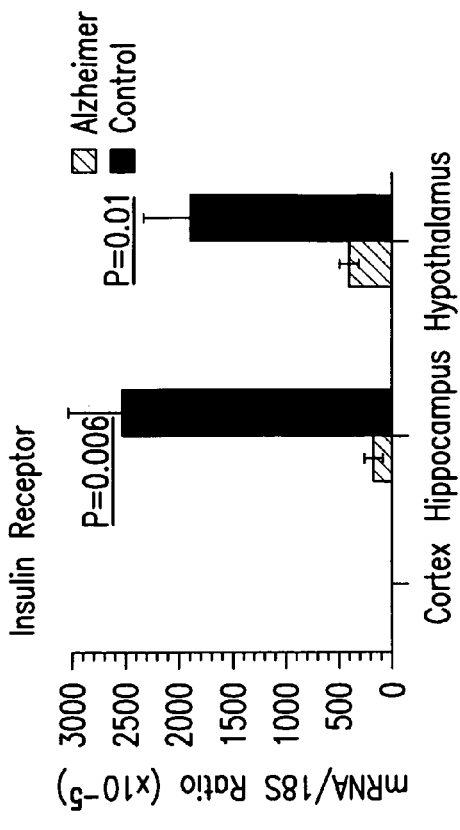
Figure 1C:
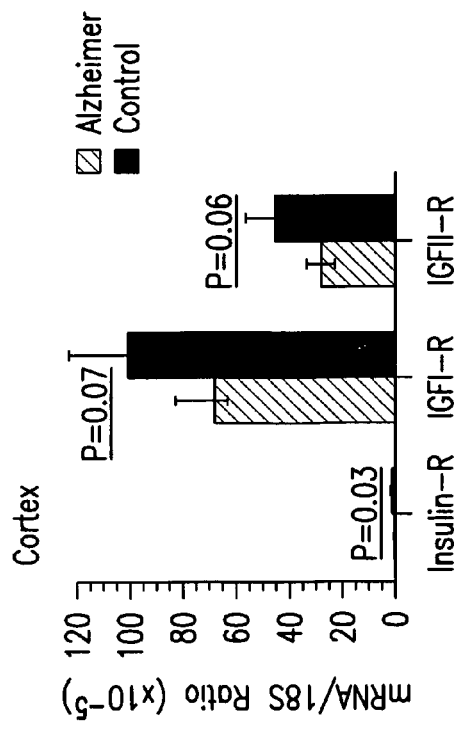
Figure 1D:
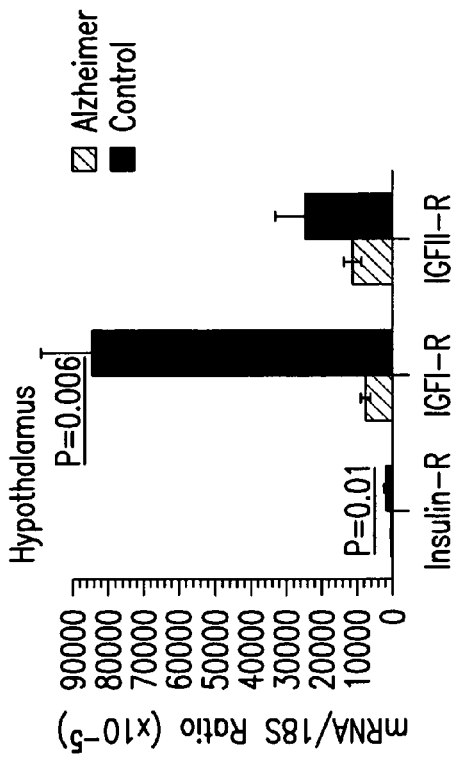
Figure 2A:
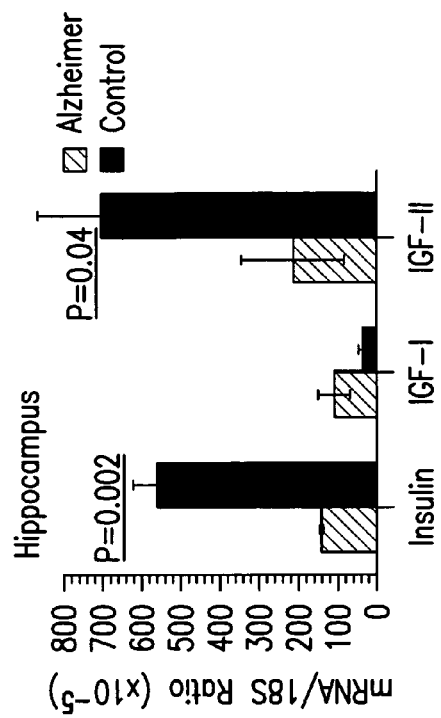
Figure 2B:
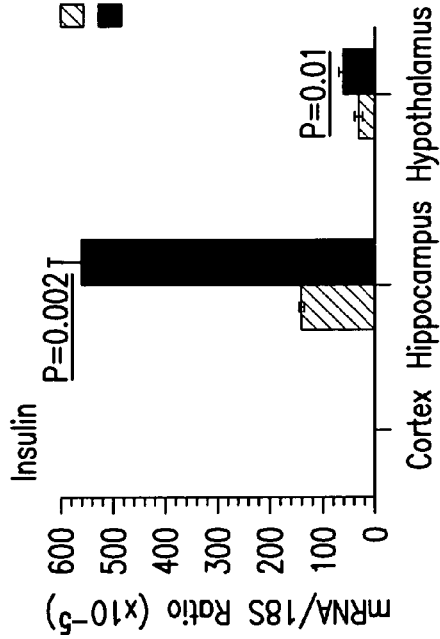
Figure 2C:
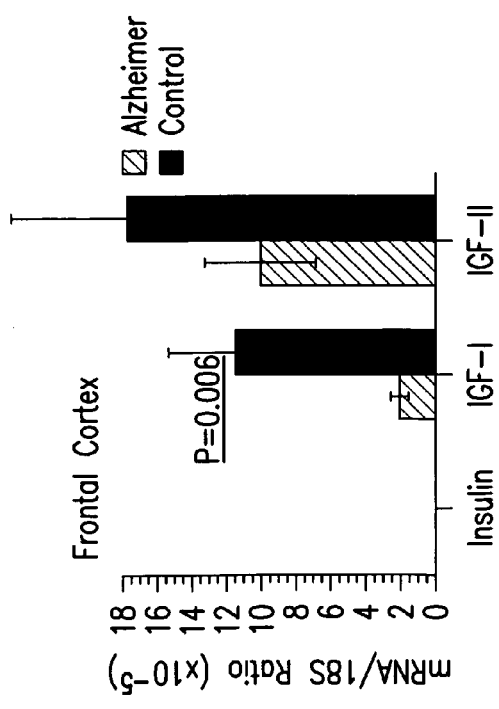
Figure 2D:
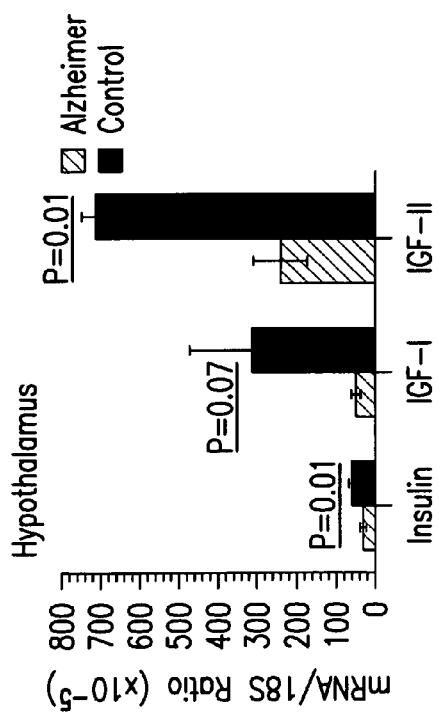

Brun, R.P., et al., "Peroxisome proliferator-activated receptor gamma and the control of adipogenesis," *Curr. Opin. Lipidol.* 8:212-218, Rapid Science Publishers (1997).

Bucht, G., et al., "Changes in Blood Glucose and Insulin Secretion in Patients with Senile Dementia of Alzheimer Type," *Acta Med. Scand.* 213:387-392, Elsevier Science Inc. (1983).

Burgering, B.M. and Coffer, P.J., "Protein kinase B (c-Akt) in phosphatidylinositol-3-OH kinase signal transduction," *Nature* 376:599-602, Macmillan Magazines Ltd. (1995).

Carantoni, M., et al., "Alzheimer Disease and Vascular Dementia: Relationships with Fasting Glucose and Insulin Levels," *Dement. Geriatr. Cogn. Disord.* 11:176-180, Karger (2000).

Carson, M.J., et al., "Insulin-like Growth Factor I Increases Brain Growth and Central Nervous System Myelination in Transgenic Mice," *Neuron* 10:729-740, Cell Press (1993).

Castellani, R.J., et al., "Active Glycation in Neurofibrillary Pathology of Alzheimer Disease: $N^\epsilon$-(Carboxymethyl) Lysine and Hexitol-Lysine," *Free Radic. Biol. Med.* 31:175-180, Elsevier Science Inc. (2001).

Chakrabarti, R. and Rajagopalan, R., "The Role of PPARs in Obesity and other Insulin Resistance Associated Disorders," *Curr. Med. Chem.—Immun., Endoc. & Metab. Agents* 4:67-73, Bentham Science Publishers Ltd. (Jun. 2004).

Chawla, A., et al., "PPARδ is a very low-density lipoprotein sensor in macrophages," *Proc. Natl. Acad. Sci. USA* 100:1268-1273, National Academy of Sciences (Feb. 2003).

Cockrell, J.R. and Folstein, M.F., "Mini-Mental State Examination (MMSE)," *Psychopharmacol. Bull.* 24:689-692, MedWorks Media (1988).

Combs, C.K., et al., "Inflammatory Mechanisms in Alzheimer's Disease: Inhibition of β-Amyloid-Stimulated Proinflammatory Responses and Neurotoxicity by PPARγ Agonists," *J. Neurosci.* 20:558-567, Society for Neuroscience (2000).

Condorelli, F., et al., "Caspase Cleavage Enhances the Apoptosis-Inducing Effects of BAD," *Mol. Cell. Biol.* 21:3025-3036, American Society for Microbiology (2001).

Connor, B., et al., "Insulin-like growth factor-I (IGF-I) immunoreactivity in the Alzheimer's disease temporal cortex and hippocampus," *Brain Res. Mol. Brain Res.* 49:283-290, Elsevier Science B.V. (1997).

Cook, D.G., et al., "Reduced Hippocampal Insulin-Degrading Enzyme in Late-Onset Alzheimer's Disease Is Associated with the Apolipoprotein E-ε4 Allele," *Am. J. Pathol.* 162:313-319, American Society for Investigative Pathology (Jan. 2003).

Craft, S., et al., "Effects of Hyperglycemia on Memory and Hormone Levels in Dementia of the Alzheimer Type: A Longitudinal Study," *Behav. Neurosci.* 107:926-940, American Psychological Association (1993).

Craft, S., et al., "Memory Improvement Following Induced Hyperinsulinemia in Alzheimer's Disease," *Neurobiol. Aging* 17:123-130, Elsevier Science Inc. (1996).

Craft, S., et al., "Insulin Metabolism in Alzheimer's Disease Differs According to Apolipoprotein E Genotype and Gender," *Neuroendocrinology* 70:146-152, Karger (1999).

Craft, S., et al., "Enhancement of Memory in Alzheimer Disease With Insulin and Somatostatin, but Not Glucose," *Arch. Gen. Psychiatry* 56:1135-1140, American Medical Association (1999).

Craft, S., et al., "Insulin dose-response effects on memory and plasma amyloid precursor protein in Alzheimer's disease: interactions with apolipoprotein E genotype," *Psychoneuroendocrinology* 28:809-822, Pergamon Press (Aug. 2003).

Craft, S., et al., "Cerebrospinal fluid and plasma insulin levels in Alzheimer's disease: Relationship to severity of dementia and apolipoprotein E genotype," *Neurology* 50:164-168, Lippincott-Raven Publishers (1998).

Craft, S., et al., "Insulin Effects on Glucose Metabolism, Memory, and Plasma Amyloid Precursor Protein in Alzheimer's Disease Differ According to Apolipoprotein-E Genotype," *Ann. N. Y. Acad. Sci.* 903:222-228, New York Academy of Sciences (2000).

Crews, F.T., et al., "Binding of [$^{125}$I]-Insulin-Like Growth Factor-1 (IGF-1) in Brains of Alzheimer's and Alcoholic Patients," *Adv. Exp. Med. Biol.* 293:483-492, Plenum Press (1991).

Crews, F.T., et al., "Insulin-Like Growth Factor I Receptor Binding in Brains of Alzheimer's and Alcoholic Patients," *J. Neurochem.* 58:1205-1210, Raven Press, Ltd. (1992).

Datta, S.R., et al.; "Akt Phosphorylation of BAD Couples Survival Signals to the Cell-Intrinsic Death Machinery," *Cell* 91:231-241, Cell Press (1997).

De Keyser, J., et al., "Insulin-like growth factor-I receptor densities in human frontal cortex and white matter during aging, in Alzheimer's disease, and in Huntington's disease," *Neurosci. Lett.* 172:93-96, Elsevier Science Ireland Ltd. (1994).

de L. A. Femandes, M.L., et al., "Effects of Age on Elements of Insulin-Signaling Pathway in Central Nervous System of Rats," *Endocrine* 16:227-234, Humana Press (2001).

de la Monte, S.M., et al., "Partial Rescue of Ethanol-Induced Neuronal Apoptosis by Growth Factor Activation of Phosphoinositol-3-Kinase," *Alcohol. Clin. Exp. Res.* 24:716-726, Lippincott Williams & Wilkins (2000).

de la Monte, S.M., et al., "Ethanol impairs insulin-stimulated mitochondrial function in cerebellar granule neurons," *Cell. Mol. Life Sci.* 58:1950-1960, Birkhauser Verlag (2001).

de la Monte, S.M. and Wands, J.R., "Chronic gestational exposure to ethanol impairs insulin-stimulated survival and mitochondrial function in cerebellar neurons," *Cell. Mol. Life Sci.* 59:882-893, Birkhauser Verlag (2002).

de la Monte, S.M. and Wands, J.R., "Review of insulin and insulin-like growth factor expression, signaling, and malfunction in the central nervous system: Relevance to Alzheimer's disease," *J. Alzheimer's Dis.* 7:45-61, IOS Press (Feb. 2005).

de la Torre, J.C., "Critically attained threshold of cerebral hypoperfusion: the CATCH hypothesis of Alzheimer's pathogenesis," *Neurobiol. Aging* 21:331-342, Elsevier Science Inc. (2000).

Delcommenne, M., et al., "Phosphoinositide-3-OH kinase-dependent regulation of glycogen synthase kinase 3 and protein kinase B/AKT by the integrin-linked kinase," *Proc. Natl. Acad. Sci. USA* 95:11211-11216, National Academy of Sciences (1998).

den Heijer, T., et al., "Type 2 diabetes and atrophy of medial temporal lobe structures on brain MRI," *Diabetologia* 46:1604-1610, Springer-Verlag Berlin (Dec. 2003).

Dentremont, K.D., et al., "Increased insulin-like growth factor-I (IGF-I) expression during early postnatal development differentially increases neuron number and growth in medullary nuclei of the mouse," *Brain Res. Dev. Brain Res.* 114:135-141, Elsevier Science B.V. (1999).

D'Ercole, A.J., "Expression of Insulin-like Growth Factor-I in Transgenic Mice," *Ann. N. Y. Acad. Sci.* 692:149-160, New York Academy of Sciences (1993).

D'Ercole, A.J., et al., "Use of Transgenic Mice for Understanding the Physiology of Insulin-Like Growth Factors," *Horm. Res.* 45:5-7, Elsevier Science B.V. (1996).

D'Ercole, A.J., et al., "The Role of the Insulin-Like Growth Factors in the Central Nervous System," *Mol. Neurobiol.* 13:227-255, Humana Press (1996).

D'Ercole, A.J., et al., "Mutant mouse models of insulin-like growth factor actions in the central nervous system," *Neuropeptides* 36:209-220, Churchill Livingstone (2002).

Doble, B.W. and Woodgett, J.R., "GSK-3: tricks of the trade for a multi-tasking kinase," *J. Cell Sci.* 116:1175-1186, Company of Biologists Ltd. (Apr. 2003).

Doré, S., et al., "Insulin-like growth factor I protects and rescues hippocampal neurons against β-amyloid- and human amylin-induced toxicity," *Proc. Natl. Acad. Sci. USA* 94:4772-4777, National Academy of Sciences (1997).

Doré, S., et al., "Protective and Rescuing Abilities of IGF-I and Some Putative Free Radical Scavengers against β-Amyloid-Inducing Toxicity in Neurons," *Ann. N. Y. Acad. Sci.* 890:356-364, New York Academy of Sciences (1999).

Doublier, S., et al., "Impaired brain development and hydrocephalus in a line of transgenic mice with liver-specific expression of human insulin-like growth factor binding protein-1," *Growth Horm. IGF Res.* 10:267-274, Harcourt Publishers Ltd. (2000).

Dressel, U., et al., "The Peroxisome Proliferator-Activated β/δ Agonist, GW501516, Regulates the Expression of Genes Involved in Lipid Catabolism and Energy Uncoupling in Skeletal Muscle Cells," *Mol. Endocrinol.* 17:2477-2493, Endocrine Society (Dec. 2003).

Dudek, H., et al., "Regulation of Neuronal Survival by the Serine-Threonine Protein Kinase Akt," *Science* 275:661-665, American Association for the Advancement of Science (1997).

Duelli, R., et al., Intracerebroventricular Injection of Streptozotocin Induces Discrete Local Changes in Cerebral Glucose Utilization in Rats, *Int. J. Devl. Neurosci.* 12:737-743, Pergamon Press (1994).

Duval, C., et al., "The role of PPARs in atherosclerosis," *Trends Mol. Med.* 8:422-430, Elsevier Science Ltd. (2002).

Etiene, D., et al., "Cerebrovascular Pathology Contributes to the Heterogeneity of Alzheimer's Disease," *J. Alzheimer's Dis.* 1:119-134, IOS Press (1998).

Eves, E.M., et at, "Akt, a Target of Phosphatidylinositol 3-Kinase, Inhibits Apoptosis in a Differentiating Neuronal Cell Line," *Mol. Cell. Biol.* 18:2143-2152, American Society for Microbiology (1998).

Evin, G. and Weidemann, A., "Biogenesis and metabolism of Alzheimer's disease Aβ amyloid peptides," *Peptides* 23:1285-1297, Elsevier Science Inc. (2002).

Farris, W., et al., "Insulin-degrading enzyme regulates the levels of insulin, amyloid β-protein, and the β-amyloid precursor protein intracellular domain in vivo," *Proc. Natl. Acad. Sci. USA* 100:4162-4167, National Academy of Sciences (Apr. 2003).

Farris, W., et al.; "Partial Loss-of-Function Mutations in Insulin-Degrading Enzyme that Induce Diabetes also Impair Degradation of Amyloid β-Protein," *Am. J. Pathol.* 164:1425-1434, American Society for Investigative Pathology (Apr. 2004).

Fisman, M., et al., "Metabolic Changes in Alzheimer's Disease," *J. Am. Geriatr. Soc.* 36:298-300, Elsevier Science Publishing Co., Inc. (1988).

Folli, F., et al., "The Early Intracellular Signaling Pathway for the Insulin/Insulin-Like Growth Factor Receptor Family in the Mammalian Central Nervous System," *Mol. Neurobiol.* 13:155-183, Human Press (1996).

Folstein, M.F., et al., "'Mini-Mental State': A Practical Method for Grading the Cognitive State of Patients for the Clinician," *J. Psychiat. Res.* 12:189-198, Pergamon Press (1975).

Frölich, L., et al., "Brain insulin and insulin receptors in aging and sporadic Alzheimer's disease," *J. Neural Transm.* 105:423-438, Springer-Verlag (1998).

Frölich, L., et al., "A Disturbance in the Neuronal Insulin Receptor Signal Transduction in Sporadic Alzheimer's Disease," *Ann. N. Y. Acad. Sci.* 893:290-293, New York Academy of Sciences (1999).

Fujisawa, Y., et al., "Increased Insulin Levels after OGTT Load in Peripheral Blood and Cerebrospinal Fluid of Patients with Dementia of Alzheimer Type," *Biol. Psychiatry* 30:1219-1228, Elsevier Science Publishing Co., Inc. (1991).

Garver, T.D., et al., "Tau Phosphorylation in Brain Slices: Pharmacological Evidence for Convergent Effects of Protein Phosphatases on Tau and Mitogen-Activated Protein Kinase," *Mol. Pharmacol.* 47:745-756, Williams & Wilkins (1995).

Gasic-Milenkovic, J., et al., "Advanced glycation endproducts cause lipid peroxidation in the human neuronal cell line SH-SY5Y," *J. Alzheimer's Dis.* 5:25-30, IOS Press (Feb. 2003).

Gasparini, L., et al., "Stimulation of β-Amyloid Precursor Protein Trafficking by Insulin Reduces Intraneuronal β-Amyloid and Requires Mitogen-Activated Protein Kinase Signaling," *J. Neurosci.* 21:2561-2570, Society for Neuroscience (2001).

Gasparini, L., et al., "Does insulin dysfunction play a role in Alzheimer's disease?," *Trends Pharmacol. Sci.* 23:288-293, Elsevier Science Ltd. (2002).

Gasparini, L. and Xu, H., "Potential roles of insulin and IGF-1 in Alzheimer's disease," *Trends Neurosci.* 26:404-406, Elsevier Applied Science Publishing (Aug. 2003).

Gerozissis, K., "Brain Insulin: Regulation, Mechanisms of Action and Functions," *Cell. Mol. Neurobiol.* 23:1-25, Kluwer Academic/Plenum Publishers (Feb. 2003).

Giovannone, B., et al., "Insulin receptor substrate (IRS) transduction system: distinct and overlapping signaling potential," *Diabetes Metab. Res. Rev.* 16:434-441, John Wiley & Sons, Ltd. (2000).

Glenner, G.G. and Wong, C.W., "Alzheimer's Disease: Initial Report of the Purification and Characterization of a Novel Cerebrovascular Amyloid Protein," *Biochem. Biophys. Res. Commun.* 120:885-890, Academic Press, Inc. (1984).

Gregoire, F.M., "Adipocyte Differentiation: From Fibroblast to Endocrine Cell," *Exp. Biol. Med.* 226:997-1002, Karger (2001).

Grünblatt, E., et al., "Gene expression profile in streptozotocin rat model for sporadic Alzheimer's disease," *J. Neural Transm.* 111:367-386, Springer-Verlag (Mar. 2004).

Halestrap, A.P., et al., "Mitochondria and cell death," *Biochem. Soc. Trans.* 28:170-177, Portland Press (2000).

Heidenreich, K.A. and Toledo, S.P., "Insulin Receptors Mediate Growth Effects in Cultured Fetal Neurons. I. Rapid Stimulation of Protein Synthesis," *Endocrinology* 125:1451-1457, Endocrine Society (1989).

Heitner, J. and Dickson, D., "Diabetics do not have increased Alzheimer-type pathology compared with age-matched control subjects: A retrospective postmortem immunocytochemical and histofluorescent study," *Neurology* 49:1306-1311, Lippincott-Raven Publishers (1997).

Hetman, M., et al., "Role of Glycogen Synthase Kinase-3β in Neuronal Apoptosis Induced by Trophic Withdrawal," *J. Neurosci.* 20:2567-2574, Society for Neuroscience (2000).

Hirsch, T., et al., "Mitochondrial permeability transition in apoptosis and necrosis," *Cell Biol. Toxicol.* 14:141-145, Kluwer Academic Publishers (1998).

Hong, M. and Lee, V.M.-Y., "Insulin and Insulin-like Growth Factor-1 Regulate Tau Phosphorylation in Cultured Human Neurons," *J. Biol. Chem.* 272:19547-19553, American Society for Biochemistry and Molecular Biology (1997).

Hoyer, S. and Nitsch, R., "Cerebral excess release of neurotransmitter amino acids subsequent to reduced cerebral glucose metabolism in early-onset dementia of Alzheimer type," *J. Neural Transm.* 75:227-232, Springer-Verlag (1989).

Hoyer, S., et al., "Predominant abnormality in cerebral glucose utilization in late-onset dementia of the Alzheimer type: a cross-sectional comparison against advanced late-onset and incipient early-onset cases," *J. Neural Transm. [P- DSect.]* 3:1-14, Springer-Verlag (1991).

Hoyer, S., "Age as Risk Factor for Sporadic Dementia of the Alzheimer Type?," *Ann. N. Y. Acad. Sci.* 719:248-256, New York Academy of Sciences (1994).

Hoyer, S., et al, "Desensitization of brain insulin receptor. Effect on glucose/energy and related metabolism," *J. Neural. Transm.* 44:259-268, Springer-Verlag (1994).

Hoyer, S., "Neurodegeneration, Alzheimer's Disease, and Beta-Amyloid Toxicity," *Life Sci.* 55:1977-1983, Pergamon Press (1994).

Hoyer, S., "Oxidative metabolism deficiencies in brains of patients with Alzheimer's disease," *Acta Neurol. Scand.* 165:18-24, Munksgaard International Publishers Ltd. (1996).

Hoyer, S., "Is sporadic Alzheimer disease the brain type of non-insulin dependent diabetes mellitus? A challenging hypothesis," *J. Neural Transm.* 105:415-422, Springer-Verlag (1998).

Hoyer, S. and Lannert, H., "Inhibition of the Neuronal Insulin Receptor Causes Alzheimer-like Disturbances in Oxidative/Energy Brain Metabolism and in Behavior in Adult Rats," *Ann. N. Y. Acad. Sci.* 893:301-303, New York Academy of Sciences (1999).

Hoyer, S., et al., "Inhibition of the Neuronal Insulin Receptor: An in Vivo Model for Sporadic Alzheimer Disease?," *Ann. N. Y. Acad. Sci.* 920:256-258, New York Academy of Sciences (2000).

Hoyer, S., "Brain glucose and energy metabolism abnormalities in sporadic Alzheimer disease. Causes and consequences: an update," *Exp. Gerontol.* 35:1363-1372, Elsevier Science (2000).

Hoyer, S., "The aging brain. Changes in the neuronal insulin/insulin receptor signal transduction cascade trigger late-onset sporadic Alzheimer disease (SAD). A mini-review," *J. Neural Transm.* 109:991-1002, Springer-Verlag (2002).

Hoyer, S., "The brain insulin signal transduction system and sporadic (type II) Alzheimer disease: an update," *J. Neural Transm.* 109:341-360, Springer-Verlag (2002).

Hoyer, S., "Causes and Consequences of Disturbances of Cerebral Glucose Metabolism in Sporadic Alzheimer Disease: Therapeutic Implications," in *Frontiers in Clinical Neuroscience: Neurodegeneration and Neuroprotection*, Vécsei, L., ed., Kluwer Academic/Plenum Publishers, New York, NY, pp. 135-152 (Feb. 2004).

Hoyer, S., "Glucose metabolism and insulin receptor signal transduction in Alzheimer disease," *Eur. J. Pharmacol.* 490:115-125, Elsevier Science B.V. (Apr. 2004).

Jafferali, S., et al., "Insulin-Like Growth Factor-I and Its Receptor in the Frontal Cortex, Hippocampus, and Cerebellum of Normal Human and Alzheimer Disease Brains," *Synapse* 38:450-459, Wiley-Liss, Inc. (2000).

Kilander, L., et al., "Peripheral glucose metabolism and insulin sensitivity in Alzheimer's disease," *Acta Neurol. Scand.* 8:294-298, Munksgaard International Publishers Ltd. (1993).

Koh, E.H., et al., "Peroxisome Proliferator-Activated Receptor (PPAR)-β Activation Prevents Diabetes in OLETF Rats: Comparison With PPAR-γ Activation," *Diabetes* 52:2331-2337, American Diabetes Association, Inc. (Sep. 2003).

Kulik, G., et al., "Antiapoptotic Signalling by the Insulin-Like Growth Factor I Receptor, Phosphatidylinositol 3-Kinase, and Akt," *Mol. Cell. Biol.* 17:1595-1606, American Society for Microbiology (1997).

Kulkarni, R.N. and Okada, T., "Tissue-Specific Targeting of the Insulin Receptor Gene," *Endocrine* 19:257-266, Humana Press (2002).

Kuusisto, J., et al., "Association between features of the insulin resistance syndrome and Alzheimer's disease independently of apolipoprotein E4 phenotype: cross sectional population based study," *BMJ* 315:1045-1049, British Medical Association (1997).

Lam, K., et al., "The Phosphatidylinositol 3-Kinase Serine Kinase Phosphorylates IRS-1: Stimulation by Insulin and Inhibition by Wortmannin," *J. Biol. Chem.* 269:20648-20652, American Society for Biochemistry and Molecular Biology (1994).

Lannert, H. and Hoyer, S., "Intracerebroventricular Administration of Streptozotocin Causes Long-Term Diminutions in Learning and Memory Abilities and in Cerebral Energy Metabolism in Adult Rats," *Behav. Neurosci.* 112:1199-1208, American Psychological Association (1998).

Leibowitz, M.D., et al., "Activation of PPARδ alters lipid metabolism in db/db mice," *FEBS Lett.* 473:333-336, Elsevier Science B.V. (2000).

Leissring, M.A., et al., "Enhanced Proteolysis of β-Amyloid in APP Transgenic Mice Prevents Plaque Formation, Secondary Pathology, and Premature Death," *Neuron* 40:1087-1093, Cell Press (Dec. 2003).

Lester-Coll, N., et al., "Intracerebral Streptozotocin Model of Type 3 Diabetes: Relevance to Sporadic Alzheimer's Disease," *J. Alzheimer's Dis.* 9:13-33, IOS Press (Mar. 2006).

Ling, X., et al., "Amyloid beta antagonizes insulin promoted secretion of the amyloid beta protein precursor," *J. Alzheimer's Dis.* 4:369-374, IOS Press (2002).

Lovestone, S., et al., "Alzheimer's disease-like phosphorylation of the microtubule-associated protein tau by glycogen synthase kinase-3 in transfected mammalian cells," *Curr. Biol.* 4:1077-1086, Current Biology Ltd. (1994).

Mauvais-Jarvis, F. and Kahn, C.R., "Understanding the Pathogenesis and Treatment of Insulin Resistance and Type 2 Diabetes Mellitus: What Can We Learn from Transgenic and Knockout Mice," *Diabetes Metab.* 26:433-448, Masson (2000).

Mauvais-Jarvis, F., et al., "Knockout models are useful tools to dissect the pathophysiology and genetics of insulin resistance," *Clin. Endocrinol.* 57:1-9, Blackwell Publishing Company (2002).

McDermott, J.R. and Gibson, A.M., "Degradation of Alzheimer's β-Amyloid Protein by Human and Rat Brain Peptidases: Involvement of Insulin-Degrading Enzyme," *Neurochem. Res.* 22:49-56, Plenum Press (1997).

Meneilly, G.S. and Hill, A., "Alterations in Glucose Metabolism in Patients with Alzheimer's Disease," *J. Am. Geriatr. Soc.* 41:710-714, Williams & Wilkins (1993).

Messier, C. and Gagnon, M., "Glucose regulation and cognitive functions: relation to Alzheimer's disease and diabetes," *Behav. Brain Res.* 75:1-11, Elsevier Science B.V. (1996).

Messier, C., "Diabetes, Alzheimer's disease and apolipoprotein genotype," *Exp. Gerontol.* 38:941-946, Elsevier Inc. (Sep. 2003).

Mill, J.F., et al., "Insulin, insulin-like growth factor II, and nerve growth factor effects on tubulin mRNA levels and neurite formation," *Proc. Natl. Acad. Sci. USA* 82:7126-7130, National Academy of Sciences (1985).

Miyachi, H., "Synthetic ligands for peroxisome proliferator-activated receptor-α, review of the patent literature 2000-2003," *Expert Opin. Ther. Patents* 14:607-618, Ashley Publications Ltd. (May 2004).

Miyachi, H., "Analysis of patent applications relating to peroxisome proliferator-activated receptor (PPAR) ligands in 2004," *Expert Opin. Ther. Patents* 15:1521-1530, Ashley Publications Ltd. (Nov. 2005).

Miyazaki, Y., et al., "Rosiglitazone Improves Downstream Insulin Receptor Signaling in Type 2 Diabetic Patients," *Diabetes* 52:1943-1950, American Diabetes Association, Inc. (Aug. 2003).

Molina, J.A., et al., "Cerebrospinal fluid levels of insulin in patients with Alzheimer's disease," *Acta Neural. Scand.* 106:347-350, Blackwell Publishing (2002).

Moroo, I., et al., "Loss of insulin receptor immunoreactivity from the substantia nigra pars compacta neurons in Parkinson's disease," *Acta Neuropathol.* 87:343- 348, Springer-Verlag (1994).

Müller, D., et al., "Intracerebroventricular Injection of Streptozotocin—An Animal Model for Sporadic Alzheimer's Disease?," in *Alzheimer's and Parkinson's Diseases*, Hanin, I., et al., eds., Plenum Press, New York, Ny, pp. 389-393 (1995).

Münch, G., et al., "Alzheimer's disease—synergistic effects of glucose deficit, oxidative stress and advanced glycation endproducts," *J. Neural Transm.* 105:439-461, Springer-Verlag (1998).

Mustafa, A., et al., "Decreased Plasma Insulin-Like Growth Factor-I Level in Familial Alzheimer's Disease Patients Carrying the Swedish APP 670/671 Mutation," *Dement. Geriatr. Cogn. Disord.* 10:446-451, S. Karger Medical and Scientific Publishers (1999).

Myers, M.G., et al., "The IRS-1 signaling system," *Trends Biochem. Sci.* 19:289-293, International Union of Biochemistry and Molecular Biology and Elsevier Trends Journals (1994).

Nakae, J., et al., "Distinct and Overlapping Functions of Insulin and IGF-I Receptors," *Endocr. Rev.* 22:818-835, Endocrine Society (2001).

Ni, W., et al., "Impaired brain development and reduced astrocyte response to injury in transgenic mice expressing IGF binding protein-1," *Brain Res.* 769:97-107, Elsevier Science B.V. (1997).

Odetti, P., et at, "Early Glycoxidation Damage in Brains from Down's Syndrome," *Biochem. Biophys. Res. Commun.* 243:849-851, Academic Press (1998).

O'Kusky, J.R., et al., "Insulin-Like Growth Factor-I Promotes Neurogenesis and Synaptogenesis in the Hippocampal Dentate Gyrus during Postnatal Development," *J. Neurosci.* 20:8435-8442, Society for Neuroscience (2000).

Oliver, W.R., et al., "A selective peroxisome proliferator-activated receptor δ agonist promotes reverse cholesterol transport," *Proc. Natl. Acad. Sci. USA* 98:5306-5311, National Academy of Sciences (2001).

Ott, A., et al., "Association of diabetes mellitus and dementia: The Rotterdam Study," *Diabetologia* 39:1392-1397, Springer-Verlag Berlin (1996).

Ott, A., et al., "Diabetes mellitus and the risk of dementia: The Rotterdam Study," *Neurology* 53:1937-1942, Lippincott Williams & Wilkins (1999).

Pap, M. and Cooper, G.M., "Role of Glycogen Synthase Kinase-3 in the Phosphatidylinositol 3-Kinase/Akt Cell Survival Pathway," *J. Biol. Chem.* 273:19929-19932, American Society for Biochemistry and Molecular Biology (1998).

Pei, J.-J., et al., "Accumulation of cyclin-dependent kinase 5 (cdk5) in neurons with early stages of Alzheimer's disease neurofibrillary degeneration," *Brain Res.* 797:267-277, Elsevier Science B.V. (1998).

Pérez, A., et al., "Degradation of Soluble Amyloid β-Peptides 1-40, 1-42, and the Dutch Variant 1-40Q by Insulin Degrading Enzyme from Alzheimer Disease and Control Brains," *Neurochem. Res.* 25:247-255, Kluwer Academic/Plenum Publishers (2000).

Perry, G., et al., "Reactive Oxygen Species Mediate Cellular Damage in Alzheimer Disease," *J. Alzheimer's Dis.* 1:45-55, IOS Press (1998).

Pete, G., et al., "Postnatal Growth Responses to Insulin-Like Growth Factor I in Insulin Receptor Substrate-I-Deficient Mice," *Endocrinology* 140:5478-5487, Endocrine Society (1999).

Plaschke, K. and Hoyer, S., "Action of the Diabetogenic Drug Streptozotocin on Glycolytic and Glycogenolytic Metabolism in Adult Rat Brain Cortex and Hippocampus," *Int. J. Devl. Neurosci.* 11:477-483, Pergamon Press (1993).

Poduslo, J.F., et al., "Permeability of Proteins at the Blood-Brain Barrier in the Normal Adult Mouse and Double Transgenic Mouse Model of Alzheimer's Disease," *Neurobiol. Dis.* 8:555-567, Academic Press (2001).

Popken, G.J., et al., "In vivo effects of insulin-like growth factor-I (IGF-I) on prenatal and early postnatal development of the central nervous system," *Eur. J. Neurosci.* 19:2056-2068, Blackwell Publishing Ltd. (Apr. 2004).

Puro, D.G. and Agardh, E., "Insulin-Mediated Regulation of Neuronal Maturation," *Science* 225:1170-1172, American Association for the Advancement of Science (1984).

Qui, W.Q., et al., "Insulin-degrading Enzyme Regulates Extracellular Levels of Amyloid β-Protein by Degradation," *J. Biol. Chem.* 273:32730-32738, American Society for Biochemistry and Molecular Biology (1998).

Razay, G. and Wilcock, G.K., "Hyperinsulinaemia and Alzheimer's Disease," *Age Ageing* 23:396-399, Oxford University Press (1994).

Reubi, J.C. And Palacios, J., "Somatostatin and Alzheimer's disease: a hypothesis," *J. Neurol.* 233:370-372, Springer-Verlag (1986).

Rivera, E.J., et al., "Insulin and Insulin-Like Growth Factor Expression and Function Deteriorate with Progression of Alzheimer's Disease," *J. Alzheimer's Dis.* 8:247-268, IOS Press (Dec. 2005).

Saltiel, A.R. and Pessin, J.E., "Insulin signaling pathways in time and space," *Trends Cell Biol.* 12:65-71, Elsevier Science Ltd. (2002).

Schubert, M., et al., "Insulin Receptor Substrate-2 Deficiency Impairs Brain Growth and Promotes Tau Phosphorylation," *J. Neurosci.* 23:7084-7092, Society for Neuroscience (Aug. 2003).

Schubert, M., et al., "Role for neuronal insulin resistance in neurodegenerative diseases," *Proc. Natl. Acad. Sci. USA* 101:3100-3105, National Academy of Sciences (Mar. 2004).

Shpakov, A.O. and Pertseva, M.N., "Structural and Functional Characterization of Insulin Receptor Substrate Proteins and the Molecular Mechanisms of Their Interaction with Insulin Superfamily Tyrosine Kinase Receptors and Effector Proteins," *Membr. Cell Biol.* 13:455-484, Harwood Academic Publishers (2000).

Spindler, A.A., et al., "Nutritional status of patients with Alzheimer's disease: a 1-year study," *J. Am. Diet. Assoc.* 96:1013-1018, American Dietetic Association (1996).

Steen, E., et al., "Impaired insulin and insulin-like growth factor expression and signaling mechanisms in Alzheimer's disease—is this type 3 diabetes?," *J. Alzheimer's Dis.* 7:63-80, IOS Press (Feb. 2005).

Sun, X.J., et al., "Pleiotropic Insulin Signals Are Engaged by Multisite Phosphorylation of IRS-1," *Mol. Cell. Biol.* 13:7418-7428, American Society for Microbiology (1993).

Tham, A., et al., "Insulin-like growth factors and somatomedin B in the cerebrospinal fluid of patients with dementia of the Alzheimer type," *Acta Psychiatr. Scand.* 77:719-723, Munksgaard International Publishers (1988).

Tham, A., et al., "Insulin-like growth factors and insulin-like growth factor binding proteins in cerbrospinal fluid and serum of patients with dementia of the Alzheimer type," *J. Neural Transm. [P-D Sect.]* 5:165-176, Springer-Verlag (1993).

Tsukamoto, E., et al., "Characterization of the Toxic Mechanism Triggered by Alzheimer's Amyloid-β Peptides Via p75 Neurotrophin Receptor in Neuronal Hybrid Cells," *J. Neurosci. Res.* 73:627-636, Wiley-Liss, Inc. (Sep. 2003).

Ullrich, A., et al., "Human insulin receptor and its relationship to the tyrosine kinase family of oncogenes," *Nature* 313:756-761, Macmillan Journals Ltd (1985).

Unger, J.W., et al., "Immunohistochemical Localization of Insulin Receptors and Phosphotyrosine in the Brainstem of the Adult Rat," *Neuroscience* 42:853-861, Pergamon Press plc (1991).

Unger, J.W., et al., "Insulin Receptors in the Central Nervous System: Localization, Signalling Mechanisms and Functional Aspects," *Prog. Neurobiol.* 36:343-362, Pergamon Press plc (1991).

van Weeren, P.C., et al., "Essential Role for Protein Kinase B (PKB) in Insulin-induced Glycogen Synthase Kinase 3 Inactivation," *J. Biol. Chem.* 273:13150-13156, American Society for Biochemistry and Molecular Biology (1998).

Vekrellis, K., et al., "Neurons Regulate Extracellular Levels of Amyloid β-Protein via Proteolysis by Insulin-Degrading Enzyme," *J. Neurosci.* 20:1657-1665, Society for Neuroscience (2000).

Virkamäki, A., et al., "Protein-protein interaction in insulin signaling and the molecular mechanisms of insulin resistance," *J. Clin. Invest.* 103:931-943, American Society for Clinical Investigation (1999).

Vollenweider, P., "Insulin Resistant States and Insulin Signaling," *Clin. Chem. Lab. Med.* 41:1107-1119, Walter De Gruyter (Sep. 2003).

Vosper, H., et al., "The Peroxisome Proliferator-activated Receptor δ Promotes Lipid Accumulation in Human Macrophages," *J. Biol. Chem.* 276:44258-44265, American Society for Biochemistry and Molecular Biology, Inc. (2001).

Wang, Y.-X., et al., "Peroxisome-Proliferator-Activated Receptor δ Activates Fat Metabolism to Prevent Obesity," *Cell* 113:159-170, Cell Press (Apr. 2003).

Watson, G.S. and Craft, S. "The role of insulin resistance in the pathogenesis of Alzheimer's disease: implications for treatment," *CNS Drugs* 17:27-45, Adis International Limited (2003).

Willson, T.M., et al., "The PPARs: From Orphan Receptors to Drug Discovery," *J. Med. Chem.* 43:527-550, American Chemical Society (2000).

Wozniak, M., et al., "The Cellular and Physiological Actions of Insulin in the Central Nervous System," *Neurochem. Int.* 22:1-10, Pergamon Press Ltd. (1993).

Xie, L., et al., "Alzheimer' β-Amyloid Peptides Compete for Insulin Binding to the Insulin Receptor," *J. Neurosci.* 22:RC221 (1-5), Society for Neuroscience (2002).

Yamaguchi, H., et al., "T-817MA, a Neurotrophic Compound, Reverses Aβ Neurotoxicity and Promotes Neurite Outgrowth Through PI3-Kinase Pathway in Rat Primary Neurons," Program No. 97.5. *2003 Abstract Viewer/Itinerary Planner*, Washington, DC, Society for Neuroscience (presented Nov. 8-12, 2003).

Yan, S.D., et al., "Non-enzymatically glycated tau in Alzheimer's disease induces neuronal oxidant stress resulting in cytokine gene expression and release of amyloid β-peptide," *Nature Med.* 1:693-699, Nature Publishing Co. (1995).

Ye, P., et al., "In vivo actions of insulin-like growth factor-I (IGF-I) on cerebellum development in transgenic mice: evidence that IGF-I increases proliferation of granule cell progenitors," *Brain Res. Dev. Brain Res.* 95:44-54, Elsevier Science B.V. (1996).

Ye, P., et al., "Regulation of Insulin-Like Growth Factor I (IGF-I) Gene Expression in Brain of Transgenic Mice Expressing an IGF-I-Luciferase Fusion Gene," *Endocrinology* 138:5466-5475, Endocrine Society (1997).

Ye, P., et al., "Deficient expression of insulin receptor substrate-1 (IRS-1) fails to block insulin-like growth factor-I (IGF-I) stimulation of brain growth and myelination," *Dev. Brain Res. Brain Res.* 136:111-121, Elsevier Science B.V. (2002).

Zhao, W.-Q. and Alkon, D., "Role of insulin and insulin receptor in learning and memory," *Mol. Cell. Endocrinol.* 177:125-134, Elsevier Science Ireland Ltd. (2001).

Zhang, F., et al., "Peroxisome Proliferator-Activated Receptors as Attractive Antiobesity Targets," *Drug News Perspect.* 17:661-669, J.R. Prous, S.A. (Dec. 2004).

Zheng, W.-H., et al., "Insulin-like growth factor-1 (IGF-1): a neuroprotective trophic factor acting via the Akt kinase pathway," in *Advances in Research on Neurodegeneration*, Reiderer, P., et al., eds., Springer-Verlag, New York, NY, pp. 261-272 (2000).

Zhong, J., et al., "Inhibition of Insulin-Like Growth Factor I Activity Contributes to the Premature Apoptosis of Cerebellar Granule Neuron in Weaver Mutant Mice: In Vitro Analysis," *J. Neurosci. Res.* 70:36-45, Wiley-Liss, Inc. (2002).

International Search Report for International Application No. PCT/US05/43856, United States Patent and Trademark Office, United States, mailed on Aug. 28, 2006.

Benedict et al., "Intranasal insulin improves memory in humans", *PNEC*, 29:1326-1334 (2004).

Zhang, et al., The role of insulin in Alzheimer's disease; *Chin J. Endocrinol Metab*, vol. 2(2)176-177 (2004).

\* cited by examiner

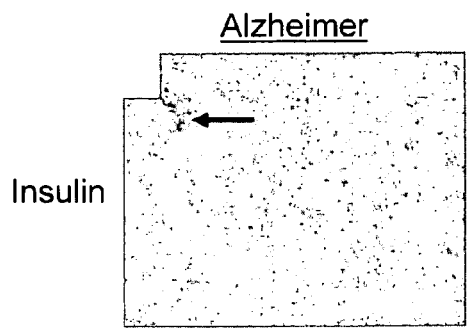
FIG.3A (Alzheimer, Insulin)
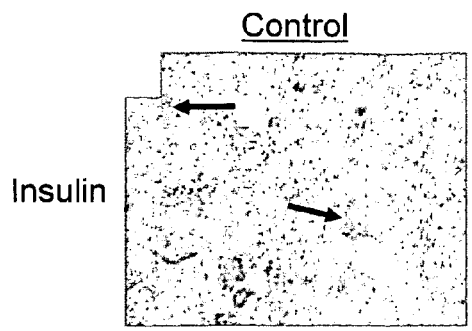
FIG.3B (Control, Insulin)
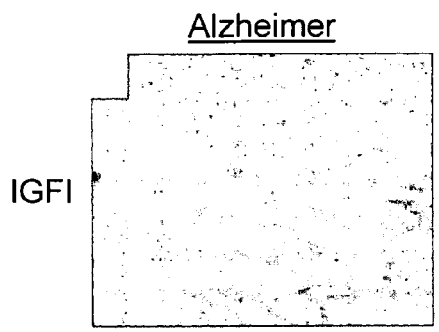
FIG.3C (Alzheimer, IGFI)
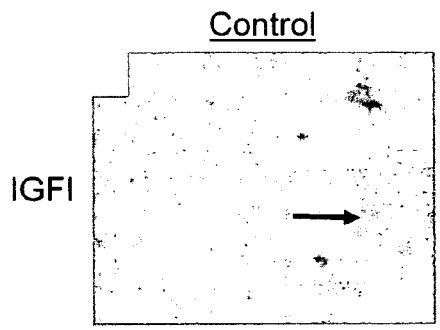
FIG.3D (Control, IGFI)
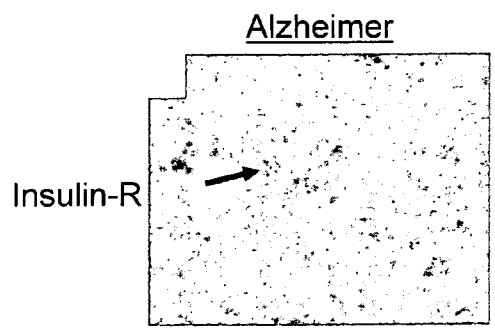
FIG.3E (Alzheimer, Insulin-R)
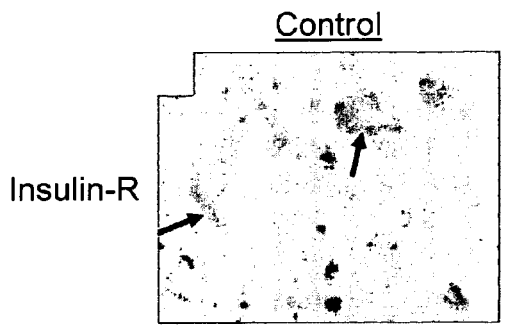
FIG.3F (Control, Insulin-R)
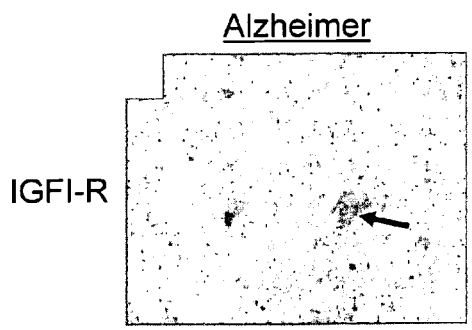
FIG.3G (Alzheimer, IGFI-R)
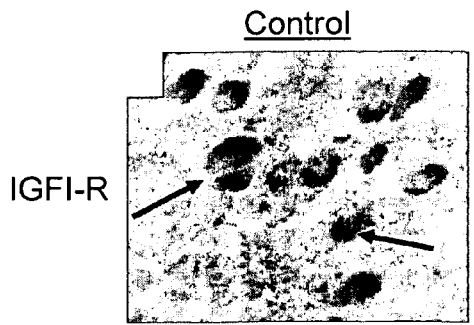
FIG.3H (Control, IGFI-R)

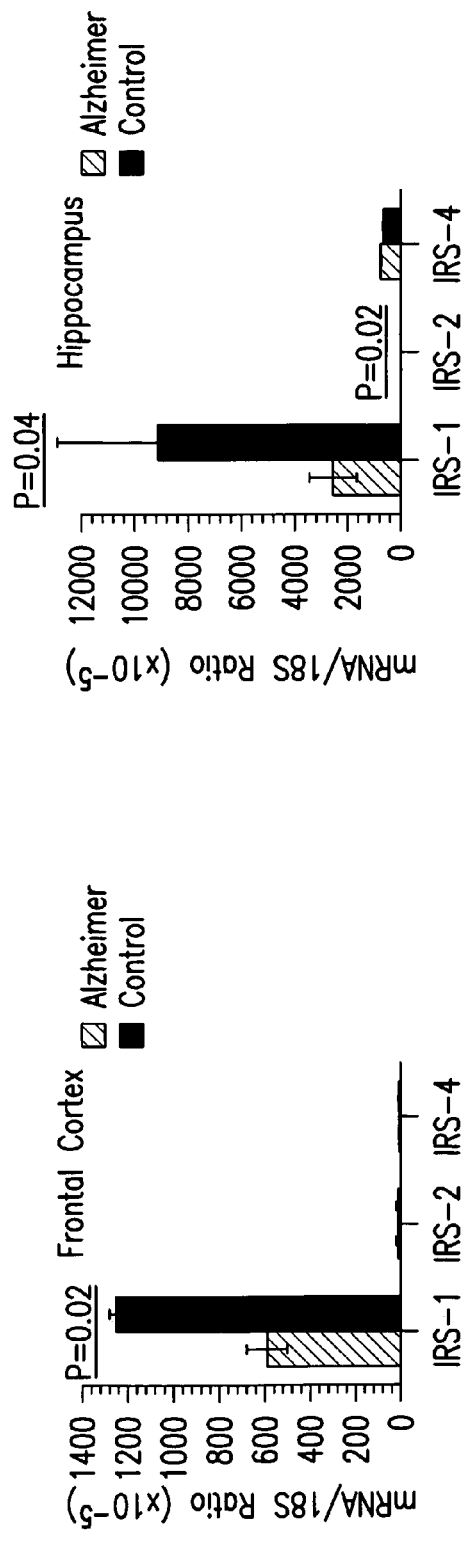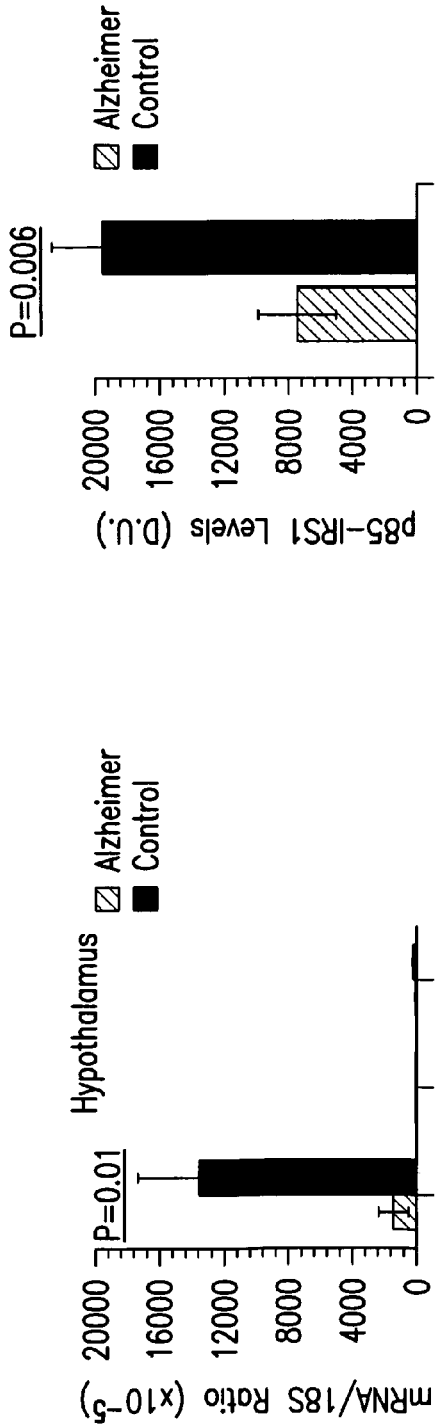

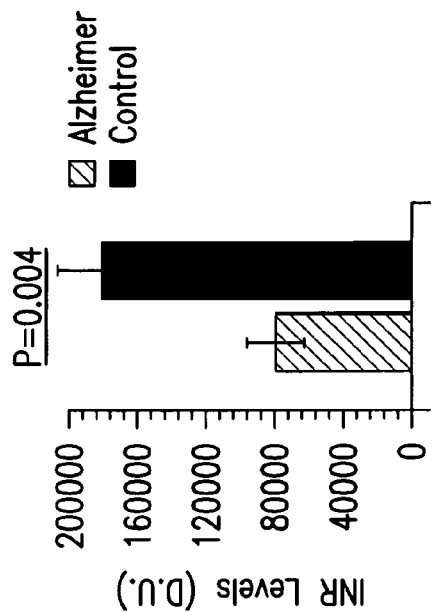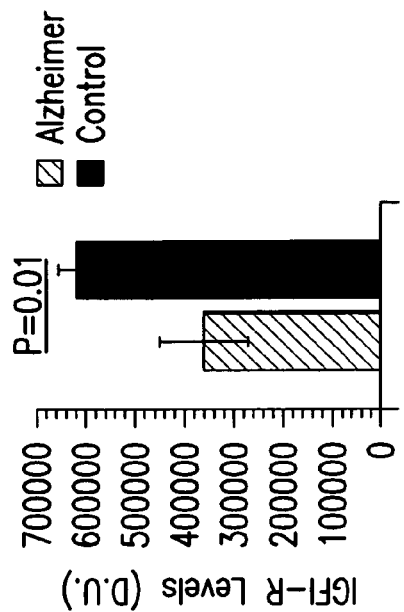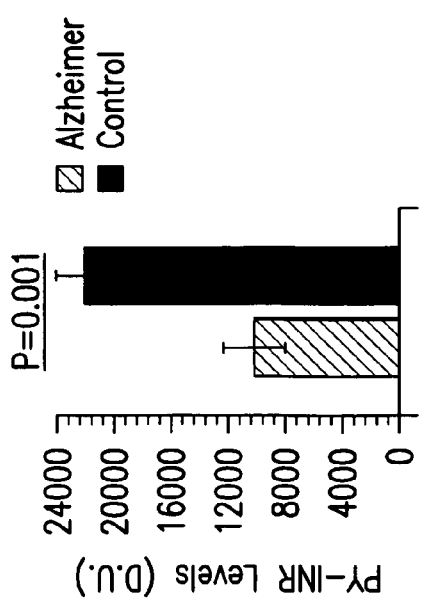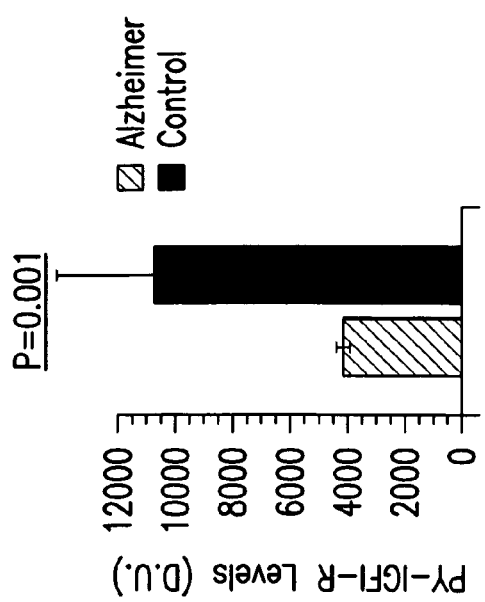

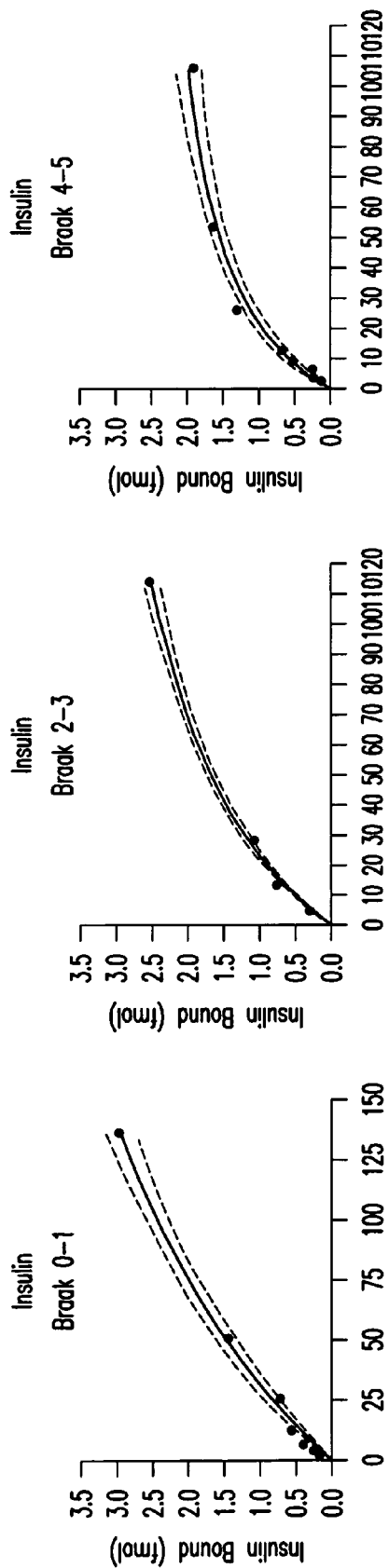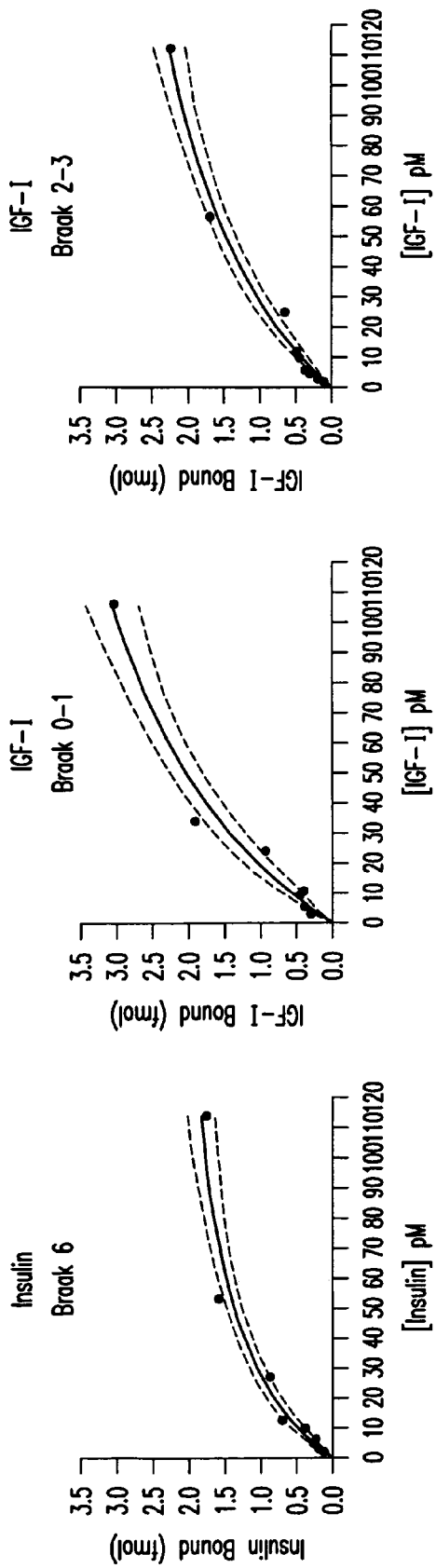
FIG. 13A  FIG. 13B  FIG. 13C
FIG. 13D  FIG. 13E  FIG. 13F

FIG.17E  FIG.17F
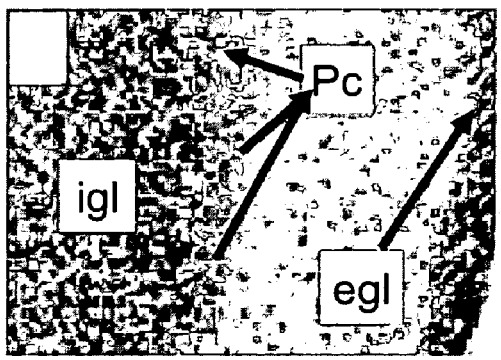
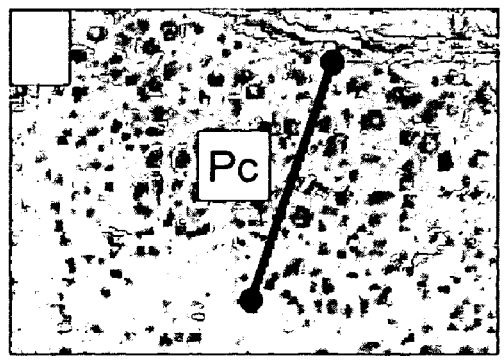
FIG.17G  FIG.17H
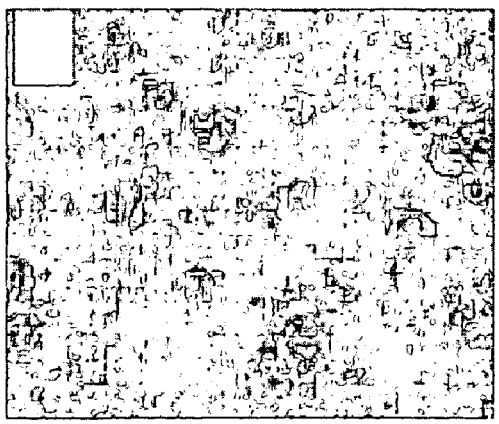
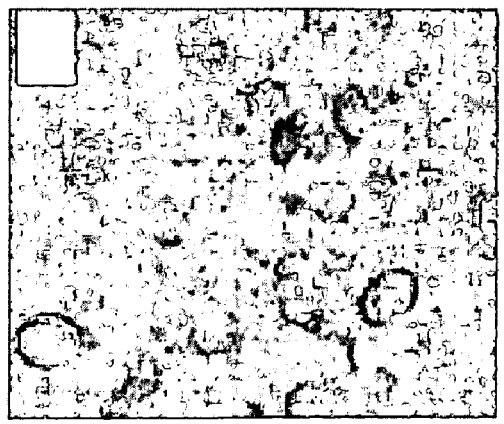
FIG.17I  FIG.17J

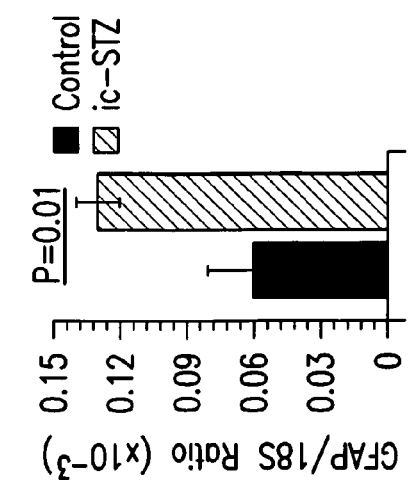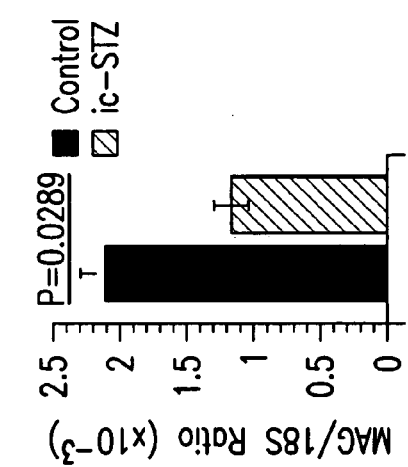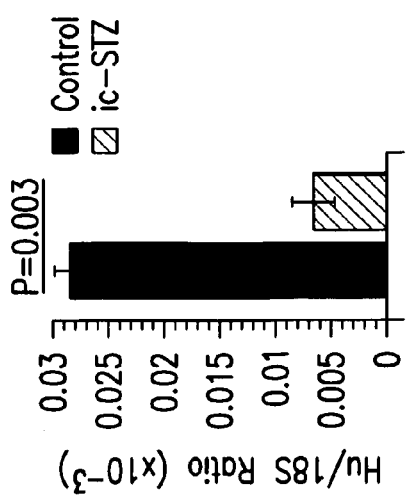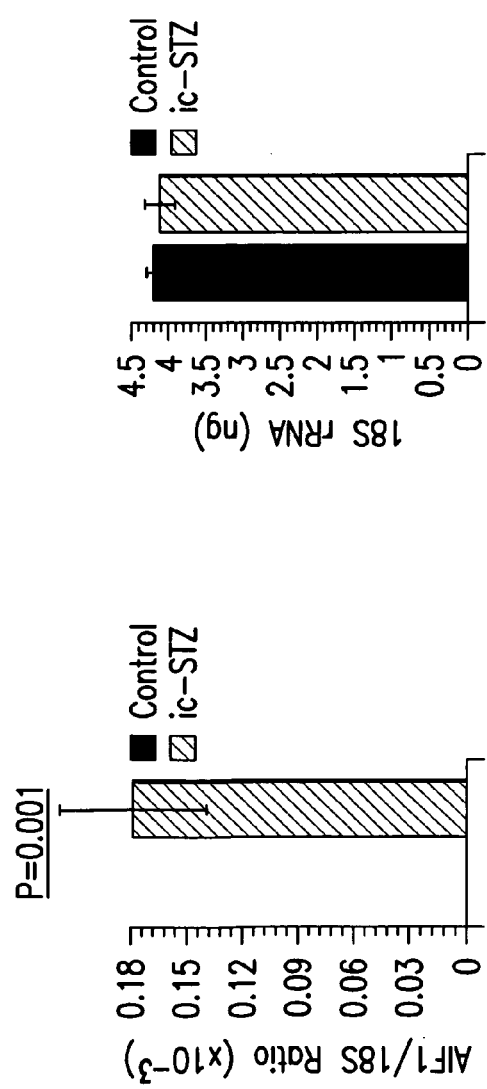

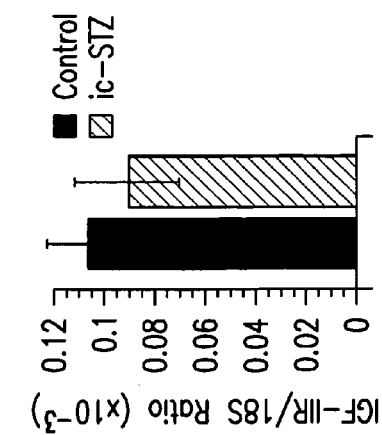
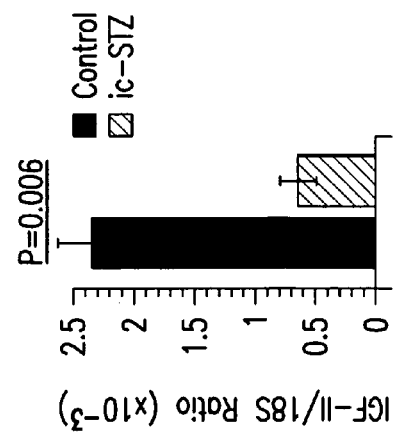
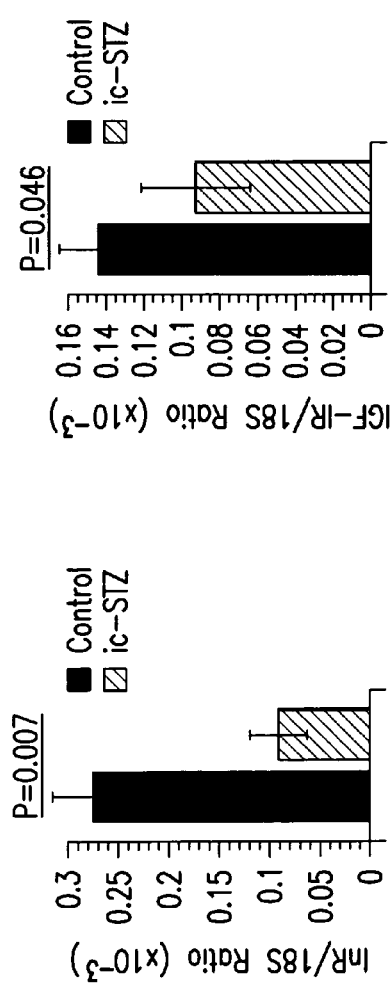
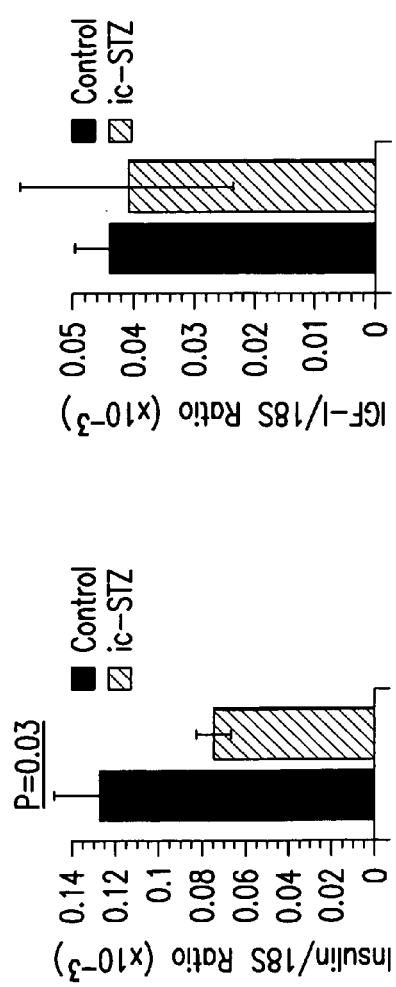
FIG. 19A  FIG. 19B  FIG. 19C
FIG. 19D  FIG. 19E  FIG. 19F

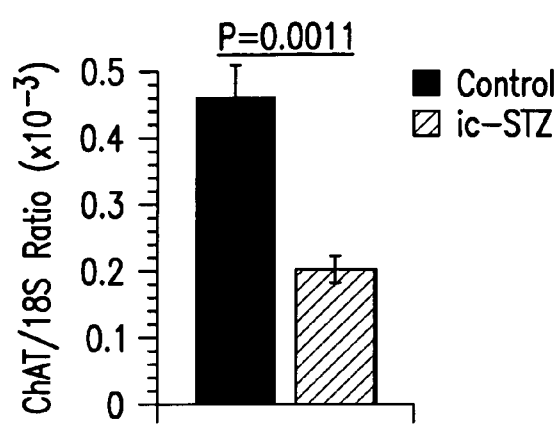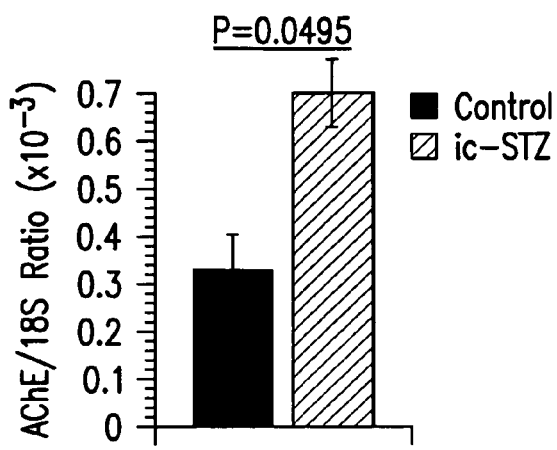
FIG.24A  FIG.24B
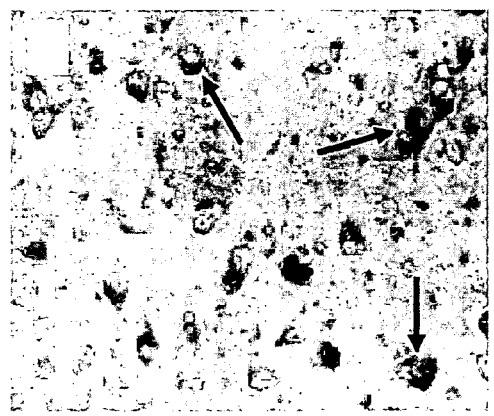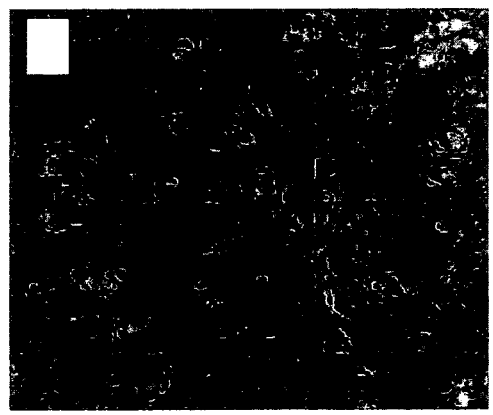
FIG.24C  FIG.24D
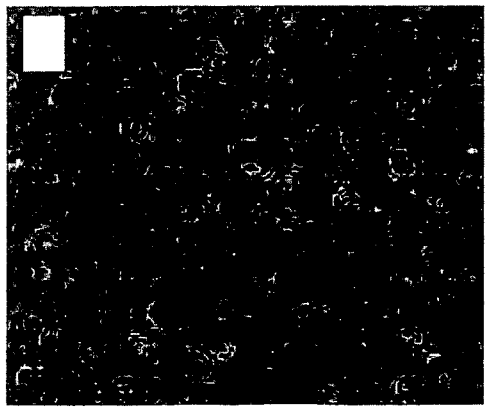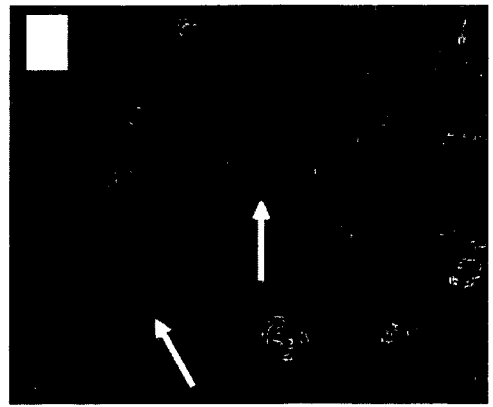
FIG.24E  FIG.24F

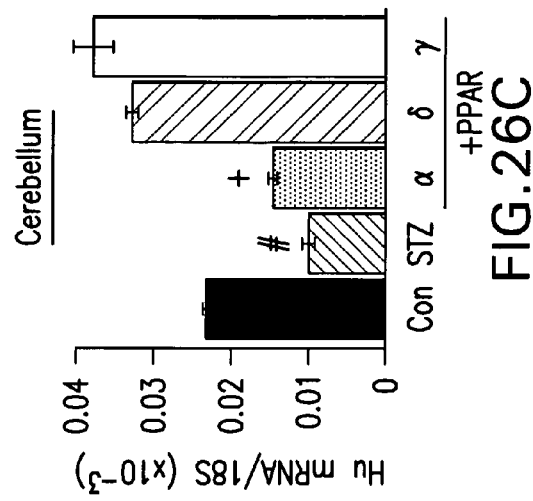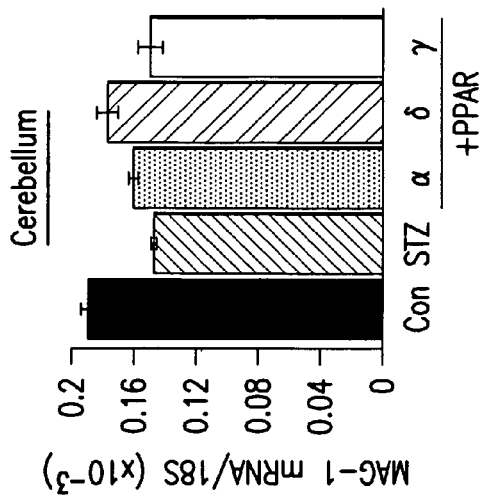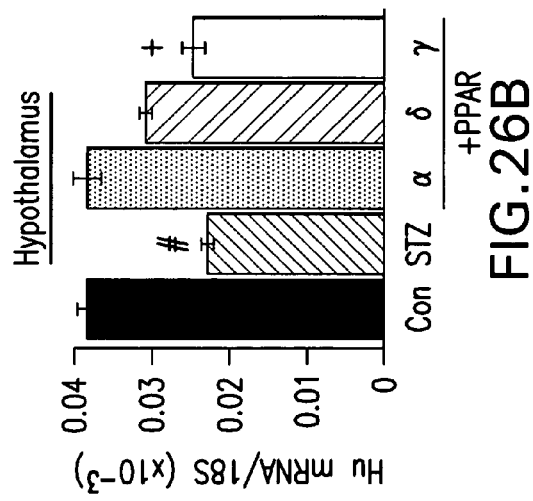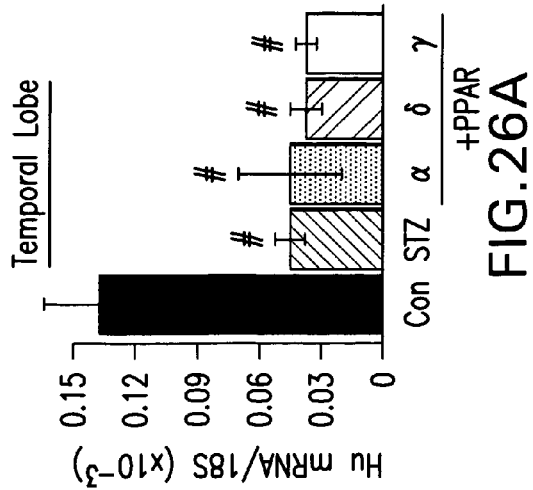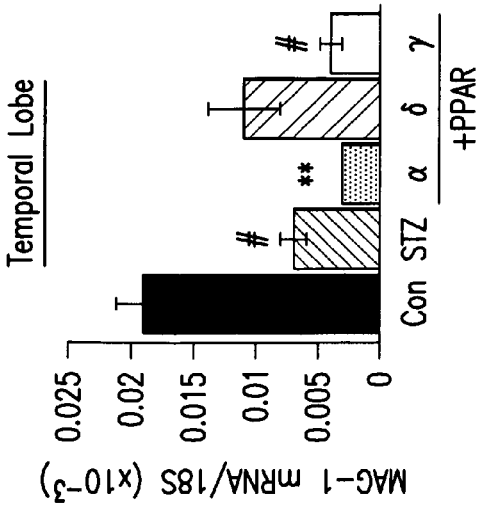
FIG. 26A FIG. 26B FIG. 26C FIG. 26D FIG. 26E FIG. 26F

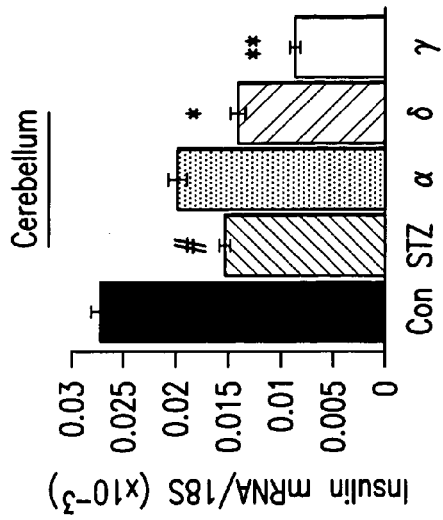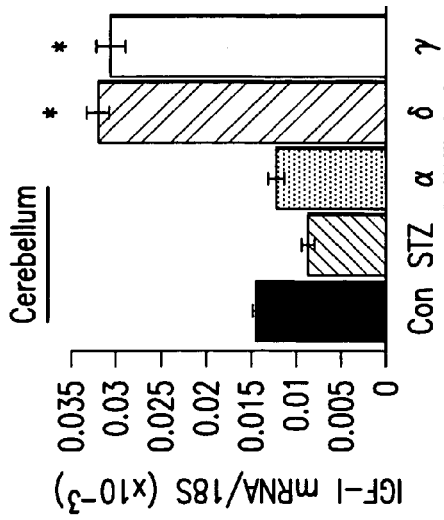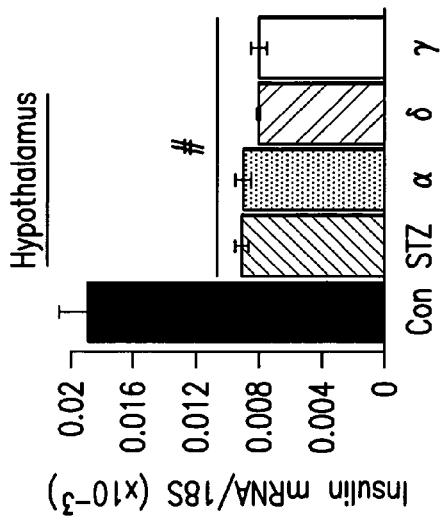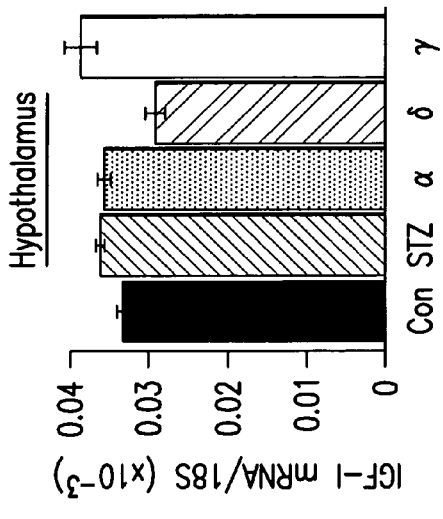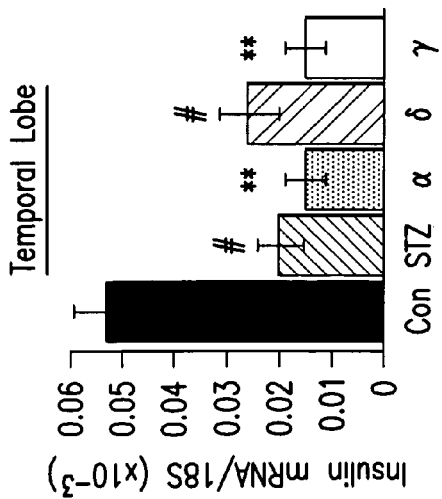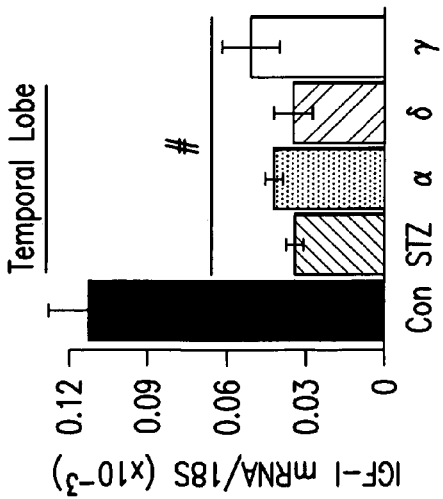

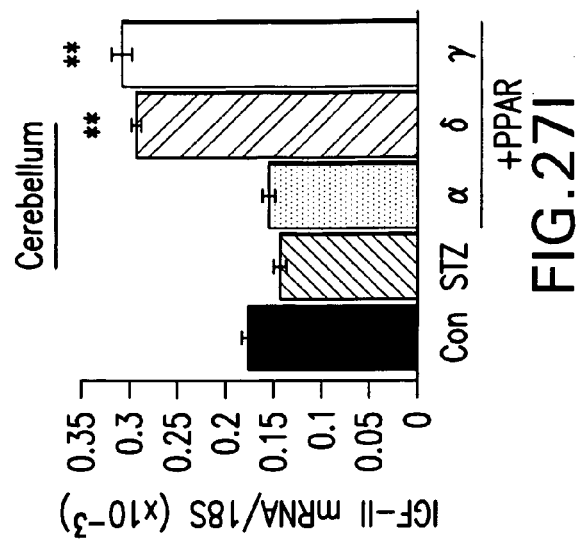
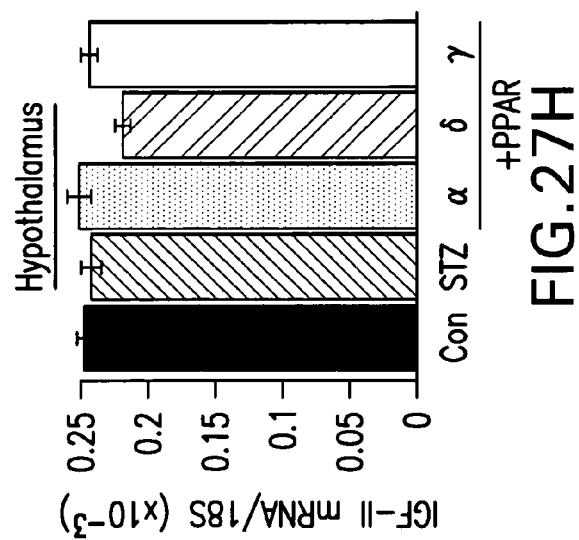
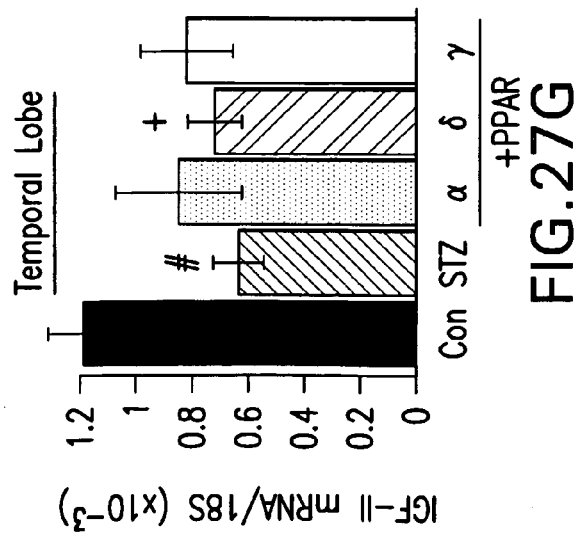
FIG. 27I
FIG. 27H
FIG. 27G

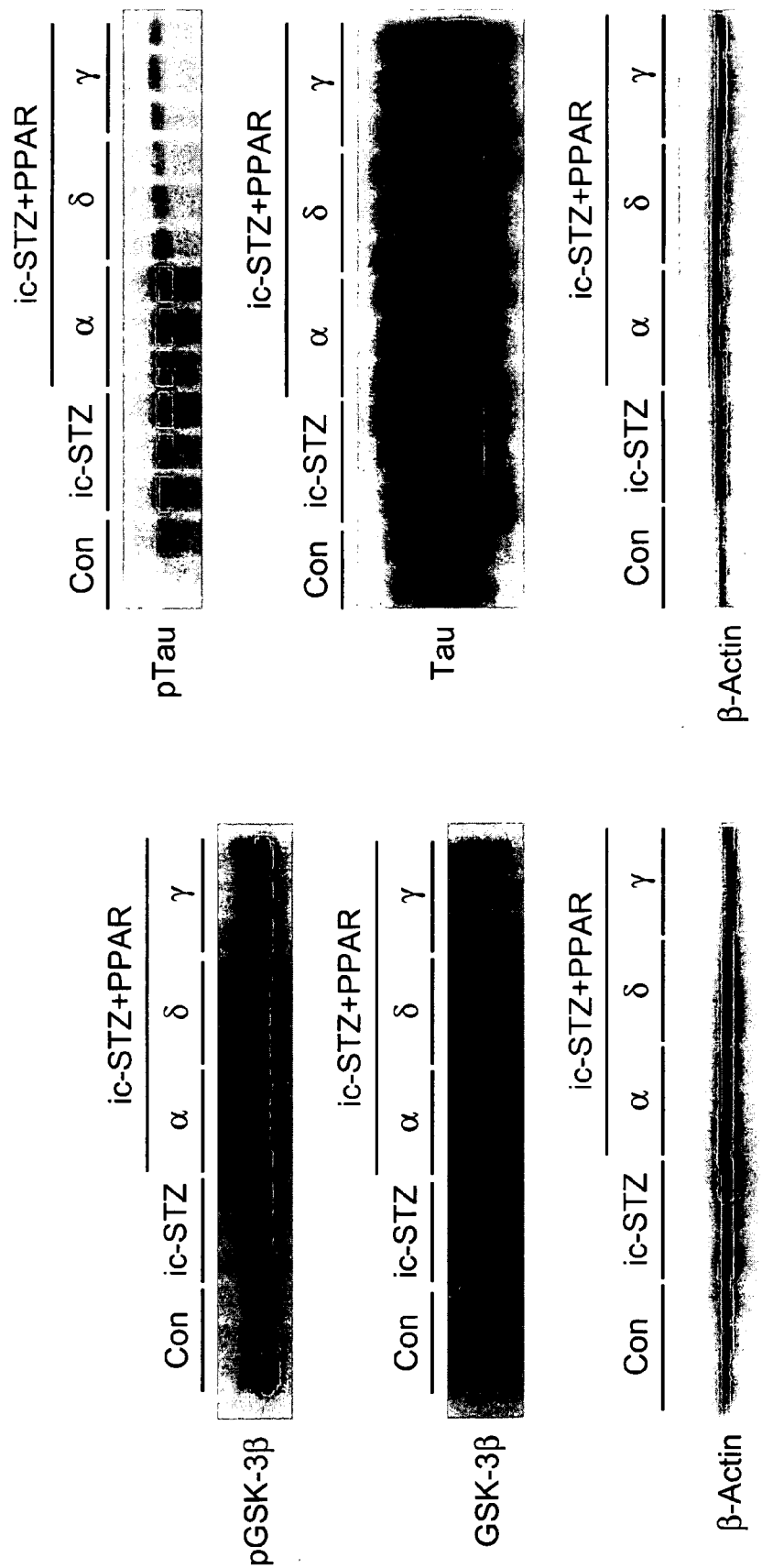

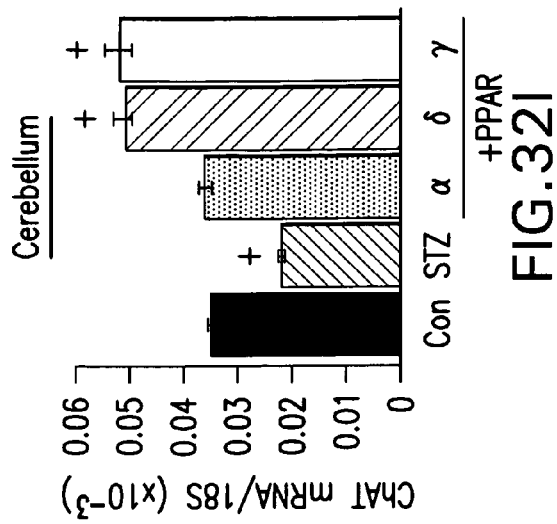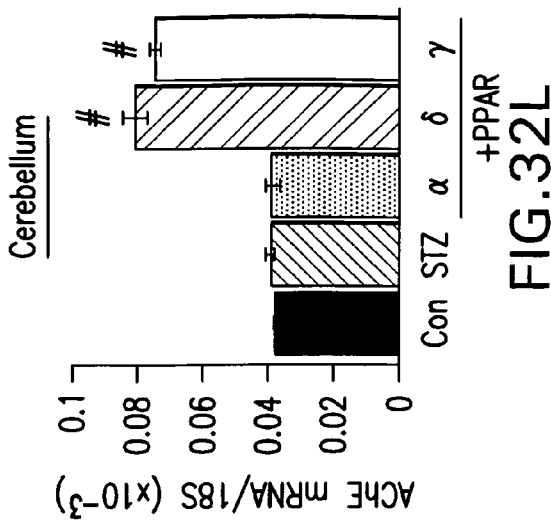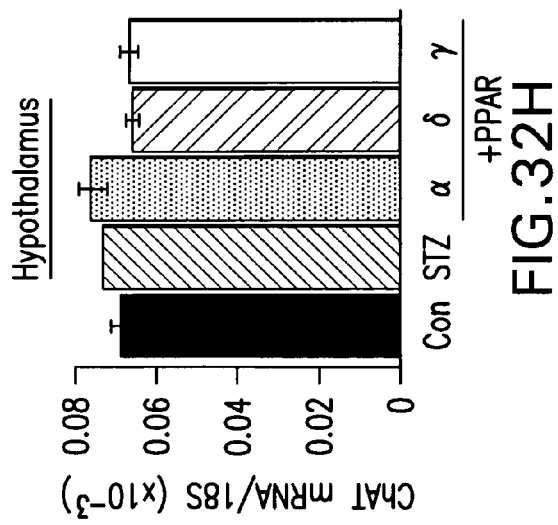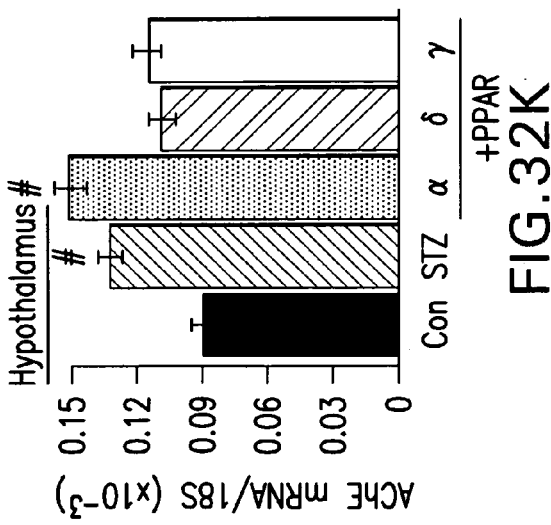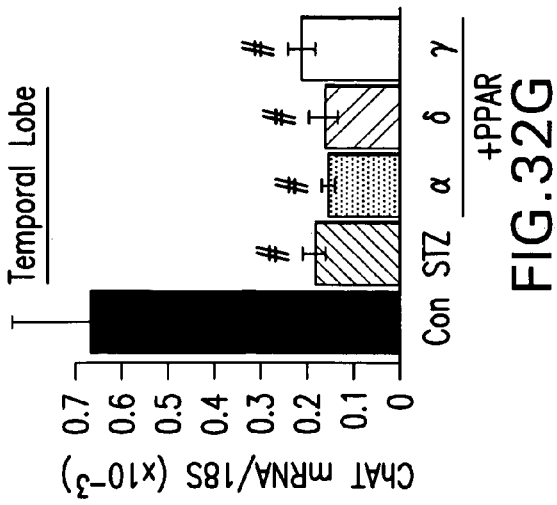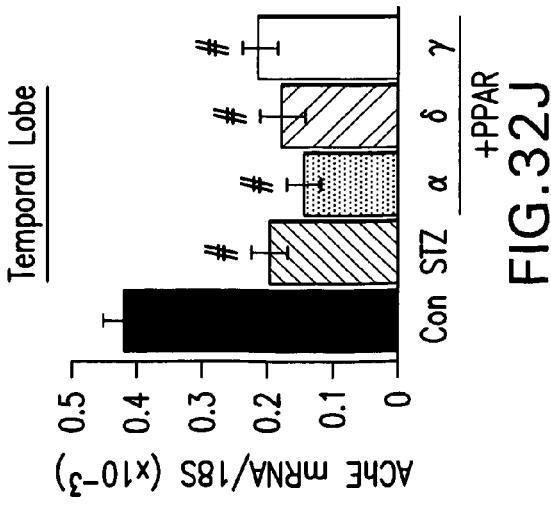

GFAP

Control

HNE

Control

GFAP ic-STZ

HNE ic-STZ

GFAP

+PPAR-α

HNE

+PPAR-α

GFAP

+PPAR-δ

HNE

+PPAR-δ

GFAP

+PPAR-γ

HNE

+PPAR-γ

TREATMENT OF ALZHEIMER'S DISEASE

BACKGROUND OF THE INVENTION

1. Field of the Invention

This invention is in the field of medical diagnostics and therapy. In particular, the invention relates to methods for diagnosing Alzheimer's Disease (AD) by determining the level or function of insulin, insulin-like growth factors, their receptors and/or their downstream signaling molecules. The invention further relates to methods for the treatment of AD by administering an insulin agonist and an insulin-like growth factor agonist. The invention additionally provides an animal model of AD and methods of screening for agents useful in the treatment, amelioration, or prevention of AD.

2. Related Art

The characteristic neuropathological and molecular lesions that correlate with dementia in Alzheimer's Disease (AD) include the accumulation of hyper-phosphorylated and poly-ubiquinated microtubule-associated proteins, such as tau, resulting in the formation of neurofibrillary tangles, dystrophic neuritis, and neuropil threads. Neuronal cytoskeletal abnormalities are associated with cerebral atrophy with cell and fiber loss, and synaptic disconnection. Increased amyloid-beta (Aβ) deposition around and within the walls of meningeal and cortical vessels, the cortical neuropil, and neuronal perikarya is a feature of both AD and normal aging. Although genetic factors can predispose individuals to develop premature and excessive cerebral deposits of Aβ in AD-type dementia, most cases are sporadic and do not exhibit clear familial or genetic clustering. Recent exploration of biochemical, molecular, and cellular abnormalities that precede or accompany classic AD demonstrated that cell loss was associated with increased activation of pro-death genes and signaling pathways, impaired energy metabolism, mitochondrial dysfunction, chronic oxidative stress, and cerebrovascular disease/cerebral hypoperfusion. However, the inability to interlink these phenomena under a single primary pathogenic mechanism resulted in the emergence and propagation of various heavily debated theories, each of which focused on how one particular component of AD could trigger a cascade that contributes to the development of all other known abnormalities. However, re-evaluation of some of the older literature revealed that impairment in cerebral glucose utilization and energy metabolism represent very early abnormalities that precede or accompany the initial stages of cognitive impairment. Additionally, there is emerging evidence that impaired insulin signaling may have an important role in the pathogenesis of AD.

Currently, there is a growing interest in clarifying the roles of insulin resistance, hyperinsulinemia, Type 2 Diabetes Mellitus, and insulin degrading enzyme in the pathogenesis of AD, and its associated neuronal cytoskeletal lesions and Aβ deposits in the brain. This relatively new wave of enthusiasm is fueled by reports showing reduced brain growth and increased tau phosphorylation in mice deficient in either the insulin receptor substrate-2 or the neuronal insulin receptor gene. (Schubert et al., *J. Neurosci.* 23:7084 (2003); Schubert et al., *Proc. Natl. Acad. Sci. USA* 101:3100 (2004)). The potential role of the neuroendocrine system in AD was raised 15 to 20 years ago when abnormalities in the hypothalamic-pituitary axis were detected. (Beal et al., *Res. Publ. Assoc. Res. Nerv. Ment. Dis.* 64:215 (1986); Reubi et al., *J. Neurol.* 233:370 (1986); Fisman et al., *J. Am. Geriatr. Soc.* 36:298 (1988); Hoyer, *J. Neurol.* 234:266 (1987); Tham et al., *Acta Psychiatr. Scand.* 77:719 (1988); Bucht et al., *Acta Med. Scand.* 213:387 (1983)). That concept nearly vanished with the tidal wave of accelerated research on Aβ and tau, although presently, the renewed interest in neuroendocrine mechanisms emphasizes systemic disease rather than intrinsic central nervous system (CNS) endocrine dysfunction. However, previous research revealed that many important components of CNS neurodegeneration that occur in AD are mediated by impaired insulin signaling in the brain. (de la Monte et al., *Cell. Mol. Life Sci.* 58:1950 (2001); de la Monte et al., *Cell. Mol. Life Sci.* 59:882 (2002); de la Monte et al., *Alcohol Clin. Exp. Res.* 24:716 (2000); Xu et al., *J. Biol. Chem.* 278:26929 (2003)).

SUMMARY OF THE INVENTION

A relationship between AD and the insulin/insulin-like growth factor (IGF) signaling pathway has been demonstrated by the finding of impaired insulin and IGF expression in the brains of AD patients. It has also been discovered that downstream mediators of insulin and IGF signaling are impaired in AD patients. These findings define a connection between AD and the insulin/IGF signaling pathway that may be exploited for both diagnostic and therapeutic purposes.

Thus, one aspect of the present invention is to a method for diagnosing AD in a subject, comprising detecting a decrease in the level or function of at least one factor in the insulin/IGF signaling pathway in said subject, wherein a decrease in the level or function of one or more of said factors relative to the level in healthy subjects is a diagnostic indicator of AD.

In another aspect the invention relates to a method for identifying a subject at risk for developing AD, comprising determining the level or function of at least one factor in the insulin/IGF signaling pathway in said subject, wherein a decrease in the level of one or more of said factors relative to the level in healthy subjects is a diagnostic indicator of a risk for developing AD.

In one embodiment of the invention, a diagnostic kit is provided for the diagnosis of AD. The kits may be used to determine the level or function of at least one factor in the insulin/IGF signaling pathway in a subject.

In one aspect of the invention, methods for the treatment, amelioration, or prevention of AD is subject are provided. In certain embodiments, the methods comprise the administration to a subject a therapeutically effective amount of an insulin agonist and a therapeutically effective amount of an IGF agonist. In one embodiment, the insulin agonist is a PPAR δ receptor selective agonist.

An additional aspect of the present invention relates to a method for improving mentation of a subject with AD, comprising administering to said subject a therapeutically effective amount of an insulin agonist and a therapeutically effective amount of an IGF agonist. In one embodiment, the agonist is a PPAR δ receptor selective agonist.

Surprisingly, it has been discovered that PPAR δ receptor selective agonists are particularly effective for rescue of animals whose brains are treated with streptozocin, a model of Alzheimer's disease. Thus, it is expected that human subjects who experience mild cognitive impairment, who may be experiencing the early stages of neurodegeneration and who may be at risk for progression to Alzheimer's disease may be "rescued" from progression to Alzheimer's disease. Thus, another aspect of this invention relates to a method for treating mild cognitive impairment in a subject, comprising administering to said subject a therapeutically effective amount of a PPAR δ receptor selective agonist. In this embodiment, the subject is rescued from early stages of neurodegeneration.

It has also been surprisingly discovered that PPAR δ receptor selective agonists are particularly effective at preserving brain size, learning and memory performance in animals whose brains are treated with streptozocin. Thus, another aspect of this invention relates to a method for preserving brain size, learning and memory performance in a subject, comprising administering to said subject a therapeutically effective amount of a PPAR δ receptor selective agonist.

A further aspect of the present invention relates to a method for reducing memory loss in a subject with AD, comprising administering to said subject a therapeutically effective amount of an insulin agonist and a therapeutically effective amount of an IGF agonist.

An additional aspect of the present invention provides compositions comprising a therapeutically effective amount of an insulin agonist and a therapeutically effective amount of an IGF agonist.

A further aspect of the invention provides a method for screening for an agent that is potentially useful for the treatment, amelioration, or prevention of AD, comprising administering the agent to an animal and determining the level or function of at least one factor in the insulin/IGF signaling pathway in said animal, wherein an increase in the level or function of one or more of said factors relative to the level in a control animal that has not had the agent administered indicates that the agent is potentially useful for the treatment, amelioration, or prevention of AD.

An additional aspect of the invention provides a method for testing potential treatments for AD comprising administering the potential treatment to an animal and determining the level or function of at least one factor in the insulin/IGF signaling pathway in said animal, wherein an increase in the level or function of one or more of said factors relative to the level in a control animal that has not had the treatment administered indicates that the treatment is potentially useful for the treatment, amelioration, or prevention of AD.

A further aspect of the invention provides a method for testing an agent for a potential deleterious effect on the onset or progression of AD, comprising administering the agent to an animal and determining the level or function of at least one factor in the insulin/IGF signaling pathway in said animal, wherein a decrease in the level or function of one or more of said factors relative to the level in a control animal that has not had the agent administered indicates that the agent potentially has a deleterious effect on the onset or progression of AD.

The invention further provides an animal model of AD produced by intracerebrally injecting a non-human animal with streptozotocin (STZ), wherein said non-human animal is injected at an age of less than 1 week. In another embodiment, the invention provides an animal model of AD produced by intracerebrally injecting a non-human animal with STZ, wherein said non-human animal is injected with a dose of STZ of at least about 10 mg/kg body weight.

The invention further relates to a method for screening for an agent that is potentially useful for the treatment, amelioration, or prevention of AD, comprising administering an agent to the animal model of AD produced by intracerebrally injecting a non-human animal with STZ and determining the level or function of at least one indicator of AD relative to the level in a control animal that has not had the agent administered, wherein an improvement in the level or function of at least one indicator of AD relative to the level in a control animal that has not had the agent administered indicates that the agent is potentially useful for the treatment, amelioration, or prevention of AD.

The invention additionally provides a method for testing a potential treatment for AD, comprising administering the potential treatment to the animal model of AD produced by intracerebrally injecting a non-human animal with STZ and determining the level or function of at least one indicator of AD relative to the level in a control animal that has not had the potential treatment administered, wherein an improvement in the level or function of at least one indicator of AD relative to the level in a control animal that has not had the potential treatment administered indicates that the treatment is potentially useful for the treatment, amelioration, or prevention of AD.

A further aspect of the invention provides a method for testing an agent for a potential deleterious effect on the onset or progression of AD, comprising administering the agent to the animal model of AD produced by intracerebrally injecting a non-human animal with STZ and determining the level or function of at least one indicator of AD relative to the level in a control animal that has not had the potential treatment administered, wherein a decrease in the level or function of at least one indicator of AD relative to the level in a control animal that has not had the agent administered indicates that the agent potentially has a deleterious effect on the onset or progression of AD.

BRIEF DESCRIPTION OF THE DRAWINGS/FIGURES

FIGS. 1A-1D show the reduced levels of insulin, IGF-I, and IGF-II receptor expression in AD brains demonstrated using real time quantitative RT-PCR. Graphs depict the mean±S.E.M. of results obtained for the frontal cortex (A), hippocampus (B), and hypothalamus (C). (D) To better depict the inter-group and regional differences in insulin receptor expression, those data were re-graphed to scale. Significant P-values (including trends) are indicated over the bar graphs.

FIGS. 2A-2D show the altered expression of insulin, IGF-I, and IGF-II in AD, demonstrated using real time quantitative RT-PCR. Graphs depict the mean±S.E.M. of results obtained for the frontal cortex (A), hippocampus (B), and hypothalamus (C). (D) To better depict the inter-group and regional differences in insulin gene expression, those data were re-graphed to scale. Significant P-values (including trends) are indicated over the bar graphs.

FIGS. 3A-3H show the localization of insulin (A-B), IGF-I (C-D), insulin receptor (E-F), and IGF-I receptor (G-H) immunoreactivity in AD (A,C,E,G) and aged control (B,D,F,H) hippocampus using immunohistochemical staining. Arrows point toward labeled neurons.

FIGS. 4A-4E show the detection of insulin, IGF-I, and IGF-II receptor expression in post-mitotic differentiated primary neuronal cultures generated from rat postnatal cerebellar cortex (CBM), and rat fetal cerebral cortex (CTX), hippocampus (HIPPO), and hypothalamus (HYPO). Graphs depict the mean±S.E.M. of results obtained for insulin receptor (A), IGF-I receptor (B), and IGF-II receptor (C) expression levels. (D, E) To better depict the inter-group and regional differences in growth factor receptor expression, the data corresponding to cerebellar neurons (D) or cortical, hippocampal, and hypothalamic neurons (E) were re-graphed to scale.

FIGS. 5A-5E show the detection of insulin, IGF-I, and IGF-II gene expression in post-mitotic differentiated primary neuronal cultures generated from rat postnatal cerebellar cortex (CBM), and rat fetal cerebral cortex (CTX), hippocampus (HIPPO), and hypothalamus (HYPO). Graphs depict the mean±S.E.M. of results obtained for insulin (A), IGF-I (B), and IGF-II (C) expression levels. (D, E) To better depict the inter-group and regional differences in growth factor expression, the data corresponding to cerebellar neurons (D) or cortical, hippocampal, and hypothalamic neurons (E) were re-graphed to scale.

FIGS. 6A-6H show the reduced levels of insulin receptor substrate, type 1 (IRS-1) and impaired insulin and IGF-I signaling mechanisms in AD brains. IRS-1, 2, and 4 mRNA levels were measured in the frontal cortex (A), hippocampus (B), and hypothalamus (C) of AD and aged control brains using real time quantitative RT-PCR. Steady state levels of tyrosine phosphorylated (PY) insulin (E) and IGF-I (G) receptors, and associations between the catalytically active p85 subunit of PI3 kinase and IRS-1 (D; reflecting PY-IRS-1-associated PI3 kinase activity) were assessed in hippocampal tissue samples by Western blot analysis of immunoprecipitates. Insulin receptor (INR; F) and IGF-I receptor (IGFI-R; H) protein expression were examined in hippocampal tissue samples by direct Western blot analysis. Significant P-values are indicated over the bar graphs.

FIGS. 7A-7E show the impaired survival signaling mechanisms in AD brains. Steady state levels of (A) phospho-Akt (p-Akt), (B) total Akt, (C) phospho-glycogen synthase kinase 3β (p-GSK-3β), (D) total GSK-3β, and (E) β-Actin were assessed in hippocampal specimens by Western blot analysis. Significant P-values are indicated over the bar graphs.

FIGS. 8A-8H show the measurement of tau (A, B), amyloid precursor protein (APP; C, D), glucose transporter 4 (GLUT4; E,F), and insulin degrading enzyme (IDE; G,H) gene expression in AD and control hippocampus (A,C,E,G) and hypothalamus (B,D,F,H) demonstrated using real time quantitative RT-PCR. Significant P-values are indicated over the bar graphs.

Figure 9A:
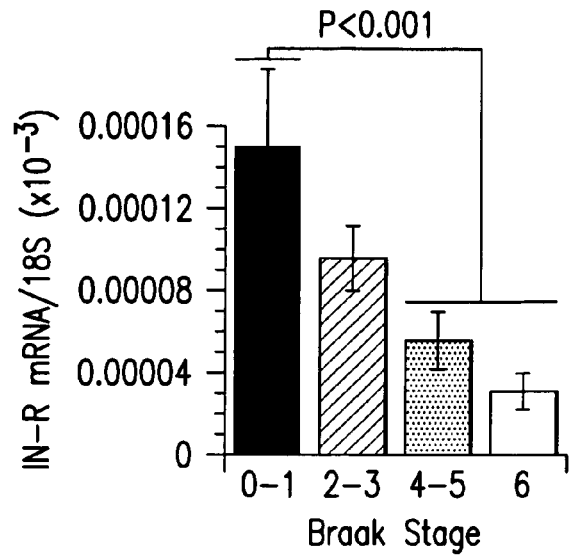
Figure 9B:
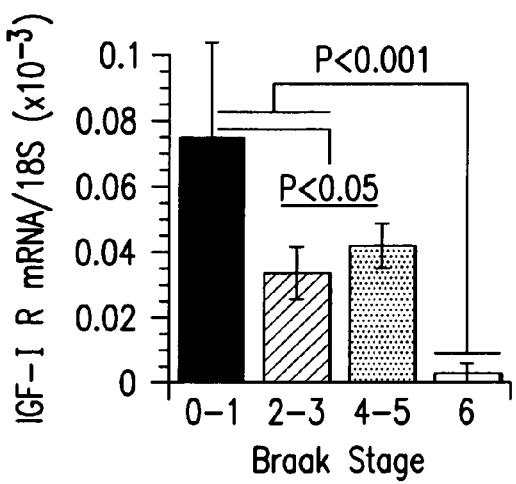
Figure 9C:
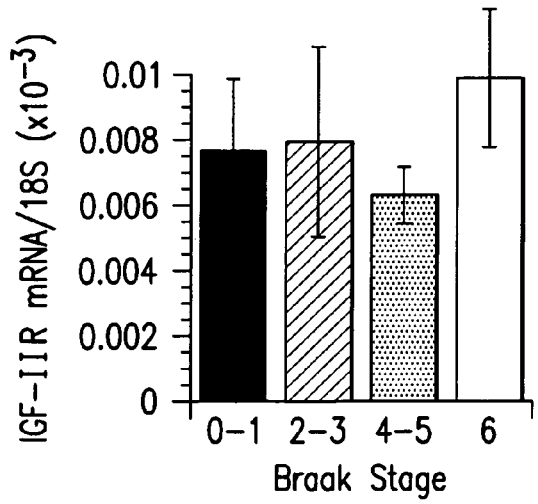

FIGS. 9A-9C show reduced levels of insulin receptor and IGF receptor expression with progression of AD demonstrated using real time quantitative RT-PCR. Graphs depict the mean±S.E.M. of results obtained for the insulin receptor (A), IGF-I receptor (B), and IGF-II receptor (C). Data were analyzed statistically using ANOVA with the post-hoc Tukey-Kramer significance test. Significant P-values are indicated over the bar graphs.

Figure 10A:
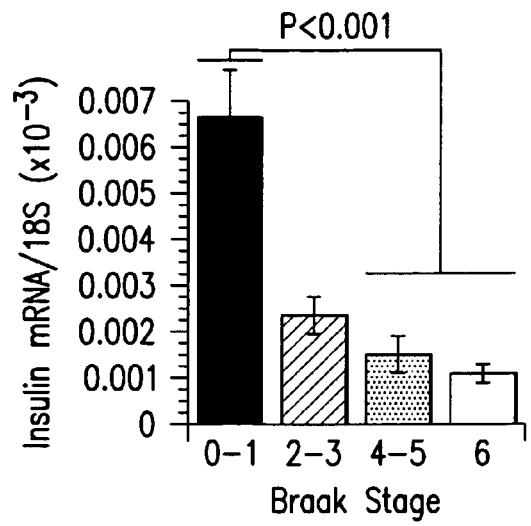
Figure 10B:
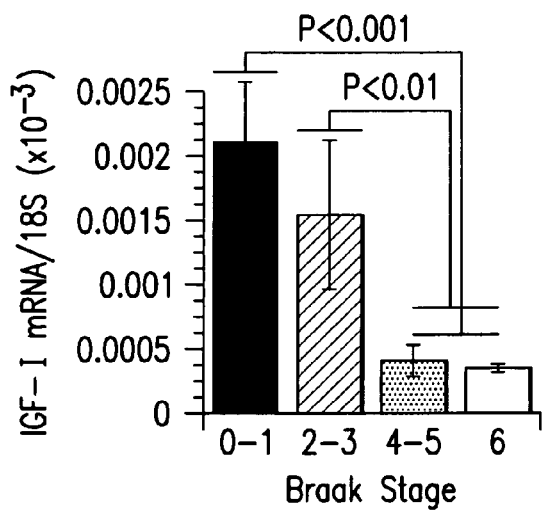
Figure 10C:
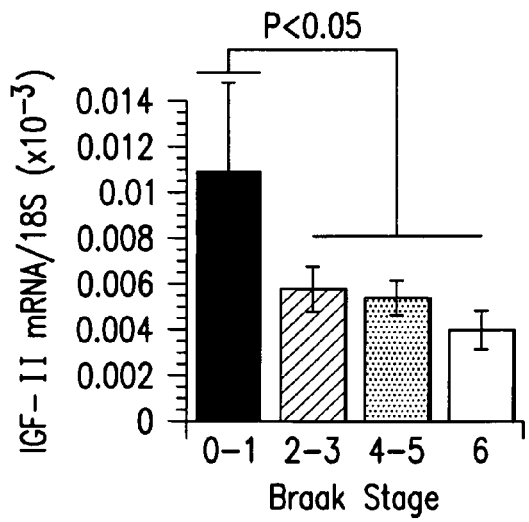

FIGS. 10A-10C show reduced expression of insulin, IGF-I, and IGF-II with progression of AD, demonstrated using real time quantitative RT-PCR. Graphs depict the mean±S.E.M. of results obtained for the insulin (A), IGF-I (B), and IGF-II (C) polypeptide genes. Data were analyzed statistically using ANOVA with the post-hoc Tukey-Kramer significance test. Significant P-values are indicated over the bar graphs.

Figure 11A:
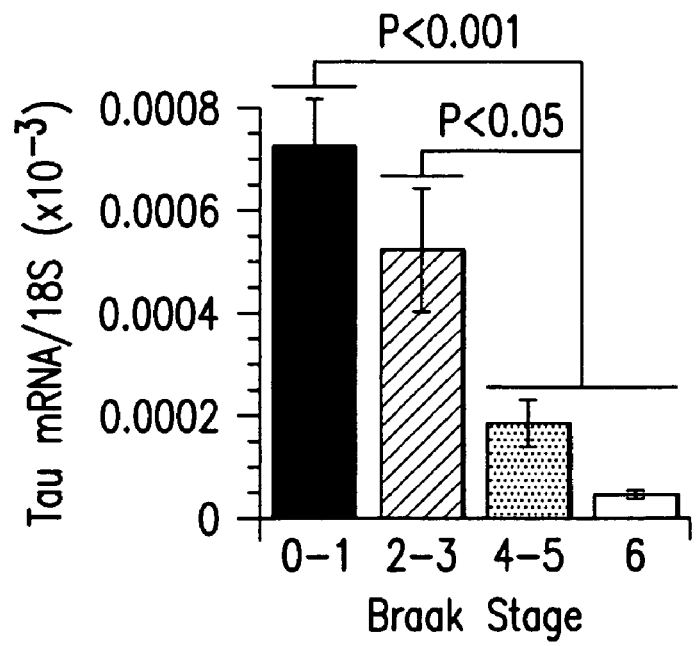
Figure 11B:
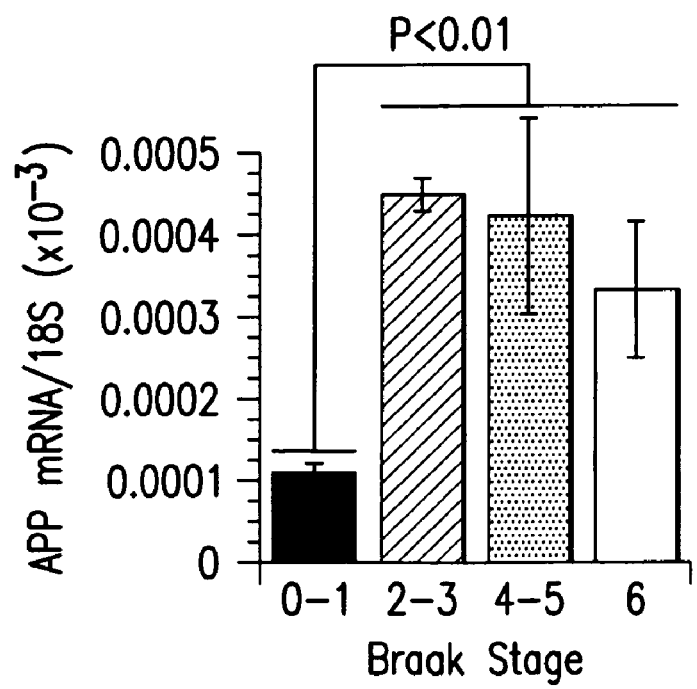

FIGS. 11A-11B show the relationship between AD progression and tau (A) or amyloid precursor protein (APP; B) mRNA expression demonstrated using real time quantitative RT-PCR. Graphs depict the mean±S.E.M. of results obtained for the tau (A) and APP (B) genes. Data were analyzed statistically using ANOVA with the post-hoc Tukey-Kramer significance test. Significant P-values are indicated over the bar graphs.

Figure 12A:
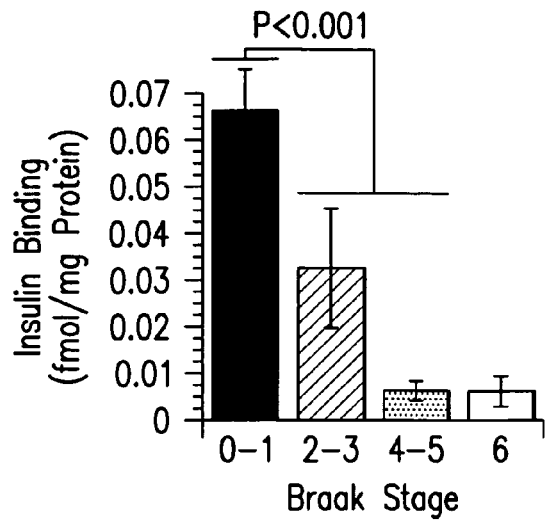
Figure 12B:
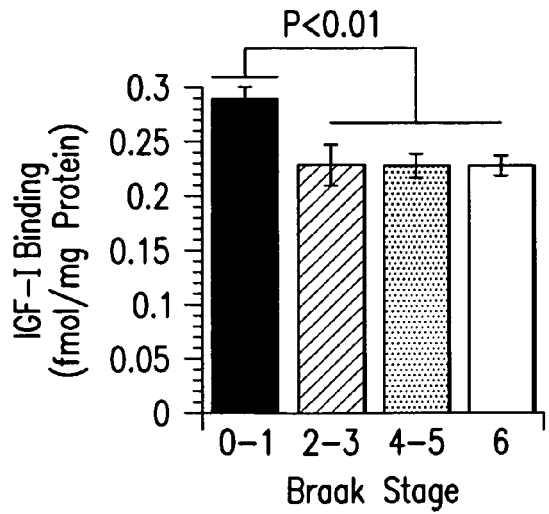
Figure 12C:
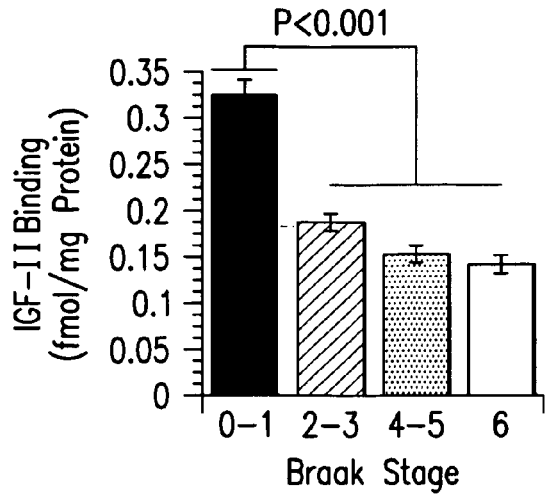
Figure 13I:
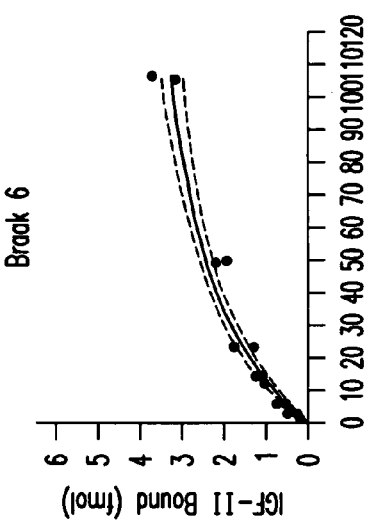
Figure 13H:
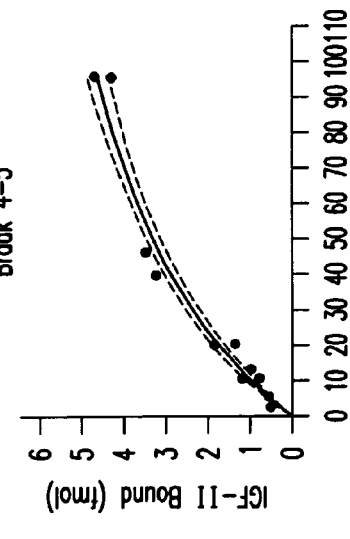
Figure 13G:
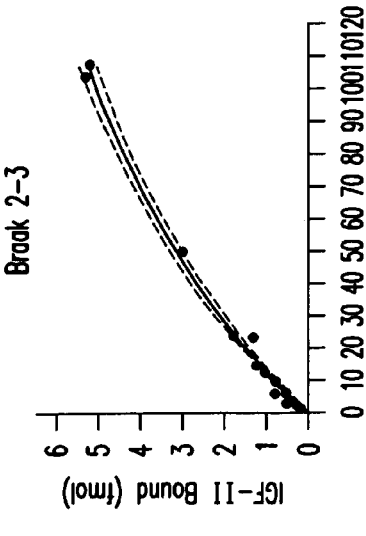
Figure 13L:
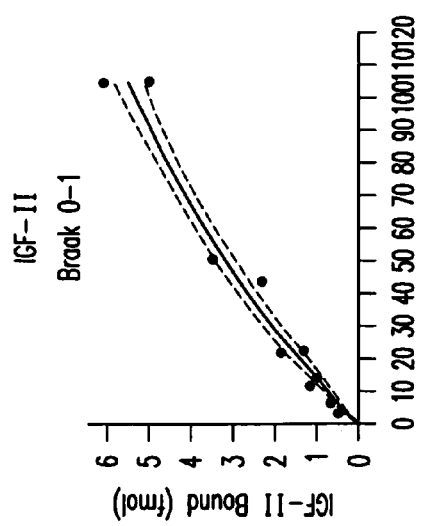
Figure 13K:
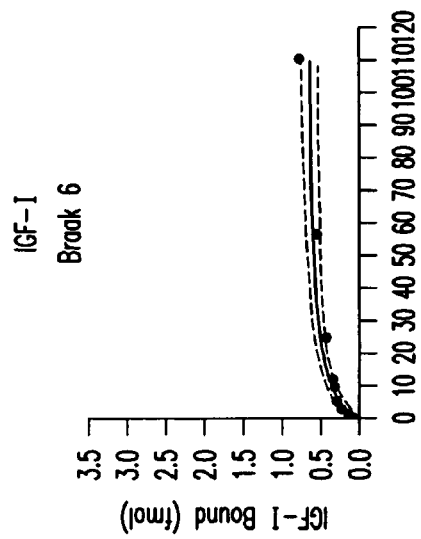
Figure 13J:
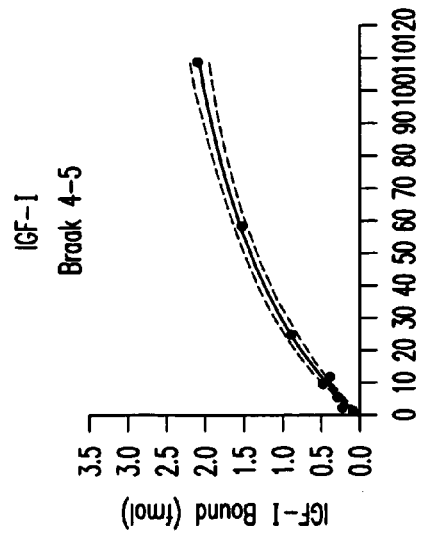

FIGS. 12A-12C show reduced growth factor binding with progression of AD neurodegeneration. Graphs depict the mean±S.E.M. of results obtained for the insulin (A), IGF-I (B), and IGF-II (C) binding. Data were analyzed statistically using ANOVA with the post-hoc Tukey-Kramer significance test. Significant P-values are indicated over the bar graphs.

FIGS. 13A-13L show reduced growth factor saturation binding levels with progression of AD. Graphs depict specific binding (fmol/mg protein)±95% CI corresponding to insulin (A-D), IGF-I (E-H), and IGF-II (I-L) binding in brains with AD Braak stages of 0-1 (A, E, I), 2-3 (B, F, J), 4-5 (C, G, K), or 6 (D, H, L).

Figure 14A:
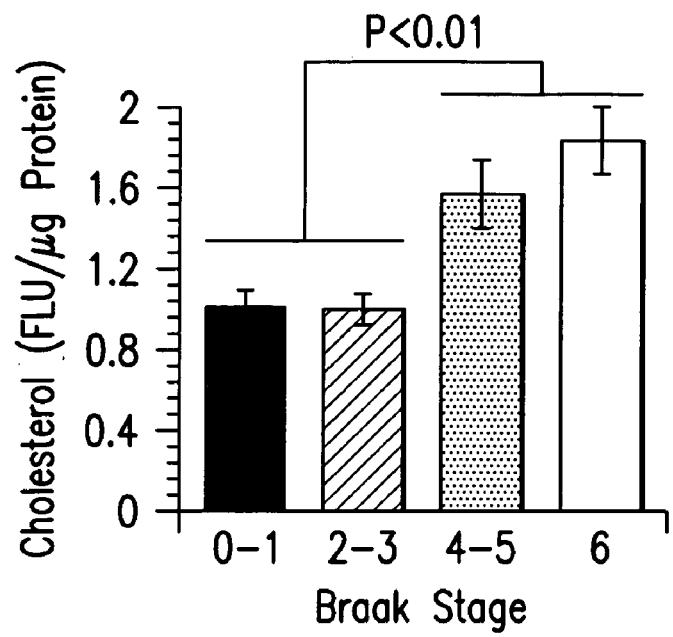
Figure 14B:
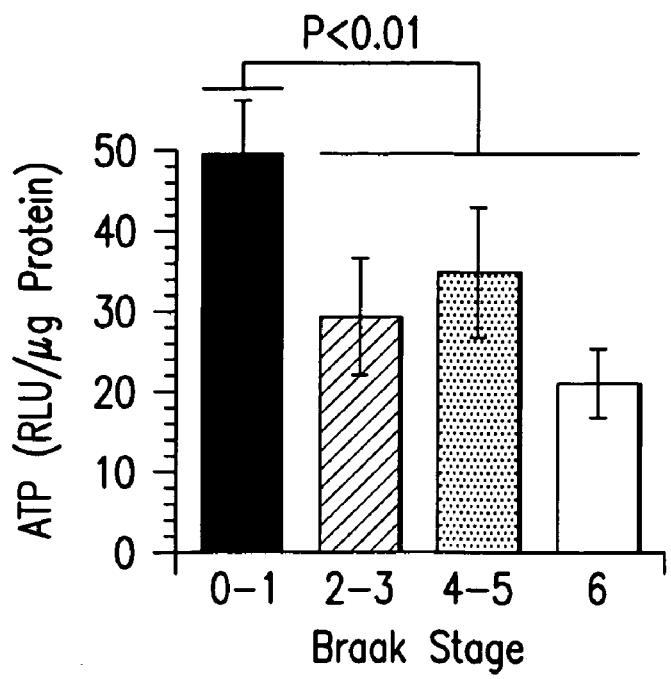

FIGS. 14A-14B show the relationship between AD progression and brain membrane cholesterol content (A) or steady state ATP levels (B). The graphs depicts the mean±S.E.M. of fluorescence light units (FLU)/μg protein (A) or luminescence (B). Data were analyzed statistically using ANOVA with the post-hoc Tukey-Kramer significance test. Significant P-values (including trends) are indicated over the bar graphs.

FIGS. 15A-15D show the absence of pancreatic islet destruction in the ic-STZ model. (A, B) Hematoxylin and eosin stained sections of control (A) and ic-STZ (B) treated pancreases demonstrating intact tissue architecture and normal appearing islets (arrows) in both groups. (C, D) Adjacent sections were immunostained with monoclonal antibodies to insulin. Immunoreactivity was revealed by the ABC method using diaminobenzidine (brown precipitate) as the chromogen. The sections were lightly were counterstained with hematoxylin. Prominent insulin immunoreactivity was detected in pancreatic islets (arrows) of both control (C) and ic-STZ-treated (D) rats. Insets (lower right of Panels C and D) show high magnification images of the insulin-immunoreactive islets.

FIGS. 16A-16D show the effects of ic-STZ on blood glucose levels, body weight, and brain size. (A) Blood glucose concentration (mg/dl) was measured just prior to sacrifice (day 14) using the One-Touch Ultra Blood Glucose Meter. (B) Body weight (gm) and (C) brain weight (mg) were measured at the time of sacrifice. The graphs depict the mean±S.D. of blood glucose level, body weight, and brain weight measured in 20 rats per group. Inter-group comparisons were made using the Student t-tests (significant P-values are indicated above the bars). (D) Representative gross photograph of control (left) and ic-STZ-treated rat brains 14 days after treatment. Note the extremely small cerebellum (arrows) and multiple small meningeal hemorrhages (double-headed arrows) in the ic-STZ-treated brain.

FIGS. 17A-17J show the neuropathology of ic-STZ. Brains harvested from control (left panel) and ic-STZ (right panel) rats (day 14) were fixed and processed for histopathology. Paraffin sections were stained with hematoxylin and eosin. Coronal sections through the frontal lobes including the caudate-putamen (cp) (A, B), and temporal lobe with hippocampal formation and thalamus (C,D), and cerebellar cortex (E,F) are shown for control (A,C,E) and ic-STZ-treated (B,D,F) rats were photographed at the same magnification. The smaller size of the cerebrum was associated with dilation of the ventricles (V), marked thinning of the temporal cortex (T), and reduced sizes of the basal ganglia (bg), hippocampus (h), hypothalamus and thalamus (Th) in ic-STZ-treated brains. The cerebella of ic-STZ-treated rats were strikingly reduced in size (F) relative to control (E, G). Cerebellum from ic-STZ-treated rats had ill-defined, simplified folia, and disorganized cortical lamination due to absence of the internal (igl) and external (egl) granule cell layers and the molecular layer. Instead, the ic-STZ cerebellar cortex was replete with a disorganized collection of large pyramidal neurons/neuroblastic elements that resembled Purkinje cells (Pc) (F,H). Adjacent sections were immunostained with monoclonal antibodies to p53. Immunoreactivity was detected using the ABC method with DAB as the chromogen (brown precipitate). Photomicrographs show representative labeling of control (I) and ic-STZ (J) temporal lobe. Note the increased p53 immunoreactivity in ic-STZ cortical neurons (J) compared with the nearly undetectable labeling in control cortical neurons (I).

FIGS. 18A-18E show the loss of neurons and oligodendroglia, and increased astrocytic and microglial cell populations in the temporal lobes of ic-STZ-treated brains (day 14). The mRNA transcript levels corresponding to (A) Hu neuronal RNA binding protein, (B) myelin-associated glucoprotein-1 (MAG-1), (C) astrocytic glial fibrillary acidic protein (GFAP), and (D) microglial AIF-1, were used to detect pathological shifts in brain cell types following ic-STZ treatment. Graphs depict the mean±S.E.M. of results obtained from 8-10 samples per group. Data were analyzed statistically using Student t-tests. Significant P-values are indicated over the bar graphs.

FIGS. 19A-19I show the effects of ic-STZ on CNS expression of insulin and insulin-like growth factor (IGF) genes and receptors (day 14). Graphs depict the mean±S.E.M. of results obtained for (A) insulin receptor (InR), (B) IGF-I receptor (IGF-IR), (C) IGF-II receptor (IGF-IIR), (D) insulin, (E) IGF-I, (F) IGF-II, (G) insulin receptor substrate, type 1 (IRS-1), (H) IRS-2, and (I) IRS-4. Data were analyzed statistically using Student T-tests. Significant P-values are indicated over the bar graphs.

Figure 20A:
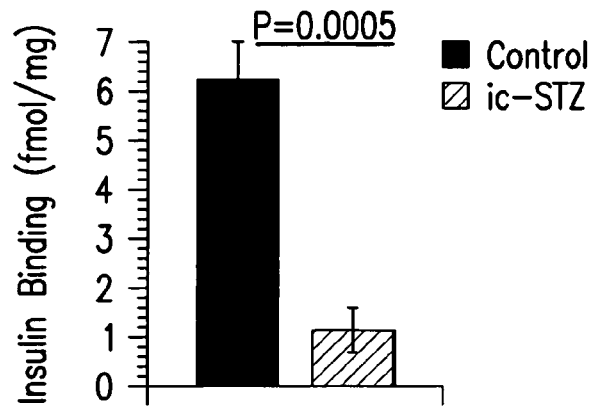
Figure 20B:
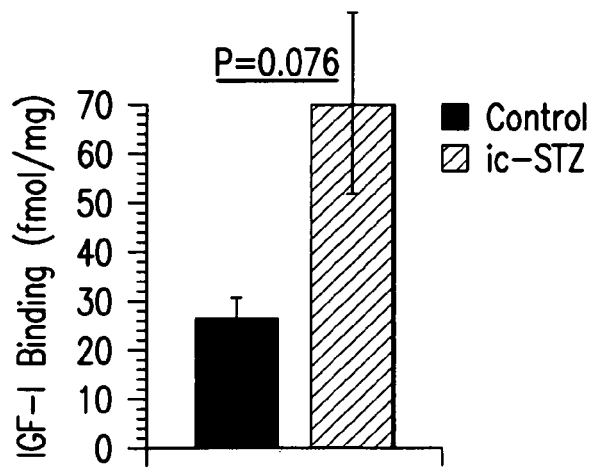
Figure 20C:
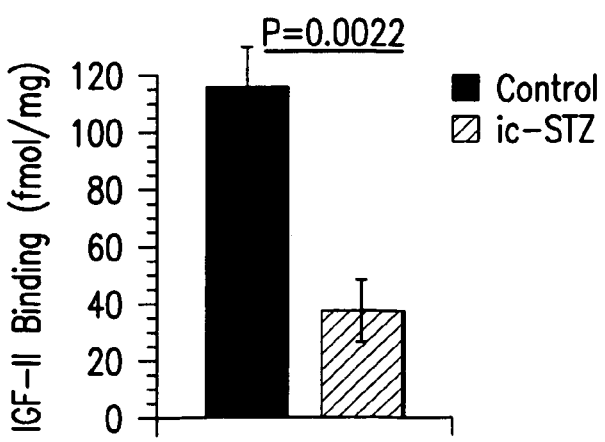
Figure 21A:
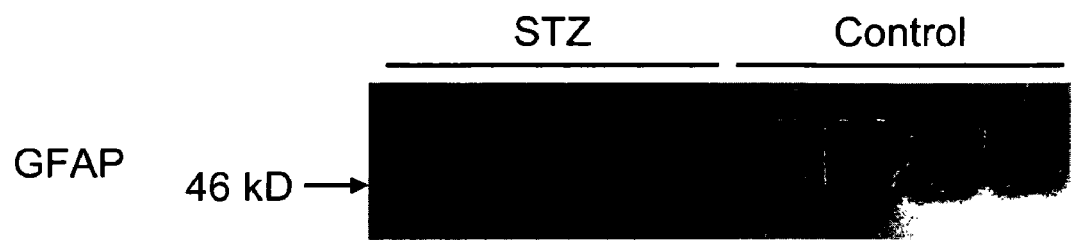
Figure 21B:
Figure 21C:
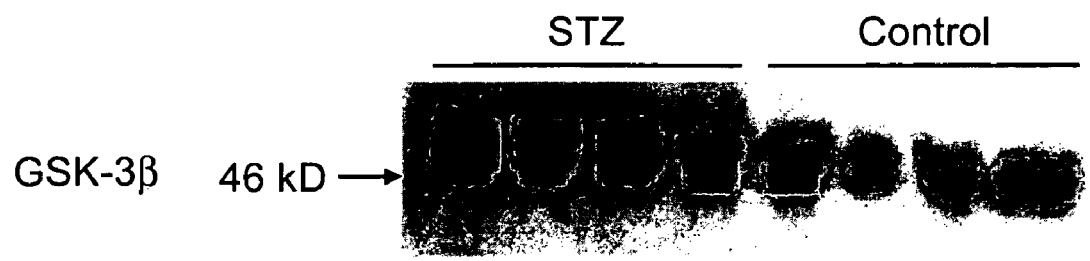
Figure 21D:
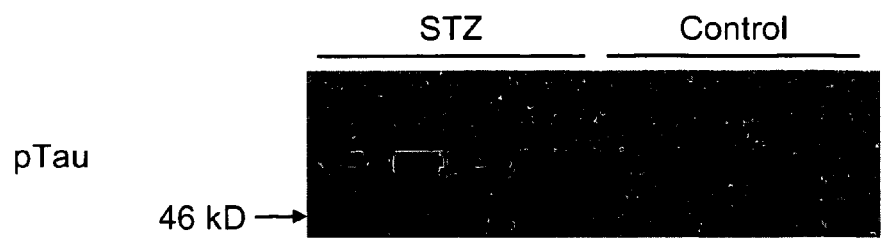
Figure 21E:
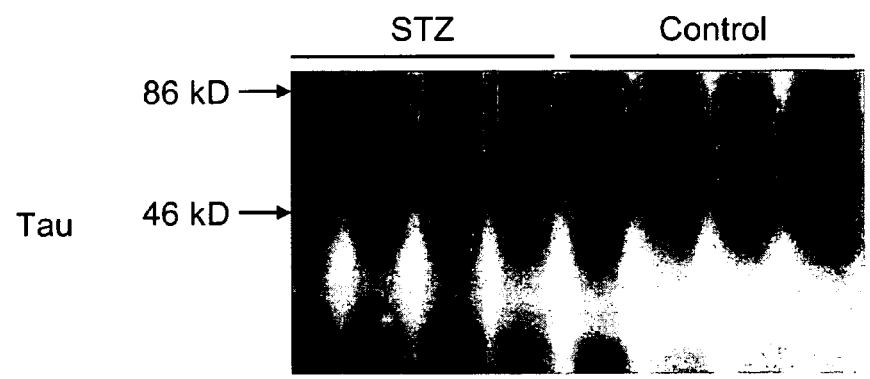
Figure 21F:
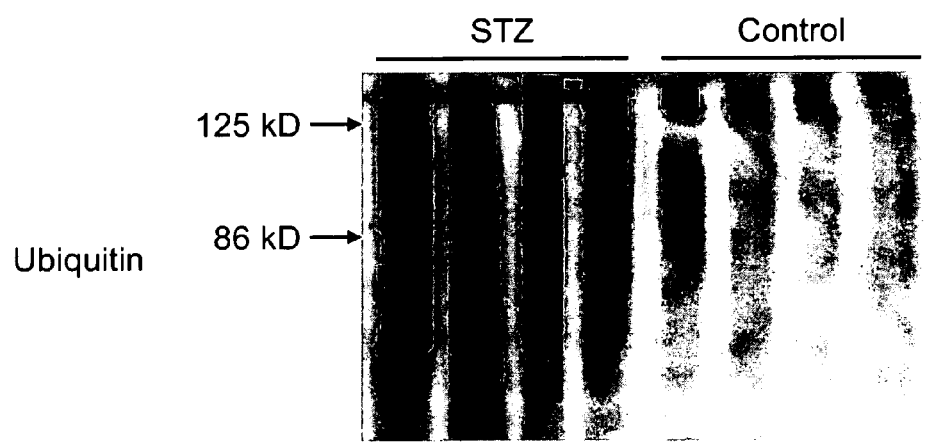
Figure 21G:
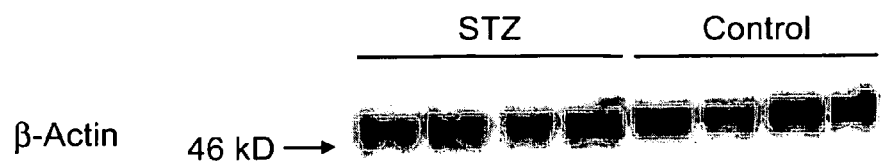

FIGS. 20A-20C show the reduced CNS growth factor binding in ic-STZ treated rats. Graphs depict the mean±S.E.M. of results obtained for (A) insulin, (B) IGF-I, and (C) IGF-II specific binding. Data were analyzed statistically using Student t-tests. Significant P-values are indicated over the bar graphs.

FIGS. 21A-21G show the increased indices of neurodegeneration in ic-STZ-treated brains demonstrated by Western blot analysis. Representative results demonstrating steady state expression levels of (A) glial fibrillary acidic protein (GFAP), (B) phospho-glycogen synthase kinase 3 (p-GSK-3β/β(Ser21/9)), (C) total GSK-3β, (D) phospho-tau (pTau), (E) tau, (F) ubiquitin, and (G) β-Actin (negative control) detected in temporal lobe tissue by Western blot analysis. The arrows to the left of each panel indicate the position of the molecular weight markers indicated below each arrow.

FIGS. 22A-22F show the increased indices of neurodegeneration in ic-STZ-treated brains demonstrated by immunohistochemical staining. Paraffin-embedded sections of brain were immunostained with monoclonal antibodies to (A, B) GFAP, (C, D) phospho-tau, or (E, F) ubiquitin to demonstrate increased gliosis, tau phosphorylation, and protein ubiquitination in the ic-STZ-treated (B, D, F) relative to control (A, C, E) brains. All panels depict representative labeling profiles in the temporal lobe. (A, B) GFAP immunoreactivity was localized in astrocytes and neuropil glial fibrils. (C, D) pTau immunoreactivity was increased in ic-STZ cortical neuronal perikarya. (E, F) Ubiquitin immunoreactivity was increased in the nuclei of ic-STZ cortical neurons as well as other cell types.

FIGS. 23A-23F show that ic-STZ increases amyloid precursor protein (APP) expression and Aβ accumulation in the brain, similar to the findings in AD. (A) Tau and (B) APP gene expression were measured using real time quantitative RT-PCR with the values normalized to 18S rRNA. Graphs depict the mean±S.E.M. of results. Data were analyzed statistically using Student t-tests. Significant P-values are indicated over the bar graphs. (C) Control brains exhibited minimal or no immunoreactivity for Aβ, whereas the ic-STZ-treated brains (D-F) had prominent Aβ immunoreactivity in (D) neuronal cell bodies (arrows), (E, F) parenchymal microvessels (by), and (E,F) extracellular dense core plaque-like structures (arrows).

FIGS. 24A-24F shows the loss of neurons and impaired insulin/IGF signaling mechanisms correlate with reduced expression of choline acetyltransferase (ChAT) in ic-STZ-treated brains. (A) ChAT and (B) acetylcholinesterase (AChE) mRNA transcripts were detected and quantified by real time RT-PCR with the values normalized to 18S ribosomal RNA measured in the same samples. Graphs depict the mean±S.E.M. of results obtained for the (A) ChAT and (B) AChE genes. Data were analyzed statistically using Student t-tests. Significant P-values are indicated over the bar graphs. To characterize the ic-STZ-induced alterations in CHAT and ACHE expression, paraffin-embedded sections of brain were immunostained with antibodies to (C, D) CHAT or (E, F) AChE. Immunoreactivity was detected with biotinylated secondary antibody, ABC reagents, and DAB. In control brains (C, E), ChAT immunoreactivity was relatively higher, whereas ACHE immunoreactivity was lower than observed in ic-STZ-treated brains (D, F). CHAT immunoreactivity was detected in control cortical neurons (C; arrows), whereas high levels of ACHE were detected in neuropil fibers and cortical neurons in the ic-STZ-treated brains (D; arrows).

FIGS. 25A-25J: Effects of PPAR agonist treatment on the neuropathology of ic-STZ. Brains harvested from vehicle control rats (A,F), and rats treated with ic-STZ (B,G), ic-STZ+PPAR-α (C,H), ic-STZ+PPAR-δ, (D,I) and ic-STZ+PPAR-γ (E,J) were fixed and embedded in paraffin, and histological sections were stained with hematoxylin and eosin. Panels A-E depict the same regions of temporal lobe with the hippocampal formation, and Panels F-J show the lateral cerebellar cortex at the same magnification. Note the absence or near absence of the hippocampal formation (HF) in Panels B and E, and relative preservation of these structures in Panels C and D. Reduced thickness of the temporal cortex can be gauged from the horizontal scale bar (A-E) which spans 30% of the control and ic-STZ+PPAR-δ cortex, and 50% or more of cortex in the other 3 groups. The severe atrophy and cystic degeneration (Cys) of the cerebellar cortex in ic-STZ-treated rats was markedly reduced by early treatment with the PPAR-α or PPAR-δ agonists. Despite the PPAR agonist rescue, the molecular (M) and granule cell (GC) layers were thinner in all ic-STZ-treated relative to control cerebella.

FIGS. 26A-26L: Partial reversal of the ic-STZ-induced pathological shifts in brain cell populations by treatment with a PPAR α, δ, or γ agonist. Cell type specific gene expression corresponding to (A-C) Hu neuronal RNA binding protein, (D-F) myelin-associated glucoprotein-1 (MAG-1), (G-I) astrocytic glial fibrillary acidic protein (GFAP), and (J-L) microglial AIF-1 was measured in the temporal cortex (A,D, G,J), hypothalamus (B,E,H,K), and cerebellar cortex (C,F,I, L) by real time quantitative RT-PCR with levels normalized to 18S rRNA. Graphs depict the mean±S.E.M. of results obtained from 6-8 samples per group. Data were analyzed statistically using ANOVA with the Fisher post hoc significance testing (+=P<0.05; #=P<0.01; *=P<0.005; **=P<0.001 relative to control).

FIGS. 27A-27I: Sustained impairment of CNS insulin, IGF-I, and IGF-II gene expression despite PPAR agonist treatment of the ic-STZ model. Gene expression corresponding to (A-C) insulin, (D-F) IGF-I, and (G-I) IGF-II was measured in the temporal cortex (A,D,G), hypothalamus (B,E,H), and cerebellar cortex (C,F,I) by real time quantitative RT-PCR with levels normalized to 18S rRNA. Graphs depict the mean±S.E.M. of results obtained from 6-8 samples per group. Data were analyzed statistically using ANOVA with the Fisher post hoc significance testing (+=P<0.05; #=P<0.01; *=P<0.005; **=P<0.001 relative to control).

FIGS. 28A-28I: Partial rescue of CNS insulin, IGF-I, and IGF-II receptor gene expression by PPAR agonist treatment of the ic-STZ model. Gene expression corresponding to (A-C) insulin receptor (IN-R), (D-F) IGF-I receptor, and (G-D) IGF-II receptor was measured in the temporal cortex (A,D,G), hypothalamus (B,E,H), and cerebellar cortex (C,F, I) by real time quantitative RT-PCR with levels normalized to 18S rRNA. Graphs depict the mean±S.E.M. of results obtained from 6-8 samples per group. Data were analyzed statistically using ANOVA with the Fisher post hoc significance testing (+=P<0.05; #=P<0.01; *=P<0.005; **=P<0.001 relative to control).

FIGS. 29A-29I: Partial rescue of ic-STZ-impaired insulin, IGF-I, and IGF-II receptor binding by PPAR agonist treatments. Equilibrium binding assays were performed by incubating temporal lobe, hypothalamus, or cerebellar cortex membrane proteins with 50 pM [$^{125}$I]-labeled insulin, IGF-I, or IGF-II as tracer, in the presence or absence of 100 nM cold ligand. Membrane bound tracer was precipitated by adding bovine gamma globulin and PEG-8000 to the reactions and centrifuging the samples (14,000×g). Radioactivity present in the supernatant fractions (containing unbound/free ligand) and the pellets (containing bound ligand) was measured in a gamma counter. Specific binding (fmol/mg) was calculated using the GraphPad Prism 4 software. Graphs depict the mean±S.E.M. of results obtained for insulin (A-C), IGF-I (D-F), and IGF-II (G-I) specific binding in the temporal lobe (A,D,G), hypothalamus (B,E,H), and cerebellar cortex (C,F,I). Data were analyzed statistically using ANOVA with the Fisher post hoc significance testing (+=P<0.05; #=P<0.01; *=P<0.005; **=P<0.001 relative to control).

Figure 30A:
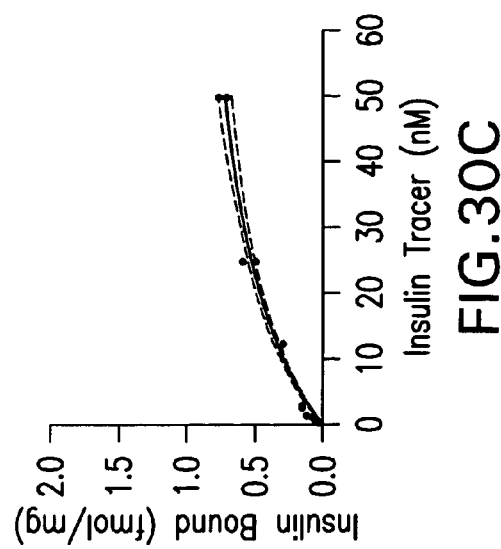
Figure 30B:
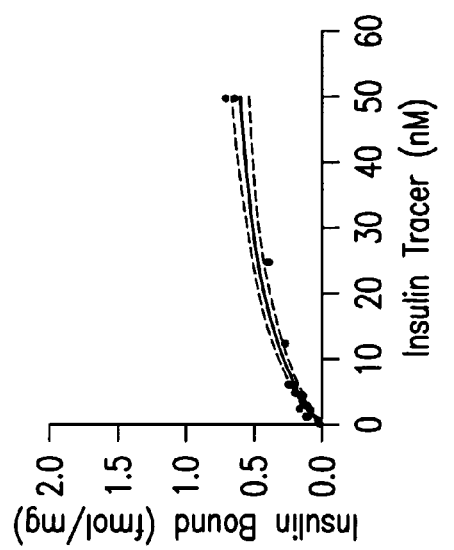
Figure 30C:
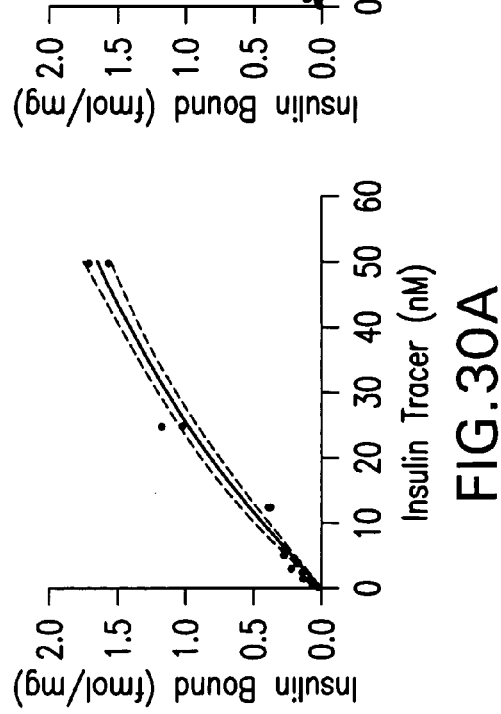
Figure 30D:
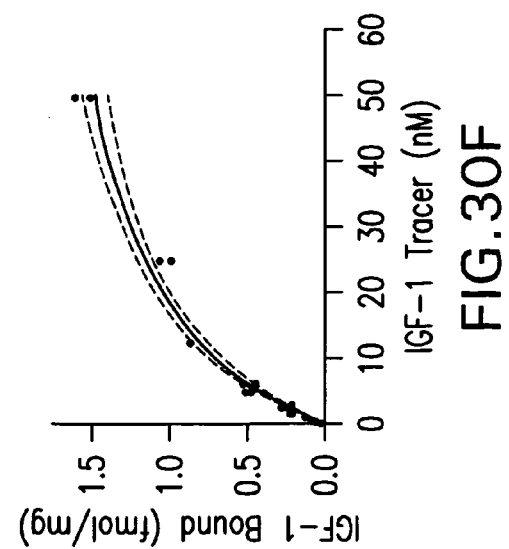
Figure 30E:
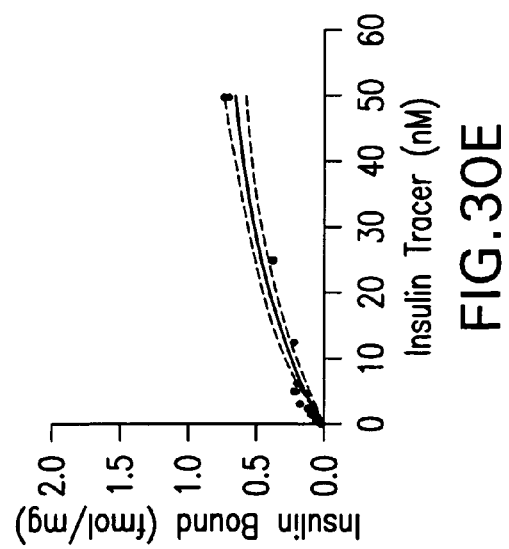
Figure 30F:
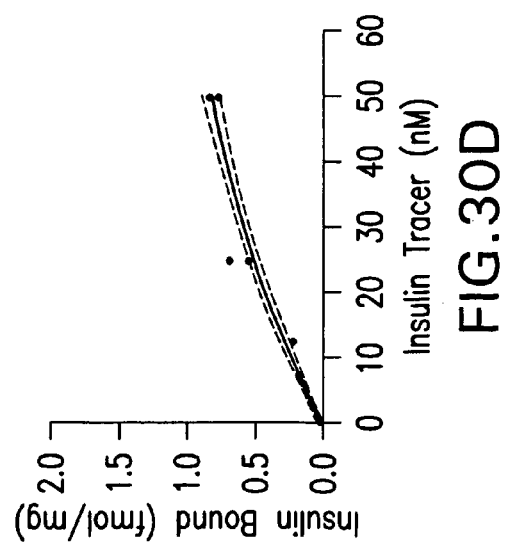
Figure 30G:
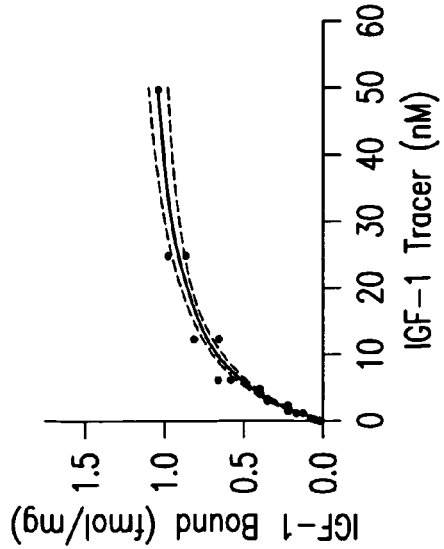
Figure 30J:
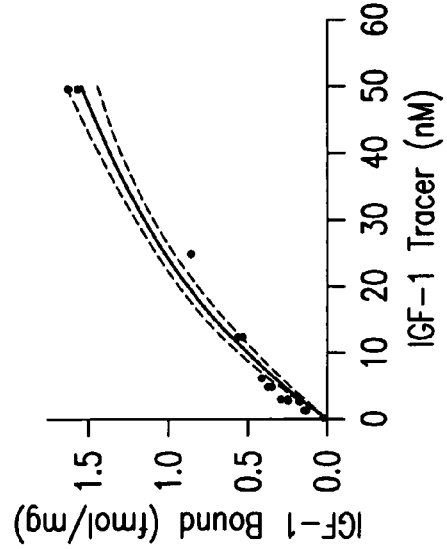
Figure 30H:
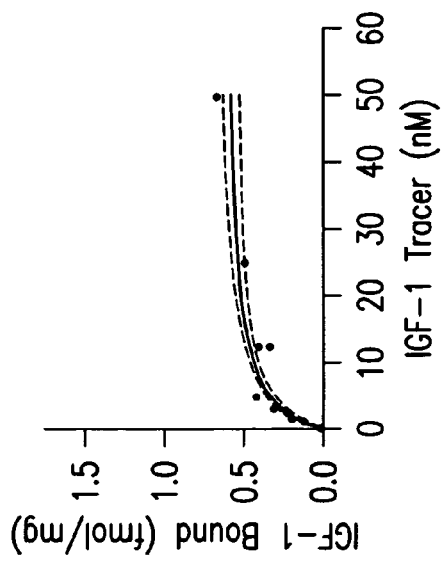
Figure 30K:
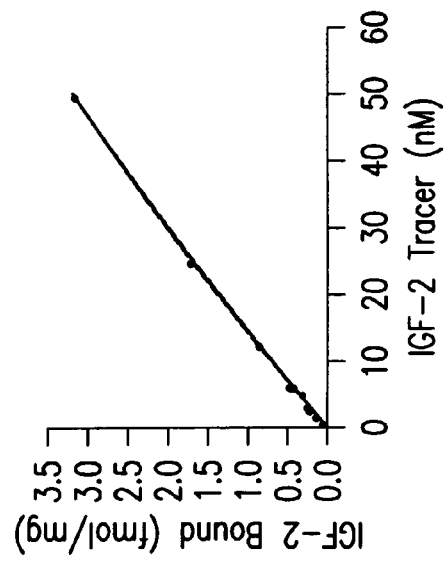
Figure 30I:
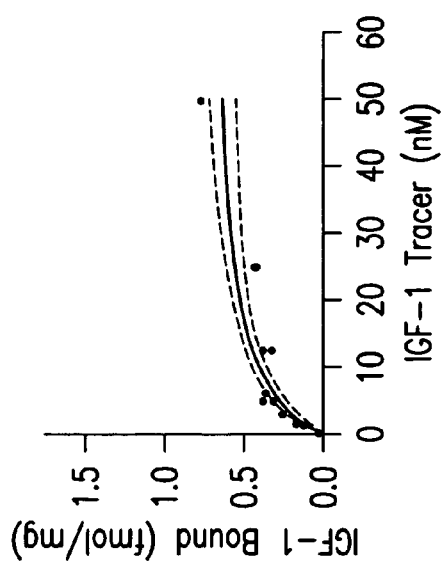
Figure 30L:
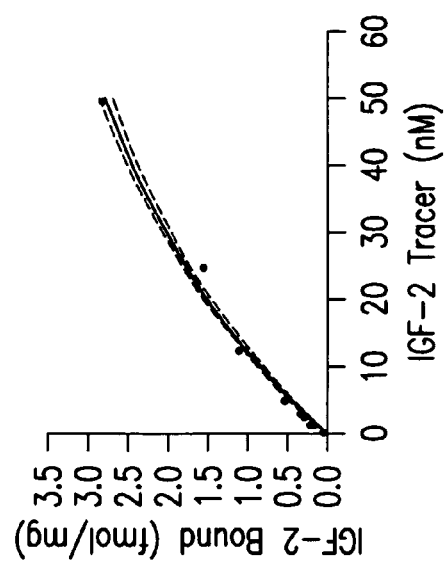
Figure 30O:
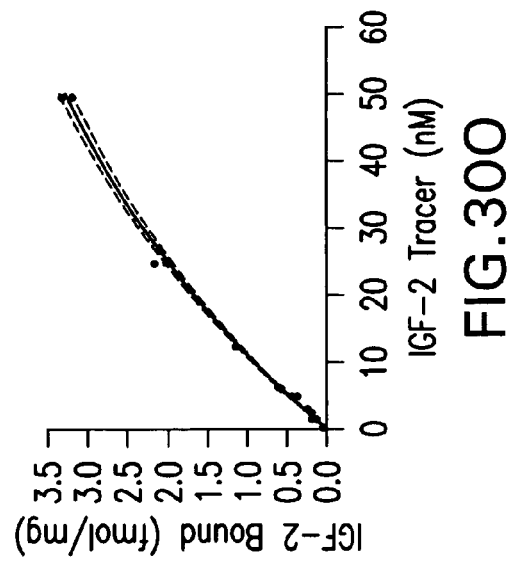
Figure 30N:
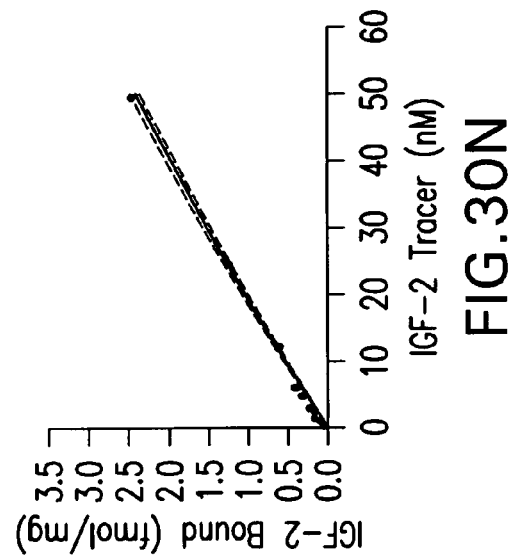
Figure 30M:
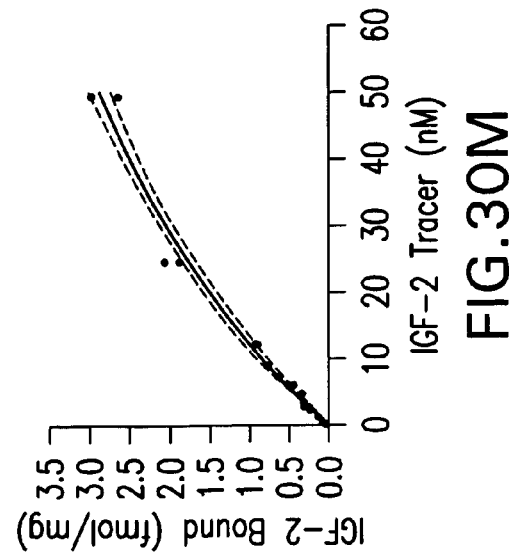

FIGS. 30A-30O: Reduced saturation binding but increased binding affinity to the insulin, IGF-I, and IGF-II receptors by PPAR agonist treatment of the ic-STZ model. Saturation binding assays were performed by incubating temporal lobe, hypothalamus, and cerebellar cortex membrane protein extracts overnight at 4° C. with 0.5-500 pM [$^{125}$I]-labeled insulin, IGF-I, or IGF-II as tracer, in the presence or absence of 100 nM cold ligand. Membrane bound tracer was precipitated by adding bovine gamma globulin and PEG-8000 to the reactions and centrifuging the samples (14,000×g). Radioactivity present in the supernatant fractions (containing unbound/free ligand) and the pellets (containing bound ligand) was measured in a gamma counter. Specific binding, saturation binding (BMAX), and dissociation constants/binding affinity (kD) and the S.D. and 95% confidence intervals (CI) were calculated using the GraphPad Prism 4 software. Graphs depict specific binding (fmol/mg protein)±95% CI corresponding to insulin (A-C), IGF-I (D-F), and IGF-II (G-I) binding in the temporal lobe (A,D,G), hypothalamus (B,E,H), and cerebellum (C,F,I). The calculated binding indices and inter-group statistical comparisons are listed in Table 3.

FIGS. 31A-31H: PPAR agonist treatment reduces GSK-3 activation and Tau phosphorylation in the ic-STZ model. Protein extracts of hypothalamus were subjected to Western blot analysis to examine (A) phospho-glycogen synthase kinase 3 (p-GSK-3β/β(Ser21/9)) and GSK-3β expression, and (E) phospho-Tau (pTau) and Tau immunoreactivity. The blots were stripped and re-probed to detect β-Actin as a negative control. Phosphorylated proteins were detected using phospho-specific antibodies. Representative results are depicted. Immunoreactivity corresponding to (B) p-GSK-3β, (C) GSK-3β, (F) pTau, and (G) Tau was quantified with digital imaging, and the calculated rations of (D) phosphor-GSK-3β/GSK-3β and (H) phosphor-Tau/Tau are depicted graphically. Data were analyzed statistically using ANOVA with the Fisher post hoc significance testing (+=P<0.05; #=P<0.01; *=P<0.005; **=P<0.001 relative to control).

FIGS. 32A-32L: PPAR agonist treatments reduce molecular indices of neurodegeneration: Rat pups were treated with ic-STZ or vehicle, followed by IP injection of saline or a PPAR-α, δ, or γ agonist. Rats were sacrificed 4 weeks later to examine expression levels of Tau (A-C), APP (D-F), ChAT (G-I), and ACHE (J-L) in the temporal lobe (A,D,G,J), hypothalamus (B,E,H,K), and cerebellum (C,F,I,L) by real time quantitative RT-PCR. Gene expression levels were normalized to 18S rRNA values. Graphs depict the group mean±S.E.M. Data were analyzed using ANOVA (+=P<0.05; #=P<0.01; *=P<0.005; **=P<0.001 relative to control).

FIGS. 33A-33E: PPAR agonist treatments reduce oxidative stress and pro-apoptosis mechanisms in the ic-STZ model. Rat pups were treated with ic-STZ or vehicle, followed by IP injection of saline or a PPAR-α, δ, or γ agonist. Rats were sacrificed 4 weeks later to examine expression levels of nitric oxide synthase (NOS) 1 (A), NOS 2 (B), NOS 3 (C), NADPH oxidase 1 (NOX-1) (D), and p53 (E) in the temporal lobe by real time quantitative RT-PCR. Gene expression levels were normalized to 18S rRNA values. Graphs depict the group mean±S.E.M. Data were analyzed using ANOVA testing (+=P<0.05; #=P<0.01; *=P<0.005; **=P<0.001 relative to control).

Figure 34A:
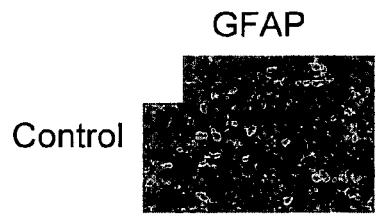
Figure 34F:
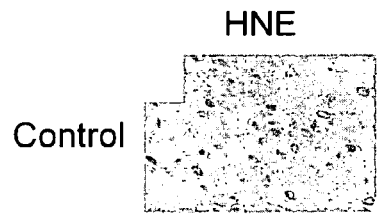
Figure 34B:
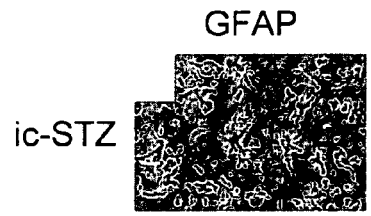
Figure 34G:
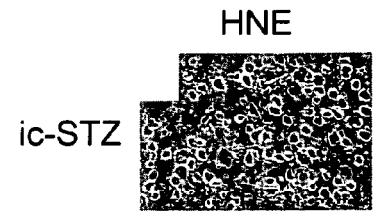
Figure 34C:
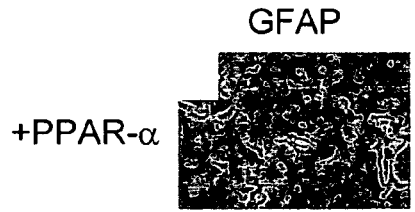
Figure 34H:
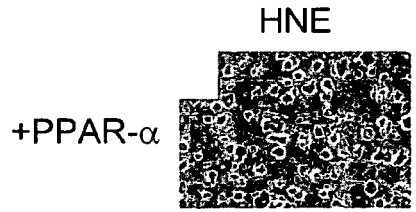
Figure 34D:
Figure 34I:
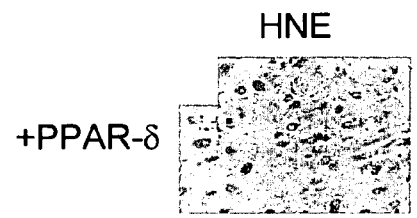
Figure 34E:
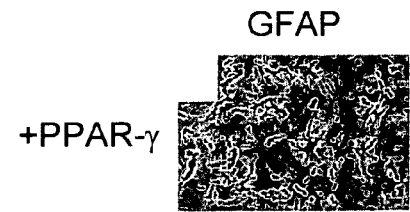
Figure 34J:
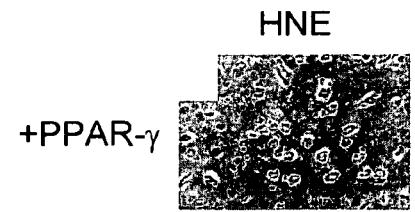
Figure 34K:
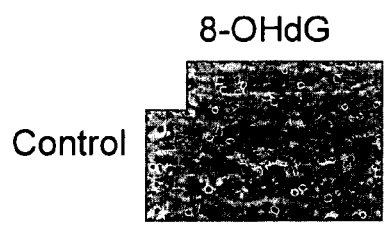
Figure 34P:
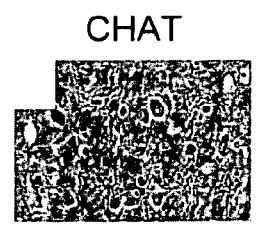
Figure 34L:
Figure 34Q:
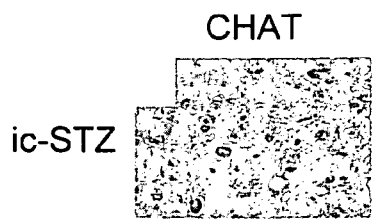
Figure 34M:
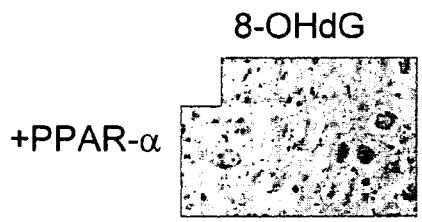
Figure 34R:
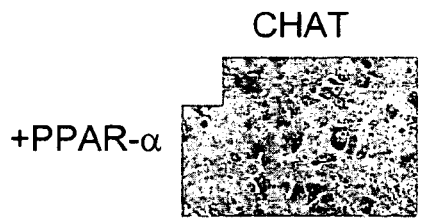
Figure 34N:
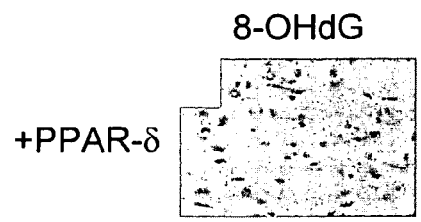
Figure 34S:
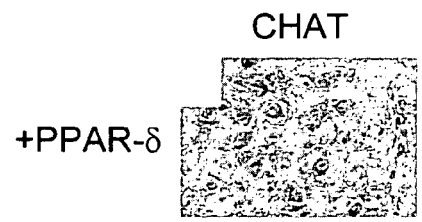
Figure 34O:
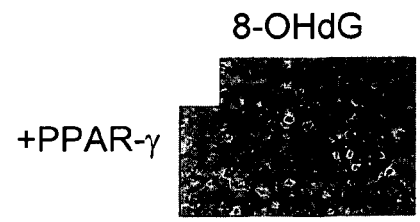
Figure 34T:
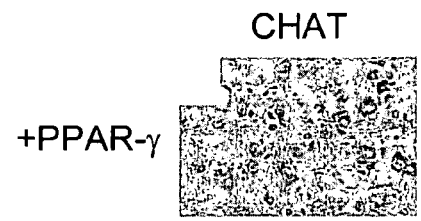

FIGS. 34A-34T: PPAR agonist treatments reduce glial fibrillary acidic protein (GFAP) and oxidative stress, and preserve choline acetyltransferase (ChAT) immunoreactivity in the ic-STZ model. Rat pups were treated with ic-STZ or vehicle, followed by IP injection of saline or a PPAR-α, δ, or γ agonist. Brains harvested 4 weeks later were fixed, sectioned along standardized landmarks, and paraffin-embedded. Histological sections were immunostained with antibodies to GFAP (A-E), HNE (F-J), 8-OHdG (K-O) or ChAT (P-T) using the ABC method with DAB as the chromogen (brown precipitate). Sections were lightly counterstained with hematoxylin. In the temporal cortex, immunoreactivity corresponding to GFAP was localized in activated astrocytes (A-E). HNE was distributed in cortical neurons and glial cells, and 8-OHdG was mainly detected in glia (L-arrows), particularly in white matter. ChAT immunoreactivity was localized in neuropil fibers and neuronal perikarya, but the most prominent ChAT expression was detected in the basal forebrain region of the brain (P-T). Representative results are shown for each experimental group.

FIGS. 35A-35E: PPAR-agonist reversal/prevention of ic-STZ-impairments in learning and memory. Learning and memory were assessed in control, ic-STZ, ic-STZ+PPAR-α, ic-STZ+PPAR-δ, or ic-STZ+PPAR-γ treated 4-week old rats by measuring the latency period required to recall and reach the location of the submerged platform in a Morris Water Maze. On Day 1 of testing, the rats were oriented to the water maze and educated about the location of the platform. On the 3 subsequent days of testing, the platform was submerged just below the surface, and the latency period (seconds) required to reach the platform was determined. Each rat was tested 3 times each day and allowed with 30 min. between trial rests. The start locations were consistent on the first two days of testing, but randomized for the last two testing days. The mean±S.E.M. latency periods measured for each group and trial are depicted graphically (A-E). Data were analyzed using ANOVA (+=P<0.05; #=P<0.01; *=P<0.005; **=P<0.001 relative to control).

DETAILED DESCRIPTION OF THE INVENTION

The present invention relates to the important role played in the occurrence of AD by the insulin/IGF signaling pathways in the brain. A significant decrease in the levels of several factors involved in these signaling pathways has been detected in the brains of subjects with AD compared to healthy subjects. Therefore, the invention relates to methods of diagnosing AD in a subject by detecting a decrease in the level or function of at least one factor in the insulin/IGF signaling pathway in said subject. The invention further relates to methods of treating, ameliorating, or preventing AD in a subject by administering to said subject a therapeutically effective amount of an insulin agonist in combination with a therapeutically effective amount of an IGF agonist.

The term "Alzheimer's Disease," as used herein, refers to a neurodegenerative disorder and encompasses familial and sporadic AD. Symptoms indicative of AD in human subjects typically include, but are not limited to, mild to severe dementia, progressive impairment of memory (ranging from mild forgetfulness to disorientation and severe memory loss), poor visio-spatial skills, personality changes, poor impulse control, poor judgment, distrust of others, increased stubbornness, restlessness, poor planning ability, poor decision making, and social withdrawal. Hallmark pathologies within brain tissues include extracellular neuritic β-amyloid plaques, neurofibrillary tangles, neurofibrillary degeneration, granulovascular neuronal degeneration, synaptic loss, and extensive neuronal cell death.

The terms "subjects displaying pathology resulting from AD" and "subjects suspected of displaying pathology resulting from AD," as used herein, refer to a subject that is identified as having or likely to have AD based on known AD symptoms and pathology.

The term "subjects at risk of displaying pathology resulting from AD," as used herein, refers to a subject at risk for developing AD (e.g., because of age or a familial inheritance pattern of AD in the subject's family).

In one aspect the invention relates to a method for diagnosing AD in a subject, comprising detecting a decrease in the level or function of at least one factor in the insulin/IGF signaling pathway in said subject, wherein a decrease in the level or function of one or more of said factors relative to the level in healthy subjects is a diagnostic indicator of AD.

In another aspect the invention relates to a method for identifying a subject at risk for developing AD, comprising determining the level or function of at least one factor in the insulin/IGF signaling pathway in said subject, wherein a decrease in the level of one or more of said factors relative to the level in healthy subjects is a diagnostic indicator of a risk for developing AD.

In certain embodiments of the invention, the level or function of at least 2, 3, 4, 5, or 6 factors in the insulin/IGF signaling pathway is determined.

The diagnostic methods of the invention may be carried out on subjects displaying pathology resulting from AD, subjects suspected of displaying pathology resulting from AD, and subjects at risk of displaying pathology resulting from AD.

In one embodiment of the invention, the level or function of at least one factor in the insulin/IGF signaling pathway in the CNS is determined.

In one embodiment, the diagnostic methods are carried out in vivo. For example, imaging techniques (e.g., magnetic resonance imaging, computed axial tomography, single photon emission computed tomography, positron emission tomography, X-ray, ultrasound) may be used in combination with detectably labeled antibodies, ligands, enzymes substrates, etc., to determine the level or function of at least one factor in the insulin/IGF signaling pathway in a subject. Examples of detectable labels include, but are not limited to, radioactive, fluorescent, paramagnetic, and superparamagnetic labels. Any suitable in vivo imaging techniques known in the art may be used in the present invention. Examples of imaging techniques are disclosed in U.S. Pat. Nos. 6,737,247, 6,676,926, 6,083,486, 5,989,520, 5,958,371, 5,780,010, 5,690,907, 5,620,675, 5,525,338, 5,482,698, and 5,223,242.

In another embodiment, the diagnostic methods are carried out in vitro, e.g., using a biological sample. A biological sample may be any tissue or fluid from a subject that is suitable for detecting the level or function of at least one factor in the insulin/IGF signaling pathway. Examples of useful samples include, but are not limited to, biopsied neurological tissues, blood (e.g., cerebral blood), plasma, serous fluid, cerebrospinal fluid, saliva, urine, and lymph.

Factors in the insulin/IGF signaling pathway that may be detected and measured include, but are not limited to, insulin, insulin-like growth factor-I (IGF-I), IGF-II, insulin receptor, IGF-I receptor, IGF-II receptor, tyrosine phosphorylated insulin receptor, tyrosine phosphorylated IGF-I receptor, tyrosine phosphorylated IGF-II receptor, insulin receptor substrate-1 (IRS-1), IRS-2, IRS-4, tyrosine phosphorylated IRS-1, tyrosine phosphorylated IRS-2, tyrosine phosphorylated IRS-4, phosphotidylinositol 3-kinase (PI3 kinase), the p85 subunit of PI3 kinase, Akt, phospho-Akt, glycogen synthase kinase-3β (GSK-3β), and phospho-GSK-3β. Functions that may be measured include, but are not limited to, ligand binding capacity of the insulin receptor, IGF-I receptor, or IGF-II receptor, kinase activity of the insulin receptor, IGF-I receptor, or IGF-II receptor, interaction of the p85 subunit of PI3 kinase with phosphorylated IRS-1, IRS-2, or IRS-4, binding of phosphorylated IRS-1, IRS-2, or IRS-4 to growth factor receptor-bound protein 2 (Grb2), SHPTP-2 protein tyrosine phosphatase, or the p85 subunit of PI3 kinase, the enzymatic activity of mitogen-activated protein kinase kinase (MAPKK), Erk MAPK, Akt/Protein kinase B, GSK-3β.

The standard level or function of a factor in the insulin/IGF signaling pathway in healthy subjects may represent the average of a suitable number of members of the general population, typically at least 10, more preferably 50, and still more preferably more than 100-500 members of the general population. In one embodiment, the standard level in healthy subjects is determined in an age-matched fashion, e.g., the subject on whom the methods of the invention are being practiced is compared to healthy subjects of the same age.

The levels of factors in the insulin/IGF signaling pathway may be measured at the protein or RNA (e.g., mRNA) levels.

Any method known in the art for quantitating specific proteins in a biological sample may be used in the present methods. Examples include, but are not limited to, immunoassays, Western blotting, immunoprecipitation, immunohistochemistry, gel electrophoresis, capillary electrophoresis, column chromatography, ligand binding assays, and enzymatic assays. See, e.g., Harlow et al., Antibodies: A Laboratory Manual, Cold Spring Harbor Laboratory, Cold Spring Harbor, N.Y., (1988); Ausubel et al., Current Protocols in Molecular Biology, John Wiley & Sons, New York 3rd Edition, (1995).

In a preferred embodiment, proteins are quantitated using immunoassays. Such assays include homogenous or heterogenous binding assays. These assays may be in the form of non-competitive binding assays or assays in which analytes compete with ligands. Any method known to one of ordinary skill in the art that detects binding between an analyte (e.g., a protein of interest) and a reagent may be used in the present invention. Assays for use in the present invention are preferably simple and inexpensive methods, and may also involve high throughput methods, capable of screening large numbers of individual samples in a rapid fashion. This includes, for example, methods that use microbeads or plates having multiple wells.

Antibodies to factors in the insulin/IGF pathway, such as insulin, IGF-I, IGF-II, insulin receptor, IGF-I receptor, IGF-II receptor, IRS-1, IRS-2, the p85 subunit of PI3 kinase, Gsk- 3β, phospho-Gsk-3β, Akt, and phospho-Akt, are commercially available (see e.g., Cell Signaling (Beverly, Mass.); Upstate Biotechnology (Lake Placid, N.Y.)). Alternatively, antibodies may be raised using standard techniques known in the art. See, e.g., Harlow et al., Antibodies: A Laboratory Manual, Cold Spring Harbor Laboratory, Cold Spring Harbor, N.Y., (1988); Ausubel et al., Current Protocols in Molecular Biology, John Wiley & Sons, New York 3rd Edition, (1995).

Examples of assays (e.g., immunohistochemistry, radioimmunoassay, ligand binding, protein:protein interaction) for the level or function of factors in the insulin/IGF pathway, including insulin, insulin receptor, IGF-I, IGF-II, IGF-I receptor, IRS subtypes 1-4, phosphorylated IRS, Grb-2, SHPTP-2, p85, PI3 kinase, Akt, and Gsk-3β, are described in Frolich et al., *J. Neural Transm.* 105:423 (1998); Folli et al., *Mol. Neurobiol.* 13:155 (1996); Unger et al., *Prog. Neurobiol.* 36:343 (1991); Saltiel et al., *Trends Cell Biol.* 12:65 (2002); Giovannone et al., *Diabetes Metab. Res. Rev.* 16:434 (2000); Shpakov et al., *Membr. Cell Biol.* 13:455 (2000); Sun et al., *Mol. Cell. Biol.* 13:7418 1993); Lam et al., *J. Biol. Chem.* 269:20648 (1994); Kulik et al., *Mol. Cell. Biol.* 17:1595 (1997); Delcommenne et al., *Proc. Natl. Acad. Sci. USA* 95:11211 (1998); Pap et al., *J. Biol. Chem.* 273:19929 (1998); Connor et al., *Brain Res. Mol. Brain Res.* 49:283 (1997); Jafferali et al., *Synapse* 38:450 (2000); Frolich et al., *Ann. NY Acad. Sci.* 893:290 (1999); Fernandes et al., *Endocrine* 16:227 (2001) and U.S. Pat. No. 5,198,340, each of which is incorporated by reference.

Any homogeneous assay well known in the art can be used in the present invention to determine the level of specific proteins. For example, radioassays, fluorescence polarization assays, time-resolved fluorescence assays, biotin-avidin assays, enzyme-linked assays, and electrochemiluminescent assays may all be used. Where the reagent is labeled, the assay may be a non-competitive binding assay in which the ability of analytes (protein of interest) to bind the reagent is determined. Where analytes are labeled, the assay may be a competitive binding assay where the ability of a protein to displace reagent-bound analyte is determined.

A homogeneous binding assay used in the present invention, and which uses fluorescence to detect the analyte/protein binding, may employ fluorescently labeled analyte or fluorescently labeled reagent. Any method known to one of ordinary skill in the art can be used to link the fluorophore to a polypeptide or reagent of interest. See, e.g., Richard P. Haugland, Molecular Probes: Handbook of Fluorescent Probes and Research Chemicals 1992-1994 (5th ed., 1994, Molecular Probes, Inc.).

One embodiment of the invention relates to a non-competitive fluorescent assay. Such an assay employs reagent covalently attached to a fluorophore. Free reagent has a higher fluorescence intensity than reagent bound to an analyte (Hwang et al., *Biochemistry* 31:11536 (1992)). Once the analyte/reagent complex is formed, it rotates and tumbles more slowly and has less fluorescence intensity ("Introduction to Fluorescence Polarization," Pan Vera Corp., Madison, Wis., Jun. 17, 1996; Perrin, *J. Phys. Rad.* 1:390 (1926)). Hence, when the analyte and reagent bind, the fluorescence intensity of the labeled reagent decreases proportional to binding.

Competitive homogenous fluorescence assays can also be used in the present invention. Competitive assays are well known in the art and any method can be used in the present invention. For example, U.S. Pat. No. 6,511,815 describes an assay for quantitating competitive binding of test compounds to proteins utilizing fluorescence polarization.

Alternative homogeneous assays for use in the invention include those described in U.S. Pat. No. 6,492,128; U.S. Pat. No. 6,406,913; U.S. Pat. No. 6,326,459; U.S. Pat. No. 5,928,862; U.S. Pat. No. 5,876,946; U.S. Pat. No. 5,612,221; and U.S. Pat. No. 5,556,758.

The skilled artisan will recognize that radiolabels can also be used in homogenous competitive binding assays. In such assays, reagent (e.g., antibody) is radiolabeled and allowed to equilibrate with protein in solution. Then, a sample is introduced into the solution and allowed to equilibrate. Antibody (bound either to radiolabeled antigen or to the sample) is then separated from unbound antigen and unbound sample. This can be detected by a scintillation counter, photoradiography, or other techniques well known in the art.

Detection and/or quantitation of a protein of interest through binding to a reagent may also be accomplished using heterogeneous assays. Heterogeneous assays for use in the present invention may be based on radioassays, fluorescence polarization assays, time-resolved fluorescence assays, biotin-avidin assays, enzyme-linked assays, and electrochemiluminescent assays. In heterogenous assays, a first component is attached to a solid phase such as a bead or other solid substrate and one or more additional components are in solution. For example, antigen may be bound to a bead or other solid substrate and labeled antibody is introduced as a solution. The label may be a radiolabel, chemiluminescent label, fluorescent label, chromogenic label, or other label well known in the art. After the mixture equilibrates and the antigen/antibody complexes form, a solution of sample is introduced and allowed to equilibrate to form antigen/antibody complexes. The beads or solid components are separated from the solutions. This can be done, for example, using magnetic fields where the beads are magnetic. Alternatively, where antigen is bound to a solid substrate, separation can occur simply by rinsing the solid substrate with water or a buffer to remove any solution containing unbound labeled antibody or unbound sample. The extent to which antigen remains associated with the detectably labeled antibody is measured. Such measurements can be performed while antigen remains bound to the bead or solid substrate. Alternatively, such measurements can be made after antigen has been removed from the bead or solid substrate. In such competitive binding assays, decreases in signal associated with the detectable label are proportionally related to increases in the ability of antibody in samples to bind antigen by displacing antibody.

The skilled artisan recognizes that the antibody may also be the component bound to the beads or solid substrate. In such assays, labeled antigen is introduced as a solution and allowed to equilibrate forming the antigen/antibody complexes. The label may be a radiolabel, chemiluminescent label, fluorescent label, chromogenic label, or other label well known in the art. Then, a sample is added as a solution. If a sample displaces antibody, then the antigen will fall back into solution and not be bound to the bead or solid substrate through antibody. As described above, the beads or solid substrate are removed from the solution but the solution is retained to measure the extent of the detectable label. Here, increases in signal associated with the detectable label are proportional to the ability of a sample to bind antigen.

Solid phase supports for use in the present invention include any insoluble support known in the art that is capable of binding antigen or antibody. This includes, for example, glass and natural and synthetic polymers such as agaroses, polystyrene, polypropylene, polyethylene, dextran, nylon, amylases, natural and modified celluloses, polyacrylamides, and magnetite. The support material may have virtually any possible structural configuration so long as the support-bound molecule is capable of binding to an antibody or antigen. Thus, the support configuration may be spherical, as in a bead, or cylindrical, as in the inside surface of a test tube, or the external surface of a rod, or hemispherical, such as the well of a microtitre plate. Alternatively, the surface may be flat such as a sheet, test strip, etc. Those skilled in the art will note many other suitable carriers for binding antibody or antigen, or will be able to ascertain the same by use of routine experimentation.

An example of a heterogeneous assay for use in the present invention is the radioassay. A good description of a radioassay may be found in Laboratory Techniques and Biochemistry in Molecular Biology, by Work, T. S., et al., North Holland Publishing Company, NY (1978), with particular reference to the chapter entitled "An Introduction to Radioimmune Assay and Related Techniques" by Chard, T. Examples of other competitive radioassays are given in U.S. Pat. Nos. 3,937, 799; 4,102,455; 4,333,918 and 6,071,705. Inherent in such assays is the need to separate the bead or substrate bound component from the solution component. Various ways of accomplishing the required separation have been developed, including those exemplified in U.S. Pat. Nos. 3,505,019; 3,555,143; 3,646,346; 3,720,760; and 3,793,445. The skilled artisan will recognize that separation can include filtering, centrifuging, washing, or draining the solid substrate to insure efficient separation of the substrate bound and solution phases.

The radioactive isotope or radiolabel can be detected by such means as the use of a gamma counter or a scintillation counter or by autoradiography. Isotopes which are particularly useful for the purpose of the present invention are: $^{3}$H, $^{123}$I, $^{125}$I, $^{131}$I, $^{35}$S, $^{31}$P, $^{14}$C, $^{111}$In, $^{97}$Ru, $^{67}$Cu, $^{67}$Ga, $^{67}$Ga, $^{72}$As, $^{89}$Zr and $^{201}$Tl. Those of ordinary skill in the art will know of other suitable labels, which may be employed in accordance with the present invention. The binding of these labels to antigen or antibody can be accomplished using standard techniques commonly known to those of ordinary skill in the art. Typical techniques are described by Kennedy, et al. (Clin. Chim. Acta 70:1 (1976)), and Schurs et al. (Clin. Chim. Acta 81:1 (1977)). In a particular embodiment, one or more hydrogen and/or carbon atoms of an antigen or antibody are replaced by $^{3}$H and $^{14}$C, by methods well known in the art.

Alternative labels for use in the heterogeneous assays of the present invention include chemiluminescent labels, such as those described in U.S. Pat. No. 4,380,580; and enzyme substrate labels, such as those assays described in U.S. Pat. No. 4,492,751. For example, a fluorescent label may be used.

An alternative heterogeneous assay for use in the present invention is a biotin/avidin based assay. For examples of the various ways in which this assay can be performed in the present invention, see, e.g., Blake et al. Anal. Biochem. 272: 123 (1999); Cho et al. Anal. Sci. 15:343 (1999); Choi et al. Bull. Korean Chem. Soc. 22:417 (2001); U.S. Pat. Nos. 6,096, 508; 4,863,876; 4,228,237. In the present invention, avidin may be labeled with any label. Preferably, avidin is fluorescently labeled or conjugated to an enzyme. Any detectably labeled enzyme can be used in the present invention. Specific examples include, but are not limited to, horseradish peroxidase, alkaline phosphatase, β-galactosidase, and glucose oxidase.

To measure the level of a specific RNA, any assay known in the art for the detection of nucleic acids may be used in the invention. Examples include, but are not limited to, reverse transcription and amplification assays, hybridization assays, Northern blotting, dot blotting, in situ hybridization, gel electrophoresis, capillary electrophoresis, and column chromatography. See, e.g., Ausubel et al., Current Protocols in Molecular Biology, John Wiley & Sons, New York 3rd Edition, (1995); Sambrook et al., Molecular Cloning—A Laboratory Manual, 2nd ed., Vol. 1-3 (1989). The assay can detect the RNA itself or a cDNA produced by reverse transcription of the RNA. Assays can be performed directly on biological samples or on nucleic acids isolated from the samples.

Nucleic acid detection assays can be predicated on any characteristic of the nucleic acid molecule, such as its size, sequence and, if DNA, susceptibility to digestion by restriction endonucleases. The sensitivity of such assays may be increased by altering the manner in which detection is reported or signaled to the observer. Thus, for example, assay sensitivity can be increased through the use of detectably labeled reagents. A wide variety of such labels have been used for this purpose. Detectable labels include, for example, radioactive isotopes, fluorescent labels, chemiluminescent labels, bioluminescent labels and enzyme labels. U.S. Pat. No. 4,581,333 describes the use of enzyme labels to increase sensitivity in a detection assay. Radioisotopic labels are disclosed in U.S. Pat. Nos. 4,358,535 and 4,446,237. Fluorescent labels (EP 144,914), chemical labels (U.S. Pat. Nos. 4,582,789 and 4,563,417), and modified bases (EP 119,448) have also been used in an effort to improve the efficiency with which detection can be observed.

Many current methods of identification and quantification of nucleic acids rely on amplification and/or hybridization techniques. While many of these involve a separation step, several that allow detection of nucleic acids without separating the labeled primer or probe from the reaction have been developed. These methods have numerous advantages compared to gel-based methods, such as gel electrophoresis and dot-blot analysis, for example, and require less time, permit high throughput, prevent carryover contamination and permit quantification through real time detection. Most of these current methods are solution-based fluorescence methods that utilize two chromophores. These methods utilize the phenomena of fluorescence resonance energy transfer (FRET) in which the energy from an excited fluorescent moiety is transferred to an acceptor molecule when the two molecules are in close proximity to each other. This transfer prevents the excited fluorescent moiety from releasing the energy in the form of a photon of light thus quenching the fluorescence of the fluorescent moiety. When the acceptor molecule is not sufficiently close, the transfer does not occur and the excited fluorescent moiety may then fluoresce. The major disadvantages of systems based on FRET are the cost of requiring the presence of two modified nucleotides in a detection oligonucleotide and the possibility that the efficiency of the quenching may not be sufficient to provide a usable difference in signal under a given set of assay conditions. Other known methods which permit detection without separation are: luminescence resonance energy transfer (LRET) where energy transfer occurs between sensitized lanthanide metals and acceptor dyes (Selvin et al., Proc. Natl. Acad. Sci. USA 91:10024 (1994)); and color change from excimer-forming dyes where two adjacent pyrenes can form an excimer (fluorescent dimer) in the presence of the complementary target, resulting in a detectably shifted fluorescence peak (Paris et al., Nucleic Acids Re. 26:3789 (1998)).

Various methods are known to those skilled in the art for the amplification of nucleic acid molecules. In general, a nucleic acid target molecule is used as a template for extension of an oligonucleotide primer in a reaction catalyzed by polymerase. For example, Panet et al. (J. Biol. Chem. 249: 5213 (1974)) demonstrate the replication of deoxyribopolynucleotide templates bound to cellulose. Kleppe et al. (J. Mol.

*Biol.* 56:341 (1971)) disclose the use of double- and single-stranded DNA molecules as templates for the synthesis of complementary DNA.

Other known nucleic acid amplification procedures include transcription based amplification systems (Kwoh et al., *Proc. Natl. Acad. Sci. USA* 86:1173 (1989); WO 88/10315). Schemes based on ligation ("Ligation Chain Reaction") of two or more oligonucleotides in the presence of a target nucleic acid having a sequence complementary to the sequence of the product of the ligation reaction have also been used (Wu et al., *Genomics* 4:560 (1989)). Other suitable methods for amplifying nucleic acid based on ligation of two oligonucleotides after annealing to complementary nucleic acids are known in the art.

WO 89/06700 discloses a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts.

EP 329,822 discloses an alternative amplification procedure termed Nucleic Acid Sequence-Based Amplification (NASBA). NASBA is a nucleic acid amplification process comprising cyclically synthesizing single-stranded RNA ("ssRNA"), ssDNA, and double-stranded DNA (dsDNA). The ssRNA is a first template for a first primer oligonucleotide, which is elongated by reverse transcriptase (RNA dependent DNA polymerase). The RNA is then removed from the resulting DNA:RNA duplex by the action of ribonuclease H (RNase H, an RNase specific for RNA in a duplex with either DNA or RNA). The resultant ssDNA is a second template for a second primer. The second primer includes the sequences of an RNA polymerase promoter (exemplified by T7 RNA polymerase) located 5' to the primer sequence which hybridizes to the ssDNA template. This primer is then extended by a DNA polymerase (exemplified by the large "Klenow" fragment of *E. coli* DNA polymerase I), resulting in the production of a dsDNA molecule, having a sequence identical to that of the portion of the original RNA located between the primers and having, additionally, at one end, a promoter sequence. This promoter sequence can be used by the appropriate RNA polymerase to make many RNA copies of the DNA. These copies can then re-enter the cycle leading to very swift amplification. With the proper choice of enzymes, this amplification can be done isothermally without the addition of enzymes at each cycle. Because of the cyclical nature of this process, the starting sequence can be chosen to be in the form of either DNA or RNA.

U.S. Pat. No. 5,455,166 and EP 684 315 disclose a method called Strand Displacement Amplification (SDA). This method is performed at a single temperature and uses a combination of a polymerase, an endonuclease and a modified nucleoside triphosphate to amplify single-stranded fragments of the target DNA sequence. A target sequence is fragmented, made single-stranded and hybridized to a primer that contains a recognition site for an endonuclease. The primer:target complex is then extended with a polymerase enzyme using a mixture of nucleoside triphosphates, one of which is modified. The result is a duplex molecule containing the original target sequence and an endonuclease recognition sequence. One of the strands making up the recognition sequence is derived from the primer and the other is a result of the extension reaction. Since the extension reaction is performed using a modified nucleotide, one strand of the recognition site is modified and resistant to endonuclease digestion. The resultant duplex molecule is then contacted with an endonuclease which cleaves the unmodified strand causing a nick. The nicked strand is extended by a polymerase enzyme lacking 5'-3' exonuclease activity resulting in the displacement of the nicked strand and the production of a new duplex molecule. The new duplex molecule can then go through multiple rounds of nicking and extending to produce multiple copies of the target sequence.

The most widely used method of nucleic acid amplification is the polymerase chain reaction (PCR). A detailed description of PCR is provided in the following references: Mullis et al., *Cold Spring Harbor Symp. Quant. Biol.* 51:263 (1986); EP 50,424; EP 84,796; EP 258,017; EP 237,362; EP 201,184; U.S. Pat. Nos. 4,683,202; 4,582,788; 4,683,194. In its simplest form, PCR involves the amplification of a target double-stranded nucleic acid sequence. The double-stranded sequence is denatured and an oligonucleotide primer is annealed to each of the resultant single strands. The sequences of the primers are selected so that they will hybridize in positions flanking the portion of the double-stranded nucleic acid sequence to be amplified. The oligonucleotides are extended in a reaction with a polymerase enzyme, nucleotide triphosphates and the appropriate cofactors resulting in the formation of two double-stranded molecules each containing the target sequence. Each subsequent round of denaturation, annealing and extension reactions results in a doubling of the number of copies of the target sequence as extension products from earlier rounds serve as templates for subsequent replication steps. Thus, PCR provides a method for selectively increasing the concentration of a nucleic acid molecule having a particular sequence even when that molecule has not been previously purified and is present only in a single copy in a particular sample. The method can be used to amplify either single- or double-stranded nucleic acids. The essence of the method involves the use of two oligonucleotides to serve as primers for the template dependent, polymerase-mediated replication of the desired nucleic acid molecule.

Methods for detecting nucleic acid amplification products commonly use gel electrophoresis, which separates the amplification product from the primers on the basis of a size differential. Alternatively, amplification products can be detected by immobilization of the product, which allows one to wash away free primer (for example, in dot-blot analysis), and hybridization of specific probes by traditional solid phase hybridization methods. Several methods for monitoring the amplification process without prior separation of primer or probes have been described. All of these methods are based on FRET.

One method, described in U.S. Pat. No. 5,348,853 and Wang et al, *Anal. Chem.* 67:1197 (1995), uses an energy transfer system in which energy transfer occurs between two fluorophores on the probe. In this method, detection of the amplified molecule takes place in the amplification reaction vessel, without the need for a separation step. The Wang et al. method uses an "energy-sink" oligonucleotide complementary to the reverse primer. The "energy-sink" and reverse primer oligonucleotides have donor and acceptor labels, respectively. Prior to amplification, the labeled oligonucleotides form a primer duplex in which energy transfer occurs freely. Then, asymmetric PCR is carried out to its late-log phase before one of the target strands is significantly overproduced.

A second method for detection of an amplification product without prior separation of primer and product is the 5' nuclease PCR assay (also referred to as the TAQMAN® assay) (Holland et al., *Proc. Natl. Acad. Sci. USA* 88:7276 (1991); Lee et al., *Nucleic Acids Res.* 21:3761 (1993)). This assay detects the accumulation of a specific PCR product by hybridization and cleavage of a doubly labeled fluorogenic probe (the TAQMAN® probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if it hybridizes to the segment being amplified. Cleavage of the probe generates an increase in the fluorescence intensity of the reporter dye. In the TAQMAN® assay, the donor and quencher are preferably located on the 3'- and 5'-ends of the probe, because the requirement that 5'-3' hydrolysis be performed between the fluorophore and quencher may be met only when these two moieties are not too close to each other (Lyamichev et al., Science 260:778 (1993)).

Another method of detecting amplification products (namely MOLECULAR BEACONS) relies on the use of energy transfer using a "beacon probe" described by Tyagi and Kramer (Nature Biotech. 14:303 (1996)). This method employs oligonucleotide hybridization probes that can form hairpin structures. On one end of the hybridization probe (either the 5'- or 3'-end), there is a donor fluorophore, and on the other end, an acceptor moiety. In the case of the Tyagi and Kramer method, the acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the beacon probe, which hybridizes to one of the strands of the PCR product, is in "open conformation," and fluorescence is detected, while those that remain unhybridized will not fluoresce. As a result, the amount of fluorescence will increase as the amount of PCR product increases, and thus may be used as a measure of the progress of the PCR.

Another method of detecting amplification products which relies on the use of energy transfer is the SUNRISE PRIMER method of Nazarenko et al. (Nucleic Acids Res. 25:2516 (1997); U.S. Pat. No. 5,866,336). SUNRISE PRIMERS are based on FRET and other mechanisms of non-fluorescent quenching. SUNRISE PRIMERS consist of a single-stranded primer with a hairpin structure at its 5'-end. The hairpin stem is labeled with a donor/quencher pair. The signal is generated upon the unfolding and replication of the hairpin sequence by polymerase.

Another method of detecting amplification products is real time quantitative PCR (Xu et al., J. Biol. Chem. 278:26929 (2003); Yeon et al., Hepatology 38:703 (2003)). In this technique a fluorescent reporter (e.g., an intercalating dye such as SYBR Green (Molecular Probes)) is used to monitor the PCR reaction as it occurs. The fluorescence of the reporter molecule increases as products accumulate with each successive round of amplification. The point at which the fluorescence rises appreciably above baseline can be used to determine the starting amount of template in a sample.

In one embodiment of the invention, a diagnostic kit is provided for the diagnosis of AD. The kits may be used to determine the level or function of at least one factor in the insulin/IGF signaling pathway in a biological sample obtained from a subject. In this embodiment, a kit is provided, with one or more containers comprising at least one detecting agent which may be used to determine the level or function of at least one factor in the insulin/IGF signaling pathway. Detecting agents include, but are not limited to, one or more antibodies that specifically bind to a factor in the insulin/IGF signaling pathway, one or more oligonucleotides capable of hybridizing to a polynucleotide encoding a factor in the insulin/IGF signaling pathway, one or more pairs of primers useful for amplifying a polynucleotide encoding a factor in the insulin/IGF signaling pathway, or one or more enzyme substrates which may be acted on by a factor in the insulin/IGF signaling pathway. In various other embodiments, the kit can also comprise, e.g., a buffering agent, a preservative, or a protein stabilizing agent. The kit also can comprise components necessary for detecting the detecting agent (e.g., an enzyme or a substrate). The kit also can contain a control sample or a series of control samples which can be assayed and compared to the test sample. Each component of the kit is usually enclosed within an individual container and all of the various containers are within a single package along with instructions for observing whether the tested subject is suffering from, or is at risk of developing AD.

In one aspect of the invention, methods for the treatment, amelioration, or prevention of AD in a subject are provided. In certain embodiments, the methods comprise the administration to the subject a therapeutically effective amount of an insulin agonist and a therapeutically effective amount of an IGF agonist.

An additional aspect of the present invention relates to a method for improving mentation of a subject with AD, comprising administering to a subject a therapeutically effective amount of an insulin agonist and a therapeutically effective amount of an IGF agonist.

A further aspect of the present invention relates to a method for reducing memory loss in a subject with AD, comprising administering to a subject a therapeutically effective amount of an insulin agonist and a therapeutically effective amount of an IGF agonist.

In one embodiment, a therapeutically effective amount of an insulin agonist and optionally a therapeutically effective amount of an IGF agonist are administered to a subject exhibiting mild cognitive impairment as a result of conditions such as Parkinson's disease, vascular dementia, limbic encephalitis, Lewy body disease, normal pressure hydrocephalus, posttraumatic dementia, Huntingdon's disease, progressive supranuclear palsy, amnesic disorders, cognitive disorders not otherwise specified, mental retardation, frontotemporal dementia (Pick's disease), multiple sclerosis, Jakob-Creutzfeldt disease, idiopathic basal ganglia calcification, transient ischemic attacks, metabolic and neutritional imbalances, febrile states, neurosyphilus, alcohol-related dementia, hypothyroidism and depression. Mild cognitive impairment is diagnosed by a physician and may be based upon a subject receiving a score of 20 or less using the Mini-Mental State Examination. Other instruments that may be employed to evaluate mental status include the Blessed Information Memory Concentration, the Blessed Orientation Memory Concentration, the Short Test of Mental Status, and the Functional Activity Questionnaire. Using these instruments, therapy may be initiated upon subject scores of greater than 10 errors, greater than 10 errors, less than 29, and less than 9, respectively. Mild cognitive impairment is generally observed in subjects corresponding to Braak stages 1-2.

In one embodiment of the invention, a therapeutically effective amount of an insulin agonist and a therapeutically effective amount of an IGF agonist are administered to a subject exhibiting early symptoms of AD or symptoms suggestive of a pre-AD condition in order to rescue the subject from further progression of AD or development of AD. Included among such subjects are those diagnosed with mild or minimal cognitive impairment, a condition characterized by cognitive deficits not severe enough to be classified as dementia, but which is a precursor of, or an early stage of, AD. Early stages of AD in which the rescue of subjects may be carried out include those corresponding to Braak stages 1-3. At these stages, the changes in expression of growth factors and growth factor receptors in the brain have begun but the expression has not fallen to the levels seen in severe stages of AD (e.g., Braak stages 4-6). Thus, subjects at early stages of AD may still be rescued by the administration of growth factors and other therapeutic agents.

The term "insulin agonist," as used herein, refers an agent which has been used, is currently, used or is known to be useful for the treatment of diabetes by increasing the level of or sensitivity to insulin.

In one embodiment, the insulin agonist is any agonist of the insulin receptor that has been used, is currently used, or is known to be useful for the stimulation of insulin dependent signaling pathways. Examples of insulin agonists include purified natural occurring insulin (e.g., ILETIN), recombinant insulin (e.g., HUMULIN), functional derivatives of insulin, and insulin analogs and mimetics (i.e., derivatives, analogs and mimetics that are capable of binding to the insulin receptor and stimulating one or more of the same signals that are stimulated by insulin). Examples of insulin analogs and mimetics include insulin aspart (NOVOLOG), insulin glargine (LANTUS), insulin lispro (HUMALOG), $Lys^{B28}Pro^{B29}$-insulin, $Asp^{B28}$-insulin, $desPro^{B28}$-insulin, $desPro^{B28}desThr^{B30}$-insulin, $desPhe^{B25}desThr^{B30}$-insulin, $desTyr^{B26}desThr^{B30}$-insulin, $Ser^{A21}desPro^{B28}$-insulin, $Gly^{A21}desPro^{B28}$-insulin, $Gly^{A21}desPhe^{B25}$-insulin, $Asp^{A21}desPhe^{B25}$-insulin, $His^{B25}desTyr^{B26}desThr^{B30}$-insulin, $Asn^{B25}desTyr^{B26}desThr^{B30}$-insulin, $Asp^{A21}desPhe^{B25}desThr^{B30}$-insulin, $Asp^{B28}desPhe^{B25}$-insulin, $Asp^{B3}desPhe^{B25}$-insulin, $Lys^{B28}Thr^{B29}$-insulin $Arg^{B28}desLys^{B29}$-insulin, $Gly^{A21}desThr^{B27}$-insulin, $Gly^{A21}Thr^{B3}desThr^{B27}$-insulin, $Ala^{A21}Thr^{B3}desThr^{B27}$-insulin, $Gly^{A21}Asp^{B3}desThr^{B27}$-insulin, $Ala^{A21}Asp^{B3}desThr^{B27}$-insulin, $desThr^{B27}desThr^{B30}$-insulin, $Glu^{B27}$-insulin, $Ile^{B12}$-insulin, $Tyr^{B12}$-insulin, $Asp^{A21}Glu^{B27}$-insulin, $Asp^{B9}$-insulin, $Asp^{A21}Asp^{B9}Glu^{B27}$-insulin, $Gly^{A12}$-insulin, $Thr^{A12}$-insulin, $Gly^{A12}His^{A19}$-insulin, $Phe^{A14}$-insulin, $Gly^{A14}$-insulin, $Thr^{A12}Gly^{A14}$-insulin, $Pro^{A10}Trp^{A13}$-insulin, $Lys^{B28}$-insulin, $desPhe^{B25}desThrB^{B30}$-insulin, $desPhe^{B25}$-insulin, and $Asp^{A21}desPhe^{B25}desThr^{B30}$-insulin. Additional examples of such agents are described in U.S. Pat. Nos. 6,800,606, 6,686,177, 6,630,348, 6,620,780, 6,610,649, 6,451,762, 6,444,641, 6,329,431, 6,323,311, 6,251,856, 6,221,837, 6,221,633, 6,197,926, 6,100,376, 6,093,697, 6,011,007, 5,970,973, 5,962,267, 5,952,297, 5,922,675, 5,851,988, 5,840,680, 5,834,422, 5,830,918, 5,750,497, 5,747,642, 5,716,927, 5,693,609, 5,656,722, 5,650,486, 5,618,913, 5,597,893, 5,559,094, 5,547,930, 5,547,929, 5,514,646, 5,506,202, 5,504,188, 5,474,978, 5,461,035, 5,461,031, 5,268,453, 5,208,217, 5,164,366, 5,157,021, 5,149,777, 5,149,716, 5,049,545, 5,028,586, 5,008,241, 4,992,418, 4,992,417, 4,959,351, 4,946,828, 4,701,440, 4,639,332, and 4,489,064, and WO 95/13823, each incorporated by reference.

In another embodiment, an insulin agonist is an agent which has been used, is currently, used or is known to be useful for the treatment of insulin resistance and/or type II diabetes. In one embodiment the agent is an insulin sensitizer. Insulin sensitizers include, but are not limited to, biguanides (such as metformin (GLUCOPHAGE)), thiazolidinediones (such as rosiglitazone (AVANDIA), pioglitazone (ACTOS), troglitazone (REZULIN), englitazone, and ciglitazone), and MBX-102 (an enantiomer of halogenate). Other useful thiazolidinediones include those disclosed in U.S. Pat. Nos. 6,787,551, 6,288,096, 6,130,216, 6,046,202, 5,990,139, 5,965,589, 5,811,439, 5,716,975, 5,489,602, 5,478,852, 5,457,109, 5,441,971, 5,326,770, 4,725,610, 4,697,020, and 4,687,777, and in Hulin et al., *J. Med. Chem.* 35:1853 (1992). Other agents useful in the treatment of insulin resistance include insulin secretagogues, including meglitinides (such as repaglinide (PRANDIN) and nateglinide (STARLIX)), sulfonylureas (such as tolbutamide, chlorpropamide (DIABINASE), tolazamide (TOLINASE), glyburide (MICRONASE, DIABETA), glypizide (GLUCOTROL), and glimepiride (AMARYL)), and alpha-glucosidase inhibitors (such as acarbose (PRECOSE) and miglitol (GLYSET)). Other useful agents include peroxisome proliferator-activated receptor (PPAR) agonists, including selective agonists of PPAR-α, PPAR-γ, and PPAR-δ, as disclosed in U.S. Pat. Nos. 6,713,514, 6,677,298, 6,462,046, 5,925,657, and 5,326,770 and in Combs et al., *J. Neurosci.* 20:558 (2000). The term selective is used to describe agents having greater than 10-fold, preferably greater than 100-fold, and most preferably greater than 1,000-fold activity at one PPAR receptor subtype than at another PPAR receptor subtype. Characterization of receptor affinities and functional activities for agents at PPAR receptor subtypes can be determined using methodology as described in WO 2005049572. The use of PPAR-δ agonists in AD patients may have an added advantage of increasing the number of type I muscle fibers, which may confer resistance to obesity and improve metabolic profiles, even in the absence of exercise (Wang et al., *PLoS Biol.* 2:3294 (2004)). Useful PPAR-δ receptor selective agonists include without limitation GW 501516, GW 0742, L-165041, and carbaprostacyclin, which are structurally defined below:

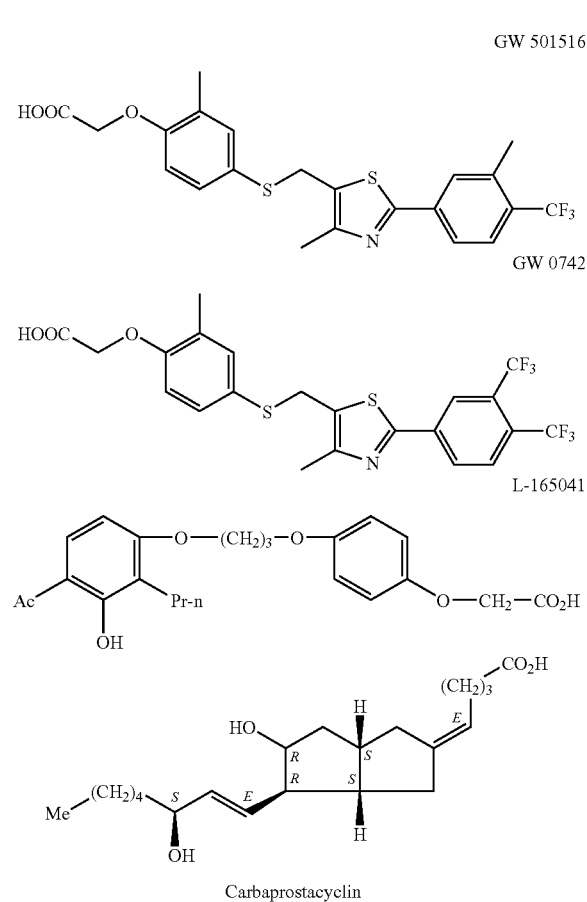

Other useful PPAR-δ agonists are disclosed in EP 1586573, US 20050245589, and WO 2005049572.

Other useful agents include $\beta_3$-adrenergic receptor agonists (U.S. Pat. Nos. 6,649,603, 6,605,618, 6,583,140, 6,569,873, 6,537,994, 6,525,202, 6,514,991, 6,509,358, 6,506,901, 6,498,170, 6,465,501, 6,458,817, 6,451,814, 6,444,685, 6,410,734, 6,395,762, 5,972,881) and retinoid X receptor agonists (U.S. Pat. Nos. 6,593,493, 6,521,633, 6,316,404, 6,228,862, 6,028,052). Additional agents that may be used include chromium, dopamine agonists (U.S. Pat. Nos. 5,468,755, 5,597,832, 5,602,120, 5,602,121), pyruvate and pyruvate precursors (U.S. Pat. Nos. 5,472,980, 5,283,260), and benzothiadiazines (e.g., diazoxide). Other examples of agents useful for the treatment of insulin resistance are disclosed in U.S. Pat. Nos. 6,787,556, 6,765,021, 6,765,013, 6,713,508, 6,699,896, 6,693,094, 6,683,107, 6,677,352, 6,673,815, 6,649,628, 6,646,004, 6,645,997, 6,624,194, 6,613,802, 6,521,665, 6,521,633, 6,515,003, 6,509,360, 6,451,845, 6,451,827, 6,444,670, 6,414,002, 6,391,897, 6,376,495, 6,369,072, 6,310,081, 6,284,787, 6,262,118, 6,251,936, 6,251,924, 6,248,764, 6,232,322, 6,221,902, 6,214,877, 6,214,842, 6,207,714, 6,166,069, 6,117,899, 6,110,962, 6,103,708, 6,063,815, 6,015,558, 5,948,810, 5,730,975, 5,693,664, 5,646,168, 5,641,796, 5,545,672, 5,463,070, and 4,980,350, and in Shinkai et al., *J. Med. Chem.* 41:1927 (1998), each incorporated by reference.

The term "IGF agonist," as used herein, refers to any agonist of the IGF receptors that has been used, is currently used, or is known to be useful for the stimulation of IGF dependent signaling pathways.

Examples of IGF agonists include purified natural or recombinant IGF proteins, functional derivatives of IGFs, and IGF analogs and mimetics (i.e., derivatives, analogs and mimetics that are capable of binding to an IGF receptor and stimulating one or more of the same signals that are stimulated by an IGF). Examples of IGF analogs include the D analog of IGF-I, long-$Arg^3$-IGF-I, $Val^{59}$-IGF-I, AlaGlu-IGF-I, $Ala^{63}$-IGF-I, $Ser^1Ala^{63}Val^{70}$-IGF-I, $Leu^{24,59,60}Ala^{31}$-IGF-II, $Gln^6Ala^7Tyr^{18}Leu^{19}Leu^{27}$-IGF-II, $Gly^1$-IGF-II, $Leu^{27}$-IGF-II, and $Gln^{37}Gln^{38}$-IGF-II. Also included are agents that interfere with the binding of IGFs to IGF binding proteins, thereby increasing the amount of circulating IGFs available for binding to IGF receptors. Examples of other IGF functional derivatives, agonists and mimetics are described in U.S. Pat. Nos. 6,750,321, 6,743,894, 6,723,699, 6,716,586, 6,713,451, 6,693,079, 6,693,078, 6,693,076, 6,689,751, 6,683,053, 6,680,298, 6,677,305, 6,645,775, 6,635,619, 6,632,794, 6,620,789, 6,608,031, 6,608,028, 6,509,443, 6,506,874, 6,420,518, 6,403,764, 6,358,916, 6,342,227, 6,251,865, 6,235,874, 6,121,416, 5,854,025, 5,776,897, 5,736,363, 5,708,134, 5,703,045, 5,652,214, 5,622,932, 5,473,054, 5,470,828, 5,273,966, 5,028,531, 5,019,500, 4,876,242, and 4,745,179, each incorporated by reference.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of AD, a therapeutically effective amount preferably refers to the amount of a therapeutic agent that decreases the symptoms of AD, increases the time to progression of the symptoms of AD, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% as compared to that which would have occurred without the present invention.

The terms "prevent," "preventing," and "prevention," as used herein, refer to a decrease in the occurrence of AD pathology in a subject. The prevention may be complete, e.g., the total absence of AD pathology in a subject. The prevention may also be partial, such that the occurrence of AD pathology in a subject is less than that which would have occurred without the present invention.

The term "synergistic," as used herein, refers to an effect obtained when a first agent and a second agent are administered together (e.g., at the same time or one after the other) that is greater than the additive effect of the first agent and the second agent when administered individually. The synergistic effect allows for lower doses of the first agent and/or the second agent to be administered or provides greater efficacy at the same doses. The synergistic effect obtained can be at least 10%, at least 20%, at least 30%, at least 40%, at least 50%, at least 60%, at least 70%, at least 80%, at least 90%, at least 100%, at least 125%, at least 150%, at least 175%, at least 200%, at least 250%, at least 300%, at least 350%, at least 400%, or at least 500% more than the additive effect of the first agent and the second agent when administered individually.

The therapeutic methods of the invention may be carried out on subjects displaying pathology resulting from AD, subjects suspected of displaying pathology resulting from AD, and subjects at risk of displaying pathology resulting from AD. For example, subjects that have a genetic predisposition to AD can be treated prophylactically. Subjects exhibiting AD symptoms may be treated to decrease the symptoms or to slow down or prevent further progression of the symptoms. The physical changes associated with the increasing severity of AD are shown herein to be progressive. Thus, in one embodiment of the invention, subjects exhibiting mild signs of AD pathology (e.g., corresponding to mild cognitive impairment or Braak stages 1-3) may be treated to improve the symptoms and/or prevent further progression of the symptoms.

Cognitive behavior in AD (e.g., mentation, memory) may be measured by any one of several tests (See Gershon et al., Clinical Evaluation of Psychotropic Drugs: Principles and Guidelines, Prien and Robinson (eds.), Raven Press, Ltd., New York, 1994, p. 467). One such test, BCRS, is designed to measure only cognitive functions: concentration, recent memory, past memory, orientation, functioning, and self-care. This test, as well as the Weschler Memory Scale and the Alzheimer's Disease-Associated Scale, may be used to determine improvement following therapeutic treatment. An increase in mentation or a reduction in memory loss is present if there is a statistically significant difference in the direction of normality in the Weschler Memory Scale test. For example, test results of the performance of treated patients are compared to members of the placebo group or between subsequent tests given to the same patient.

The most frequently used instrument to evaluate cognitive impairment is the Mini-Mental State Examination (MMSE) (see Cockrell, J. R., et al., Psychopharmacology 1988; 24:689-692, Crumb, R. M., et al., JAMA 1993; 269:2386-2391). The MMSE includes measures of memory, orientation to place and time, naming, reading, copying (visuospatial organization), writing, and the ability to follow a three-stage command. A score of less than 24 points on the MMSE is generally accepted as signifying cognitive impairment. The Blessed Information Memory Concentration instrument (Blessed, G., et al., Br. J. Psychiatry 1968; 114:797-811) primarily evaluates orientation, memory, and concentration. The Blessed Orientation Memory Concentration instrument (Katzman, R., et al., Am. J. Psychiatry 1983; 140:734-739)

assesses orientation to time, recall of a short phrase, the ability to count backward, and the ability to recite months in reverse order. The Short Test of Mental Status (Kokmen, E., et al., Mayo Clin. Proc., 1987; 62(4):281-289) evaluates orientation, attention, recall, concentration, abstraction, clock drawing, and copying. The Functional Activities Questionnaire (Pfeffer, R. I., et al., J. Gerontol. 1982; 37:323-329) employs responses from a family member or a friend of the subject to evaluate functional activities that may be impaired by dementia.

The insulin agonist and the IGF agonist may be administered in any appropriate manner, e.g., intraventricularly (e.g., with an intraventricular stent), intracranially, intraperitoneally, intravenously, intraarterially, nasally, or orally. In one embodiment, the insulin agonist and the IGF agonist may be capable of crossing the blood brain barrier. The blood brain barrier of subjects suffering from AD is often found in deteriorated condition, and this facilitates the ability of agents administered parenterally to traverse the barrier. In another embodiment, the agents can be conjugated with a targeting molecule, such as transferrin, for which there are receptors on the blood brain barrier. See, e.g., U.S. Pat. No. 4,902,505. In a further embodiment, the agents can be modified to have decreased polarity, or increased hydrophobicity, as more hydrophobic (less polar) agents cross the blood brain barrier more readily. See, e.g., U.S. Pat. No. 5,260,308. In a further embodiment, hydrophobic (non-polar) agents can be selected and used. In yet another embodiment, the agents can be administered in a liposome, particularly a liposome targeted to the blood brain barrier. See, e.g., U.S. Pat. No. 6,372,250. Administration of pharmaceutical agents in liposomes is known.

In one embodiment, cells that express an insulin agonist and/or an IGF agonist (e.g., by recombinant expression) may be administered to the central nervous system. In another embodiment, the cells express both an insulin agonist and an IGF agonist. Any type of cell that can be genetically altered to express an insulin agonist and/or an IGF agonist may be used. In one embodiment, the cells are stem cells, e.g., embryonic, juvenile, or adult stem cells, neural stem cells, progenitor cells, multipotent cells, and the like. Cells to be administered may be heterologous, autologous, or xenogeneic to the recipient.

Embryonic stem cells may be obtained by isolating cells from the inner cell mass of blastocysts and culturing the cells on a feeder cell layer (e.g., fibroblasts) in the presence of a growth factor that inhibits cell differentiation (e.g., leukemia inhibitory factor). See, e.g., U.S. Pat. Nos. 6,200,806, 5,843,780, 5,690,926, and 5,453,357. Alternatively, isolated inner cell mass cells may be cultured on extracellular matrix (e.g., from lysed feeder cell layers) in the presence of culture medium optionally conditioned by feeder cells, as disclosed in U.S. Pat. Nos. 6,800,480 and 6,642,048. Further methods of isolating embryonic stem cells are disclosed in U.S. Pat. No. 5,166,065.

Neural stem cells may be isolated from any area of the CNS known to contain stem cells, such as the forebrain, cerebral cortex, cerebellum, midbrain, hippocampus, brainstem, spinal cord, and ventricular tissue, and specific sub-areas thereof, e.g., basal ganglia, anterior subventricular zone, diencephalon, telencephalon, or ependymal/subependymal zone. Human neural stem cells may be obtained from aborted fetal tissue, juvenile or adult organ donors, neural tissue biopsies, or tissues removed during neurosurgery. Cells obtained from neural tissue can be proliferated in vitro by culturing in suspension or on a substrate, preferably with a defined medium to avoid differentiation of the cells. Proliferation-inducing growth factors may be added to the culture, such as epidermal growth factor, amphiregulin, acidic fibroblast growth factor, basic fibroblast growth factor, transforming growth factor alpha, and combinations thereof. Cells may also be differentiated in vitro, e.g., into neurons, astrocytes, and/or oligodendrocytes, by adding differentiation-inducing growth factors, such as nerve growth factor, platelet derived growth factor, thyrotropin releasing hormone, transforming growth factor beta, or insulin like growth factors. Cells may also be differentiated by culturing on substrates that cause differentiation, e.g., MATRIGEL, collagen, fibronectin, laminin, or poly-L-lysine. Examples of suitable neural stem cells and methods of isolation include those disclosed in U.S. Pat. Nos. 6,812,027, 6,787,353, 6,734,015, 6,497,872, 6,251,669, 5,968,829, 5,851,832, 5,753,505, 5,589,376, and 5,411,883. Examples of non-neural stem cells that can differentiate into neural cells include those disclosed in U.S. Pat. No. 6,749,850 and U.S. Published Application No. 2004/0107453.

Cells may be genetically engineered to express an insulin agonist and/or an IGF agonist using any method known in the art. See, e.g., Ausubel et al., Current Protocols in Molecular Biology, John Wiley & Sons, New York 3rd Edition, (1995); Sambrook et al., Molecular Cloning: A Laboratory Manual, Cold Spring Harbor Laboratory Press, $2^{nd}$ Edition, (1989). Nucleic acids (DNA or RNA) encoding an insulin agonist and/or an IGF agonist may be synthetic or naturally derived or a combination of both and may contain genes, portions of genes, or other useful DNA sequences, e.g., selectable markers or regulatory sequences such as promoters, enhancers, and the like. Promoters may be exogenous promoters, such as cytomegalovirus or simian virus 40, non-specific endogenous promoters such as collagen, or neural cell specific promoters such as tyrosine hydroxylase, phenylethanolamine N-methyltransferase, or choline acetyltransferase. The nucleotide and amino acid sequences for insulin, IGF-I, and IGF-II are readily available. The nucleotide sequence can be modified by methods well known in the art to encode an insulin agonist and/or an IGF agonist such as those listed above. The nucleic acid encoding an insulin agonist and/or an IGF agonist may be incorporated into any suitable vector for delivery into a cell, e.g., plasmids, viruses, artificial chromosomes, homologous recombination sequences, and the like. The nucleic acid may be introduced into the cells by viral vectors (e.g., retrovirus, herpesvirus, adenovirus, adeno-associated virus) or direct transfection (e.g., lipofection, calcium phosphate transfection, electroporation). Examples of methods for preparing nucleic acid constructs and delivering the constructs to stem cells, particularly embryonic stem cells or neural stem cells, are disclosed in U.S. Pat. Nos. 6,713,247, 6,541,255, 6,528,306, 6,514,761, 6,399,384, 6,392,118, 6,312,949, 6,284,539, 6,281,009, 6,054,575, 5,958,767, 5,849,553, 5,750,376, 5,032,407, and 4,959,313.

Cells that express an insulin agonist and/or an IGF agonist may be administered directly to the central nervous system, e.g., directly to the brain, into ventricular cavities, or subdurally. In one embodiment, the cell are transplanted into the region of damage or dysfunction. Methods of administering cells to the central nervous system for the expression of therapeutic proteins or other factors are known in the art. Cells are preferably administered to a particular region, preferably a region where neurodegeneration is occurring or has occurred. Cells may be introduced alone or with suitable biocompatible carriers, matrices, physical barriers, etc. Cells may be administered in a single injection or multiple injections in one or more sites. In one embodiment, about $10^4$ to about $10^8$ cells are administered. Suitable methods for administering cells to the CNS include those disclosed in U.S. Pat. Nos. 6,497,872, 5,871,767, 5,762,926, 5,650,148, and 5,082,670.

Some embodiments of the present invention provide methods for administering a therapeutically effective amount of an insulin agonist and an IGF agonist. In some embodiments, the combination of an insulin agonist and an IGF agonist is expected to have a greater effect as compared to the administration of either agent alone. In other embodiments, the combination of an insulin agonist and an IGF agonist is expected to result in a synergistic effect (i.e., more than additive) as compared to the administration of either one alone.

In some embodiments of the invention, an insulin agonist and an IGF agonist are administered to a subject separately, e.g., as two separate compositions. In other embodiments an insulin agonist and an IGF agonist are administered as a part of a single composition.

In some embodiments of the present invention, an insulin agonist and an IGF agonist are administered to a subject under one or more of the following conditions: at different periodicities, at different durations, at different concentrations, by different administration routes, etc. In some embodiments, an insulin agonist is administered prior to an IGF agonist, e.g., 0.5, 1, 2 3, 4, 5, 10, 12, or 18 hours, 1, 2, 3, 4, 5, or 6 days, or 1, 2, 3, or 4 weeks prior to the administration of an IGF agonist. In some embodiments, an insulin agonist is administered after an IGF agonist, e.g., 0.5, 1, 2, 3, 4, 5, 10, 12, or 18 hours, 1, 2, 3, 4, 5, or 6 days, or 1, 2, 3, or 4 weeks after the administration of an IGF agonist. In some embodiments, an insulin agonist and an IGF agonist are administered concurrently but on different schedules, e.g., an insulin agonist is administered daily while an IGF agonist is administered once a week, once every two weeks, once every three weeks, or once every four weeks. In other embodiments, an insulin agonist is administered once a week while an IGF agonist is administered daily, once a week, once every two weeks, once every three weeks, or once every four weeks.

The administration of an insulin agonist may be continued concurrently with the administration of an IGF agonist. Additionally, the administration of an insulin agonist may be continued beyond the administration of an IGF agonist or vice versa.

In certain embodiments of the invention, the method of administering an insulin agonist in combination with an IGF agonist may be repeated at least once. The method may be repeated as many times as necessary to achieve or maintain a therapeutic response, e.g., from one to about 10 times or more. With each repetition of the method the insulin agonist and the IGF agonist may be the same or different from that used in the previous repetition. Additionally, the time period of administration of the insulin agonist and the IGF agonist and the manner in which they are administered can vary from repetition to repetition.

The agents of the present invention may be linked to a carrier molecule to enhance the cellular uptake of the compounds. Examples of such carrier molecules include carrier peptides such as those described by Fulda et al., *Nature Med.* 8:808 (2002), Arnt et al., *J. Biol. Chem.* 277:44236 (2002), and Yang et al., *Cancer Res.* 63:831 (2003), fusogenic peptides (see, e.g., U.S. Pat. No. 5,965,404), and viruses and parts of viruses such as empty capsids and virus hemagglutinin (see, e.g., U.S. Pat. No. 5,547,932). Other carrier molecules include ligands for cell surface receptor such as asialoglycoprotein (which binds to the asialoglycoprotein receptor; see U.S. Pat. No. 5,166,320) and antibodies to cell surface receptors such as antibodies specific for T-cells, e.g., anti-CD4 antibodies (see U.S. Pat. No. 5,693,509).

Compositions within the scope of this invention include all compositions wherein the agents of the present invention are contained in an amount which is effective to achieve its intended purpose. While individual needs vary, determination of optimal ranges of effective amounts of each component is within the skill of the art. The actual dosage and treatment regimen can be readily determined by the ordinary skilled physician, taking into account the route of administration, age, weight, and health of the subject, as well as the stage of AD, and, of course, any side effects of the agents, efficacy of the agents, and in accordance with customary medical procedures and practices. Typically, the agents may be administered to mammals, e.g. humans, orally at a dose of 0.0025 to 50 mg/kg, or an equivalent amount of the pharmaceutically acceptable salt thereof, per day of the body weight of the mammal being treated for AD. Preferably, about 0.01 to about 10 mg/kg is orally administered to treat, ameliorate, or prevent AD. For intramuscular injection, the dose is generally about one-half of the oral dose. For example, a suitable intramuscular dose would be about 0.0025 to about 25 mg/kg, and most preferably, from about 0.01 to about 5 mg/kg. In certain embodiments, either or both of the insulin agonist and the IGF agonist may be administered at doses lower than those used in the art due to the additive or synergistic effect of the combination.

The unit oral dose may comprise from about 0.01 to about 50 mg, preferably about 0.1 to about 10 mg of each agent. The unit dose may be administered one or more times daily as one or more tablets or capsules each containing from about 0.1 to about 10, conveniently about 0.25 to 50 mg of the agents.

In addition to administering agents as raw chemicals, the agents of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

The pharmaceutical compositions of the invention may be administered to any subject which may experience the beneficial effects of the compounds of the invention. Foremost among such subjects are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

A further aspect of the invention provides methods for screening for an agent that is potentially useful for the treatment, amelioration, or prevention of AD, comprising administering the agent to an animal and determining the level or function of at least one factor in the insulin/IGF signaling pathway in said animal, wherein an increase in the level or function of one or more of said factors relative to the level in a control animal that has not had the agent administered indicates that the agent is potentially useful for the treatment, amelioration, or prevention of AD. The invention further provides methods for testing potential treatments for AD comprising administering the potential treatment to an animal and determining the level or function of at least one factor in the insulin/IGF signaling pathway in said animal, wherein an increase in the level or function of one or more of said factors relative to the level in a control animal that has not had the treatment administered indicates that the treatment is potentially useful for the treatment, amelioration, or prevention of AD.

A further aspect of the invention provides a method for testing an agent for a potential deleterious effect on the onset or progression of AD, comprising administering the agent to an animal and determining the level or function of at least one factor in the insulin/IGF signaling pathway in said animal, wherein a decrease in the level or function of one or more of said factors relative to the level in a control animal that has not had the agent administered indicates that the agent potentially has a deleterious effect on the onset or progression of AD.

The animals used in the screening assay may be any animal, including non-human animals (e.g., mouse, rat, dog, or primate) that do not exhibit the hallmarks of AD. Alternatively, known animal models of AD may be used. Examples of animal models are disclosed in U.S. Pat. Nos. 6,717,031, 6,710,226, and 5,811,633. Finally, individuals with AD may be used.

Methods for determining the level or function of at least one factor in the insulin/IGF signaling pathway in the subject are the same as discussed above for diagnosis of AD. The level or function may be determined in the same subject before and after administration of an agent. In other embodiments, the function or level in a subject that has been administered an agent is compared to one or more subjects that have not been administered the agent.

Agents that may be screened include proteins, polypeptides, peptides, antibodies, nucleic acids, organic molecules, natural products, chemical libraries, and the like.

An additional aspect of the invention provides an experimental animal model of AD produced by intracerebral injection of streptozotocin (STZ). The animal may be a mammal such as a rodent, dog, cat, horse, sheep, cow, pig, non-human primate (e.g., chimpanzee, macaque, lemur, orangutan, gorilla, bonobo). In one embodiment, the animal is a rodent, e.g., a rat or mouse. The animal is preferably injected with STZ at a young age, e.g., less than one week old, e.g., 2, 3, or 4 days old. The STZ may be prepared in any formulation suitable for administration to the brain of an animal, e.g., saline or artificial cerebrospinal fluid. The amount of STZ injected is sufficient to induce AD-like pathology and/or symptoms in the animal. In one embodiment, STZ is injected at a dose of at least about 10 mg/kg body weight (BW), e.g., about 20 to about 80 mg/kg BW, e.g., about 30 to about 60 mg/kg BW, e.g., about 40 mg/kg BW. The STZ may be injected bilaterally, e.g., 1.0 mm posterior and 1.0 mm lateral to the bregma, and 2.5 mm deep to the skull surface of each hemisphere using a microsyringe, e.g., a 30-gauge needle affixed to a Hamilton microliter syringe. The accuracy of the injection procedure may be confirmed by injecting a dye such as methylene blue. Studies on the STZ-injected animals may be performed about 1 week to about 8 weeks after injection of the STZ, e.g., about 1 week to about 3 weeks after injection, e.g., about 2 weeks after injection.

A further aspect of the invention provides methods for screening for an agent that is potentially useful for the treatment, amelioration, or prevention of AD using the STZ-injected animal model of AD. In one embodiment, methods for screening for an agent that inhibits neurodegeneration in AD are provided. In another embodiment, methods for screening for an agent that inhibits cognitive impairment in AD are provided. The invention further provides methods for testing potential treatments for AD comprising administering the potential treatment to a STZ-injected animal model of AD. The methods comprise administering the agent to an animal and determining the level or function of at least one indicator of AD relative to the level in a control animal that has not had the agent administered. Indicators of AD that may be measured include the level or function of one or more factors in the insulin/IGF signaling pathway, histopathological signs of AD such as brain weight, neurodegeneration, neurofibrillary tangles, or plaques, levels of apoptosis-related factors or other indicators of cell death (e.g., p53), changes in the number of cells of different cell types, levels of AD related proteins or nucleic acids such as tau, phospho-tau, ubiquitin, amyloid precursor protein, amyloid, levels of acetylcholine, acetylcholinesterase, or choline acetyltransferase, and cognitive impairment. Cognitive impairment may be tested by any method known in the art (e.g., Morris water maze, memory-related feeding behavior, spatial recognition memory, locomotor activity, emotional reactivity, object recognition). An improvement in the level or function of one or more of said indicators relative to the level in a control animal that has not had the agent or treatment administered indicates that the agent or treatment is potentially useful for the treatment, amelioration, or prevention of AD. The level or function may be determined in the same animal before and after administration of an agent or treatment. In other embodiments, the function or level in an animal that has been administered an agent or treatment is compared to one or more animals that have not been administered the agent or treatment.

The invention additionally provides a method for testing a potential treatment for AD, comprising administering the potential treatment to the animal model of AD produced by intracerebrally injecting a non-human animal with STZ and determining the level or function of at least one indicator of AD relative to the level in a control animal that has not had the potential treatment administered, wherein an improvement in the level or function of at least one indicator of AD relative to the level in a control animal that has not had the potential treatment administered indicates that the treatment is potentially useful for the treatment, amelioration, or prevention of AD.

A further aspect of the invention provides a method for testing an agent for a potential deleterious effect on the onset or progression of AD, comprising administering the agent to the animal model of AD produced by intracerebrally injecting a non-human animal with STZ and determining the level or function of at least one indicator of AD relative to the level in a control animal that has not had the potential treatment administered, wherein a decrease in the level or function of at least one indicator of AD relative to the level in a control animal that has not had the agent administered indicates that the agent potentially has a deleterious effect on the onset or progression of AD.

Agents that may be screened include proteins, polypeptides, peptides, antibodies, nucleic acids, organic molecules, natural products, chemical libraries, and the like.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

General Methods

Source of Tissue

Postmortem brains were obtained from the Massachusetts General Hospital Alzheimer Disease Research Center brain bank, the Brown University Brain Bank, and the Kathleen Price Bryan Brain Bank at Duke University Medical Center. The diagnoses of AD (Braak and Braak Stages 5-6) and normal aging (Braak and Braak Stages 0-1) were confirmed by review of the clinical histories and postmortem histopathological sections of brain, including the Bielschowsky stained, and phospho-Tau, ubiquitin, and amyloid-β immunostained sections of pre-frontal cortex, temporal cortex, amygdala, and hippocampus. (Braak et al., *Neurobiol. Aging* 18:S85 (1997); Nagy et al., *Dement. Geriatr. Cogn. Disord.* 9:140 (1998)). Snap frozen tissues (~100 mg each) from the hippocampus, hypothalamus, and frontal lobe (Brodmann Area 11) were used to extract RNA and protein. Adjacent formalin fixed paraffin-embedded tissue blocks were used for immunohistochemical staining. A total of 28 AD and 26 control cases were included in this study. Postmortem intervals were all less than 14 hours. Cases were rejected if RNA degradation was detected by real time quantitative RT-PCR.

Real Time Quantitative RT-PCR

Total RNA was isolated from brain tissue using TRIzol reagent (Invitrogen, Carlsbad, Calif.) according to the manufacturer's protocol. RNA concentrations were determined from the absorbances measured at 260 nm and 280 nm. RNA (2 μg) was reverse transcribed using the AMV First Strand cDNA synthesis kit (Roche Diagnostics Corporation, Indianapolis, Ind.) and random oligodeoxynucleotide primers. The mRNA levels of insulin, IGF-I, and IGF-II growth factors, their corresponding receptors, insulin receptor substrate (IRS subtypes 1, 2, and 4, Tau, amyloid precursor protein (APP), glucose transporter 4 (GLUT4), and insulin degrading enzyme (IDE) were measured using real time quantitative RT-PCR amplification. Ribosomal 18S RNA levels measured in parallel reactions were used to calculate relative abundance of each mRNA transcript. (Xu et al., *J. Biol. Chem.* 278:26929 (2003); Yeon et al., *Hepatology* 38:703 (2003)).

PCR amplifications were performed in 25 μL reactions containing the cDNA generated from 2.5 ng of original RNA template, 300 nM each of gene specific forward and reverse primer for human genes (Table 1) or rat genes (Table 2), and 12.5 μL of 2× QuantiTect SYBR Green PCR Mix (Qiagen Inc., Valencia, Calif.). The amplified signals were detected continuously with the BIO-RAD iCycler iQ Multi-Color RealTime PCR Detection System (Bio-Rad, Hercules, Calif.). The amplification protocol used was as follows: initial 15-minute denaturation and enzyme activation at 95° C., 40 cycles of 95° C.×30 sec, 55-60° C.×45 sec, and 72° C.×60 sec. Annealing temperatures were optimized using the temperature gradient program provided with the iCycler software. The mRNA levels were determined using the equations of the regression lines generated with serial 10-fold dilutions of 20 ng of recombinant plasmid DNA containing the target sequences studied. Relative mRNA abundance was determined from the ng ratios of specific mRNA to 18S. (Xu et al., *J. Biol. Chem.* 278:26929 (2003); Yeon et al., *Hepatology* 38:703 (2003)).

TABLE 1

| Primer | Sequence (5'-->3') | Position (mRNA) | Amplicon size (bp) |
|---|---|---|---|
| Insulin | TTC TAC ACA CCC AAG TCC CGT C (SEQ ID NO: 1) | 189 | 134 |
|  | ATC CAC AAT GCC ACG CTT CTG C (SEQ ID NO: 2) | 322 |  |
| Insulin Receptor | GGT AGA AAC CAT TAC TGG CTT CCT C (SEQ ID NO: 3) | 1037 | 125 |
|  | CGT AGA GAG TGT AGT TCC CAT CCA C (SEQ ID NO: 4) | 1161 |  |
| IGF-I | CAC TTC TTT CTA CAC AAC TCG GGC (SEQ ID NO: 5) | 1032 | 147 |
|  | CGA CTT GCT GCT GCT TTT GAG (SEQ ID NO: 6) | 1178 |  |
| IGF-I Receptor | AGG GCG TAG TTG TAG AAG AGT TTC C (SEQ ID NO: 7) | 395 | 101 |
|  | TAC TTG CTG CTG TTC CGA GTG G (SEQ ID NO: 8) | 295 |  |
| IGF-II | CTG ATT GCT CTA CCC ACC CAA G (SEQ ID NO: 9) | 996 | 76 |
|  | TTG CTC ACT TCC GAT TGC TGG C (SEQ ID NO: 10) | 1071 |  |
| IGF-II Receptor | CAC GAC TTG AAG ACA CGC ACT TAT C (SEQ ID NO: 11) | 403 | 132 |
|  | GCT GCT CTG GAC TCT GTG ATT TG (SEQ ID NO: 12) | 534 |  |
| IRS-1 | TGC TGG GGG TTT GGA GAA TG (SEQ ID NO: 13) | 3559 | 68 |
|  | GGC ACT GTT TGA AGT CCT TGA CC (SEQ ID NO: 14) | 3626 |  |
| IRS-2 | AAA ATT GGC GGA GCA AGG C (SEQ ID NO: 15) | 753 | 64 |
|  | ATG TTC AGG CAG CAG TCG AGA G (SEQ ID NO: 16) | 816 |  |
| IRS-4 | CCG ACA CCT CAT TGC TCT TTT C (SEQ ID NO: 17) | 570 | 74 |

TABLE 1-continued

| Primer | Sequence (5'-->3') | Position (mRNA) | Amplicon size (bp) |
|---|---|---|---|
|  | TTT CCT GCT CCG ACT CGT TCT C (SEQ ID NO: 18) | 643 |  |
| Tau | AGA AGC AGG CAT TGG AGA CAC C (SEQ ID NO: 19) | 543 | 81 |
|  | AAG CAG CCA CTT TGG GTT CC (SEQ ID NO: 20) | 251 |  |
| APP | CAA TCC AGG CAC AGA AAG AGT CC (SEQ ID NO: 21) | 478 | 96 |
|  | TTC CAT AAC CAA GAG AGG CTG C (SEQ ID NO: 22) | 573 |  |
| GLUT4 | GTA TCA TCT CTC AGT GGC TTG GAA G (SEQ ID NO: 23) | 394 | 111 |
|  | TTT CAT AGG AGG CAG CAG CG (SEQ ID NO: 24) | 504 |  |
| IDE | TGA TGA ATG ATG CCT GGA GAC TC (SEQ ID NO: 25) | 635 | 130 |
|  | TCA ATC CCT TCT TGG TTT GGT C (SEQ ID NO: 26) | 764 |  |
| 18S | GGA CAC GGA CAG GAT TGA CA (SEQ ID NO: 27) | 1278 | 50 |
|  | ACC CAC GGA ATC GAG AAA GA (SEQ ID NO: 28) | 1327 |  |
| 28S | GGT AAA CGG CGG GAG TAA CTA TG (SEQ ID NO: 29) | 3712 | 107 |
|  | TAG GTA GGG ACA GTG GGA ATC TCG (SEQ ID NO: 30) | 3818 |  |

TABLE 2

| Primer | Sequence (5'-->3') | Position (mRNA) | Amplicon size (bp) |
|---|---|---|---|
| Insulin | TTC TAC ACA CCC AAG TCC CGT C (SEQ ID NO: 31) | 189 | 134 |
|  | ATC CAC AAT GCC ACG CTT CTG C (SEQ ID NO: 32) | 322 |  |
| Insulin Receptor | GGT AGA AAC CAT TAC TGG CTT CCT C (SEQ ID NO: 33) | 1037 | 125 |
|  | CGT AGA GAG TGT AGT TCC CAT CCA C (SEQ ID NO: 34) | 1161 |  |

TABLE 2-continued

| Primer | Sequence (5'-->3') | Position (mRNA) | Amplicon size (bp) |
|---|---|---|---|
| IGF-I | CAC TTC TTT CTA CAC AAC TCG GGC (SEQ ID NO: 35) | 1032 | 147 |
|  | CGA CTT GCT GCT GCT TTT GAG (SEQ ID NO: 36) | 1178 |  |
| IGF-I Receptor | AGG GCG TAG TTG TAG AAG AGT TTC C (SEQ ID NO: 37) | 395 | 101 |
|  | TAC TTG CTG CTG TTC CGA GTG G (SEQ ID NO: 38) | 295 |  |
| IGF-II | CTG ATT GCT CTA CCC ACC CAA G (SEQ ID NO: 39) | 996 | 76 |
|  | TTG CTC ACT TCC GAT TGC TGG C (SEQ ID NO: 40) | 1071 |  |
| IGF-II Receptor | CAC GAC TTG AAG ACA CGC ACT TAT C (SEQ ID NO: 41) | 403 | 132 |
|  | GCT GCT CTG GAC TCT GTG ATT TG (SEQ ID NO: 42) | 534 |  |

In preliminary studies, SYBR Green-labeled PCR products were evaluated by agarose gel electrophoresis, and the authenticity of each amplicon was verified by nucleic acid sequencing. Serial dilutions of known quantities of recombinant plasmid DNA containing the specific target sequences were used as standards in the PCR reactions, and the regression lines generated from the $C_t$ values of the standards were used to calculate mRNA abundance. Results were normalized with respect to 18S RNA because the levels were highly abundant and essentially invariant, whereas housekeeping genes were modulated with disease state. Between-group statistical comparisons were made using the calculated mRNA/18S ratios.

Western Blot Analysis

Western blot analysis was used to assess the levels of Akt, phospho-Akt, GSK-3β, phospho-GSK-3β, Tau, and β-actin. Fresh frozen tissue (~100 mg) was homogenized in 5 volumes of radio-immunoprecipitation assay RIPA) buffer (50 mM Tris-HCl, pH 7.5, 1% NP-40, 0.25% Na-deoxycholate, 150 mM NaCl, 1 mM EDTA, 2 mM EGTA) containing protease (1 mM PMSF, 0.1 mM TPCK, 1 µg/ml aprotinin, 1 µg/ml pepstatin A, 0.5 µg/ml leupeptin, 1 mM NaF, 1 mM $Na_4P_2O_7$) and phosphatase (2 mM $Na_3VO_4$) inhibitors. Protein concentration was determined using the bicinchoninic acid (BCA) assay (Pierce, Rockford, Ill.). Samples containing 100 µg of protein were fractionated by sodium dodecyl sulfate, polyacrylamide gel electrophoresis (SDS-PAGE). (Ausubel et al., *Current Protocols in Molecular Biology* (2000)). Proteins were transferred to Immobilon-P (Millipore Corporation, Bedford, Mass.) PVDF membranes and non-specific binding sites were adsorbed with SuperBlock-TBS (Pierce, Rockford, Ill.). Membranes were incubated over night at 4° C. with primary antibody (0.5-1 µg/ml) diluted in Tris-buffered saline (TBS; 50 mM Tris, 150 mM NaCl, pH 7.4) containing 1% bovine serum albumin and 0.05% Tween-20 (TBST-BSA). Immunoreactivity was detected using horseradish peroxidase (HRP) conjugated IgG (Pierce, Rockford, Ill.), Western Lightning chemiluminescence reagents (Perkin Elmer Life Sciences Inc., Boston, Mass.), and film autoradiography. All incubations were performed using gentle platform agitation. Immunoreactivity was quantified using the Kodak Digital Science Imaging Station (NEN Life Sciences, Boston, Mass.).

Immunoprecipitation

Immunoprecipitation studies were used to examine interactions between the p85 subunit of PI3 kinase and insulin receptor substrate (IRS) types 1 and 2. The tissue samples were homogenized in RIPA buffer containing protease and phosphatase inhibitors (1 µg/ml aprotinin, 0.5 µg/ml leupeptin, 1 mM PMSF, 0.1 mM TPCK, 1 µg/ml pepstatin A, 2 mM sodium vanadate), and diluted in HEPES lysis buffer containing 10 mM HEPES, 100 mM NaCl, 1 mM EDTA, and 0.1% Triton X-100 just prior to use in immunoprecipitation assays. After pre-clearing, samples containing 250 µg of protein were incubated with primary antibody for 2 hours at 4° C. with constant rotation. Immune complexes were captured on UltraLink immobilized Protein A/G (Pierce, Rockford, Ill.) by a two-hour incubation at 4° C. with gentle rotation. The immunoprecipitates were washed 3 times in 0.5 ml of Hepes lysis buffer, and then used in kinase assays. (Ausubel et al., *Current Protocols in Molecular Biology* (2000)).

Immunohistochemical Staining

Buffered formalin fixed, paraffin embedded sections (8 µM thick) of hypothalamus and temporal or frontal neocortex were immunostained with antibodies to insulin receptor, IGF-I receptor, insulin, and IGF-I using the avidin biotin horseradish peroxidase method and either NovaRed or diaminobenzidine (Vector Laboratories, Burlingame, Calif.) as the chromogen. (de la Monte et al., *Lab. Invest.* 80:1323 (2000)). The sections were counterstained with hematoxylin and examined by light microscopy.

Source of Reagents

Antibodies to insulin receptor, IGF-I receptor, IRS-1, IRS-2, and the p85 subunit of PI3 kinase were obtained from Cell Signaling (Beverly, Mass.). Antibodies to GSK-3β, Akt, and phospho-specific antibodies to GSK-3β and Akt were purchased from Upstate Biotechnology (Lake Placid, N.Y.). Protein A/G agarose was obtained from Pierce Chemical Company (Rockford, Ill.). Reagents for immunohistochemical staining were purchased from Vector Laboratories, (Burlingame, Calif.). All other fine chemicals were purchased from either CalBiochem (Carlsbad, Calif.) or Sigma-Aldrich (St. Louis, Mo.).

Statistical Analysis

Data depicted in the graphs represent the means±S.E.M.s for each group. Inter-group comparisons were made using Student t-tests or repeated measures analysis of variance (ANOVA) with the Tukey-Kramer post-hoc test for significance. Statistical analyses were performed using the Number Cruncher Statistical System (Dr. Jerry L. Hintze, Kaysville, Utah). The computer software generated P-values are indicated in the graphs. P-values<0.05 were regarded as statistically significant.

Example 2

Reduced Growth Factor Receptor Expression in AD

Real time quantitative RT-PCR studies demonstrated mRNA transcripts corresponding to insulin, IGF-I, and IGF- II receptors in the cerebral cortex, hippocampus, and hypothalamus of both control and AD brains (FIG. 1). Insulin, IGF-I, and IGF-II receptors were expressed at 400- to 2000-fold higher levels in the hippocampus and hypothalamus than in the frontal cortex. IGF-I and IGF-II receptors were overall more abundantly expressed than insulin receptors, and in control brains, IGF-I receptors were more abundantly expressed than IGF-II receptors. In AD, IGF-I and IGF-II mRNA transcripts were expressed at similar levels, except in the frontal cortex where IGF-I receptor was expressed at higher levels than IGF-II receptors, as was the case for the control group. The levels of insulin and IGF-I receptor expression were significantly higher in control frontal cortex, hippocampus, and hypothalamus, than in corresponding regions of AD brains, whereas the mean levels of IGF-II receptor mRNA were similar in the control and AD samples (FIG. 1). After re-plotting the insulin receptor data to highlight the regional and inter-group differences, it became evident that the mean levels of insulin and IGF-I receptor mRNA transcripts in the hippocampus and hypothalamus were 8- to 10-fold lower in AD than corresponding regions of control brains, whereas in the frontal cortex, the inter-group differences were much smaller since the insulin and IGF-I receptor mRNA transcripts were reduced by approximately 40% in AD (FIG. 1D).

The reduced expression levels of the insulin and IGF-I receptors could not be explained solely on the basis of neuronal loss because many histologically intact neurons in AD brains exhibited low levels or absent immunoreactivity. Moreover, the hypothalamus, which does not exhibit extensive cell loss or neurodegeneration until late in the course of disease, showed striking reductions in receptor mRNA expression and immunoreactivity in AD. Reduced levels of growth factor receptor expression could impair signaling, and effectively result in insulin/IGF-I resistance in the brain. Here, it is important to emphasize that the abnormalities in AD are not restricted to insulin signaling pathways, since they also clearly involve IGF-I and possibly IGF-II stimulated mechanisms. A second conclusion is that abnormalities in growth factor activated cascades exist at the receptor level.

Example 3

Reduced Local Growth Factor Expression in AD Brains

Real time quantitative RT-PCR studies detected insulin, IGF-I, and IGF-II mRNA expression in aged control and AD brains. The highest levels of growth factor expression were observed in the hippocampus and hypothalamus where the mean levels were 30-fold to 50-fold higher than in the frontal cortex (FIG. 2). Insulin gene expression was highest in the hippocampus, but was undetectable in the frontal cortex. IGF-I mRNA expression was 10- to 30-fold higher in the hippocampus than the hypothalamus or frontal cortex. IGF-II mRNA was expressed at similarly high levels in the hippocampus and hypothalamus, and both were approximately 40-fold higher than in the frontal cortex. Re-analysis of the data by region demonstrated relatively high levels of insulin and IGF-II in the hippocampus, and IGF-II>IGF-I>>insulin expression in the hypothalamus and frontal cortex (FIG. 2).

In AD, insulin gene expression in the hippocampus and hypothalamus was significantly reduced relative to control (insulin gene expression was not detected in the frontal cortex). The mean levels of insulin mRNA transcripts in the hippocampus and hypothalamus were 4-fold to 5-fold lower than in controls. The mean levels of IGF-I gene expression in the AD hypothalamus and frontal cortex were significantly (4- to 5-fold) lower than in corresponding regions of control brains (FIG. 2). Finally, IGF-II mRNA levels were also significantly reduced in AD frontal cortex, hippocampus, and hypothalamus. Again, the biggest inter-group differences (4 to 5-fold) were observed in the hippocampus and hypothalamus, whereas in the frontal cortex, IGF-II expression was only modestly reduced (~35%) in AD.

Therefore, in AD, the problem is not simply insulin/IGF-I resistance since there is also a significant deficiency in local CNS growth factor production. The paucity of CNS growth factor gene expression would certainly be expected to substantially impair growth factor signaling. Moreover, if the CNS were dependent on local growth factor production, reduced supply would produce a state of growth factor withdrawal, which is a well established mechanism of neuronal cell death. In order to maintain the integrity of insulin/IGF-I-dependent CNS functions, either the receptor sensitivity or expression levels must be increased, or a mechanism for increasing CNS uptake of growth factors from peripheral blood must be activated or enhanced. It should be emphasized that: 1) the problem in AD is not just insulin resistance since related growth factors are also affected; and 2) the insulin, IGF-I, and possibly IGF-II resistances stem from problems related to impaired CNS growth factor production, and either down-regulation of the corresponding receptor genes or progressive loss of neurons that bear those receptors.

Example 4

Reduced Neuronal Insulin, IGF-I, Insulin Receptor and IGF-I Receptor Immunoreactivity in AD Brains The cellular distributions of insulin, IGF-I, and the corresponding receptors were examined by immunohistochemical staining of formalin fixed, paraffin embedded sections of frontal cortex, hippocampus, and hypothalamus from 14 AD brains and 10 controls. Immunoreactivity corresponding to insulin or IGF-I polypeptides was observed in neurons and neuritic processes, whereas the insulin and IGF-I receptors were found to be expressed in neurons, neuropil neurites, glia, and smooth muscle cells of both parenchymal and leptomeningeal vessels. Corresponding with the real time quantitative RT-PCR results, insulin-, IGF-I-, insulin receptor-, and IGF-I receptor-positive neurons were less abundant in the AD compared with the normal aged control hippocampal samples (FIG. 3). Reduced neuronal labeling in the AD cases was attributable to loss of neurons as well as reduced neuronal expression of the growth factors and corresponding growth factor receptors. The latter was evident from the negative immunostaining reactions observed in histologically intact appearing neurons (FIG. 3). In contrast, the degrees of growth factor receptor labeling in vessels were similar in the AD and control samples.

The immunohistochemical staining studies demonstrated expression of both the growth factors and growth factor receptors in CNS neurons. Although growth factor immunoreactivity was mainly identified in neurons, other cell types including glia may also express these same growth factors as well as the corresponding receptors. One potential explanation for the shift in growth factor and receptor expression profiles observed in AD relative to control brains is that glial cell activation combined with cell loss may play a role. Insulin and IGF-I receptor expression was detected in the vasculature, as well as in choroid plexus epithelial cells, neurons, and glia. Insulin/IGF-I receptor expression in the vasculature has been previously reported, and suggests that CNS vessels may be responsive to changes in circulating growth factor levels. There were no obvious differences between the AD and control groups with respect to growth factor receptor expression in vessels, suggesting that alterations in peripheral blood levels of insulin or IGF-I may not adversely affect CNS function to a greater extent in AD than in normal aging. Instead, the local endogenous CNS production may be most relevant with regard to growth factor regulation of CNS neuronal functions.

Example 5

Figure 4A:
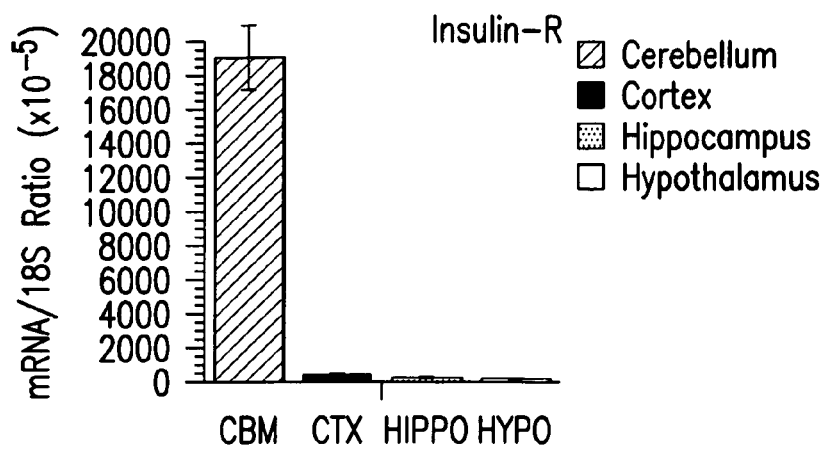
Figure 4B:
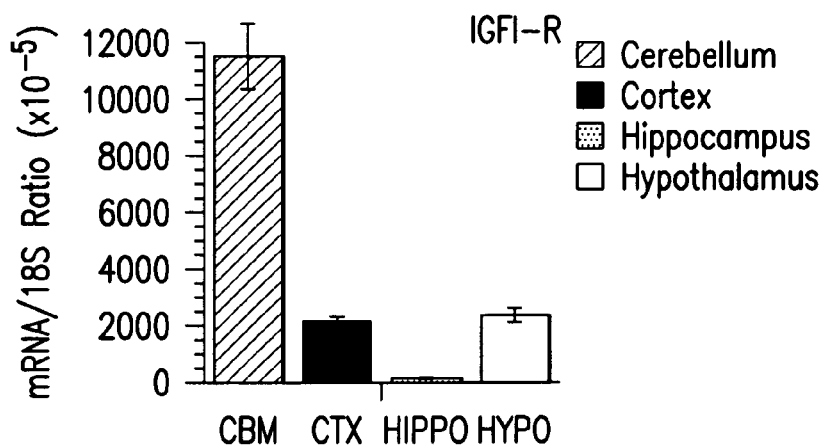
Figure 4C:
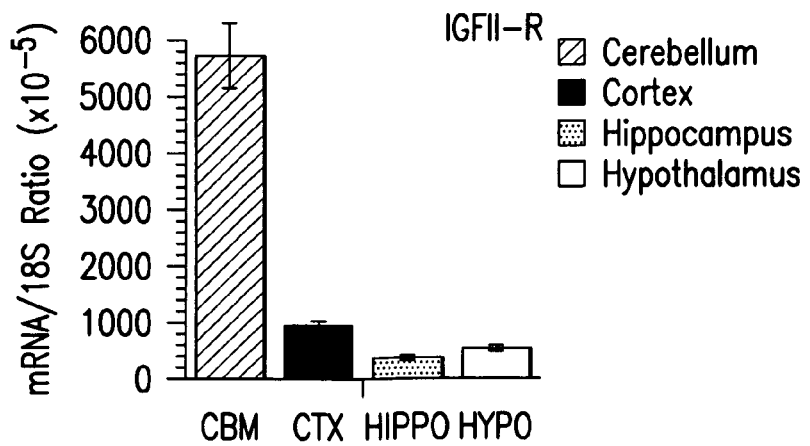
Figure 4D:
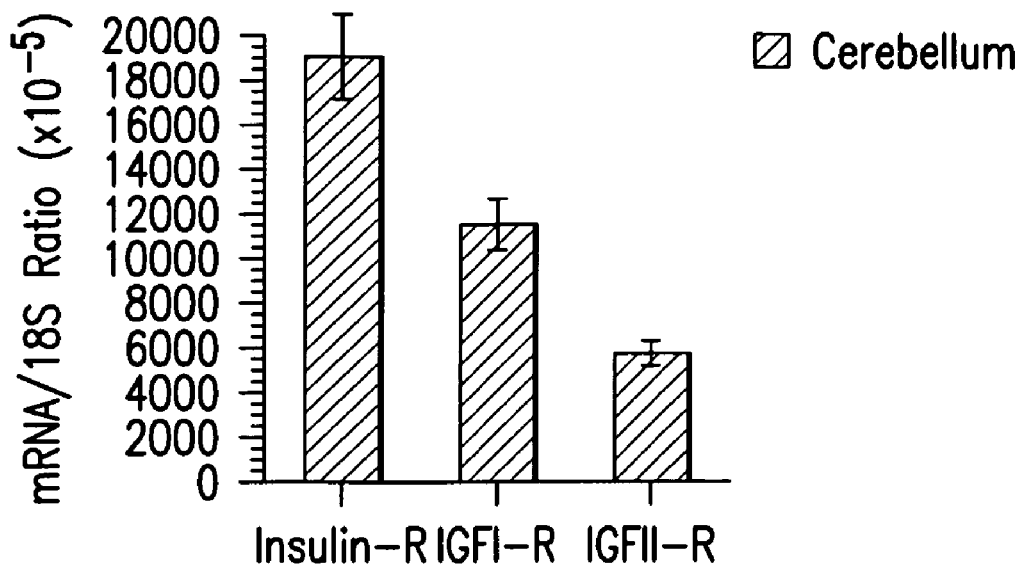
Figure 4E:
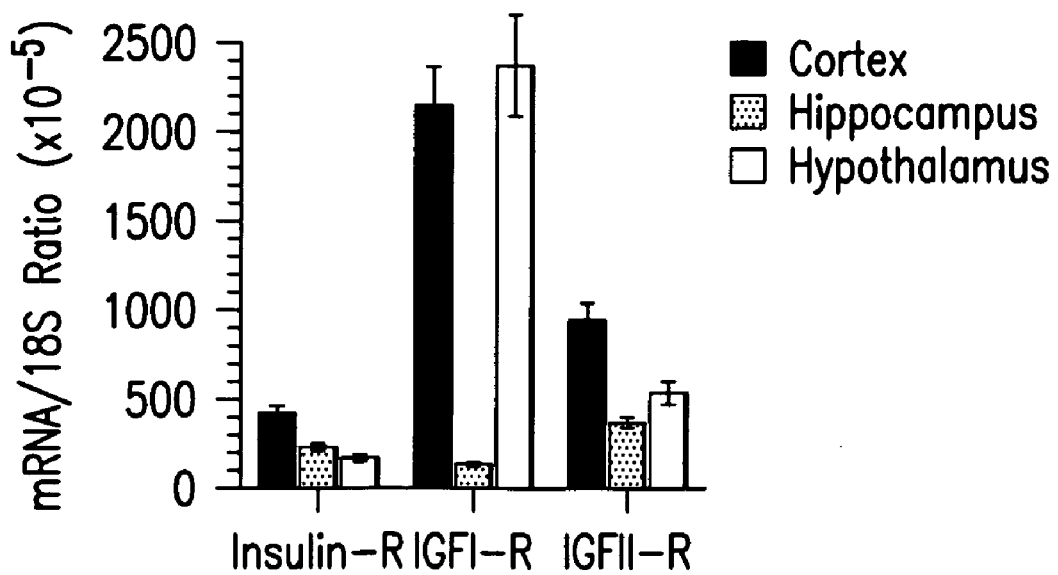

Detection of Insulin, IGF-I, IGF-II, and the Corresponding Receptor mRNA Transcripts in Primary Neuronal Cultures To confirm the findings of neuronal growth factor and growth factor receptor expression in the CNS, investigations were extended by measuring the levels of the same mRNA transcripts in cultured CNS neurons by real time quantitative RT-PCR using rat gene specific primers (Table 2). Primary neuronal cultures were generated from fetal rat cerebral cortex, hypothalamus, and hippocampus, and postnatal rat cerebellar granule neurons, as previously described. (de la Monte et al., *Cell. Mol. Life Sci.* 58:1950 (2001); de la Monte et al., *Cell. Mol. Life Sci.* 59:882 (2002); Xu et al., *J. Biol. Chem.* 278:26929 (2003); Chen et al., *J Alzheimers Dis.* 5:209 (2003); Nillni et al., *Endocrinology* 137:5651 (1996)). At the time of harvesting, the neurons were post-mitotic and had abundant processes characteristic of differentiated cells. The real time quantitative RT-PCR studies demonstrated expression of insulin, IGF-I, IGF-II, insulin receptor, IGF-I receptor, and IGF-II receptor mRNA transcripts in cultured neurons (FIG. 4). Insulin, IGF-I, and IGF-II receptors were expressed at strikingly higher levels in cerebellar granule neurons compared with neurons of cerebral origin (FIGS. 4A-4C). Among the cerebral structures, insulin and IGF-I receptors were expressed at higher levels in cortical neurons followed by hypothalamic neurons, while hippocampal neurons had the lowest expression levels of insulin and IGF-I receptors. The cortical, hippocampal, and hypothalamic cultures had similarly low levels of IGF-II receptor expression, although cortical neurons had the highest levels. Further analysis of the data to highlight the regional differences in growth factor receptor expression demonstrated that in the cerebellum, insulin receptor expression was most abundant, followed by IGF-I receptor, and then IGF-II receptor, whereas in cortical and hypothalamic neurons, the order of receptor abundance was IGF-I>IGF-II>Insulin (FIGS. 4D and 4E). In hippocampal neurons, IGF-II receptor mRNA was most abundant, followed by insulin receptor, and then IGF-I receptor.

Figure 5A:
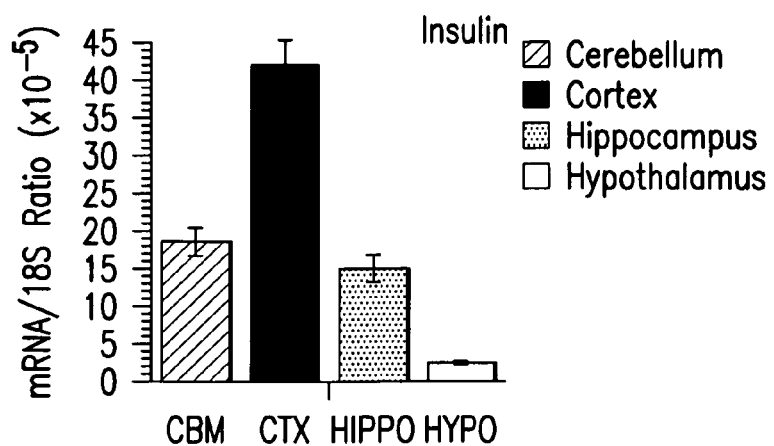
Figure 5B:
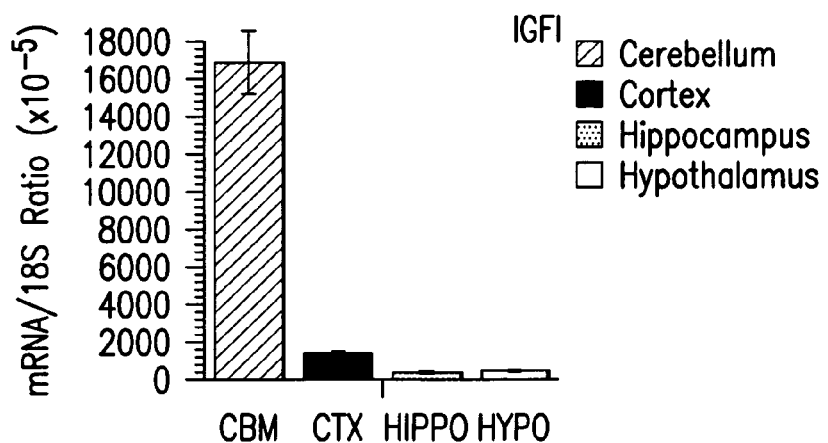
Figure 5C:
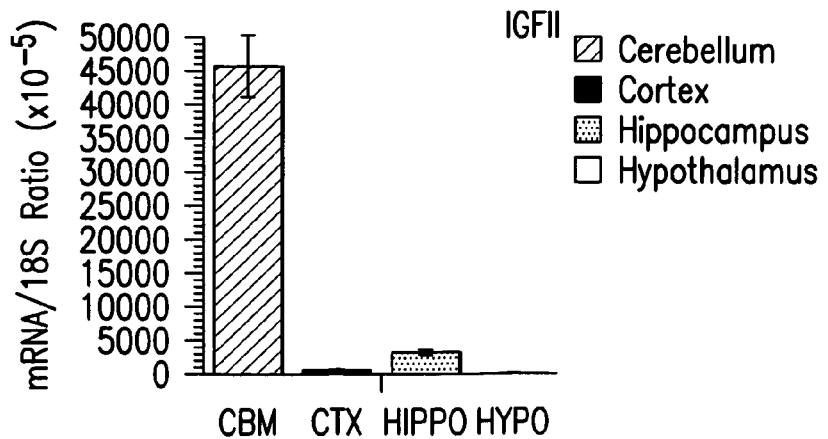
Figure 5D:
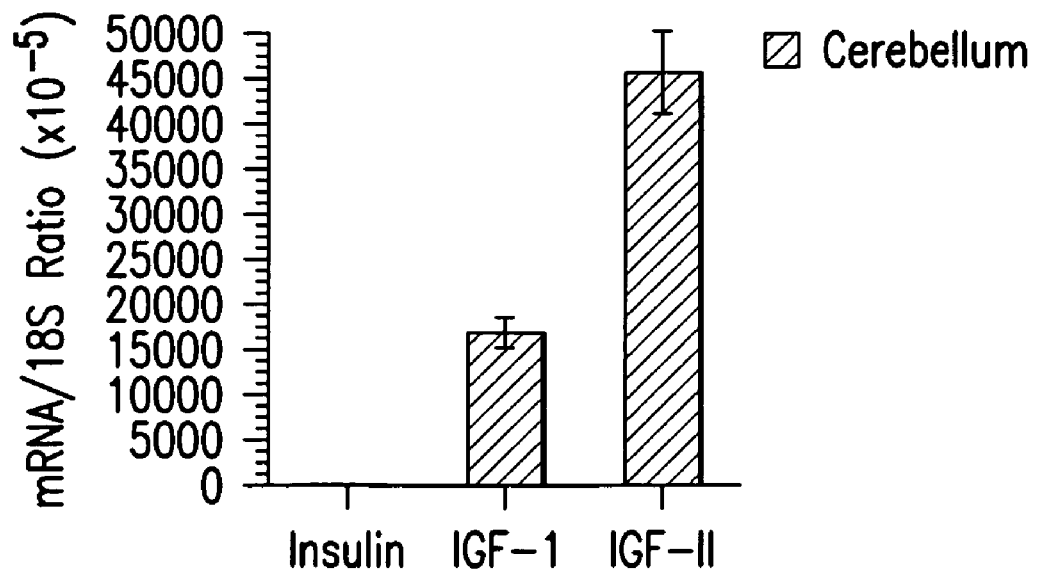
Figure 5E:
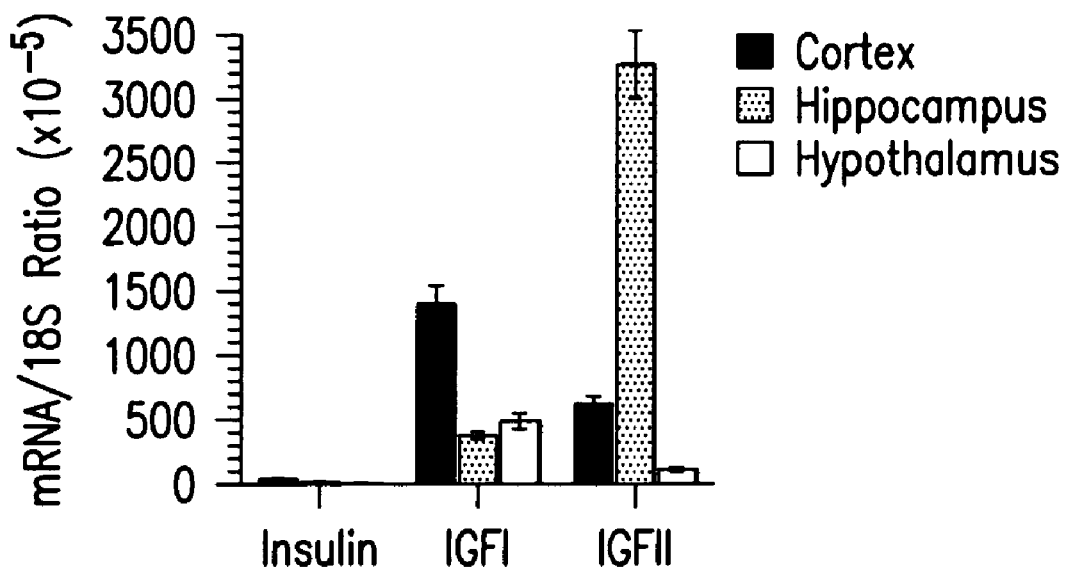

Insulin, IGF-I, and IGF-II genes were expressed at significantly higher levels in cerebellar neurons compared with neurons isolated from the hippocampus, hypothalamus, or cerebral cortex. Among the cerebral structures studied, insulin gene expression was highest in hippocampal neurons followed by hypothalamic neurons (FIG. 5A). Cortical neurons had very low but nonetheless detectable insulin gene expression. In contrast, IGF-I mRNA transcripts were expressed at relatively low levels in hippocampal and hypothalamic neurons, and high levels in cultured cortical neurons (FIG. 5B). IGF-II gene expression was highest in hippocampal neurons, followed by cortical, and hypothalamic neurons (FIG. 5C). Further analysis of the regional differences in growth factor gene expression revealed that IGF-II was the most abundantly expressed growth factor in both cerebellar and hippocampal neurons, followed by IGF-I, and insulin. In cortical and hypothalamic neurons, the order of growth factor mRNA abundance was: IGF-I>IGF-II>insulin. (FIGS. 5D and 5E).

Example 6

Analysis of Key Signaling Molecules Downstream of the Insulin/IGF-I Receptors

Insulin and IGF-I mediate their effects by activating complex intracellular signaling pathways initiated by ligand binding to cell surface receptors and attendant activation of intrinsic receptor tyrosine kinases. (Ullrich et al., *Nature* 313:756 (1985); Myers et al., *Trends Biochem. Sci.* 19:289 (1994); O'Hare et al., *Int J Biochem* 22:315 (1990)). Insulin/IGF-I receptor tyrosine kinases phosphorylate IRS molecules. (Myers et al., *Trends Biochem. Sci.* 19:289 (1994); Sun et al., *Nature* 352:73 (1991); White et al., *Nature* 318:183) 1985); Sun et al., *Mol. Cell. Biol.* 13:7418 (1993)). Tyrosyl phosphorylated IRS-1 (PY-IRS-1) transmits intracellular signals that mediate growth, metabolic functions, and survival by interacting with downstream src-homology 2 (SH2)-containing molecules through specific motifs located in the C-terminal region of IRS-1, with attendant activation of Erk MAPK and PI3 kinase/Akt, and inhibition of GSK-3β. (Giovannone et al., *Diabetes Metab. Res. Rev.* 16:434 (2000)). In this regard, binding of PY-IRS-1 to p85 stimulates glucose transport, and inhibits apoptosis by activating Akt/Protein kinase B or inhibiting GSK-3β. (Kulie et al., *Mol. Cell. Biol.* 17:595 (1997); Dudek et al., *Science* 275:661 (1997); Burgering et al., *Nature* 376:599 (1995); Delcommenne et al., *Proc. Natl. Acad. Sci. USA* 95:11211 (1998); Kido et al., *J. Clin. Endocrinol. Metab.* 86:972 (2001)). Akt kinase inhibits apoptosis by phosphorylating GSK-3β and BAD, rendering them inactive. (Delcommenne et al., *Proc. Natl. Acad. Sci. USA* 95:11211 (1998); Datta et al., *Cell* 91:231 (1997); Kennedy et al., *Mol. Cell. Biol.* 19:5800 (1999); Brunet et al., *Cell* 96:857 (1999)). Low levels of Akt kinase, and high levels of GSK-3β activity or activated BAD are associated with increased apoptosis and mitochondrial dysfunction in neuronal cells. BAD disrupts mitochondrial membrane permeability and promotes cytochrome c release, which activates caspases. (Kennedy et al., *Mol. Cell. Biol.* 19:5800 (1999); Brunet et al., *Cell* 96:857 (1999)). Perturbations in mitochondrial membrane permeability may increase cellular free radicals that cause mitochondrial DNA damage, impair mitochondrial function, and activate pro-apoptosis cascades. Jaeschke et al., *Toxicol. Sci.* 65:166 (2002); Pastorino et al., *J. Biol. Chem.* 273:7770 (1998)).

To examine the integrity of signaling pathways that are activated by insulin/IGF-I, IRS-1, IRS-2, and IRS-4 gene expression was measured. IRS-3 was not examined because that isoform is only expressed in rodent adipose tissue. Since one of the key signaling pathways activated by insulin/IGF-I signaling downstream through IRS is PI3 kinase-Akt, which is mediated by binding of the p85 subunit of PI3 kinase to a specific motif located within the carboxyl terminal region of IRS proteins, we investigated the integrity of this pathway in AD. Giovannone et al., *Diabetes Metab. Res. Rev.* 16:434 (2000)). This was accomplished by examining the levels of tyrosine phosphorylated (PY) insulin and IGF-II receptors, insulin and IGF-I protein expression, and the degrees of interaction between the p85 subunit of PI3 kinase and PY-IRS by immunoprecipitation/Western blot analysis (FIG. 6). The levels of Akt, phospho-Akt, GSK-3β, phospho-GSK-3β, and β-actin (control) were assessed by direct Western blot analysis with digital image densitometry (FIG. 7). In addition, tau and amyloid precursor protein mRNA levels were measured (FIG. 8) because both molecules are abnormally expressed or processed in AD, and previous studies demonstrated that tau, but not APP expression is regulated by insulin/IGF-I stimulation. (de la Monte et al., *Cell. Mol. Life Sci.* 60:2679 (2003); Hong et al., *J. Biol. Chem.* 272:19547 (1997)). Analyses focused on the hippocampal and hypothalamic regions, given their relatively high levels of growth factor and growth factor receptor expression compared to the frontal cortex.

IRS-1 mRNA transcripts were significantly more abundant than IRS-2 or IRS-4 (P<0.001). IRS-4 was next in abundance, while IRS-2 was expressed at very low levels (FIGS. 6A-6C). In AD, IRS-1 mRNA levels in the frontal cortex, hippocampus and hypothalamus were significantly reduced relative to control, whereas IRS-4 expression was similar in the AD and control samples. Immunoprecipitation/Western blot analyses demonstrated significantly reduced levels of tyrosine phosphorylated insulin and IGF-I receptors, as well as reduced insulin and IGF-I receptor expression (FIGS. 6E-6G). As expected, the reduced levels of tyrosine phosphorylated insulin/IGF-I receptors and receptor protein expression were associated with significantly reduced levels of p85-associated IRS-1 in AD relative to control hippocampal and hypothalamic tissues (FIG. 6D), reflecting impaired signaling downstream through IRS molecules. IRS-2 and IRS-4 interactions with p85 were not pursued because these molecules were difficult to detect by Western blot analysis due to low expression levels.

Figure 7A:
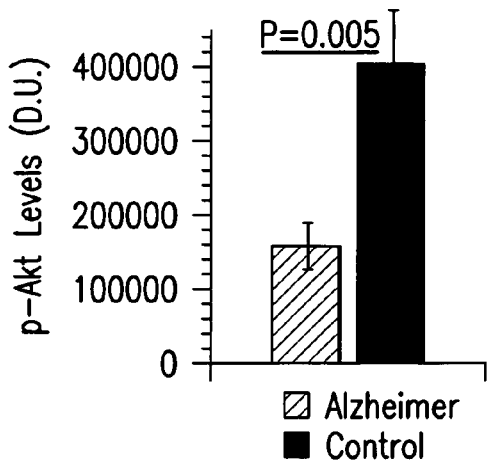
Figure 7B:
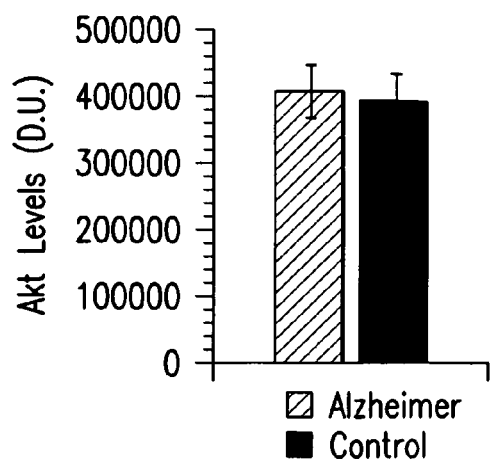
Figure 7C:
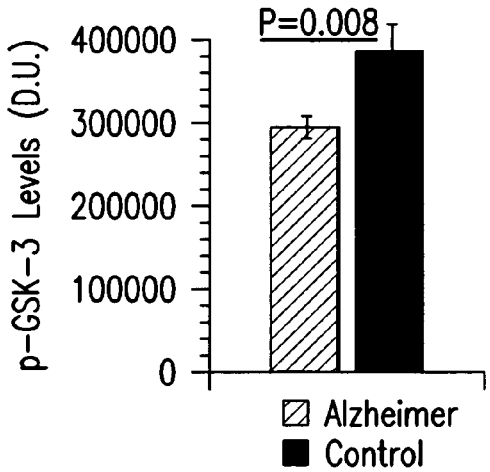
Figure 7E:
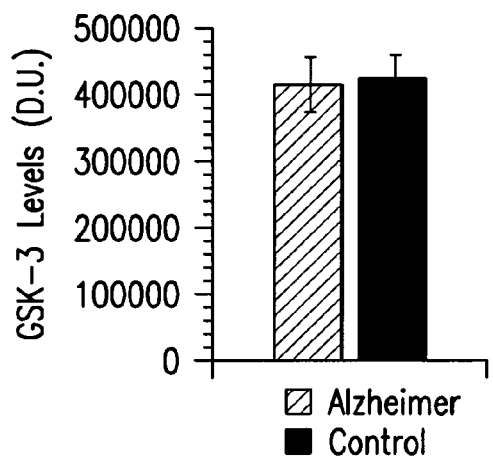
Figure 7D:
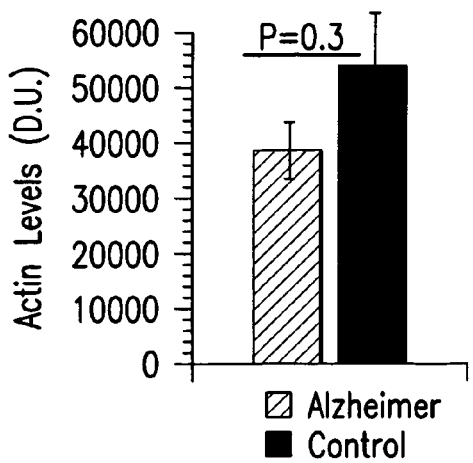
Figure 8A:
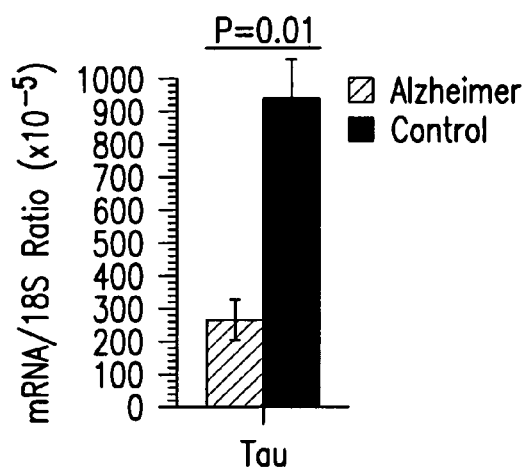
Figure 8C:
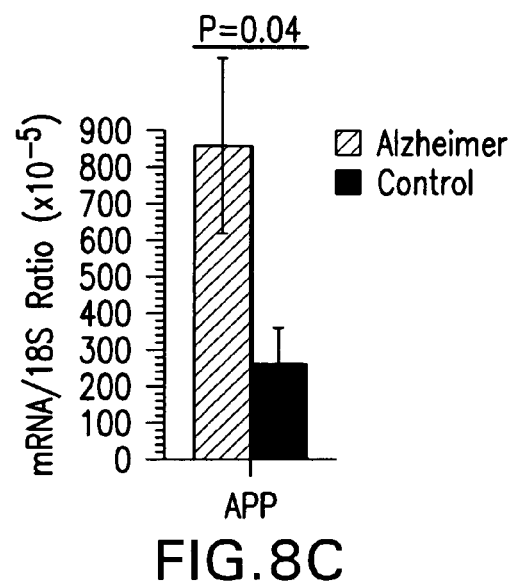
Figure 8B:
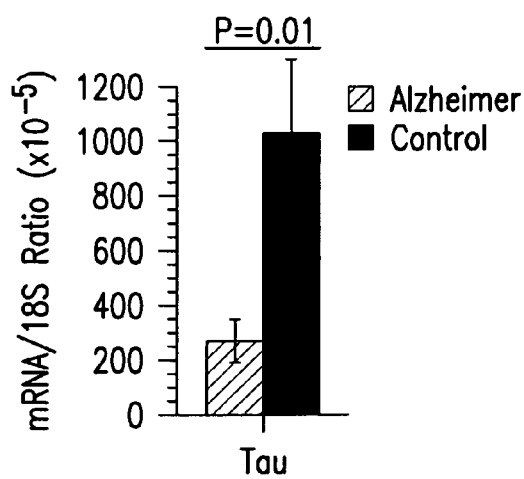
Figure 8D:
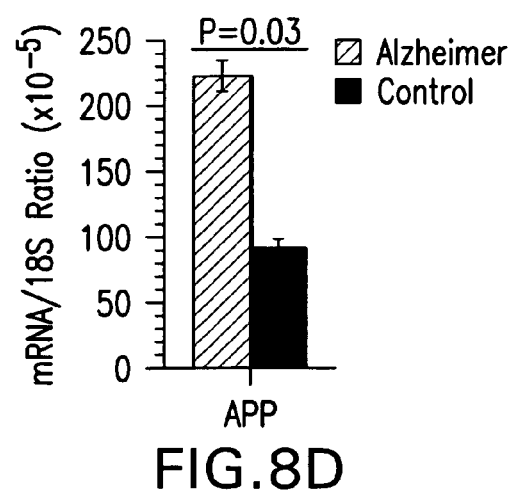
Figure 8E:
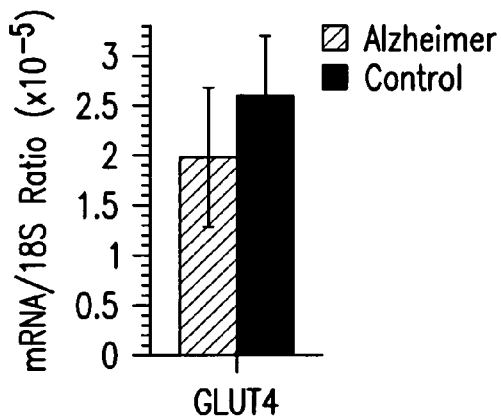
Figure 8G:
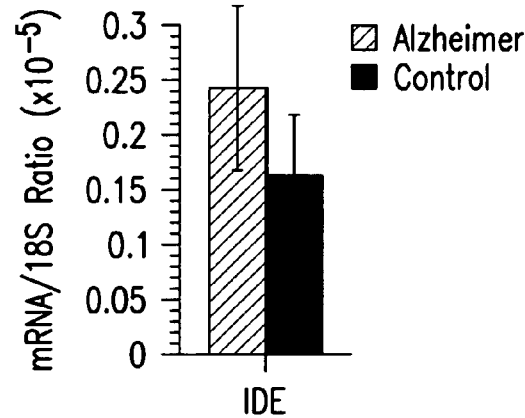
Figure 8F:
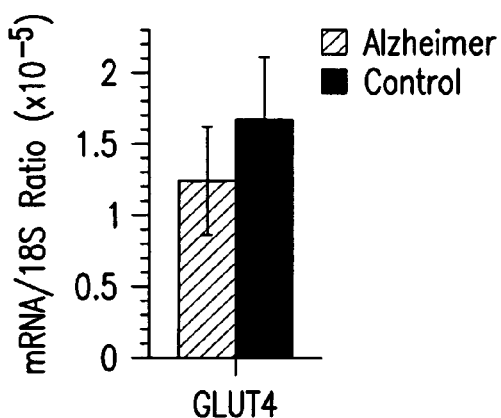
Figure 8H:
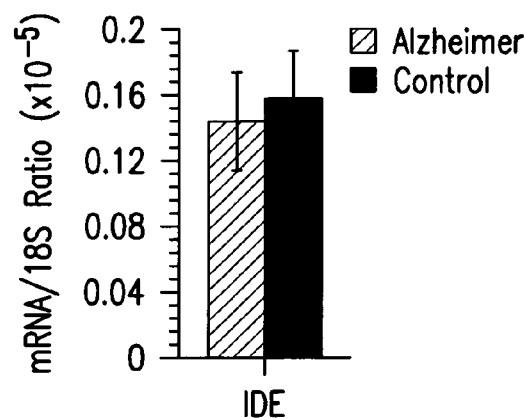

Further investigations of insulin and IGF-I stimulated survival signaling mechanisms were conducted using hippocampal and hypothalamic tissue samples due to their relatively high levels of growth factor and growth factor receptor expression compared with the frontal cortex. Survival signaling downstream of PI3 kinase is associated with increased levels of phospho-Akt and phospho-GSK-3β since phosphorylation leads to activation of Akt kinase and inhibition of GSK-3β activity. Western blot analysis with densitometry demonstrated significantly reduced mean levels of phospho-Akt (FIG. 7A) and phospho-GSK-3β (FIG. 7C) but similar mean levels of total Akt (FIG. 7B) and GSK-3β (FIG. 7D) protein in hippocampal tissue. Similar results were obtained using hippocampal tissue samples. The relatively reduced levels of phosphor-Akt and phosphor-GSK-3β reflect constitutively reduced levels of Akt kinase activity and increased levels of GSK-3β activity in AD. In contrast, β-actin expression was not significantly reduced in AD relative to aged control brains (FIG. 7E).

Since tau expression is regulated by insulin/IGF-I and Aβ turnover is mediated in part by insulin degrading enzyme (IDE), studies were conducted to measure the mRNA levels of tau and IDE. In addition, since glucose uptake and utilization are regulated in part by glucose transporter molecules, including GLUT4, and increased APP expression could account for Aβ accumulation in the brain, the real time RT-PCR studies were extended to measure the mRNA levels of GLUT4 and APP mRNA transcripts in hippocampal and hypothalamic tissues. Those studies demonstrated significantly reduced levels of tau and significantly increased levels of APP mRNA transcripts in AD relative to control cases (FIGS. 8A-8D). In contrast, no significant differences in the mean levels of GLUT4 or IDE mRNA transcripts were observed between the AD and control groups (FIGS. 8E-8H).

The studies demonstrated that IRS-1 mRNA was more abundantly expressed than IRS-2 or IRS-4, and in AD, the levels of IRS-1 mRNA were significantly reduced. Although the mechanism of reduced IRS-1 expression is not known, exploratory studies in neuronal cell lines demonstrated that IRS-1 expression is regulated by insulin and IGF-I stimulation (Carter, et al, 2004, Unpublished). The markedly reduced levels of IRS-1 gene expression are reminiscent of the murine IRS-1 and insulin receptor knock-out models which exhibit reduced brain and body weight due to impaired insulin stimulated growth and survival signaling. (Schubert et al., *J. Neurosci.* 23:7084 (2003); Doublier et al., *Growth Horm. IGF Res.* 10:267 (2000); Nishiyama et al., *Gene* 141:187 (1994)). In addition, humans with Type 2 diabetes and Syndrome X have significantly reduced levels of IRS-1 expression that is associated with impaired insulin signaling downstream through PI3 kinase and Akt. (Smith et al., *Ann. NY Acad. Sci.* 892:119 (1999)).

Since insulin and IGF-I transmit pro-survival and pro-growth signaling through IRS molecules, reduced levels of IRS expression could contribute to growth factor resistance in the CNS. Corresponding with the reduced levels of growth factor, growth factor receptor, and IRS gene expression, further analysis of the downstream signaling pathways demonstrated reduced level of IRS-associated PI3 kinase activity (reflected by reduced levels of p85-associated IRS-1), decreased levels of phospho-Akt (reflecting decreased Akt activity), and reduced levels of phospho-GSK-3β (reflecting increased GSK-3β activity). Therefore, the impaired growth factor and receptor expression were associated with impaired survival signaling mechanisms in AD.

The finding of reduced levels of tau mRNA in AD is of interest because previous studies demonstrated that IGF-I and insulin regulate tau mRNA expression in neurons. (de la Monte et al., *Cell. Mol. Life Sci.* 60:2679 (2003)). Therefore, low-level tau mRNA correlates with impaired insulin and IGF-I signaling mechanisms. Moreover, the increased levels of phospho-tau in AD brains could also reflect impaired insulin/IGF-I signaling with attendant increased levels of GSK-3β activity, since GSK-3β is one of the major kinases responsible for hyper-phosphorylating tau. (Hong et al., *J. Biol. Chem.* 272:19547 (1997)). The increased level of APP mRNA in AD brains is of interest because that suggests a transcription-based mechanism for increased amyloid-β deposition in the brain. This result is also consistent with previous demonstrations that APP expression is increased with oxidative stress (Chen et al., *J Alzheimers Dis.* 5:209 (2003)), and that increased levels of amyloid-β can be neurotoxic (Lorenzo et al., *Ann. NY Acad. Sci.* 777:89 (1996); Niukura et al., *J. Neurosci. Res.* 70:380 (2002); Tsukamoto et al., *J. Neurosci. Res.* 73:627 (2003)). Impaired insulin signaling has already been linked to increased oxidative stress and mitochondrial dysfunction in neuronal cells. (de la Monte et al., *Cell. Mol. Life Sci.* 59:882 (2002); Hoyer et al., *Ann. NY Acad. Sci.* 920:256 (2000); Hoyer et al., *Ann. NY Acad. Sci.* 893:301 (1999)). Additional studies demonstrated that the AD-associated abnormalities in insulin/IGF-I signaling mechanisms were not accompanied by reduced expression of GLUT4 or IDE. Altogether, the results suggest that impaired insulin/IGF-I stimulated survival signaling and attendant chronic oxidative stress represent major abnormalities in AD.

Example 7

Reduction of Growth Factor Receptor Expression During Progression of AD

The reduction in growth factor receptor expression was further analyzed by examining postmortem brain tissue with different degrees of AD severity. Snap frozen tissue (~100 mg each) from the anterior frontal cortex was used to extract RNA and protein. The samples were divided into four groups:

Control (Braak 0-1), Braak 2-3, Braak 4-5, and Braak 6. Real time quantitative RT-PCR studies demonstrated mRNA transcripts corresponding to insulin, IGF-I and IGF-II receptors in the frontal cortex from both control and AD brains (FIG. X). Among the Braak 0-1 cases, IGF-I receptor mRNA transcripts were most abundant and nearly ten-fold higher than the IGF-II receptor gene and 500-fold higher that the insulin receptor. With increasing Braak stage/severity of AD neurodegeneration, the mean levels of insulin and IGF-I receptor mRNA declined and were significantly lower than control even in the brain with Braak 2-3 disease severity (FIGS. 9A and 9B). The lowest mean levels of insulin and IGF-I receptor expression were observed in brains with Braak 6 AD. Consequently, the mean insulin and IGF-I receptor mRNA levels were significantly higher in the Braak 2-3 group relative to Braak 4-5 and Braak 6. IGF-II receptor expression was not significantly altered in any of the AD groups relative to control (FIG. 9C).

The finding of reduced insulin and IGF-I receptor expression in AD is consistent with results from the previous study demonstrating significant reductions in the levels of both mRNA transcripts in late stage AD relative to control brains. In that study, evidence was also obtained that insulin and IGF-I receptors were expressed in CNS neurons and that in AD, the reduced receptor expression was related to both neuronal loss and down-regulation of the genes. The findings herein suggest that loss of insulin and IGF-I receptor bearing neurons occurs early in the course of AD neurodegeneration, but the most precipitous decline is evident at Braak Stage 6 or end-stage disease. Reduced levels of growth factor receptor expression could impair signaling, and effectively cause insulin/IGF-I resistance in the brain. Importantly, these results provide evidence that the abnormalities in AD are not restricted to insulin signaling pathways, since they also clearly involve IGF-I stimulated mechanisms.

Example 8

Reduction of Growth Factor Expression During Progression of AD

Real time quantitative RT-PCR studies detected insulin, IGF-I, and IGF-II polypeptide mRNA transcripts in age control and AD brains (FIGS. 10A-10C). In Braak 0-1 brains, IGF-II mRNA levels were highest, followed by insulin, and then IGF-I. Striking and significant reductions in both insulin and IGF-II gene expression were observed in the Braak stages 2-3 cases, and although the levels declined further with increasing severity of AD, they were not significantly reduced relative to Braak 2-3 (FIGS. 10A and 10C). IGF-I mRNA expression was only slightly reduced in the Braak 2-3 group, but substantially and significantly reduced in both the Braak 4-5 and Braak 6 groups relative to control (FIG. 10B).

The studies demonstrated progressive reductions in growth factor gene expression with increasing severity of AD neurodegeneration. Therefore, in AD, the problem is not simply insulin/IGF-I resistance since there are also deficiencies in local CNS growth factor production. Importantly, significantly reduced levels of growth factor gene expression were detected in Braak Stage 2-3 brains, indicating that the abnormality develops early in the course of disease.

The disease-severity declines in growth factor gene expression indicate that these abnormalities worsen with progression of disease. At least with regard to insulin and IGF-II, the relative reductions in growth factor gene expression were steeper than the corresponding receptor expression, suggesting that local growth factor withdrawal may precede the loss of growth factor receptor-bearing neurons. A paucity of local growth factor gene expression could substantially impair growth factor signaling in the CNS. Moreover, if the CNS were dependent on local growth factor production, reduced supply would produce a state of growth factor withdrawal, which is a well established mechanism of neuronal death. In order to maintain the integrity of insulin/IGF-I-dependent CNS functions, either the receptor sensitivity or expression levels must be increased, or a mechanism for increasing CNS uptake of growth factors from peripheral blood must be activated or enhanced.

Example 9

Alterations in Tau and Amyloid Precursor Protein Expression During Progression of AD Real time RT-PCR studies found that tau mRNA transcripts were most abundant in the Braak 0-1 control cases and the levels progressively and significantly declined with increasing Braak stage, i.e., severity of AD neurodegeneration (FIG. 11A), corresponding with the trends observed with respect to the insulin and IGF-I polypeptide genes. The Braak 0-1 group had the lowest mean level of APP mRNA. In brains with Braak stage 2 or higher, the APP mRNA levels were similarly elevated and approximately 4-fold higher than control (FIG. 11B).

The reduced tau expression observed in AD is of interest because previous studies demonstrated that neuronal tau mRNA expression was regulated by IGF-I and insulin stimulation. Therefore, the AD-associated reductions in tau mRNA correlated with the significantly reduced levels of insulin and IGF-I polypeptide and receptor gene expression in AD. It was particularly noteworthy that the AD stage-associated decline in insulin and insulin receptor expression paralleled the trend with respect to tau.

The present work shows that APP expression is significantly elevated in Braak Stage 2-3 disease, indicating that this abnormality occurs early in the course of AD. In this regard, increased amyloid-β deposition, which is prevalent in AD brains, may be mediated by elevated levels of APP mRNA, since more abundant transcripts would provide additional substrate for potentially aberrant enzymatic cleavage and processing of the protein. Previous studies demonstrated that APP expression and cleavage increase with oxidative stress, and that impaired insulin signaling causes oxidative stress and mitochondrial dysfunction in neuronal cells. Since high levels of amyloid-β can be neurotoxic, oxidative stress-induced APP expression may potentiate the AD neurodegeneration cascade secondarily following the accumulation of amyloid-β. Altogether, the results suggest that impaired insulin/IGF-I stimulated signaling and attendant chronic oxidative stress represent major abnormalities that develop early in the course of AD.

Example 10

Analysis of Ligand Binding to Growth Factor Receptors During Progression of AD

Insulin and IGF-I mediate their effects by activating complex intracellular signaling pathways that are initiated by ligand binding to the corresponding cell surface receptors. Therefore, effective ligand binding is critical to the signaling cascade, and many of the downstream effects of impaired insulin signaling that have already been identified in brains with AD, including reduced neuronal survival, increased GSK-3β activation, and increased tau phosphorylation could be mediated by reduced insulin binding in the CNS. To examine this aspect of growth factor signaling, competitive equilibrium and affinity binding assays were performed using [$^{125}$I]-labeled insulin, IGF-I or IGF-II as tracers and membrane extracts of postmortem frontal lobe tissue as the sources of receptors.

Fresh frozen tissue (~100 mg) was homogenized in 5 volumes of radio-immunoprecipitation assay (RIPA) buffer (50 mM Tris-HCl, pH 7.5, 1% NP-40, 0.25% Na-deoxycholate, 150 mM NaCl, 1 mM EDTA, 2 mM EGTA) containing protease (1 mM PMSF, 0.1 mM TPCK, 1 µg/ml aprotinin, 1 µg/ml pepstatin A, 0.5 µg/ml leupeptin, 1 mM NaF, 1 mM Na$_4$P$_2$O$_7$) and phosphatase (2 mM Na$_3$VO$_4$) inhibitors. Protein concentration was determined using the bicinchoninic acid (BCA) assay (Pierce, Rockford, Ill.). Preliminary studies determined the amounts of protein and concentrations of radiolabeled ligand required to achieve 20% specific binding.

Insulin receptor binding assays were performed using 200 µg protein. IGF-I binding assays required 25 µg protein per sample, and IGF-II receptor binding assays were performed with 10 µg protein. Equilibrium binding assays were used to assess growth factor binding levels in relation to AD stage severity. This was accomplished by determining net specific binding after incubating the protein samples at 4° C. overnight with a fixed amount of radioligand, in the presence or absence of excess cold ligand and then subtracting the values obtained for non-specific binding from those corresponding to the total binding. To measure total binding, individual protein samples were incubated in 100 µl reactions containing binding buffer (100 mM HEPES, pH 8.0, 118 mM NaCl, 1.2 mM MgSO$_4$, 8.8 mM dextrose, 5 mM KCl, 1% bovine serum albumin) and 100 nCi/ml [$^{125}$I] (2000 Ci/mmol; 50 pM) of insulin, IGF-I, or IGF-II. To measure non-specific binding, replicate samples were prepared as indicated with the addition of 0.1 µM unlabeled (cold) ligand.

Saturation binding assays were performed to assess top-level (maximum) binding and binding affinity in relation to AD stage severity. Samples from 8-12 brains per Braak stage group were pooled in equal proportions and used to generate binding curves. Protein concentrations of the pooled homogenates were determined with the BCA assay. Duplicate samples were incubated in 100 µl reaction volumes containing binding buffer and 0.0031 to 1 µCi/ml of [$^{125}$I] (2000 Ci/mmol) of insulin, IGF-I, or IGF-II. To measure non-specific binding, duplicate reactions were incubated with the same concentrations of radiolabeled ligand plus 0.1 µM unlabeled (cold) competitive ligand. The data were graphed and analyzed using the GraphPad Prism 4 software to calculate the $B_{max}$, kD (dissociation constant), and their standard deviations and 95% confidence intervals.

Reactions were performed in 1.5 ml Eppendorff tubes at 4° C. for 16 hours with gentle platform agitation. Bound radiolabeled tracer ligand was then precipitated by adding 500 µl of 0.15% bovine gamma globulin (prepared in 100 mM Tris-HCl, pH 8.0) followed by 400 µl 37.5% polyethylene glycol 6000 (PEG-6000; prepared in 100 mM Tris-HCl, pH 8.0) to each tube, thoroughly vortexing the samples, and incubating them on ice for at least 2 hours. The precipitates were collected by centrifuging the samples at 15,000×g for 15 minutes at room temperature. The supernatant fractions containing unbound (free) ligand, were transferred in their entirety to individual Gamma counting tubes (Sarstedt). The tips of the Eppendorff tubes with the pellets were cut and released directly into separate Gamma counting tubes. The samples were counted for 1 minute each in an LKB CompuGamma CS Gamma counter. Specific binding was calculated by subtracting CPM or fmol of non-specific binding, i.e., amount bound in the presence of cold ligand, from the total CPM or fmol bound (absence of unlabeled competitive ligand). After determining that the data fit a one-site rather than a two-site model, the results were analyzed using non-linear regression to calculate saturation binding ($B_{max}$) and binding affinity (kD) with Scatchard analysis performed to measure saturation binding and binding affinity using GraphPad Prism 4 software (GraphPad Software, Inc., San Diego, Calif.).

The equilibrium binding studies demonstrated significantly higher levels of specific binding to the insulin receptor in control (Braak 0-1) relative to AD brains. Significantly reduced binding was detected in Braak Stages 2-3 brains, and with increasing severity of AD, the mean levels of insulin binding (fmol/mg protein) were further reduced (FIG. 12A). IGF-I binding was also significantly higher in the Braak 0-1 compared with Braak 2-3 or later stages of AD. However, corresponding with the modest or absent further reductions in receptor expression with progression of AD, the mean levels of IGF-I binding (fmol/mg) also did not significantly decline with severity of neurodegeneration (FIG. 12B). The AD-associated profiles concerning IGF-II binding were more similar to those already described for insulin. Control brains (Braak 0-1) had significantly higher mean levels of IGF-II binding (fmol/mg) compared with all other AD groups (FIG. 12C). In addition, with progression of AD neurodegeneration, the mean levels of IGF-II binding declined such that the lowest levels were observed in the Braak 6 cases. IGF-II binding was not reduced in the AD relative to control brains. Instead, significantly increased mean levels of specific binding were detected in brains with Braak 2-3 or more advanced stages of AD (FIG. 12C). In contrast to the findings obtained with respect to insulin binding, progressive reductions in IGF-I binding with increasing severity of AD were not observed (FIG. 12B).

Scatchard analysis was used to determine if, in addition to reduced receptor expression, the lower levels of ligand binding were associated with altered receptor binding affinity. The Scatchard plots revealed lower $B_{max}$ (top-level) binding for insulin, IGF-I, and IGF-II in all AD relative to the control groups (FIGS. 13A-13L and Tables 3-5). The trend for progressively reduced $B_{max}$ levels with increasing severity of AD was statistically significant for both insulin and IGF-II ($P<0.001$). Receptor binding affinities (kD) were calculated using Graphpad Prism 4 software. The analysis showed higher insulin, IGF-I, and IGF-II receptor binding affinities (lower kDs) in AD relative to control brains. In addition, correlation analysis revealed significant negative associations between Braak stage and insulin or IGF-II binding affinity, i.e., higher grades of AD were correlated with lower levels of maximum/saturation binding and higher binding affinities (lower kD's) (Tables 3-5). In contrast, these trend lines were not statistically significant with respect to the $B_{max}$ or kD of the IGF-I receptor.

TABLE 3

Scatchard Analysis of Insulin binding in the Brain

| Best-fit values | Braak 0-1 | Braak 2-3 | Braak 4-5 | Braak 6 |
|---|---|---|---|---|
| BMAX* | 7.155 | 3.974 | 2.638 | 2.508 |
| KD* | 195.2 | 69.23 | 39.99 | 42.23 |
| Std. Error | | | | |
| BMAX | 1.209 | 0.1915 | 0.201 | 0.2242 |
| KD | 49.57 | 6.303 | 6.73 | 8.13 |

TABLE 3-continued

Scatchard Analysis of Insulin binding in the Brain

| Best-fit values | Braak 0-1 | Braak 2-3 | Braak 4-5 | Braak 6 |
|---|---|---|---|---|
| 95% Confidence Intervals | | | | |
| BMAX | 4.461 to 9.849 | 3.547 to 4.400 | 2.190 to 3.086 | 2.009 to 3.008 |
| KD | 84.80 to 305.7 | 55.19 to 83.28 | 24.99 to 54.98 | 24.12 to 60.35 |
| Goodness of Fit | | | | |
| $R^2$ | 0.9876 | 0.9964 | 0.9833 | 0.9777 |

*$P < 0.001$ for AD Stage-associated declines in BMAX (reduced top-level binding) and KD (increased affinity) by Pearson correlation analysis tests.

TABLE 4

Scatchard Analysis of IGF-I binding in the Brain

| Best-fit values | Braak 0-1 | Braak 2-3 | Braak 4-5 | Braak 6 |
|---|---|---|---|---|
| BMAX* | 5.607 | 3.957 | 3.381 | 0.6775 |
| KD* | 89.36 | 85.41 | 70.48 | 9.342 |
| Std. Error | | | | |
| BMAX | 0.9428 | 0.5355 | 0.2632 | 0.06524 |
| KD | 25.57 | 20.7 | 10.35 | 2.622 |
| 95% Confidence Intervals | | | | |
| BMAX | 3.506 to 7.707 | 2.764 to 5.150 | 2.795 to 3.968 | 0.5321 to 0.8228 |
| KD | 32.39 to 146.3 | 39.29 to 131.5 | 47.42 to 93.53 | 3.499 to 15.18 |
| Goodness of Fit | | | | |
| $R^2$ | 0.9673 | 0.9789 | 0.9912 | 0.8841 |

*$P < 0.001$ for AD Stage-associated declines in BMAX (reduced top-level binding) and KD (increased affinity) by Pearson correlation analysis tests.

TABLE 5

Scatchard Analysis of IGF-II Binding in the Brain

| Best-fit values | Braak 0-1 | Braak 2-3 | Braak 4-5 | Braak 6 |
|---|---|---|---|---|
| BMAX* | 16.83 | 12.53 | 8.136 | 4.713 |
| KD* | 196.9 | 137.5 | 74.31 | 43.2 |
| Std. Error | | | | |
| BMAX | 3.638 | 1.257 | 0.6763 | 0.3796 |
| KD | 57.77 | 20.43 | 10.72 | 6.974 |
| 95% Confidence Intervals | | | | |
| BMAX | 9.281 to 24.37 | 9.918 to 15.13 | 6.734 to 9.539 | 3.926 to 5.500 |
| KD | 77.05 to 316.7 | 95.13 to 179.9 | 52.07 to 96.54 | 28.74 to 57.67 |
| Goodness of Fit | | | | |
| $R^2$ | 0.9757 | 0.9895 | 0.9816 | 0.9618 |

*$P < 0.001$ for AD Stage-associated declines in BMAX (reduced top-level binding) and KD (increased affinity) by Pearson correlation analysis tests.

These studies demonstrated significantly reduced saturation (maximum) binding to the insulin, IGF-I, and IGF-II receptors in AD relative to control brains. The levels of insulin and IGF-II binding declined with severity stage of AD, whereas the mean levels of IGF-I binding were similarly reduced across the different stages of AD neurodegeneration. Scatchard analysis of the insulin, IGF-I, and IGF-II data demonstrated higher binding affinities (lower dissociation constants-kD) with lower levels of saturation binding and receptor expression in AD. Therefore, impaired insulin, IGF-I, and probably IGF-II signaling mechanisms in AD are likely mediated by decreased receptor expression as well as reduced local availability of ligand, rather than reduced binding affinity.

Example 11

Alterations in Cholesterol Content During Progression of AD

Membrane cholesterol content can influence ligand binding to cell surface receptors. For example, decreased or increased cholesterol content in membranes has been associated with altered or impaired growth factor binding and signal transduction. To determine if the observed differences in receptor binding affinity were correlated with membrane cholesterol content, cholesterol levels were measured in frontal lobe extracts using the Amplex Red assay kit (Molecular Probes, Eugene, Oreg.) according to the manufacturer's protocol. Briefly, tissue homogenates were prepared in RIPA buffer as described above. The samples were serially diluted in 1× reaction buffer (provided with the kit) and incubated with 150 µM Amplex Red reagent, 1 U/ml horseradish peroxidase, 1 U/ml cholesterol oxidase, and 0.1 U/ml cholesterol esterase in a final reaction volume of 100 µl. Reactions were incubated at 37° C. for 30 minutes and fluorescence was measured in a Fluorocount microplate reader (Packard Instrument Co., Meriden, Conn.) (Ex 560 nm/Em 590 nm). A standard curve was simultaneously generated using a cholesterol standard provided with the kit. The levels of cholesterol were normalized to protein concentration in the samples. Preliminary studies demonstrated that the measured cholesterol levels and inter-group differences were the same in lipid extracts compared with RIPA buffer extracts, as indicated by the manufacturer. Therefore, it was not necessary to perform the analysis with lipid extracts. The studies demonstrated significantly increased levels of cholesterol in brains with Braak Stages 4-5 or 6 relative to brains with Braak stages 0-1 or 2-3 (FIG. 14A). The mean cholesterol levels were similar in brains with Braak 4-5 and Braak 6 stages of AD.

Example 12

Alterations in ATP Levels During Progression of AD

Impaired insulin and IGF-I signaling can result in reduced mitochondrial function, energy metabolism, and ATP production. To investigate the effects of impaired insulin/and IGF-I function in AD, the steady-state levels of ATP were measured in frontal cortex homogenates using the ATPLite assay system (Perkin Elmer, Boston, Mass.). The lysates were serially diluted and 50 µl ATP substrate were added per 150 µl lysate. Snap frozen brain tissue samples were Polytron (Glen Mills Inc., Clifton, N.J.) homogenized in three volumes of PBS containing 20 mM glycine, 50 mM $MgSO_4$, and 4 mM EDTA. 100 µl aliquots were transferred to 96-well black plates, and 50 µl of ATPLite lysis buffer were added to each sample. The plates were covered with adhesive plastic sheets and agitated at 700 rpm for 5 minutes at room temperature. Then, 50 µl of ATPLite substrate were added to each sample, and the sealed plates, covered with aluminum foil, were agitated for an additional 5 minutes (700 rpm at room temperature). Luminescence was measured in a TopCount machine (Packard Instrument Co., Meriden, Conn.), and ATP luminescence values were normalized to protein concentration. The studies demonstrated significantly reduced levels (~50%) of ATP in AD (all groups) relative to control brains (FIG. 14B). In AD, the mean ATP levels were consistently reduced and did not decline significantly with progression or severity of neurodegeneration.

Example 13

Diagnostic Assay for Alzheimer's Disease

Subjects displaying pathology resulting from AD or at risk of displaying pathology resulting from AD will be screened for a diagnosis of AD. Samples of brain tissue will be obtained from each subject. RNA will then be isolated from the samples and subjected to real time quantitative RT-PCR as described in Examples 2 and 3 above to determine the level of expression of insulin, IGF-I, IGF-II, insulin receptor, IGF-I receptor, and IGF-II receptor in the brain tissue. The measured expression levels will then be compared to expression levels in age matched healthy subjects. If the measured expression level of two or more of the measured factors is found to be at least 2-fold lower than the expression level in the healthy subjects than the test subject is considered to have AD.

Example 14

Animal Model of Alzheimer's Disease

In previous studies, intracerebral streptozotocin (ic-STZ) treatment was used to generate a model of AD-type neurodegeneration in adult rats. Plaschke et al., *Int. J. Dev. Neurosci.* 11:477 (1993); Duelli et al., *Int. J. Dev. Neurosci.* 12:737 (1994); Hoyer et al., *J. Neural Transm. Suppl.* 44:259 (1994); Lannert et al., *Behav. Neurosci.* 112:1199 (1998). The chemical name of STZ is 2-Deoxy-2{[methyl-nitrosoamino)carbonyl]amino}D-glucopyranose ($C_8H_{15}N_3O_7$), and its molecular mass is 265 daltons. STZ is a glucosamine-nitrosourea compound which when metabolized, generates a cytotoxic product that preferentially destroys beta cells in pancreatic islets and produces diabetes mellitus. Although the precise mechanism of cytotoxicity is not understood, the alkylating properties of STZ metabolites generate reactive oxygen species and cause oxidative stress and DNA damage. These effects led to the use of intracerebroventricular STZ to produce a model of neurodegeneration. In adult rats, intracerebroventricular injection of STZ causes chronic reductions (10-30%) in glucose and glycogen metabolism in the cerebral cortex and hippocampus. Plaschke et al., *Int. J. Dev. Neurosci.* 11:477 (1993). These effects are associated with significantly reduced brain oxidative metabolism (Duelli et al., *Int. J. Dev. Neurosci.* 12:737 (1994)), inhibition of insulin receptor function (Hoyer et al., *Ann. NY Acad. Sci.* 920:256 (2000)), and progressive deficits in learning, memory, cognitive behavior, cerebral energy balance (Lannert et al., *Behav. Neurosci.* 112: 1199 (1998); Hoyer et al., *Ann. NY Acad. Sci.* 893:301 (1999). Therefore, this model provides at least a partial match with the biochemical and physiological abnormalities occurring in AD. However, previous studies did not characterize the neuropathology, molecular pathology, abnormalities in genes expression pertinent to the insulin and IGF-1 signaling, or intactness of architecture and insulin expression in the pancreas.

The present example demonstrates that intracerebral (ic) STZ treatment of young animals produces neurodegeneration that bears a striking resemblance to the molecular and pathological features of sporadic AD, including impairments of both insulin and IGF signaling mechanisms. A major distinguishing feature between this model and the previously characterized ic-STZ model is that this rat pups instead of adult rats. The rationale for using pups was as follows. Our initial objective in generating the ic-STZ model was to demonstrate the critical roles of insulin and IGF signaling during cerebellar development since we had already discovered that cerebellar hypoplasia caused by chronic gestational exposure to ethanol was associated with impairments in insulin signaling and insulin gene expression. de la Monte et al., *Cell Mol. Life Sci.* 62:1131 (2005). However, our neuropathological assessments of the brains revealed striking cerebral atrophy, neuronal loss, and senile plaque-like structures in the cerebral cortex of the ic-STZ-treated rats. Those observations prompted us to pursue this line of investigation by further characterizing the ic-STZ model with regard to the neuropathological and molecular abnormalities, and in relation to our recent findings in human brains with AD. Rivera et al., *J. Alzheimers Dis.* 7 (2005), (In Press); Steen et al., *J. Alzheimers Dis.* 7:63 (2005).

Experimental Model:

Three-day-old Long Evans rat pups were given bilateral intra-cerebral (ic) injections of STZ. The STZ was injected 1.0 mm posterior and 1.0 mm lateral to the bregma, and 2.5 mm deep to the skull surface of each hemisphere using a 30-gauge needle affixed to a Hamilton microliter syringe. Control rats were identically injected with sterile saline. Initial studies evaluated the effects of different doses of STZ ranging from 5 to 70 mg/kg as reported previously to generate models of diabetes mellitus. Andican et al., *Clin. Exp. Pharmacol. Physiol.* 32:663 (2005); Saad et al., *Arch. Toxicol.* (2005); Srinivasan et al., *Pharmacol. Res.* 52:313 (2005); Karabatas et al., *Pancreas* 30:318 (2005); Mabley et al., *Pancreas* 28:E39 (2004). The preliminary studies demonstrated STZ-mediated neurodegeneration at all doses tested, but consistent results were achieved using at least 25 mg/kg. The results shown herein were obtained from rat pups treated with 40 mg/kg ic-STZ. The injections were completed within 3 minutes and the needle was withdrawn slowly from the brain. All pups recovered immediately and therefore were quickly returned to the dams with 100% acceptance by the dams. The accuracy of injection procedure was confirmed by injecting methylene blue dye, which was found localized in subcortical white matter and within the lateral ventricles. All animals survived the injections and were monitored daily until they were sacrificed 7, 14, or 21 days after the STZ or saline treatments.

At the termination point of the experiment, the rats were weighed and then sacrificed by isofluorane inhalation. Blood was obtained by cardiac puncture to measure glucose concentration using the OneTouch Ultra Blood Glucose Meter (Lifescan, Inc). The pancreases were harvested and immersion fixed in Histofix (Amresco Corp, Solon, Ohio) for paraffin embedding. Fresh brains were weighed and then cut in the coronal plane to obtain a ~3 mm thick slice that flanked the infundibulum. The 3-mm brain slice was snap frozen between two slabs of dry ice, and stored at −80° C. for later RNA and protein extractions. The residual tissue was immersion fixed (Histofix) and embedded in paraffin for histopathological study and immunohistochemical staining. In approximately 20% of the cases, the brains were weighed, immersion fixed whole, and then sectioned in the coronal plane along standardized landmarks for paraffin embedding and histopathological sectioning. The ic-STZ model was generated in 4 independent experiments using 180 rat pups. A comparable number of controls were studied in parallel.

Histopathological and Immunohistochemical Staining Studies:

Paraffin-embedded histological sections of pancreas (5 μm thick) and brain (8 μm thick) were stained with hematoxylin and eosin (H&E) and examined for histopathological lesions, i.e., inflammation, necrosis, and islet cell degeneration. Adjacent sections of pancreas were immunostained to detect insulin immunoreactivity in the islets. Paraffin sections of brain were immunostained with monoclonal or polyclonal antibodies to phospho-tau, Aβ, p53, ubiquitin, glial fibrillary acidic protein (GFAP), choline acetyltransferase (ChAT), and acetylcholinesterase (AChE) to characterize the nature of ic-STZ-induced AD-type neurodegeneration. As negative controls for the immunostaining reactions, either the primary antibody was omitted or non-relevant monoclonal antibody to Hepatitis B virus was used in place of the relevant antibody.

Prior to immunostaining, the deparaffinized, re-hydrated tissue sections were sequentially treated with 0.1 mg/ml saponin in phosphate buffered saline (10 mM sodium phosphate, 0.9% NaCl, pH 7.4; PBS), for 20 minutes at room temperature. Endogenous peroxidase activity was quenched by treating the tissue sections with 3% hydrogen peroxide in methanol for 10 minutes, and non-specific binding sites were blocked by a 30-minute incubation in SuperBlock-TBS (Pierce Chemical Co., Rockford, Ill.) at room temperature. After overnight incubation at 4° C. with antibodies diluted to 0.1-1 μg/ml (according to the manufacturer's recommendations), immunoreactivity was detected using rat tissue-pre-adsorbed biotinylated secondary antibodies, avidin biotin horseradish peroxidase complex (ABC) reagents, and diaminobenzidine as the chromogen (Vector Laboratories, Burlingame, Calif.). de la Monte et al., *Lab. Invest.* 80:1323 (2000). The sections were counterstained with hematoxylin and preserved with mounting medium and coverglass. All sections were examined under code.

RT-PCR

The mRNA levels of insulin, IGF-I, and IGF-II growth factors, their corresponding receptors, insulin receptor substrate (IRS) subtypes 1, 2, and 4, tau, amyloid precursor protein (APP), ACHE, and CHAT were measured by real time quantitative RT-PCR amplification as described above and using the primers shown in Table 6. In addition, studies were performed to detect pathological shifts in cell types associated with ic-STZ-mediated neurodegeneration as described in a previous study of AD. Steen et al., *J Alzheimers Dis* 7:63 (2005). Briefly, real time quantitative RT-PCR was performed with gene-specific primer pairs designed to detect Hu (neurons), GFAP (astrocytes), myelin-associated glycoprotein (MAG-1; oligodendroglia), and allograft inflammatory factor-1 (AIF-1; microglia) mRNA transcripts as shown in Table 6.

TABLE 6

| Primer | Direction | Sequence (5'→3') | Position (mRNA) | Amplicon Size (bp) |
|---|---|---|---|---|
| 18S | For | GGA CAC GGA CAG GAT TGA CA (SEQ ID NO: 43) | 1278 | 50 |
| 18S | Rev | ACC CAC GGA ATC GAG AAA GA (SEQ ID NO: 44) | 1327 | |
| Insulin | For | TTC TAC ACA CCC AAG TCC CGT C (SEQ ID NO: 31) | 145 | 135 |
| Insulin | Rev | ATC CAC AAT GCC ACG CTT CTG C (SEQ ID NO: 32) | 279 | |
| Insulin Receptor | For | TGA CAA TGA GGA ATG TGG GGA C (SEQ ID NO: 45) | 875 | 129 |
| Insulin Receptor | Rev | GGG CAA ACT TTC TGA CAA TGA CTG (SEQ ID NO: 46) | 1003 | |
| IGF-I | For | GAC CAA GGG GCT TTT ACT TCA AC (SEQ ID NO: 47) | 65 | 127 |
| IGF-I | Rev | TTT GTA GGC TTC AGC GGA GCA C (SEQ ID NO: 48) | 191 | |
| IGF-I Receptor | For | GAA GTC TGC GGT GGT GAT AAA GG (SEQ ID NO: 49) | 2138 | 113 |
| IGF-I Receptor | Rev | TCT GGG CAC AAA GAT GGA GTT G (SEQ ID NO: 50) | 2250 | |
| IGF-II | For | CCA AGA AGA AAG GAA GGG GAC C (SEQ ID NO: 51) | 763 | 95 |
| IGF-II | Rev | GGC GGC TAT TGT TGT TCA CAG C (SEQ ID NO: 52) | 857 | |
| IGF-II Receptor | For | TTG CTA TTG ACC TTA GTC CCT TGG (SEQ ID NO: 53) | 1066 | 91 |

TABLE 6-continued

| Primer | Direction | Sequence (5'→3') | Position (mRNA) | Amplicon Size (bp) |
|---|---|---|---|---|
| IGF-II Receptor | Rev | AGA GTG AGA CCT TTG TGT CCC CAC (SEQ ID NO: 54) | 1156 | |
| IRS 1 | For | GAT ACC GAT GGC TTC TCA GAC G (SEQ ID NO: 55) | 604 | 134 |
| IRS 1 | Rev | TCG TTC TCA TAA TAC TCC AGG CG (SEQ ID NO: 56) | 737 | |
| IRS 2 | For | CAA CAT TGA CTT TGG TGA AGG GG (SEQ ID NO: 57) | 255 | 109 |
| IRS 2 | Rev | TGA AGC AGG ACT ACT GGC TGA GAG (SEQ ID NO: 58) | 363 | |
| IRS 4 | For | ACC TGA AGA TAA GGG GTC GTC TGC (SEQ ID NO: 59) | 2409 | 132 |
| IRS 4 | Rev | TGT GTG GGG TTT AGT GGT CTG G (SEQ ID NO: 60) | 2540 | |
| Tau | For | CGC CAG GAG TTT GAC ACA ATG (SEQ ID NO: 61) | 244 | 65 |
| Tau | Rev | CCT TCT TGG TCT TGG AGC ATA GTG (SEQ ID NO: 62) | 308 | |
| APP | For | GCA GAA TGG AAA ATG GGA GTC AG (SEQ ID NO: 63) | 278 | 199 |
| APP | Rev | AAT CAC GAT GTG GGT GTG CGT C (SEQ ID NO: 64) | 476 | |
| AChE | For | TTC TCC CAC ACC TGT CCT CAT C (SEQ ID NO: 65) | 420 | 123 |
| AChE | Rev | TTC ATA GAT ACC AAC ACG GTT CCC (SEQ ID NO: 66) | 542 | |
| ChAT | For | TCA CAG ATG CGT TTC ACA ACT ACC (SEQ ID NO: 67) | 478 | 106 |
| ChAT | Rev | TGG GAC ACA ACA GCA ACC TTG (SEQ ID NO: 68) | 583 | |
| Hu | For | CAC TGT GTG AGG GTC CAT CTT CTG (SEQ ID NO: 69) | 271 | 50 |
| Hu | Rev | TCA AGC CAT TCC ACT CCA TCT G (SEQ ID NO: 70) | 320 | |
| GFAP | For | TGG TAA AGA CGG TGG AGA TGC G (SEQ ID NO: 71) | 1245 | 200 |
| GFAP | Rev | GGC ACT AAA ACA GAA GCA AGG GG (SEQ ID NO: 72) | 1444 | |
| MAG-1 | For | AAC CTT CTG TAT CAG TGC TCC TCG (SEQ ID NO: 73) | 18 | 63 |
| MAG-1 | Rev | CAG TCA ACC AAG TCT CTT CCG TG (SEQ ID NO: 74) | 80 | |
| AIF-1 | For | GGA TGG GAT CAA CAA GCA CT (SEQ ID NO: 75) | 168 | 158 |
| AIF-1 | Rev | GTT TCT CCA GCA TTC GCT TC (SEQ ID NO: 76) | 325 | |

Receptor Binding Assays:

Studies were performed to determine if ic-STZ treatment impaired insulin, IGF-I, and IGF-II receptor binding in the brain. Membrane proteins were extracted from fresh frozen temporal lobe tissue (~100 mg) by Polytron (Glen Mils Inc., Clifton, N.J.) homogenization in 5 volumes of NP-40 lysis buffer (50 mM Tris-HCl, pH 7.5, 150 mM NaCl, 1 mM EDTA, 2 mM EGTA, 1% NP-40) containing protease (1 mM PMSF, 0.1 mM TPCK, 1 µg/ml aprotinin, 1 µg/ml pepstatin A, 0.5 µg/ml leupeptin, 1 mM NaF, 1 mM Na$_4$P$_2$O$_7$) and phosphatase (2 mM Na$_3$VO$_4$) inhibitors. The supernatant fractions obtained after centrifuging the samples at 10,000×g for 15 minutes at 4° C. were used in the binding assays. Steen et al., *J Alzheimers Dis* 7:63 (2005). Protein concentrations were measured with the bicinchoninic acid (BCA) assay (Pierce, Rockford, Ill.).

Competitive equilibrium binding assays were used to assess growth factor binding in relation to ic-STZ-treatment. For total binding, duplicate individual protein samples were incubated in 100 µl reactions containing binding buffer (100 mM HEPES, pH 8.0, 118 mM NaCl, 1.2 mM MgSO$_4$, 8.8 mM dextrose, 5 mM KCl, 1% bovine serum albumin) and 100 nCi/ml of [$^{125}$I] (2000 Ci/mmol; 50 pM) insulin, IGF-I, or IGF-II. To measure non-specific binding, replicate samples were identically prepared but with the addition of 0.1 µM unlabeled (cold) ligand. Exploratory studies were used to determine the amounts of protein and concentrations of radiolabeled ligand required to achieve 20% specific binding. Insulin receptor binding assays were performed using 100 µg protein. IGF-I binding assays required 25 µg protein per sample, and IGF-II receptor binding assays were performed with 10 µg protein.

All reactions were performed in 1.5 ml Eppendorff tubes, and the incubations were performed at 4° C. for 16 hours with gentle platform agitation. Bound radiolabeled tracer was then precipitated by adding 500 µl of 0.15% bovine gamma globulin (prepared in 100 mM Tris-HCl, pH 8.0) followed by 400 µl 37.5% polyethylene glycol 8000 (PEG-8000; prepared in 100 mM Tris-HCl, pH 8.0) to each tube. The samples were thoroughly mixed by vortexing, and then they were incubated on ice for at least 2 hours. The precipitates were collected by centrifuging the samples at 15,000×g for 5 minutes at room temperature. The supernatant fractions, which contained unbound (free) ligand, were transferred to Gamma counting tubes (Sarstedt, Newton, N.C.). The Eppendorff tube tips with pellets were cut and released directly into separate Gamma counting tubes. Each sample was counted for 1 minute in an LKB CompuGamma CS Gamma counter. Specific binding was calculated by subtracting fmols of non-specific binding, i.e. amount bound in the presence of excess cold ligand, from total fmols bound (absence of unlabeled competitive ligand). The binding assay results were analyzed using the GraphPad Prism 4 software (GraphPad Software, Inc., San Diego, Calif.).

Western Blot Analysis:

Western blot analysis was used to assess the levels of tau, phospho-tau, ubiquitin, GSK-3β, phospho-GSK-3β, GFAP, and β-actin as described above.

Figure 15A:
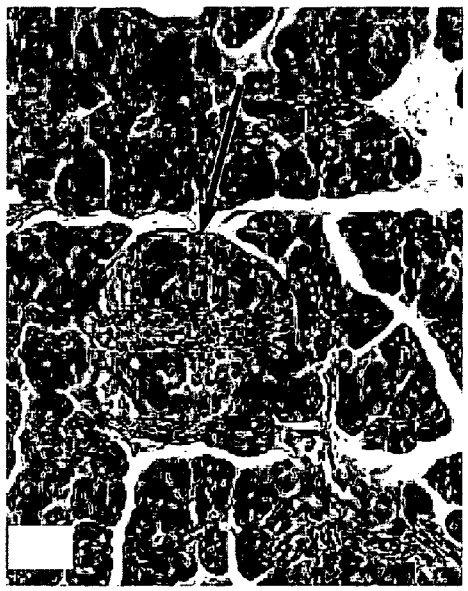
Figure 15B:
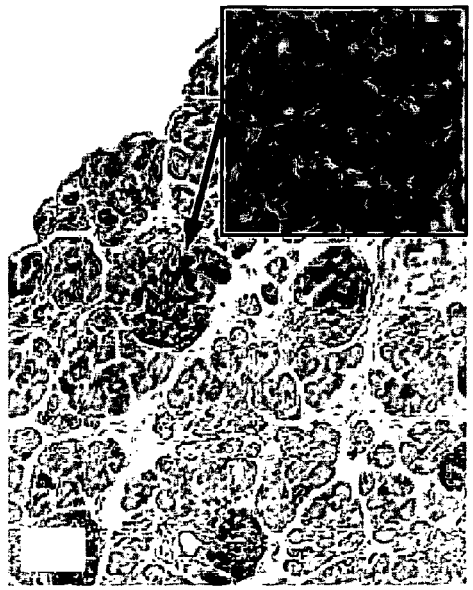
Figure 15C:
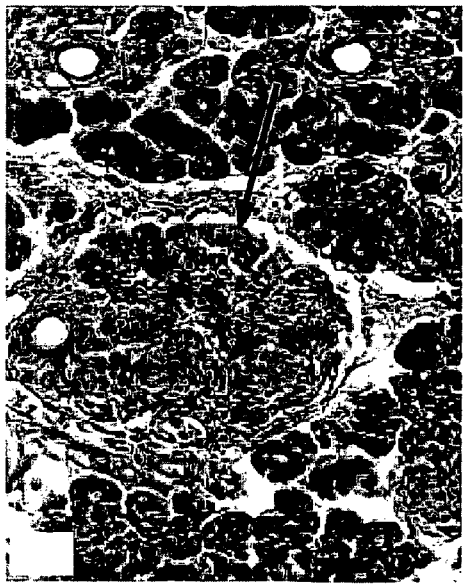
Figure 15D:
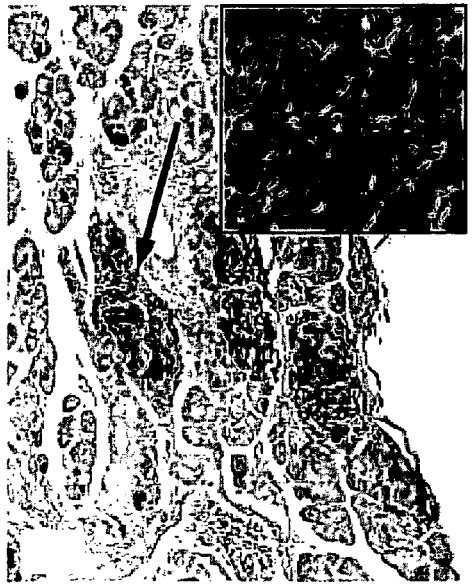
Figure 16A:
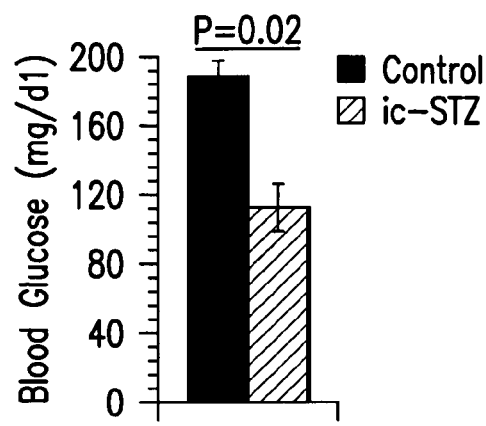
Figure 16B:
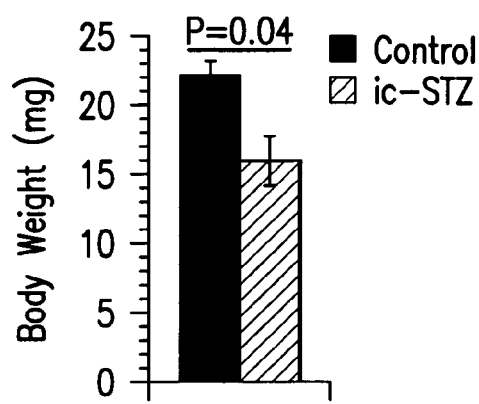

Pancreatic Islets Remain Intact Following ic-STZ Treatment:

Although the brains and pancreases were examined at various intervals after ic-STZ or vehicle treatment, most of the data presented was obtained from rats that were sacrificed on day 14 because prominent AD-type neurodegeneration and molecular indices of impaired insulin/IGF signaling were not consistently detected until at least 7 days after the ic-STZ treatment. Due to growing interest in characterizing the roles of Type 1 and Type 2 diabetes mellitus in the pathogenesis of cognitive impairment and AD-type neurodegeneration, studies were conducted to determine if the ic-STZ-mediated neurodegeneration was associated with inflammation, degeneration, necrosis, and loss of insulin immunoreactivity in the pancreatic islets as characteristically occur following parenteral administration of 40 mg/kg STZ. Mythili et al., *Microsc. Res. Tech.* 63:274 (2004). Histopathological studies demonstrated intact exocrine and endocrine architecture with no evidence of inflammation, necrosis, or islet cell degeneration in both control and ic-STZ-treated rats (FIGS. 15A and 15B). In addition, immunohistochemical staining demonstrated prominent insulin immunoreactivity in all pancreatic islets in both control and ic-STZ-treated rats (FIGS. 15C and 15D). Correspondingly, the mean random blood glucose concentration was not elevated in the ic-STZ-treated relative to control rats (FIG. 16A), and none of the ic-STZ-treated rats had random blood glucose concentrations >180 mg/dl. In fact, the mean blood glucose levels in the ic-STZ-treated group was significantly lower than control, perhaps due to reduced feeding since their mean body weight was also significantly reduced (P=0.04; FIG. 16B).

Figure 16C:
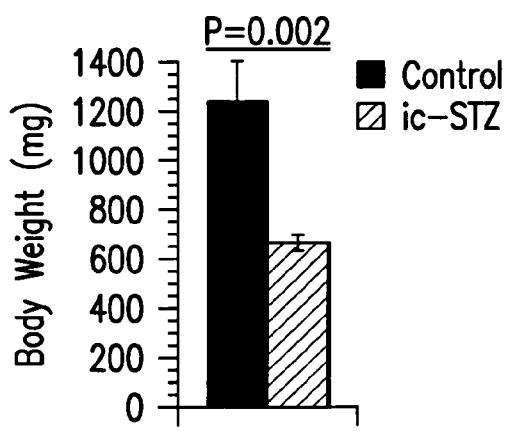

Intracerebral STZ Causes Neurodegeneration:

The mean brain weight in the ic-STZ-treated group was significantly reduced relative to control (P=0.002; FIG. 16C). The ic-STZ-injected brains were conspicuously smaller and tended to have multiple small foci of acute subarachnoid hemorrhage (FIG. 16D), suggesting increased cerebrovascular fragility. One potential explanation for this phenomenon is that increased Aβ immunoreactivity (see below) rendered the vessels more susceptible to traumatic and flow-related injury. However, there were no occurrences of intracerebral hemorrhage in either the ic-STZ-treated or control rats.

Figure 16D:
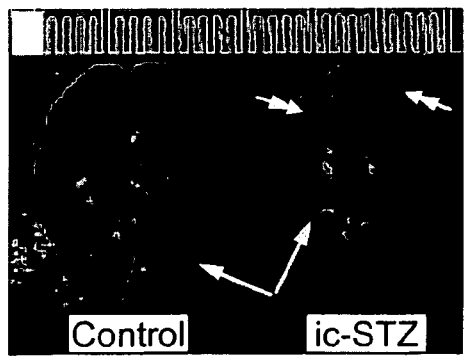
Figure 17A:
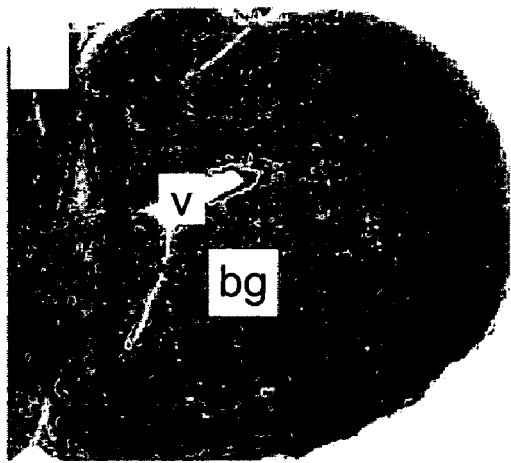
Figure 17B:
Figure 17C:
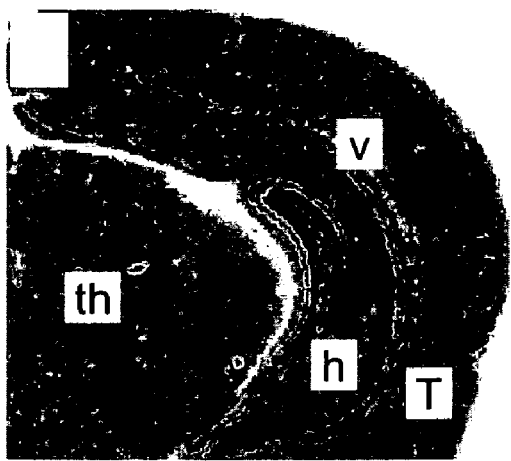
Figure 17D:
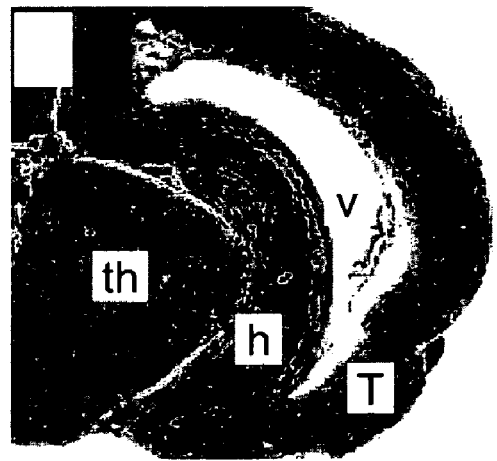

In ic-STZ treated rats, both the cerebral and cerebellar hemispheres were conspicuously reduced in size, but the cerebella were severely diminished relative to control (FIG. 16D). The greater vulnerability of the cerebellum to ic-STZ-mediated neurodegeneration was likely due to the fact that in rodents, this structure primarily develops within the first 10 postnatal days. Sotelo et al., *Philos. Trans. R. Soc. Lond. B Biol. Sci.* 331:307 (1991). Histopathological studies revealed striking abnormalities in the cerebral hemispheres of ic-STZ-treated rats, including: 1) diffuse narrowing of the cortical ribbon; 2) reduced cerebral white matter volume; 3) reduced sizes of the thalamus and hypothalamus; and 4) ventriculomegaly, i.e. hydrocephalus-probably ex vacuo (FIGS. 17A-17D). The most prominent abnormalities observed in the cerebella of ic-STZ-treated rats were: 1) reduced and simplified foliation of the cortex; 2) hypoplasia or aplasia of both external and internal granule cell layers; 3) expansion and disorganization of the Purkinje cell layer; and 4) attenuation of subcortical white matter fiber/tracts (FIGS. 17E-17H). Immunohistochemical staining of Day 7 post-treatment samples revealed prominently increased p53 immunoreactivity (pro-apoptosis molecule) throughout the ic-STZ-treated brains, but particularly in the temporal cortex, hippocampus, hypothalamus/thalamus, white matter, and cerebellum (FIGS. 17I-17J). However, at the 14- and 21-day post-treatment time points, the levels of p53 immunoreactivity in the ic-STZ-treated brains were only slightly increased relative to control, indicating that the wave of apoptosis occurs early and prior to the molecular indices of AD-type neurodegeneration.

Since neurodegeneration is frequently associated with altered architecture and parenchymal remodeling, it is difficult to characterize and quantify cell loss and cellular responses to injury using in situ histological methods. For example, cell loss that results in tissue atrophy may be associated with apparently normal or increased cell densities due to remodeling. To circumvent this problem, a molecular method of detecting and quantifying pathological shifts in cell type associated with injury or degeneration in the brain was developed by measuring the relative mRNA abundance of genes expressed in specific cell types. Steen et al., *J Alzheimers Dis* 7:63 (2005). In the present study, the expression levels of genes that are selectively expressed in neurons (Hu), astrocytes (GFAP), microglia (AIF-1), and oligodendroglia (MAG-1) were examined. Since 18S levels were used as the denominator, this approach enabled a determination of whether the relative abundance of a particular cell type was reduced or increased by the ic-STZ treatment. The results demonstrated that ic-STZ-treated brains had significantly reduced Hu (FIG. 18A) and MAG-1 (FIG. 18B) gene expression, and increased GFAP (FIG. 18C) and AIF-1 (FIG. 18D) expression. In contrast, there were no significant inter-group differences in the mean levels of 18S ribosomal RNA (FIG. 18E).

Intracerebral STZ Impairs Insulin and Insulin-Like Growth Factor Signaling Mechanisms in the Brain:

Exploratory studies demonstrated that STZ significantly impairs growth factor and growth factor receptor expression in several brain regions including the hypothalamus, hippocampus, temporal cortex, and cerebellum. Therefore, results generated with temporal lobe samples are presented as representative of the overall trends. In addition, since the alterations in gene expression were somewhat variable through the first 7 days post ic-STZ treatment, but remained stable between days 14 and 21, results from brains harvested on day 14 after treatment are shown and discussed.

Real time quantitative RT-PCR studies demonstrated expression of mRNA transcripts corresponding to the insulin, IGF-I, and IGF-II receptors in the temporal cortex of both control and ic-STZ-treated rats. However, brains from the ic-STZ-treated group had significantly reduced expression levels of both the insulin and IGF-I receptors relative to control (FIGS. 19A and 19B), whereas similar levels of IGF-II receptor mRNA transcripts were measured in the ic-STZ-treated and control brains (FIG. 19C). Insulin, IGF-I, and IGF-II polypeptide mRNA transcripts were detected in both control and ic-STZ-treated brains, but the mean levels of insulin (FIG. 19D) and IGF-II (FIG. 19F) mRNA transcripts were significantly reduced in the ic-STZ-treated relative to control brains. In contrast, IGF-I mRNA transcripts were similarly abundant in the ic-STZ treated and control groups (FIG. 19E).

Figure 19G:
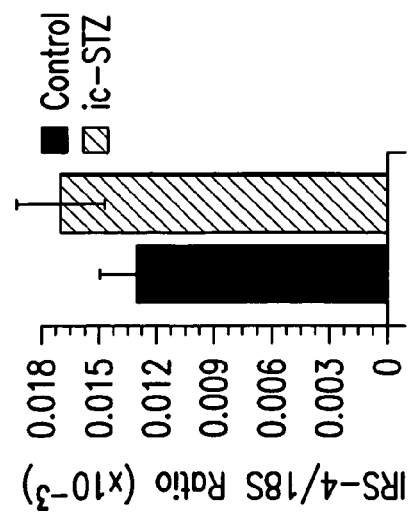
Figure 19H:
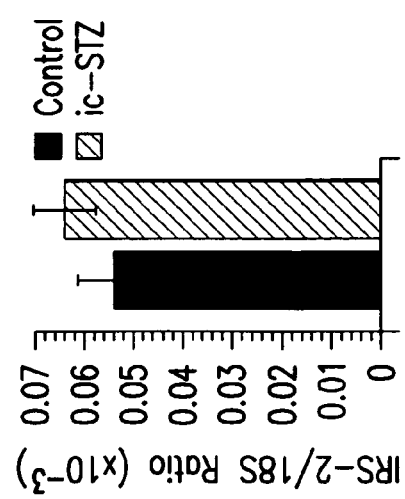
Figure 19I:
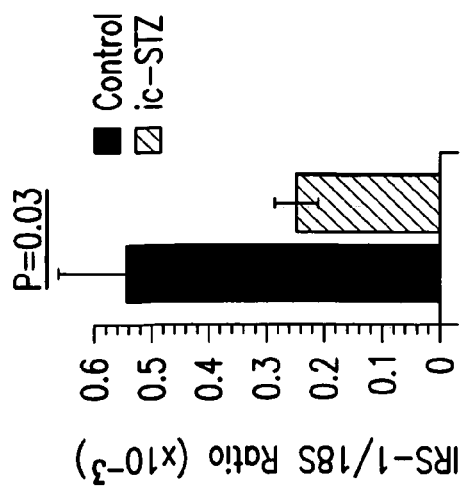

To examine the integrity of signaling pathways that are activated by insulin/IGF-I, IRS-1, IRS-2, and IRS-4 expression levels were measured. IRS-3 was not examined because it is only expressed in rodent adipose tissue. Real time quantitative RT-PCR detected expression of IRS-1, IRS-2, and IRS-4 mRNA transcripts in both control and ic-STZ-treated brains. As reported previously, IRS-1 mRNA transcripts were significantly more abundant than IRS-2 and IRS-4 (P=0.001). In the ic-STZ-treated brains, the mean levels of IRS-1 mRNA were significantly reduced relative to control (P=0.004), whereas the mean levels of IRS-2 and IRS-4 were similar to control (FIGS. 19G-19I).

Analysis of Ligand Binding to Growth Factor Receptors:

Effective ligand binding is critical to the signaling cascade, and many of the downstream effects of impaired insulin signaling that have already been identified in AD, including reduced neuronal survival, increased GSK-3β activation, and increased tau phosphorylation could be mediated by reduced insulin or IGF receptor binding in the CNS. To examine this aspect of growth factor signaling in the ic-STZ-injected brains, competitive equilibrium binding assays were performed using [$^{125}$I]-labeled insulin, IGF-I or IGF-II as tracers and membrane extracts of temporal lobe tissue as the source of receptors. The results demonstrated significantly higher levels of specific binding to the insulin receptor in control relative to ic-STZ-treated brains. Mean equilibrium binding to the insulin receptor was reduced by approximately 85% in the ic-STZ-treated relative to control brains (FIG. 20A). IGF-II binding was also significantly reduced in the ic-STZ-treated brains (FIG. 20C), while IGF-I binding was increased, although the difference was not statistically significant due to the large standard error of the mean (FIG. 20B).

AD-Type Neurodegeneration Following ic-STZ Treatment:

Studies were performed to determine if ic-STZ-induced neurodegeneration was associated with increased activation of GSK-3β (reduced phospho-GSK-3β/total GSK-3β ratio) and increased levels of phospho-tau. Since characteristic features of AD-type neurodegeneration also include increased ubiquitination of proteins, including tau (Godbolt et al., *Arch. Neurol.* 62:1097 (2005); Kosik et al., *Biochim. Biophys. Acta* 1739:298 (2005); de Vrij et al., *Prog. Neurobiol.* 74:249 (2004)) and gliosis associated with cell loss, Western blot analysis was used to measure ubiquitin and GFAP immunoreactivity as well. β-actin expression was measured as a negative control.

Figure 22A:
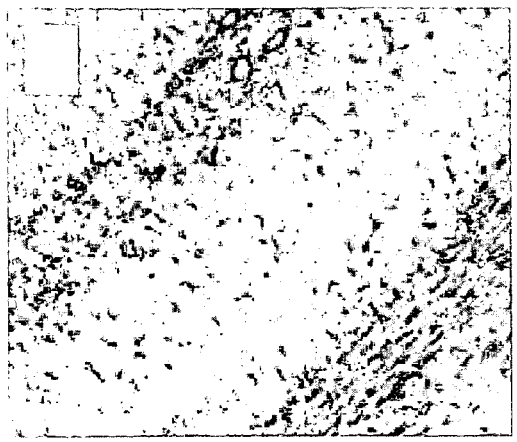
Figure 22B:
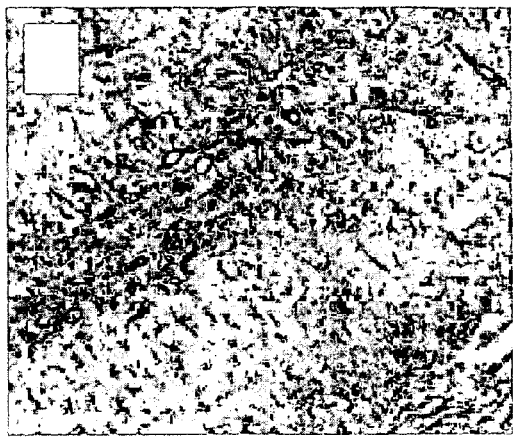
Figure 22C:
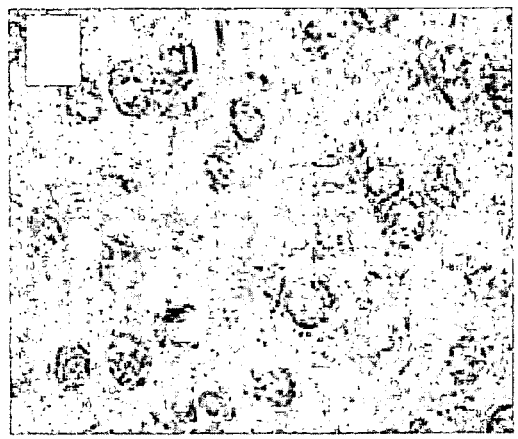
Figure 22D:
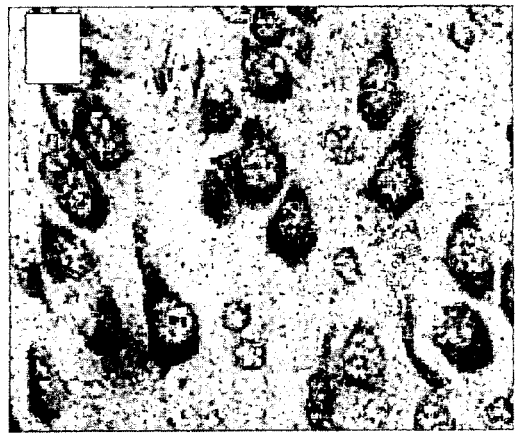
Figure 22E:
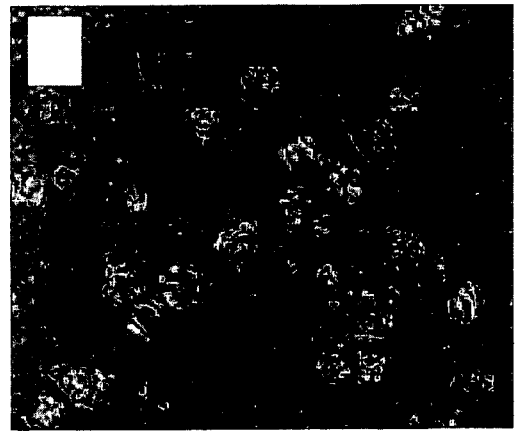
Figure 22F:
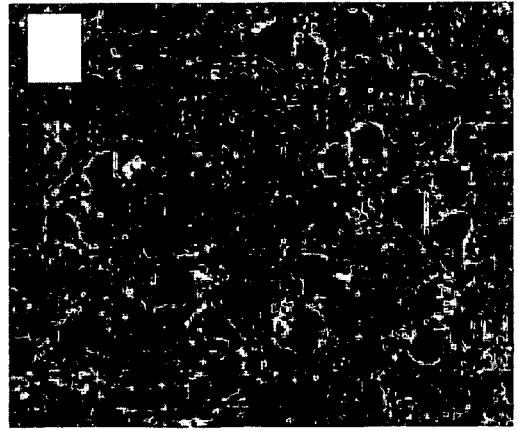
Figure 23A:
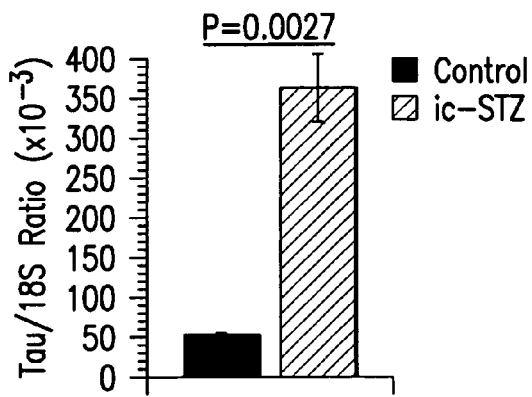
Figure 23B:
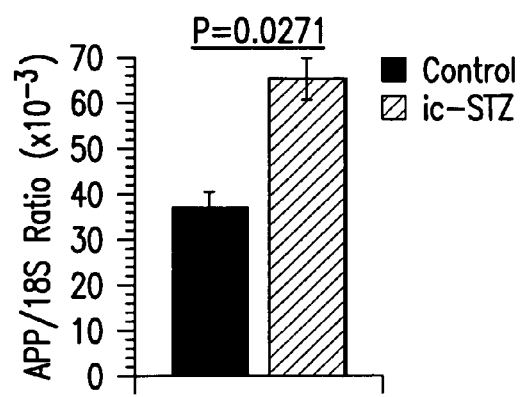
Figure 23C:
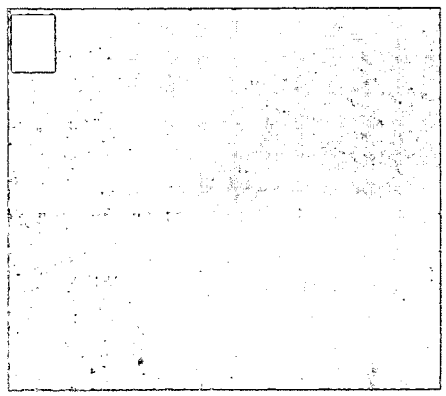
Figure 23D:
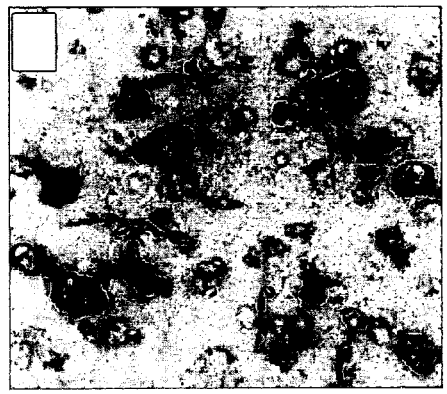
Figure 23E:
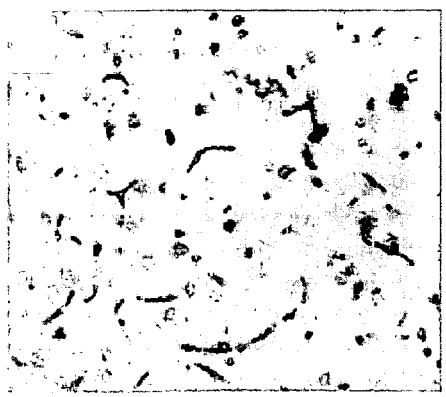
Figure 23F:
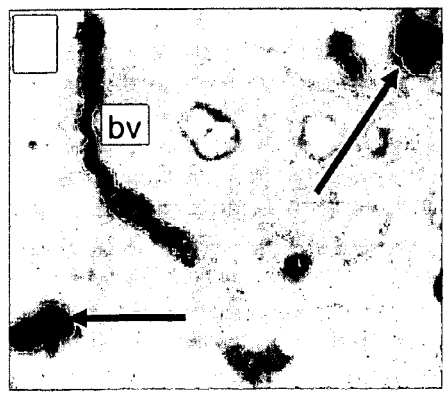

Western blot analyses demonstrated significantly increased levels of GFAP, total GSK-3β, phospho-tau, and ubiquitin, and reduced levels of phospho-GSK-3β in the ic-STZ-treated relative to control brains (FIG. 21 and Table 7). In contrast, tau and β-actin protein expression were similar for the two groups (FIG. 21 and Table 7). The calculated (densitometry units) mean ratios of phospho-GSK-3β/total GSK-3β and phospho-tau/tau were also significantly reduced in the ic-STZ-treated group (Table 7), reflecting significant activation of GSK-3β and increased tau phosphorylation. Immunohistochemical staining demonstrated globally increased GFAP immunoreactivity in the ic-STZ-treated brains, but prominent labeling in the temporal lobe (FIGS. 22A and 22B), hippocampus, hypothalamus/thalamus, and cerebellum, corresponding with the distribution of conspicuously increased p53 immunoreactivity. In the ic-STZ-treated brains, increased phospho-tau and ubiquitin immunoreactivity were observed in the temporal cortex, hippocampus, hypothalamus/thalamus, and cerebellar cortex. Increased phospho-tau immunoreactivity was localized in neuronal cell bodies and clusters of neuropil neurites distributed in the cerebral cortex (FIGS. 22C and 22D). Phospho-tau immunoreactive intra-neuronal inclusions (neurofibrillary tangles) were not observed. Increased ubiquitin immunoreactivity was localized in various cell types in both gray and white matter. Aside from higher densities of cellular labeling, a major difference between the ic-STZ and control groups was the increased localization of ubiquitin immunoreactivity in nuclei of ic-STZ-treated brains (FIGS. 22E and 22F).

TABLE 7

| Protein | Control | ic-STZ | P-Value |
| --- | --- | --- | --- |
| GFAP | 308370 ± 77143 | 983591 ± 113549 | P = 0.002 |
| GSK-3β | 68131 ± 12374 | 149945 ± 15588 | P = 0.0043 |
| p-GSK-3β | 4326 ± 496 | 2811 ± 296 | P = 0.009 |
| p-GSK-3β/GSK-3β | 0.066 ± 0.014 | 0.0204 ± 0.0022 | P = 0.0168 |
| Ubiquitin | 765286 ± 61857 | 1390824 ± 133586 | P = 0.0011 |
| Tau | 606944 ± 24733 | 686442 ± 65138 | P = 0.03 |
| p-Tau | 1129 ± 147 | 3378 ± 920 | P = 0.04 |
| p-Tau/Tau | 0.0016 ± 0.011 | 0.0025 ± 0.038 | P = 0.02 |
| β-Actin | 188261 ± 6302 | 196548 ± 14314 | N.S. |

Values correspond to arbitrary densitometry units (Mean±S.E.M.). Results were analyzed using Student t-tests.

The real time RT-PCR studies demonstrated significantly higher mRNA levels of tau (FIG. 23A) and APP (FIG. 23B) in the ic-STZ-treated brains. In addition, immunohistochemical staining demonstrated increased Aβ immunoreactivity in neurons (FIGS. 23C and 23D), leptomeningeal vessels, cerebral micro-vessels (FIGS. 23E and 23F), and scattered extracellular plaque-like deposits (FIG. 23F) in the ic-STZ-treated relative to control brains. The plaque-like deposits were visible by H&E staining, and they were present to variable degrees in all ic-STZ-treated brains. The Aβ-immunoreactive plaque-like deposits had a dense core rather than a neuritic or fibrillar morphology. The "plaques" were mainly distributed in the cerebral cortex, particularly in the temporal lobes (quite distant from the injection sites), but they were also present in subcortical structures including the hypothalamus/thalamus. Numerous thin-walled microvessels distributed in both cortical and subcortical gray matter structures and cerebral white matter had increased Aβ immunoreactivity. However, unlike AD, the Aβ deposits were not localized in the immediate perivascular spaces. Occasional leptomeningeal microhemorrhages were observed in association with the Aβ angiopathy, but no parenchymal hemorrhages or obvious ischemic or hemorrhagic lesions were detected in the ic-STZ-treated brains.

Relationship Between Impaired Insulin/IGF Signaling and Acetylcholine Production in ic-STZ-Treated Brains:

A major correlate of cognitive impairment in AD is acetylcholine deficiency in the cerebral cortex. Recently, it was demonstrated that ChAT gene expression was regulated by insulin and IGF-1 stimulation, and that in AD brains, impairment of insulin/IGF-1 signaling mechanisms correlates with deficits in acetylcholine production. Steen et al., *J Alzheimers Dis* 7:63 (2005). Therefore, it was of interest to determine if the ic-STZ treated brains had reduced levels of ChAT expression. Real time quantitative RT-PCR analysis of temporal lobe tissue demonstrated significantly reduced levels of ChAT and increased levels of AChE mRNA transcripts in the ic-STZ-treated relative to control brains (FIGS. 24A and 24B). Immunohistochemical staining studies corroborated the real time RT-PCR results by demonstrating decreased levels of ChAT (FIGS. 24C and 24D) and increased levels of ACHE (FIGS. 24E and 24F) immunoreactivity in the ic-STZ-treated relative to control brains. Similar alterations in CHAT and AChE expression were observed in the hypothalamus, hippocampal formation, and cerebellar cortex of the ic-STZ-treated rats.

CONCLUSION

In previous reports, ic-STZ was used to generate a model of sporadic AD in adult rodents, with emphasis on the role of oxidative stress as a mediator of neurodegeneration. These studies investigated the effects of ic-STZ on genes in the insulin and IGF signaling pathways, and examined the associated molecular pathology in the context of what was recently reported about AD. In this regard, the results demonstrated that ic-STZ treatment caused CNS depletion of cells expressing insulin, IGF-II, insulin receptor, and IGF-I receptor, but did not cause hyperglycemia, degeneration of pancreatic islets, or loss of insulin immunoreactivity in the pancreas. Therefore, the ic-STZ model produces CNS and not pancreatic disease, indicating that peripheral and CNS sources of insulin are separately and distinctly regulated. Moreover, this model provides good evidence that impairments in insulin/IGF signaling mechanisms in the CNS can occur in the absence of any peripheral abnormalities in insulin/IGF biosynthesis and function. Finally, in recent preliminary studies of rats that were allowed to survive for 4 weeks or longer after treatment, Morris Water Maze testing revealed striking impairments in learning and memory in the ic-STZ group relative to controls. Overall, this model supports the hypothesis that sporadic AD represents a neuro-endocrine disease caused by intrinsic CNS deficiencies in insulin and IGF polypeptide gene and receptor expression and responsiveness (resistance).

Altogether, the results obtained with the ic-STZ model link impairments in insulin/IGF actions in the brain to prominent dementia-associated abnormalities that closely mimic molecular and pathological indices of neurodegeneration that are characteristically observed in sporadic AD. Moreover, this study provides definitive evidence that impairments in insulin/IGF signaling and deficiencies in the corresponding growth factors can occur in the CNS independent of Type 1 or Type 2 diabetes. In this regard, the data argue strongly in favor of the concept that AD-type neurodegeneration represents an intrinsic neuroendocrine disease caused by selective impairments in insulin and IGF signaling mechanisms, including deficiencies in local insulin production. Three additional concepts stemming from this body of research are that: 1) abnormalities in tau expression and phosphorylation can be mediated by impairments in insulin and IGF signaling; 2) APP gene up-regulation accompanies both sporadic AD and the experimental model of ic-STZ, which resembles sporadic AD; and 3) persistent oxidative stress with activation of microglia is an early event that may play a critical role in exacerbating and perpetuating the AD neurodegeneration cascade. The ic-STZ model appears to be an excellent in vivo tool for studying the cascade of sporadic AD-type neurodegeneration, and could be used for rational design of drugs to treat or prevent AD. A striking feature of the ic-STZ phenotype described herein is that it truly is a model of progressive neurodegeneration. The initial event was the activation of pro-apoptosis molecules (days 3-5). Impairments in insulin/IGF signaling and related gene expression occurred subsequently. This suggests that AD-type neurodegeneration occurs secondary to the loss of insulin- and IGF-producing cells in the brain. The evidence supplied by the both the ic-STZ experimental model and the findings in early AD suggests that the mechanisms and etiologies of impaired insulin/IGF signaling must be addressed in order to make significant progress in the treatment and prevention of sporadic AD.

STZ is nitrosamide methylnitrosourea (MNU) linked to the C2 position of D-glucose. The MNU functions as an alkylating agent that causes DNA damage, while the glucose moiety is taken up as glucose in insulin- (and possibly also IGF-) producing cells. Once metabolized, the N-nitrosoureido is liberated to cause DNA damage through generation of reactive oxygen species such as superoxide, hydrogen peroxide, and nitric oxide. The ic-STZ model of neurodegeneration differs from the effects of oxidative stress-induced CNS injury because, in addition to mitochondrial DNA damage and metabolic dysfunction, ic-STZ causes striking impairments of insulin and IGF signaling mechanisms in the brain. Human brains with genuine AD show unequivocal evidence of oxidative stress, mitochondrial dysfunction, and DNA damage, and since many indices of oxidative stress are detectable early in the course of disease, it is likely that oxidative injury plays an important if not critical role in the pathogenesis of AD. This line of reasoning has been bolstered by the finding of AD-type biochemical and molecular abnormalities in experimental models of oxidative stress, hypoxia, or ischemia, and increased oxidative stress in the context of increased cerebral Aβ deposition, which is not sufficient to cause AD. Yet, there are three reasons to pause in the apparently logical steps toward deducing that oxidative stress is THE answer: 1) the neuropathological lesions caused by hypoxia, ischemia, or acute ischemia-reperfusion in human brains are clearly distinguishable from the neurodegenerative changes associated with cognitive impairment in AD; 2) hypoxic and ischemic injuries are either global or they follow vascular territories with relatively little selectiveness for cell type, whereas AD preferentially damages neurons in corticolimbic structures in the brain; and 3) recent studies of human brains with AD demonstrated prominent impairments in insulin and IGF signaling mechanisms that begin early in the course of disease and worsen with disease progression.

Although experimental depletion of CNS neuronal insulin receptors or IRS-2 which transmits insulin and IGF-I signals causes molecular and biochemical abnormalities similar to those observed in AD, the associated neuropathology is clearly different from AD. The explanation could be that the genetic insulin receptor depletion models lack brain aging and mitochondrial dysfunction which are pivotal in the pathogenesis of AD. In addition, these studies showed that both insulin and IGF signaling mechanisms are impaired in AD, as well as in our ic-STZ model, which does resemble AD. Finally, a role for impaired synaptic plasticity must be incorporated into the hypothetical equation. It is suggested that AD requires three important CNS functional disturbances: 1) perturbation of insulin/IGF signaling, caused by trophic factor deficiency and/or insulin resistance; 2) progressive oxidative stress with mitochondrial dysfunction; and 3) impaired neuronal plasticity caused by inhibition of acetylcholine biosynthesis and homeostasis. It is hypothesized that the ic-STZ model utilized in the present study produced a sporadic-type AD phenotype because the treatment: 1) impaired insulin/IGF signaling due to selective killing of specific growth factor producing cells followed by growth factor responsive cells in the brain; 2) caused progressive oxidative stress, DNA damage, and mitochondrial dysfunction due to the alkylating properties of the drug; and 3) inhibited acetylcholine production during a critical period of CNS neuronal plasticity. The alkylating properties of STZ probably mimic the effects of aging on mitochondrial function and mitochondrial DNA integrity, and the use of pups instead of adult rats may have been instrumental in generating the phenotype due to the high natural levels of CNS neuronal plasticity that exist during early postnatal development.

Example 15

Therapeutic Rescue of Experimental Type 3 Diabetes: Relevance to Sporadic Alzheimer's Disease Methods Experimental Model: Three-day old Long Evans rat pups were given bilateral intra-cerebral (ic) injections of STZ (40 µg/kg) or vehicle as previously described. On the same day, sub-sets of the ic-STZ group were given a single intra-peritoneal injection of vehicle (saline), or a PPAR-$\alpha$ (GW7647; 25 ug/Kg), PPAR-$\delta$ (L-165,041; 2 µg/Kg), or PPAR-$\gamma$ (F-L-Leu; 20 µg/Kg) activator (CalBiochem, Carlsbad, Calif.). The rationale for evaluating the effects of these three classes of PPAR agonists is that initial studies demonstrated similar mean levels of PPAR-$\alpha$, -$\delta$, and -$\gamma$ in control and ic-STZ treated brains, and in the CNS, PPAR-$\delta$ was found to be the most abundant of the PPAR mRNA transcripts (Table 8). The rats were monitored daily, and 4 weeks after the ic-STZ±PPAR agonist treatments, they were sacrificed by isofluorane inhalation, and brains were harvested to examine histopathology, gene expression, and insulin/IGF receptor binding. In addition, at 4 weeks of age, memory and learning were evaluated using a Morris Water Maze (R. W. Hickey, M. Akino, S. Strausbaugh, G. M. De Courten-Myers. Use of the Morris water maze and acoustic startle chamber to evaluate neurologic injury after asphyxial arrest in rats. Pediatr Res 39(1) (1996), 77-84). The procedures and use of rats in these experiments were approved by the Lifespan-Rhode Island Hospital IACUC committee.

Histopathological and Immunohistochemical Staining Studies: Whole fresh brains were immersion fixed in Histofix (Amresco, Solon, Ohio) and then sectioned in the coronal plane along standardized landmarks, embedded in paraffin, and processed for histopathological studies. In addition, fresh brains were sectioned in the coronal plane to obtain a ~3 mm thick slice that flanked the infundibulum. The 3-mm brain slice was snap frozen between two slabs of dry ice, and then stored at −80° C. for later RNA and protein studies. The residual tissue was immersion fixed and processed for histopathological studies. Paraffin-embedded sections of brain (8 µM thick) were stained with hematoxylin and eosin (H&E), and adjacent sections were used for immunohistochemical staining to detect glial fibrillary acidic protein (GFAP), APP-A$\beta$, 8-OHdG, 4-hydroxynonenol (HNE), or choline acetyltransferase (ChAT) to characterize the degree to which PPAR agonist treatment prevents the development of ic-STZ-induced AD-type neurodegeneration. As negative controls for the immunostaining reactions, either the primary antibody was omitted or non-relevant monoclonal antibody to Hepatitis B virus was used in place of the relevant antibody. Immunoreactivity was detected using the avidin-biotin horseradish peroxidase complex method (S. M. de la Monte, T. Luong, T. R. Neely, D. Robinson, J. R. Wands. Mitochondrial DNA damage as a mechanism of cell loss in Alzheimer's disease. Lab Invest 80(8) (2000), 1323-35). All sections were examined under code.

Real Time Quantitative RT-PCR: Total RNA isolated from the temporal lobe, hypothalamus, and cerebellum was reverse transcribed using the AMV First Strand cDNA synthesis kit (Roche Diagnostics Corporation, Indianapolis, Ind.) and random oligodeoxynucleotide primers. The mRNA levels of insulin, IGF-I, and IGF-II growth factors, their corresponding receptors, Tau, amyloid precursor protein (APP), ACHE, and ChAT were measured by real time quantitative RT-PCR amplification using QuantiTect SYBR Green PCR Mix (Qiagen Inc, Valencia, Calif.), gene specific oligodeoxynucleotide primers (Table 9), and the BIO-RAD iCycler iQ Multi-Color RealTime PCR Detection System (Bio-Rad, Hercules, Calif.). In addition, pathological shifts in cell type associated with ic-STZ-mediated neurodegeneration were detected by measuring the mRNA levels of Hu (neurons), GFAP (astrocytes), myelin-associated glycoprotein (MAG-1; oligodendroglia), and allograft inflammatory factor-1 (AIF-1; microglia) (E. J. Rivera, A. Goldin, N. Fulmer, R. Tavares, J. R. Wands, S. M. de la Monte, J. Alzheimers Dis 8(3) (2005), 247-68). Ribosomal 18S RNA levels measured in parallel reactions were used to calculate the relative abundance of each mRNA transcript (J. E. Yeon, S. Califano, J. Xu, J. R. Wands, S. M. De La Monte. Potential role of PTEN phosphatase in ethanol-impaired survival signaling in the liver. Hepatology 38(3) (2003), 703-14, J. Xu, J. Eun Yeon, H. Chang, G. Tison, G. Jun Chen, J. R. Wands, et al. Ethanol impairs insulin-stimulated neuronal survival in the developing brain: Role of PTEN phosphatase. J Biol Chem (2003)). The gene expression levels were measured by real time quantitative RT-PCR Relative mRNA abundance was determined from the ng ratios of specific mRNA to 18S (J. E. Yeon, S.

Califano, J. Xu, J. R. Wands, S. M. De La Monte. Potential role of PTEN phosphatase in ethanol-impaired survival signaling in the liver. Hepatology 38(3) (2003), 703-14, J. Xu, J. Eun Yeon, H. Chang, G. Tison, G. Jun Chen, J. R. Wands, et al. Ethanol impairs insulin-stimulated neuronal survival in the developing brain: Role of PTEN phosphatase. J Biol Chem (2003)).

Receptor Binding Assays: Studies were performed to determine if the PPAR agonist treatments reduced the previously detected ic-STZ mediated impairments in insulin, IGF-I, and IGF-II receptor binding in the brain. Membrane protein extracted from fresh frozen brain tissue was used for competitive equilibrium and saturation binding assays. For total binding in equilibrium binding assays, duplicate samples were incubated in 100 µl reactions containing binding buffer (100 mM HEPES, pH 8.0, 118 mM NaCl, 1.2 mM $MgSO_4$, 8.8 mM dextrose, 5 mM KCl, 1% bovine serum albumin) and 100 nCi/ml of [$^{125}$I] (2000 Ci/mmol; 50 pM) insulin, IGF-I, or IGF-II. To achieve 20% specific binding, insulin receptor binding assays required 100 µg protein, IGF-I binding assays required 25 µg protein per sample, and IGF-II receptor binding assays were performed with 10 µg protein. To measure total binding in saturation binding assays, samples from 8-12 brains per group were pooled in equal proportions, and duplicate samples were incubated in 100 µl reactions containing binding buffer and 0.0031 to 1 µCi/ml of [$^{125}$I] (2000 Ci/mmol) insulin, IGF-I, or IGF-II. To detect non-specific binding in the equilibrium and saturation binding assays, duplicate reactions were incubated with the same concentrations of radiolabeled tracer plus 0.1 µM unlabeled (cold) competitive ligand. After 16 hours incubation at 4° C., bound radiolabeled tracer was precipitated with bovine gamma globulin and polyethylene glycol 8000. The precipitate (bound ligand) and supernatant (free ligand) fractions were counted in an LKB CompuGamma CS Gamma counter. Specific binding was calculated by subtracting fmols of non-specific binding, i.e. amount bound in the presence of excess cold ligand, from total fmols bound in the absence of unlabeled competitive ligand. GraphPad Prism 4 software (San Diego, Calif.) was used to calculate saturation binding (BMAX) and binding affinity (Kd) for each data set.

Western Blot Analysis: Western blot analysis was used to assess the levels of Tau, phospho-Tau, GSK-3β, phospho-GSK-3β, and β-actin in temporal lobe tissue (E. J. Rivera, A. Goldin, N. Fulmer, R. Tavares, J. R. Wands, S. M. de la Monte, J. Alzheimers Dis 8(3) (2005), 247-68). Briefly, samples containing 40 µg protein were fractionated by sodium dodecyl sulfate, polyacrylamide gel electrophoresis (SDS-PAGE) (F. Ausubel, R. Brent, R. Kingston, D. Moore, J. Seidman, J. Smnith, et al. Current Protocols in Molecular Biology. (2000)). and transferred to PVDF membranes. Non-specific binding sites were adsorbed with SuperBlock-TBS (Pierce, Rockford, Ill.). Membranes were incubated over night at 4° C. with primary antibody (0.1-1 µg/ml-individually optimized) diluted in Tris-buffered saline (TBS; 50 mM Tris, 150 mM NaCl, pH 7.4) containing 0.5% bovine serum albumin, 0.05% Tween-20, and 0.025% $NaN_3$ (TBST-BSA). Immunoreactivity was detected using horseradish peroxidase (HRP) conjugated IgG (Pierce, Rockford, Ill.) diluted to 1:50,000 in TBST+0.5% cassein, Western Lightning enhanced chemiluminescence reagents (Perkin Elmer Life Sciences Inc., Boston, Mass.), and digital imaging. Immunoreactivity was quantified using the Kodak Digital Science Imaging Station (NEN Life Sciences, Boston, Mass.).

Morris Water Maze Behavioral Tests: A standard Morris Water Maze was used to measure learning (R. W. Hickey, M. Akino, S. Strausbaugh, G. M. De Courten-Myers. Use of the Morris water maze and acoustic startle chamber to evaluate neurologic injury after asphyxial arrest in rats. Pediatr Res 39(1) (1996), 77-84). On the first day of testing, the rats were oriented to the water maze and educated about the location of the platform. On the 3 subsequent days of testing, the platform was submerged just below the surface, and the rats were tested for their learning and memory of the platform location by measuring the latency period required to reach and recognize the platform. The rats were allowed 120 seconds to locate the platform, after which they were guided to it. After landing on the platform, the rats were allowed to orient themselves for 15 seconds prior to being rescued. The rats were tested three times each day, with 30 min. intervals between trials. The rats were placed in the same quadrant of the water maze for every trial, except for trials 2 and 3 on the final day testing, when the start locations were randomized to test mastery of platform memory.

Source of Reagents: Human recombinant [$^{125}$I] Insulin, IGF-I, and IGF-II were purchased from Amersham Biosciences (Piscataway, N.J.). Unlabeled human insulin was purchased from Sigma-Aldrich (St. Louis, Mo.). Recombinant IGF-I and IGF-II were obtained from Bachem (King of Prussia, Pa.). Antibodies to GSK-3β, and phospho-specific antibodies to GSK-3α/β (Ser21/9) were purchased from Cell Signaling Technology (Beverly, Mass.). Antibodies to Tau, phospho-Tau, APP-Aβ, and β-actin were purchased from CalBiochem (Carlsbad, Calif.). Antibodies to ChAT were purchased from Abcam, Inc. (Cambridge, Mass.). Reagents for immunohistochemical staining were purchased from Vector Laboratories, (Burlingame, Calif.). All other fine chemicals were purchased from CalBiochem or Sigma-Aldrich.

Statistical Analysis: Experiments were conducted using 12-20 rats per group. All studies were repeated at least twice with separate groups of animals. Representative data are depicted as means±S.E.M. in the graphs. Inter-group comparisons were made using Analysis of Variance with post-hoc Fisher Least Significant Difference tests. Statistical analyses were performed using the Number Cruncher Statistical System (Kaysville, Utah). Significant P-values (<0.05) are indicated over the graphs.

Results

Figure 25A:
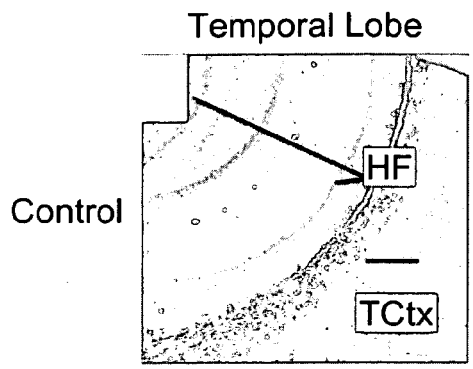
Figure 25B:
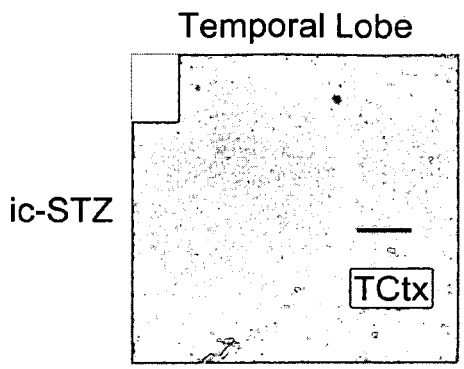
Figure 25C:
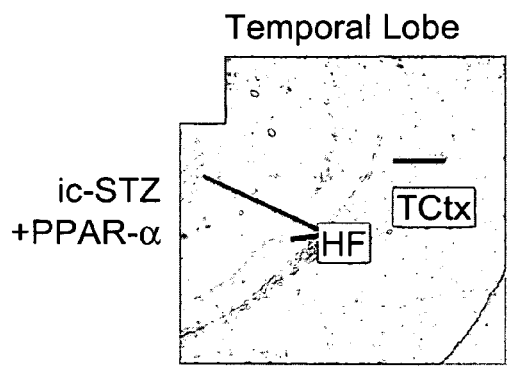
Figure 25D:
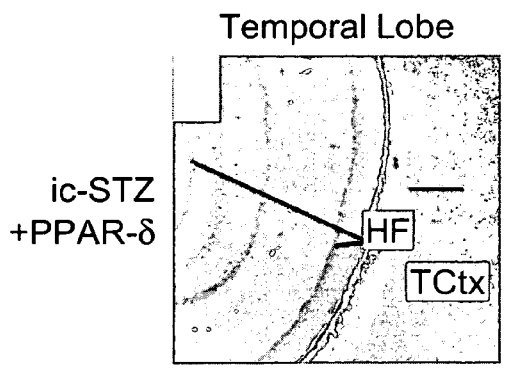
Figure 25E:
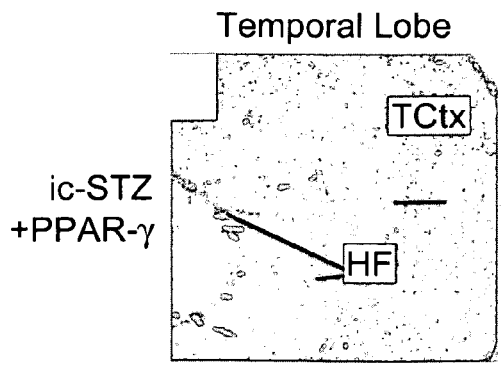
Figure 25F:
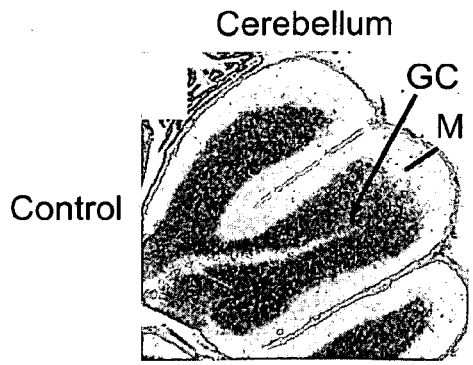
Figure 25G:
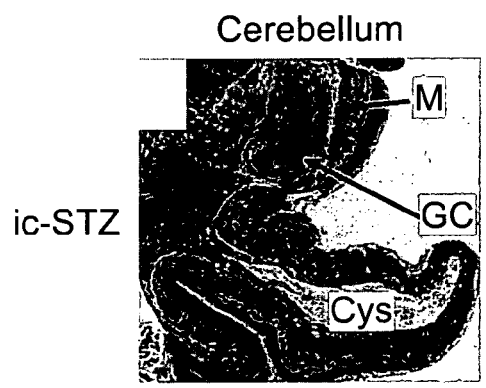
Figure 25H:
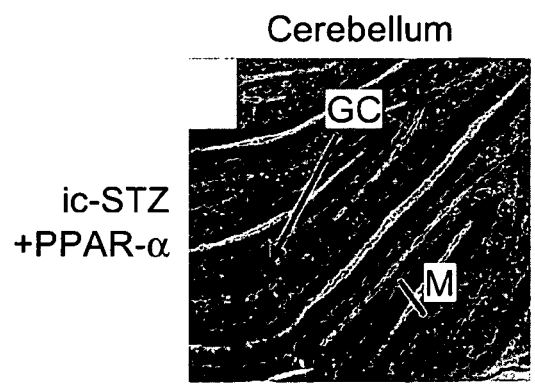
Figure 25I:
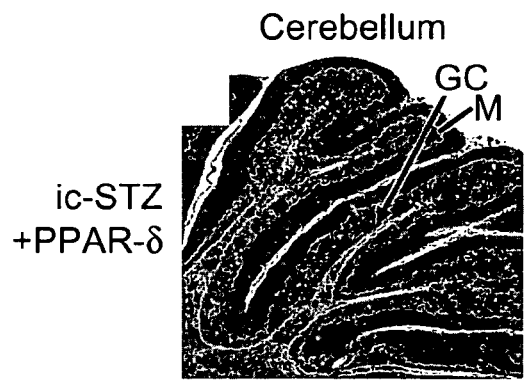
Figure 25J:
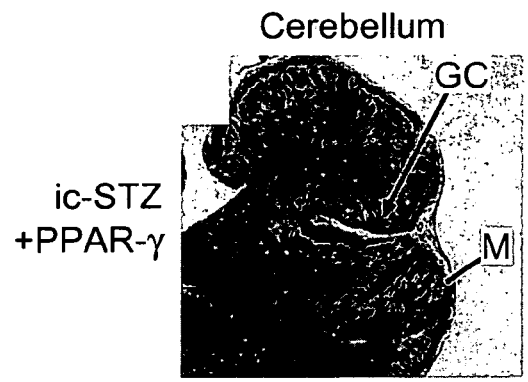
Figure 26G:
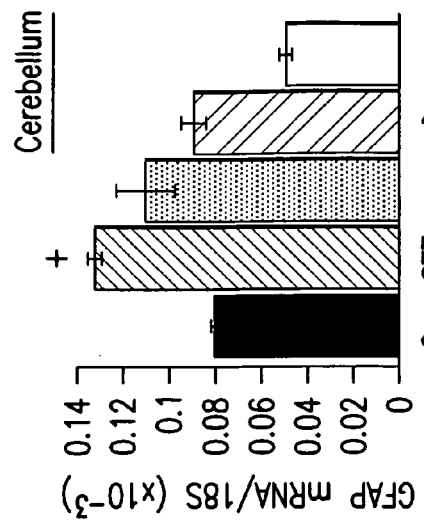
Figure 26H:
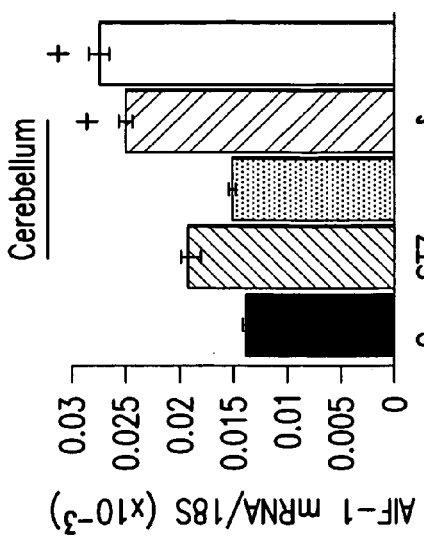
Figure 26I:
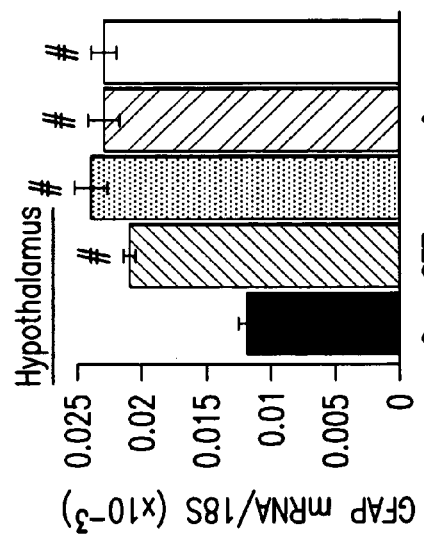
Figure 26J:
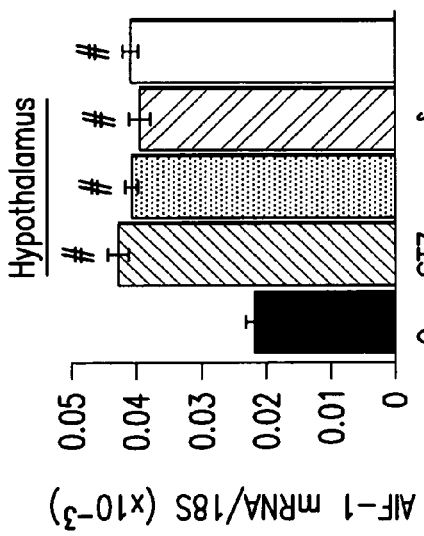
Figure 26K:
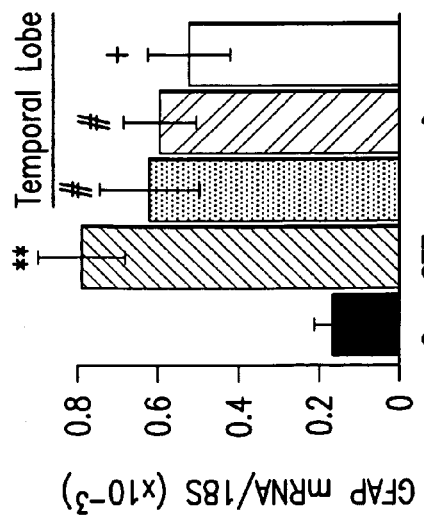
Figure 26L:
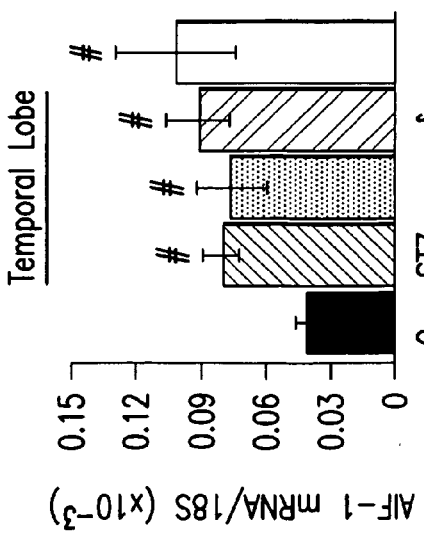

PPAR Agonist Treatments Reduce ic-STZ-induced Neurodegeneration: We have shown that the major CNS abnormalities produced by ic-STZ treatment include brain atrophy with narrowing of the cortical ribbon, reduced volumes of white matter and subcortical nuclei, ventriculomegaly, and cerebellar hypoplasia. The ic-STZ-associated cerebellar abnormalities detected at 14-17 days of age were striking due to the virtual absence of the internal and external granule cell layers, expansion and disorganization of the Purkinje cell layer, and simplification of the folia. The mechanism of ic-STZ-mediated cell loss in the brain was determined to be apoptosis. In the present study, the brains were examined in 4-week old rats when the brains were fully developed. The ic-STZ-treated brains showed degeneration of the hippocampal formation and marked hypoplasia, degeneration, and focal cystic cavitation of the cerebellar cortex (FIGS. 25A, 25B, 25F, 25G). In rats treated with ic-STZ+PPAR-α, -δ, or -γ agonists, many of the abnormalities associated with the ic-STZ treatment were reduced and nearly abrogated as evidenced by the relative preservation of the temporal lobe (including hippocampal formation) and cerebellar cortex architectures (FIGS. 25C-25E, 25H-25J). Treatment with PPAR-δ produced the most striking therapeutic rescue with respect to preserving hippocampi and temporal lobes (FIG. 25D). PPAR-α (FIG. 25C)

was less effective than the PPAR-δ agonist, and the PPAR-γ agonist was least effective (FIG. 25E). With regard to the cerebellar cortex, control rats exhibited the expected lamination with abundant cellularity in the granule cell layer and a thick molecular layer (FIG. 25F). The ic-STZ treatment caused marked thinning of both the granule and molecular layers, and atrophy with cystic degeneration of the cerebellar cortex (FIG. 25G). Treatment with the PPAR-δ and PPAR-α agonists were moderately effective in preserving the cerebellar cortical architecture, although the granule and molecular layers were still thinner than control (FIGS. 25H and 25I). The PPAR-γ agonist was ineffective in preserving the cerebellar architecture following STZ treatment (FIG. 25J).

In previous studies, we used molecular profiling with cell type specific genes to demonstrate that neurodegeneration in AD and in the ic-STZ model was associated with prominent loss of neurons and oligodendroglia, and increased expression of genes corresponding to astrocytes and microglia (E. J. Rivera, A. Goldin, N. Fulmer, R. Tavares, J. R. Wands, S. M. de la Monte, J. Alzheimers Dis 8(3) (2005), 247-68). In the present study, utilizing the same approach, we confirmed that these pathological shifts in cell populations persist in the temporal lobe, hypothalamus, and cerebellar cortex of ic-STZ treated rats (FIGS. 26A-26C). Treatment with PPAR agonists did not prevent the ic-STZ-induced neuronal (Hu gene expression) or oligodendroglial (MAG-1) cell loss, or the astrocyte (GFAP) and microglial cell (AIF-1) proliferation in the temporal lobe (FIG. 26). In contrast, PPAR-A and PPAR-δ agonists significantly increased Hu gene expression (neuronal cell density) in the hypothalamus, and the PPAR-α agonist increased MAG-1 gene expression in the hypothalamus. In the cerebellum, the PPAR-δ and PPAR-γ agonists increased Hu (neurons) and AIF-1 (microglia), and decreased GFAP (astrocytes) expression relative to the ic-STZ-treated group (FIG. 26).

PPAR Agonists Partially Restores Insulin/IGF Receptor Expression, Despite Local CNS Growth Factor Depletion: The mean levels of insulin mRNA were significantly reduced in the temporal lobe, hypothalamus, and cerebellar cortex of all ic-STZ-treated groups relative to control, irrespective of PPAR agonist treatment (FIGS. 27A-27C). IGF-I mRNA levels were also significantly reduced in the temporal lobes of all ic-STZ-treated groups. In contrast, in the hypothalamus and cerebellum, IGF-I mRNA levels were not significantly reduced by ic-STZ, and with respect to the cerebellum, treatment with PPAR-δ or PPAR-γ agonists significantly increased the IGF-I mRNA levels relative to control (FIGS. 27D-27F). Similarly, ic-STZ associated reductions in IGF-II expression were variably prevented by the PPAR-α or PPAR-γ agonist treatments (FIGS. 27G-27I).

Figure 28A:
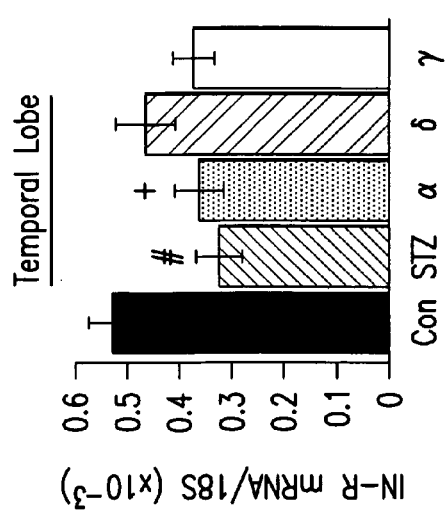
Figure 28B:
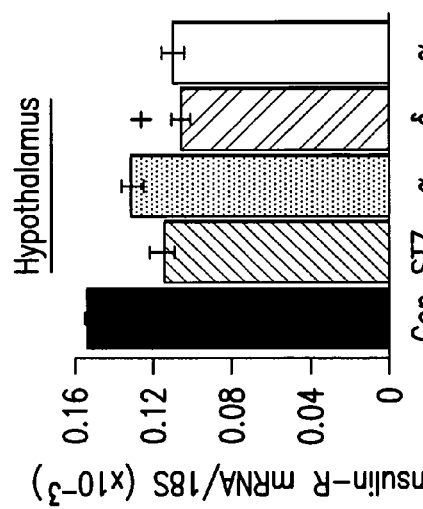
Figure 28C:
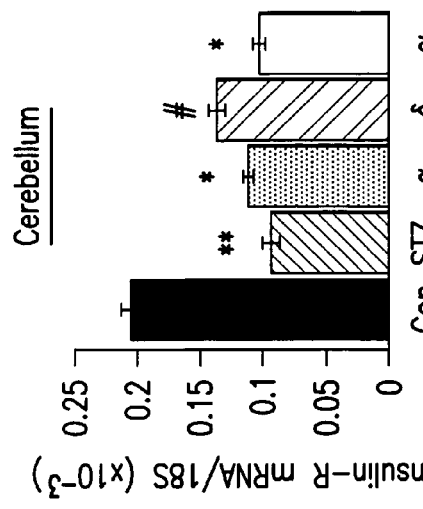
Figure 28D:
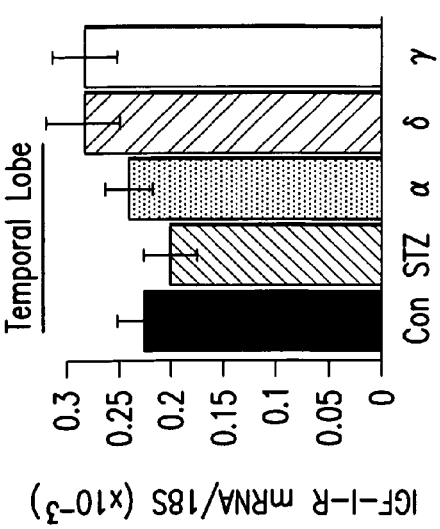
Figure 28E:
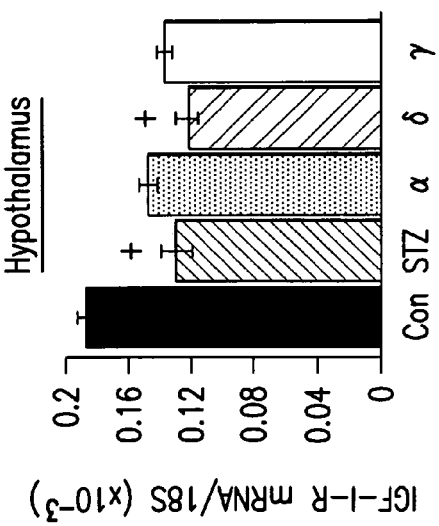
Figure 28F:
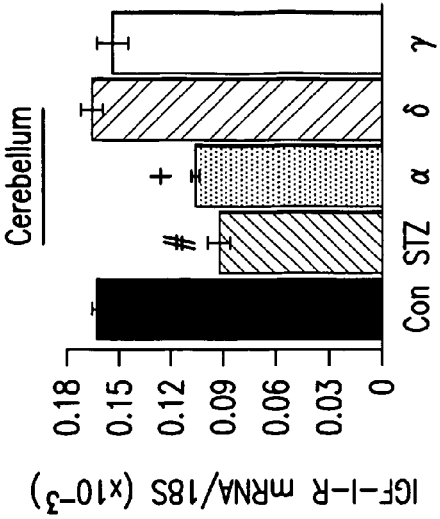
Figure 28G:
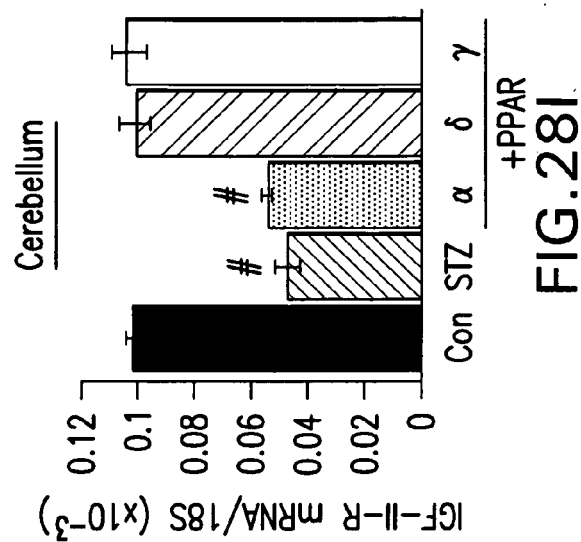
Figure 28H:
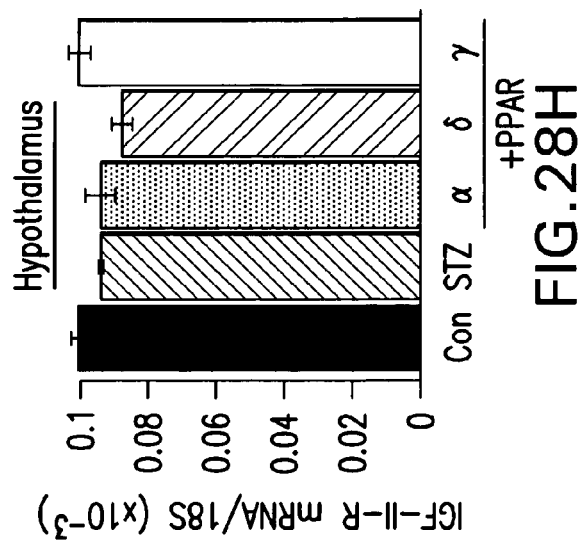
Figure 28I:
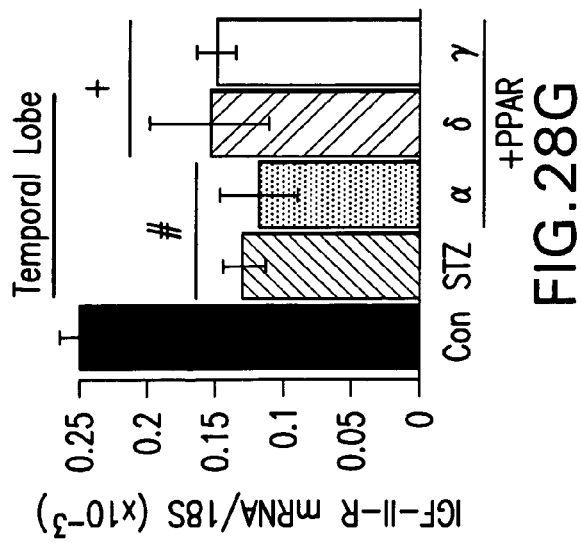

The ic-STZ treatment significantly reduced insulin receptor gene expression in the temporal lobe, hypothalamus, and cerebellum (FIGS. 28A-28C), IGF-I receptor expression in the hypothalamus and cerebellum (FIGS. 28D-28F), and IGF-II receptor expression in the temporal lobe and cerebellum (FIGS. 28G-28I). The ic-STZ treatment did not significantly impair the expression of IGF-I receptor in the temporal lobe, or IGF-II, receptor expression in the hypothalamus. Treatment with PPAR agonists variably increased insulin receptor mRNA levels, but the effects were slight and mainly not statistically significant. In contrast, the ic-STZ+PPAR-δ and ic-STZ+PPAR-γ groups had significantly increased mRNA levels of IGF-I receptor in the temporal lobe and cerebellum (FIGS. 28D-28I), and IGF-II receptor in the cerebellum (FIGS. 28G-28I).

Figure 29A:
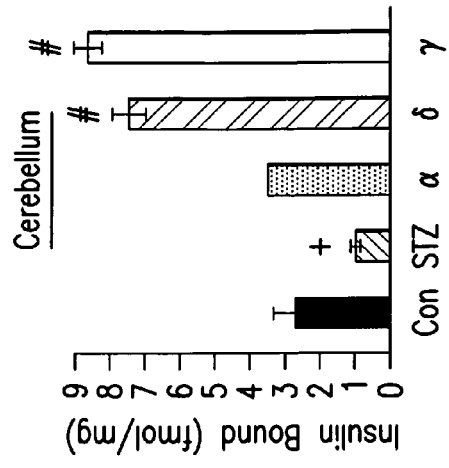
Figure 29B:
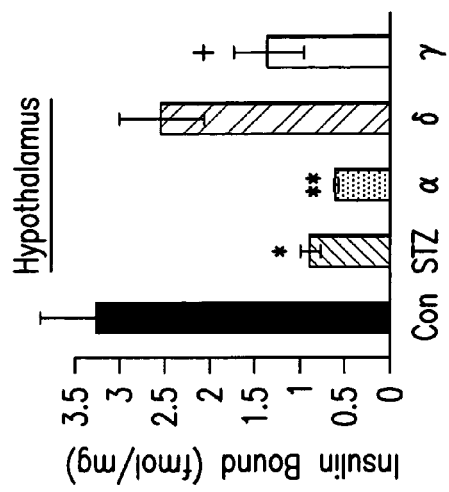
Figure 29C:
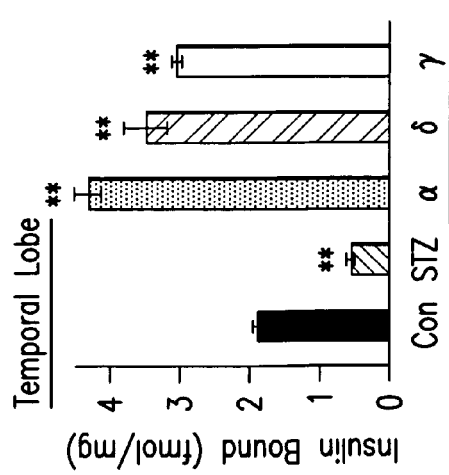
Figure 29D:
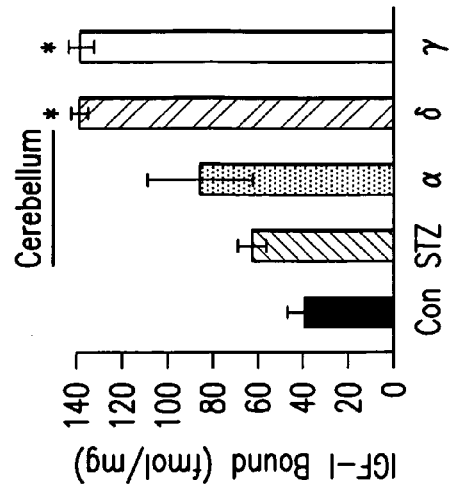
Figure 29E:
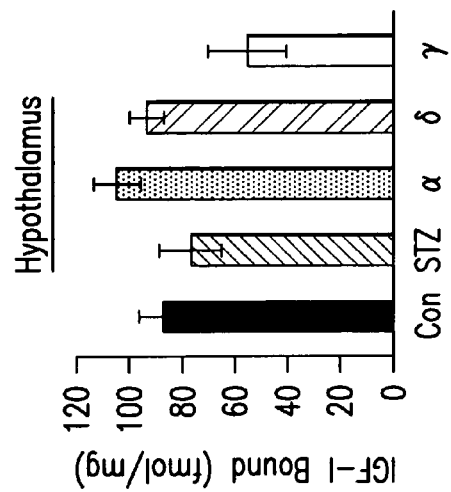
Figure 29F:
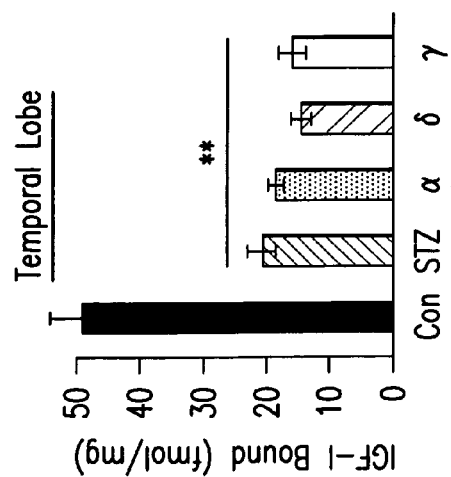
Figure 29I:
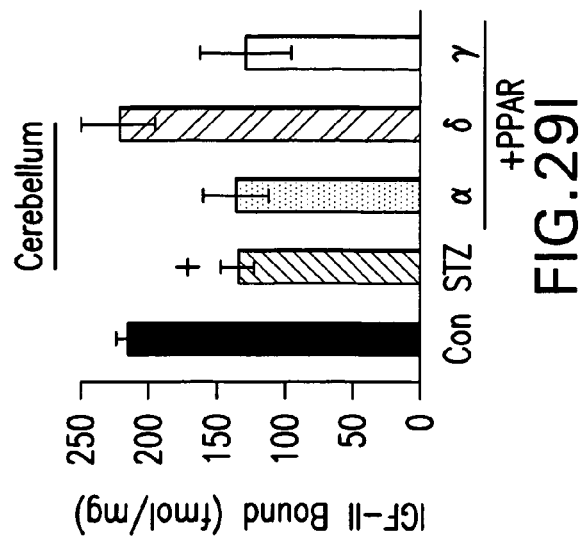
Figure 29H:
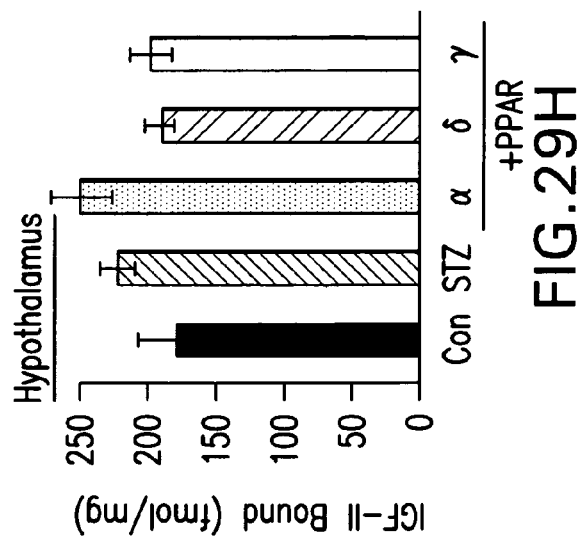
Figure 29G:
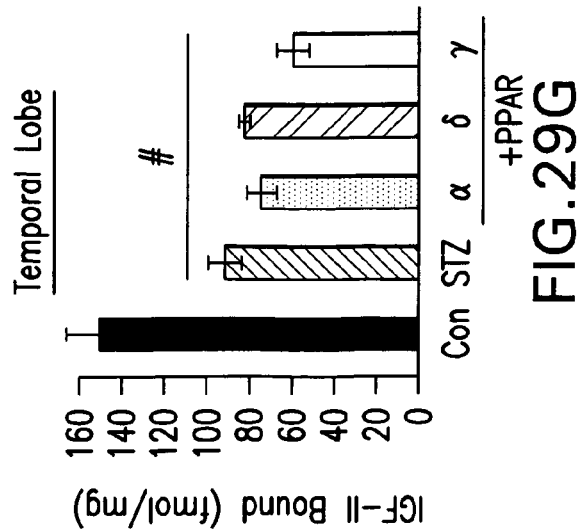

PPAR Agonist Treatment Restores Ligand Binding to Growth Factor Receptors in ic-STZ-Treated Rats: Effective ligand binding is critical to the signaling cascade, and many of the downstream effects of impaired insulin signaling that have already been identified in AD, including reduced neuronal survival, increased GSK-3β activation, and increased Tau phosphorylation could be mediated by reduced insulin or IGF receptor binding in the CNS. The ic-STZ treatment significantly reduced the steady-state levels of insulin receptor binding in the temporal lobe, hypothalamus, and cerebellum (FIGS. 29A-29C). In addition, ic-STZ treatment significantly reduced binding to IGF-I receptors in the temporal lobe but not in the hypothalamus or cerebellum, and it reduced binding to IGF-II receptors in the temporal lobe and cerebellum, but not in the hypothalamus (FIGS. 29D-29F). Treatment with PPAR-α, -δ, or -γ agonists significantly increased the mean levels of insulin receptor binding in the temporal lobe and cerebellum, whereas only the PPAR-δ agonist significantly increased insulin receptor binding in the hypothalamus. The PPAR-δ and PPAR-γ agonists significantly increased IGF-I receptor binding in the cerebellum, and PPAR-δ agonists significantly increased IGF-II receptor binding in the cerebellum of ic-STZ treated relative to control rats (FIGS. 29D-29I).

Competitive saturation binding assays were used to determine if the PPAR agonist treatments altered the top-level binding (BMAX) or binding affinity (Kd) to insulin and IGF receptors in the brain. The graphed data depict mean fmols of insulin, IGF-I, or IGF-II bound per mg of protein, and the calculated 95% confidence interval limits for pooled samples of temporal lobe, hypothalamus, or cerebellar cortex from each experimental group (FIG. 30). The calculated values for BMAX and Kd are presented in Table 10. The results demonstrated higher BMAX values for insulin, IGF-I, and IGF-II receptor binding in the control samples relative to the ic-STZ-treated cases. Although the BMAX levels corresponding to insulin receptor binding were increased by the PPAR agonist treatments, the effects were relatively small such that the differences from control remained statistically significant. The Kd values were significantly lower, i.e. binding affinity was higher in the ic-STZ treated groups, and higher BMAX values were associated with higher Kd's (lower binding affinities) in the ic-STZ+PPAR-α, PPAR-δ and PPAR-γ treated groups (FIGS. 30A-30E and Table 10). Similarly, with respect to IGF-I and IGF-II receptor binding, the major effect of the ic-STZ±PPAR agonist treatment was to reduce both the BMAX and Kd values relative to control, i.e. reduce maximum binding while increasing binding affinity to the receptors. However, treatment with the PPAR-γ agonist increased the BMAX for IGF-I receptor, and the PPAR-δ agonist increased the BMAX for IGF-II receptor to levels that were significantly higher than observed in the ic-STZ treated group (FIGS. 30F-30O and Table 10).

PPAR Agonist Treatment Reduces ic-STZ-Mediated AD-Type Neurodegeneration: In AD, the neuronal cytoskeletal lesions that correlate with dementia, i.e. neurofibrillary tangles, dystrophic neuritis, and neuropil threads, contain insoluble fibrillar structures that are generated in part from hyper-phosphorylated Tau (K. Iqbal, C. Alonso Adel, S. Chen, M. O. Chohan, E. El-Akkad, C. X. Gong, et al. Tau pathology in Alzheimer disease and other tauopathies. Biochim Biophys Acta 1739(2-3) (2005), 198-210). Tau hyperphosphorylation is mediated by increased activation of GSK-3β (S. Lovestone, C. H. Reynolds, D. Latimer, D. R. Davis, B. H. Anderton, J. M. Gallo, et al. Alzheimer's disease-like phosphorylation of the microtubule-associated protein tau by glycogen synthase kinase-3 in transfected mammalian cells. Curr Biol 4(12) (1994), 1077-86, M. Schubert, D. P. Brazil, D. J. Burks, J. A. Kushner, J. Ye, C. L. Flint, et al. Insulin receptor substrate-2 deficiency impairs brain growth and promotes tau phosphorylation. J Neurosci 23(18) (2003), 7084-92, M. Schubert, D. Gautam, D. Surjo, K. Ueki, S. Baudler, D. Schubert, et al. Role for neuronal insulin resistance in neurodegenerative diseases. Proc Natl Acad Sci USA 101(9) (2004), 3100-5), and in AD, high levels of GSK-3β activity and Tau phosphorylation correlate with impairments in insulin and IGF-1 mediated survival signaling (E. Steen, B. M. Terry, E. J. Rivera, J. L. Cannon, T. R. Neely, R. Tavares, et al. Impaired insulin and insulin-like growth factor expression and signaling mechanisms in Alzheimer's disease—is this type 3 diabetes? J Alzheimers Dis 7(1) (2005), 63-80). In addition, recent studies demonstrated increased levels of activated GSK-3β (reduced phospho-GSK-3β/total GSK-3β ratio) and phospho-Tau in rat brains with ic-STZ-induced neurodegeneration. Therefore, it was of interest to characterize the effects of PPAR agonists on GSK-3β activity and Tau phosphorylation in ic-STZ-treated brains. The levels of phospho-GSK-3β, GSK-3β, phospho-Tau, Tau, and β-actin (negative control) were examined in temporal lobe and hypothalamus homogenates by Western blot analysis. Immunoreactivity was detected and quantified by digital imaging, and the mean levels of protein expression and ratios of phospho-GSK-3β/GSK-3β and phospho-Tau/Tau measured in 4 replicate samples are depicted graphically (FIG. 31). Phospho-GSK-3β immunoreactivity was detected with antibodies directed against the Ser21/9 motif, corresponding to the inactivate form of the kinase.

In the hypothalamus of ic-STZ-treated rats, the levels of phospho-GSK-3β were similar to control. Treatment with the PPAR-α or PPAR-δ agonist significantly increased the levels of phospho-GSK-3β, whereas treatment with the PPAR-γ agonist significantly reduced the mean level of phospho-GSK-3β (FIG. 31A). Total GSK-3β protein expression was significantly increased in the ic-STZ+PPAR agonist treated groups (FIG. 31C) and the phospho-GSK-3β/GSK-3β ratios were significantly reduced relative to control in the ic-STZ±PPAR agonist treated groups (FIG. 31D). Therefore, relatively higher levels of GSK-3β activity were detected in ic-STZ-treated brains, irrespective of PPAR agonist treatment. Similar results were obtained with temporal lobe protein samples.

Figure 31B:
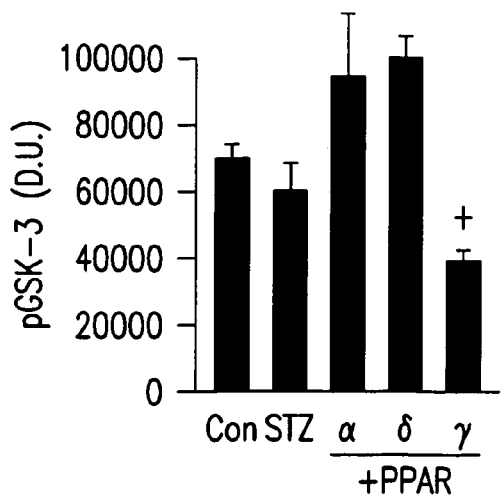
Figure 31F:
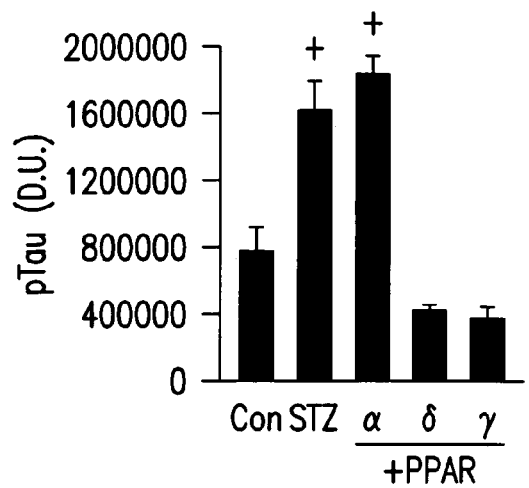
Figure 31C:
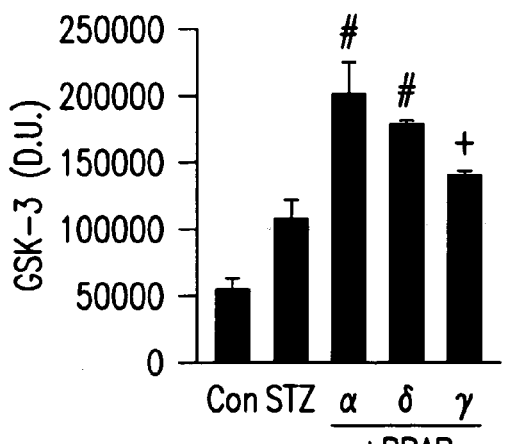
Figure 31G:
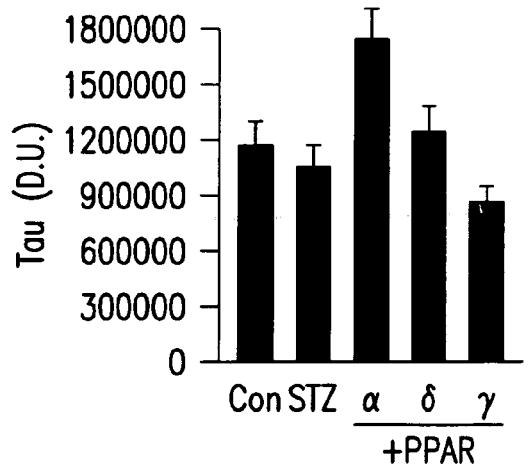
Figure 31D:
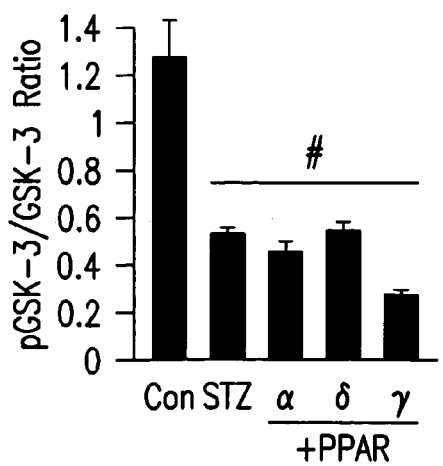
Figure 31H:
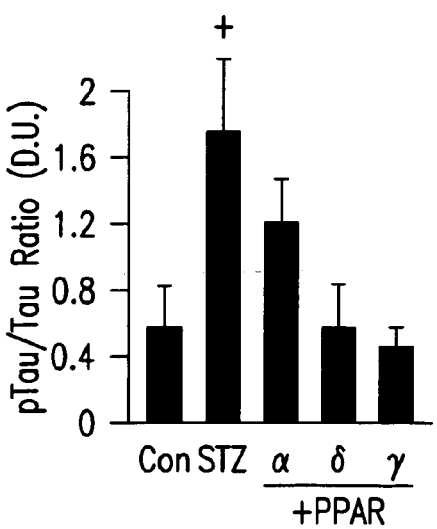

Phospho-Tau levels were significantly higher in ic-STZ and ic-STZ+PPAR-α agonist treated relative to control brains (FIG. 31F). In contrast, phospho-Tau levels were moderately reduced in the ic-STZ+PPAR-δ and ic-STZ+PPAR-γ agonist treated relative to control brains (FIG. 31F). Total Tau protein levels were similar among the groups, except for the ic-STZ+PPAR-α agonist treated group, which had slightly higher levels of Tau relative to all other groups (FIG. 31G). The ic-STZ treated group had significantly higher mean pTau/Tau ratios relative to control, whereas treatment with a PPAR agonist reduced the pTau/Tau to levels that were not significantly different from control (FIG. 31H). Similar observations were made with respect to the temporal lobe samples. As a negative control, the blots were stripped and re-probed with antibodies to β-actin (FIGS. 31A and 31E).

Figure 32A:
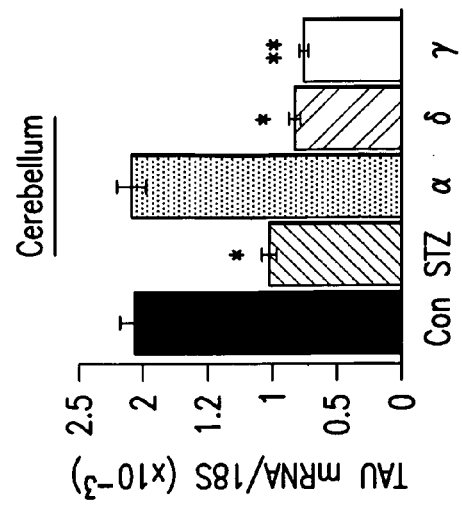
Figure 32B:
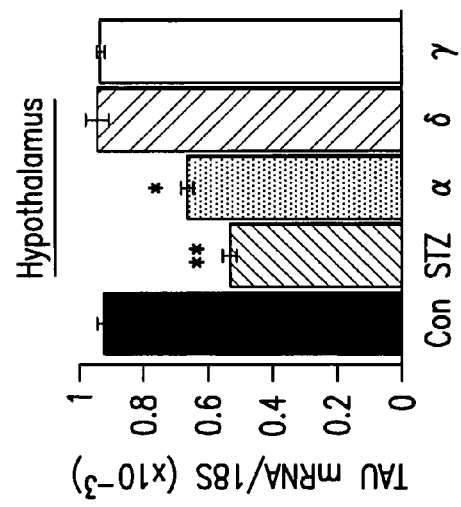
Figure 32C:
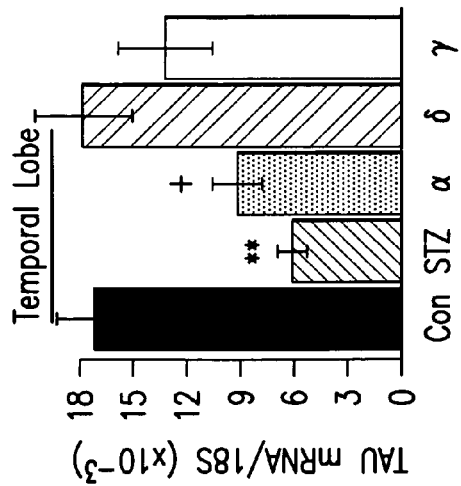
Figure 32D:
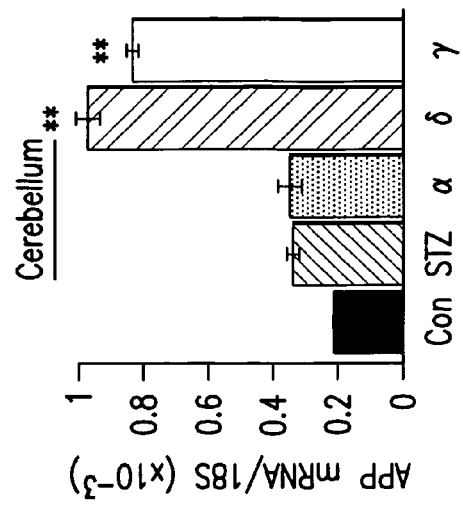
Figure 32E:
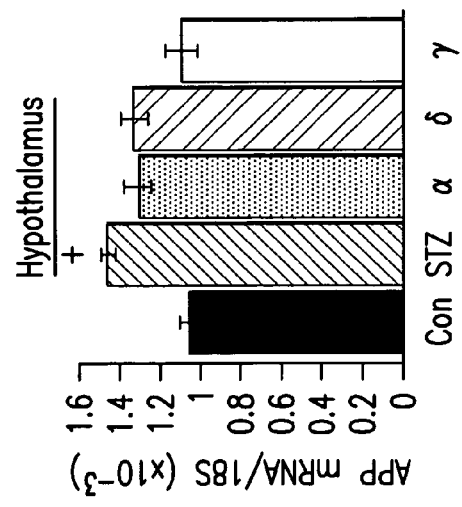
Figure 32F:
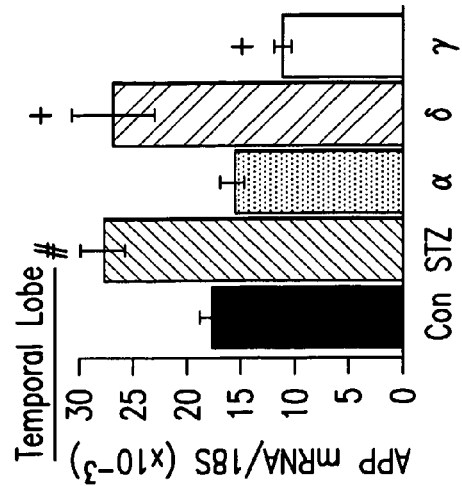
Figure 33A:
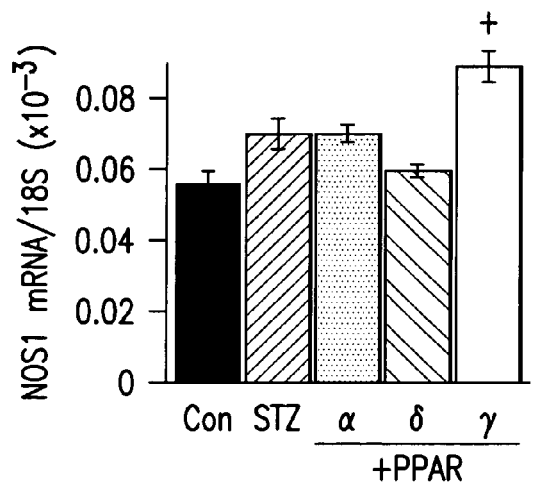
Figure 33D:
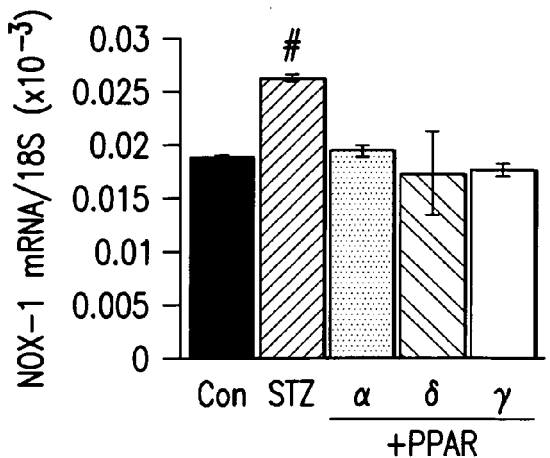
Figure 33B:
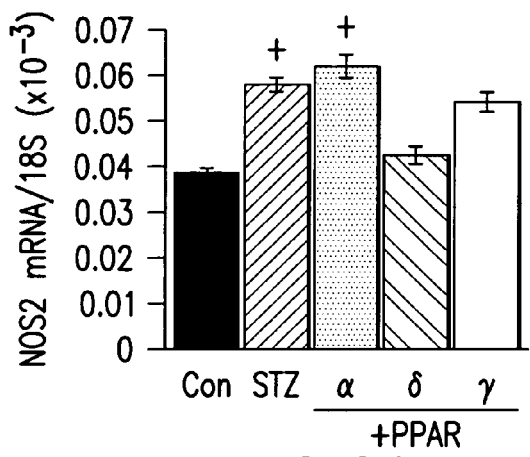
Figure 33E:
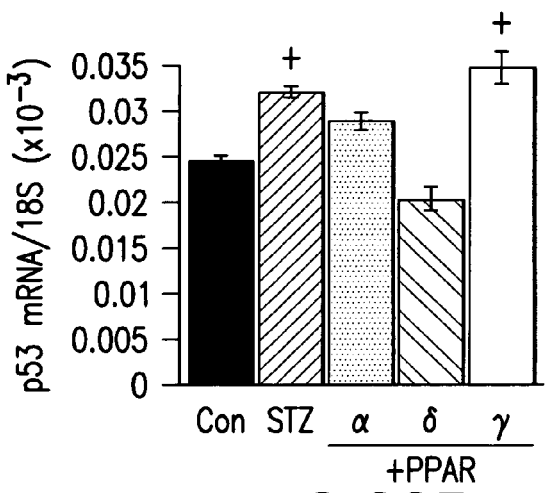
Figure 33C:
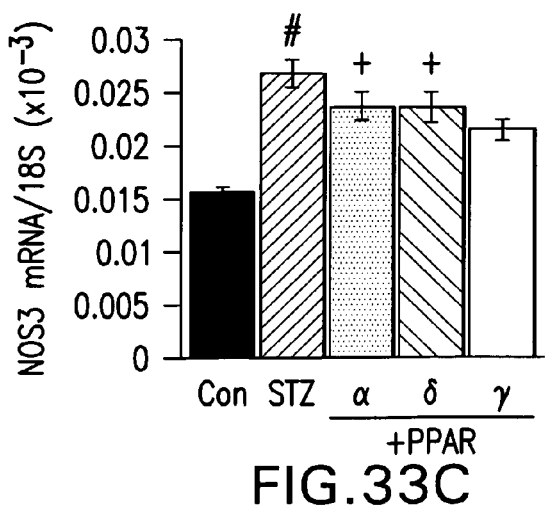

Previous studies demonstrated that Tau, but not APP mRNA was regulated by insulin/IGF-I stimulation (S. M. de la Monte, G. J. Chen, E. Rivera, J. R. Wands. Neuronal thread protein regulation and interaction with microtubule-associated proteins in SH-Sy5y neuronal cells. Cell Mol Life Sci 60(12) (2003), 2679-91, M. Hong, V. M. Lee. Insulin and insulin-like growth factor-1 regulate tau phosphorylation in cultured human neurons. J Biol Chem 272(31) (1997), 19547-53), and that Tau mRNA levels were reduced whereas APP mRNA levels were increased in both AD (E. Steen, B. M. Terry, E. J. Rivera, J. L. Cannon, T. R. Neely, R. Tavares, et al. Impaired insulin and insulin-like growth factor expression and signaling mechanisms in Alzheimer's disease—is this type 3 diabetes? J Alzheimers Dis 7(1) (2005), 63-80, E. J. Rivera, A. Goldin, N. Fulmer, R. Tavares, J. R. Wands, S. M. de la Monte. Insulin and insulin-like growth factor expression and function deteriorate with progression of Alzheimer's disease: Link to brain reductions in acetylcholine. J Alz Dis 8 (2005), E. J. Rivera, A. Goldin, N. Fulmer, R. Tavares, J. R. Wands, S. M. de la Monte, J. Alzheimers Dis 8(3) (2005), 247-68) and ic-STZ-treated brains. Therefore, further studies were conducted to determine the extent to which the PPAR agonist treatments restored Tau and APP gene expression to control levels in brains treated with ic-STZ. Real time quantitative RT-PCR analysis demonstrated significantly reduced levels of Tau (FIGS. 32A-32C) and increased levels of APP (FIGS. 32D-32F) mRNA in the temporal lobe, hypothalamus, and cerebellar cortex of ic-STZ treated relative to control rats. The PPAR agonist treatments had variable effects on the levels of Tau and APP gene expression in the different brain regions examined. The major findings were that the PPAR-δ and PPAR-γ agonists restored Tau gene expression to control levels in the temporal lobe and hypothalamus, and the PPAR-α and/or PPAR-γ agonists significantly reduced APP gene expression in the temporal lobe and hypothalamus of ic-STZ-treated rats (FIGS. 32D, 32E). However, APP mRNA levels were significantly higher in the cerebella of ic-STZ+PPAR-δ and ic-STZ+PPAR-γ agonist treated relative to control and ic-STZ treated rats (FIG. 32F).

PPAR Agonist Treatments Partially Restore Acetylcholine Homeostasis Mechanisms in the ic-STZ Model: A major correlate of cognitive impairment in AD is acetylcholine deficiency in the cerebral cortex. Recently, we demonstrated that ChAT gene expression was regulated by insulin and IGF-1 stimulation, and that in AD as well as in the ic-STZ model, impaired insulin and IGF-1 signaling mechanisms correlate with deficits in acetylcholine production (E. J. Rivera, A. Goldin, N. Fulmer, R. Tavares, J. R. Wands, S. M. de la Monte, J. Alzheimers Dis 8(3) (2005), 247-68). Therefore, it was of interest to determine if the PPAR agonist treatments restored acetylcholine homeostasis in the ic-STZ model. Real time quantitative RT-PCR analyses demonstrated significantly reduced levels of ChAT mRNA in the temporal lobe and cerebellum, but not in the hypothalamus of ic-STZ-treated rats (FIGS. 32G-32I). Treatment with PPAR-α, -δ, or -γ agonists significantly increased ChAT expression in the cerebellum but not in the temporal lobes of the ic-STZ treated rats. Acetylcholinesterase (ACHE) expression, which negatively regulates acetylcholine levels, was significantly reduced in the temporal lobe, and significantly increased in the hypothalamus of ic-STZ treated rats (FIGS. 32J-32L). The PPAR agonist treatments did not significantly alter the expression of ACHE in the temporal lobes. However, with respect to the hypothalamus, ACHE mRNA levels were significantly increased in the ic-STZ+PPAR-δ and ic-STZ+PPAR-γ agonist treated groups, and in the cerebellum, ACHE mRNA expression was significantly reduced compared with the levels observed after ic-STZ treatment alone (FIGS. 32J-32L).

Effects of PPAR Agonist Treatments on Oxidative Stress and Pro-Apoptosis Mechanisms: Recent studies demonstrated significantly increased expression of the p53 pro-apoptosis gene, all 3 isoforms of nitric oxide synthase (NOS 1-3), and NADPH-oxidase (NOX) 1 and NOX 3 in AD brains, beginning early in the course of disease. In this regard, it is noteworthy that STZ is nitrosamide methylnitrosourea that functions as an alkylating agent and causes DNA damage through the generation of reactive oxygen species such as superoxide, hydrogen peroxide, and nitric oxide (A. D. Bolzan, M. S. Bianchi. Genotoxicity of streptozotocin. Mutat Res 512(2-3) (2002), 121-34., T. Szkudelski. The mechanism of alloxan and streptozotocin action in B cells of the rat pancreas. Physiol Res 50(6) (2001), 537-46). To determine if the ic-STZ treatment caused oxidative stress of the types seen in AD, real time quantitative RT-PCR analysis was used to measure the expression levels of p53, NOS 1-3 and NOX 1 and 3 in temporal lobe samples. The studies demonstrated significantly increased mean levels of NOS 2, NOS 3, NOX 1, and p53 in the ic-STZ-treated group (FIGS. 33A-33E). Treatment with the PPAR-δ agonist reduced the NOS 2, NOX 1 and p53 mRNA expression to levels that were comparable to control. In addition, treatment with the PPAR-α or PPAR-γ agonist significantly reduced NOX 1 expression in ic-STZ-treated brains.

Increased levels of 8-OHdG and 4-hydroxynonenol (HNE) have been detected in brains with AD (W. R. Markesbery, J. M. Carney. Oxidative alterations in Alzheimer's disease. Brain Pathol 9(1) (1999), 133-46, L. M. Sayre, D. A. Zelasko, P. L. Harris, G. Perry, R. G. Salomon, M. A. Smith. 4-Hydroxynonenal-derived advanced lipid peroxidation end products are increased in Alzheimer's disease. J Neurochem 68(5) (1997), 2092-7). Since 8-OHdG is incorporated into DNA during repair and can serve as a marker of oxidative damage, and HNE is an abundant, highly toxic lipid-derived aldehyde that is generated by lipid peroxidation, the findings of increased immunoreactivity corresponding to these compounds in AD brains suggests roles for chronic DNA damage and lipid peroxidation in AD type neurodegeneration. Therefore, further studies were used to determine the extent to which the PPAR agonist treatments reduced DNA damage and lipid peroxidation in ic-STZ treated rats. In addition, it was of interest to relate indices of oxidative stress to GFAP immunoreactivity, which reflects astrocytic responses to tissue injury. Paraffin-embedded histological sections of brain were immunostained to detect GFAP, 8-OHdG or HNE using the ABC method with DAB as the chromogen (brown precipitate) and light hematoxylin as the counterstain. Increased levels of GFAP (FIGS. 34A-34B), HNE (FIGS. 34F-34G), and 8-OHdG (FIGS. 34K-34L) immunoreactivity were detected in neuronal and glial cells within the temporal cortex of ic-STZ treated relative to control rats. Treatment with the PPAR-δ agonist conspicuously reduced the levels of GFAP (FIG. 34D), HNE (FIG. 34I), and 8-OHdG (FIG. 34N) immunoreactivity relative to ic-STZ treatment. HNE immunoreactivity was also moderately reduced in the ic-STZ+PPAR-γ agonist (FIG. 34J) relative to the ic-STZ treated group. In contrast, the PPAR-α agonist had no clear effect on the levels of GFAP or HNE immunoreactivity in the temporal lobes of ic-STZ treated rats (FIGS. 34B-34C and 34G-34H). However, treatment with a PPAR-α, PPAR-δ, or PPAR-γ agonist conspicuously reduced the levels of 8-OHdG immunoreactivity (FIGS. 34M-34O).

Chat immunoreactivity was most prominent in neuropil fibers and large neurons in the basal forebrain region of control brains (FIG. 34P), although ChAT immunoreactivity was also readily detected in the temporal cortex (data not shown). The ic-STZ treatment resulted in markedly reduced levels of ChAT immunoreactivity in the basal forebrain region (FIG. 34Q). In the ic-STZ+PPAR-α, ic-STZ+PPAR-6, and ic-STZ+PPAR-γ groups, the levels of CHAT immunoreactivity in the basal forebrain region were variably increased relative to ic-STZ treatment alone, but they were still reduced relative to control (FIGS. 34R-34T). Similar observations were made with respect to the temporal lobe (data not shown).

Figure 35A:
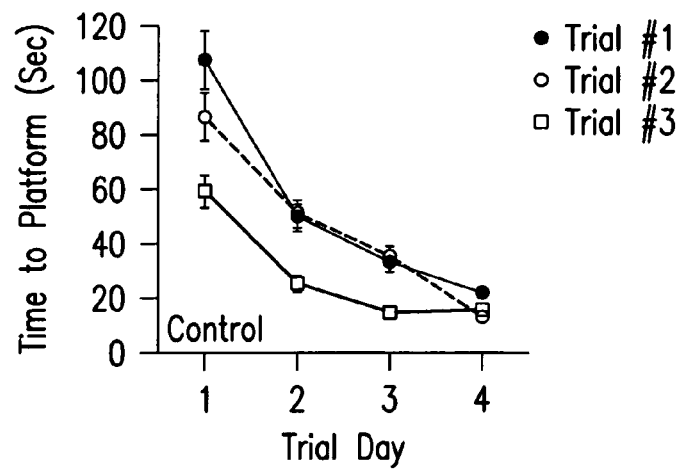
Figure 35B:
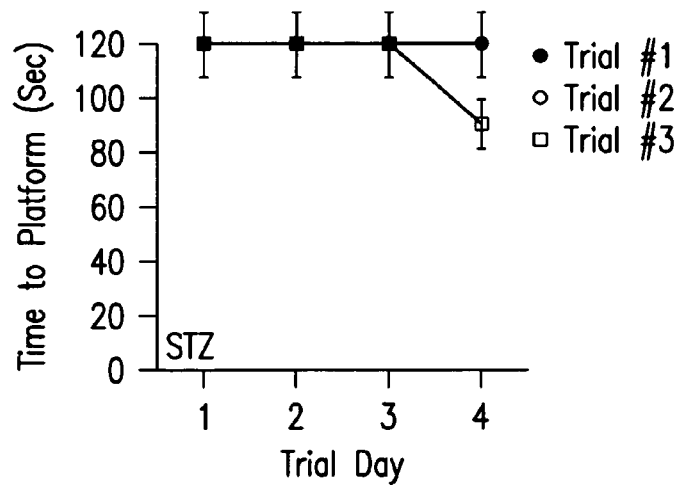
Figure 35C:
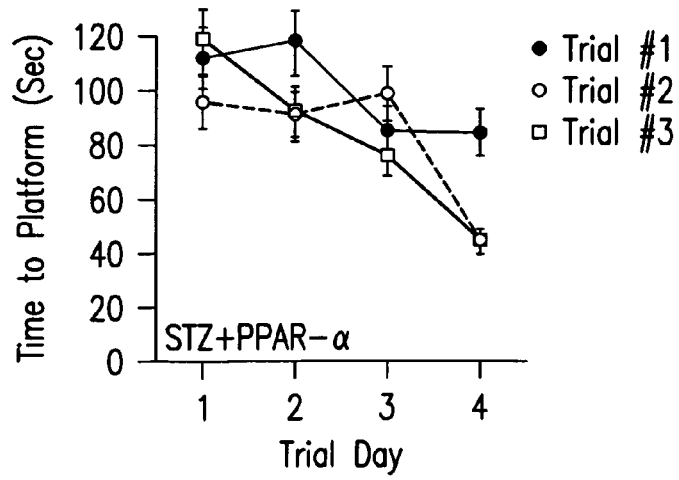
Figure 35D:
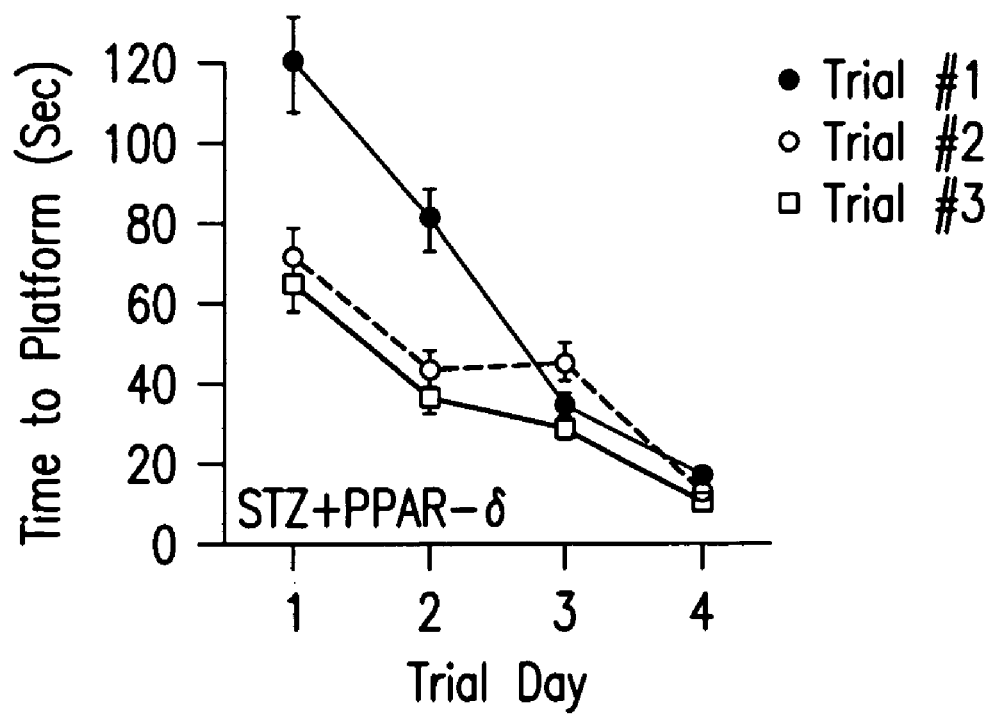
Figure 35E:
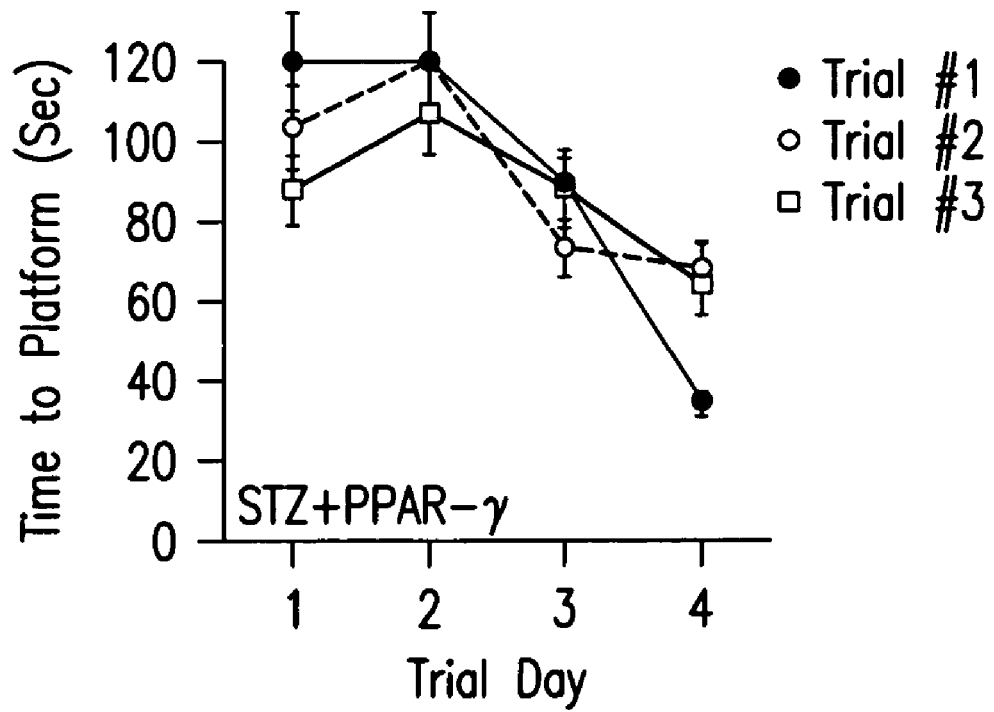

Effects of PPAR Agonist Treatment Learning and Memory in ic-STZ-Treated Rats: Learning and memory were assessed by measuring the latency periods required to recall and reach the location of the submerged platform in a Morris Water Maze. Within the first 3 days of testing, the mean latency period for the ic-STZ injected rats was approximately twice as long as control. However, by the fourth day, no significant differences in mean latency were detected between the ic-STZ and control groups (FIGS. 35A-35B). Therefore, although the ic-STZ treated rats had greater difficulty recalling the location of the platform relative to controls, they eventually learned over time through continuous reinforcement. The ic-STZ treated rats also had difficulty recalling the platform rescue event in that, after they eventually located the hidden platform, they immediately jumped back into the water rather than await rescue. Rats treated with ic-STZ+PPAR-α or ic-STZ+PPAR-γ agonists also exhibited delayed learning and impaired memory during the training period, but by the final period of testing, their performances were similar to control (FIGS. 35C and 35E). In contrast, the ic-STZ+PPAR-δ activator treated group exhibited no detectable abnormalities in behavior, learning, or memory during the trial and final testing period, such that their performances at all stages of testing were not significantly different from control (FIG. 35D). The mean latency period required to arrive at the hidden platform on Trial Day 4 was significantly higher in the ic-STZ, ic-STZ+PPAR-α and ic-STZ+PPAR-γ agonist treated relative to control (FIG. 35F). In contrast, there was no significant difference between the control and ic-STZ+PPAR-δ agonist treated groups with respect to the mean latency periods measured on the final day of testing.

Discussion

The results obtained with the ic-STZ model link impairments in insulin/IGF actions in the brain to prominent dementia-associated abnormalities that closely mimic molecular and pathological indices of AD-type neurodegeneration (E. Steen, B. M. Terry, E. J. Rivera, J. L. Cannon, T. R. Neely, R. Tavares, et al. Impaired insulin and insulin-like growth factor expression and signaling mechanisms in Alzheimer's disease—is this type 3 diabetes? J Alzheimers Dis 7(1) (2005), 63-80, E. J. Rivera, A. Goldin, N. Fulmer, R. Tavares, J. R. Wands, S. M. de la Monte, J. Alzheimers Dis 8(3) (2005), 247-68). Moreover, the findings provide evidence that, impairments in insulin/IGF signaling, and deficiencies in the corresponding growth factors in the CNS impair learning and memory. Since the ic-STZ-mediated CNS abnormalities are not associated with destruction of pancreatic islets or hyperglycemia, the data argue strongly in favor of the concept that AD-type neurodegeneration represents an intrinsic neuroendocrine disease caused by selective impairments in insulin and IGF signaling mechanisms, due to deficiencies in local insulin and IGF production, and insulin and IGF resistance. The PPAR agonist rescue results support this hypothesis since these insulin sensitizer agents function at the level of the nucleus to activate insulin-responsive genes and signaling mechanisms. One unexpected finding was that in addition to preserving insulin-receptor positive (responsive) cells, IGF-II receptor bearing cells were also relatively preserved, despite deficiencies in the local CNS production of these growth factors. This suggests that in the brain, PPAR agonists may have broader stimulatory effects on insulin and IGF signaling, rather than function as selective insulin sensitizer agents.

One of the most exciting findings was that peripheral (intraperitoneal) injection of the PPAR agonists partially rescued the brains from ic-STZ-mediated neurodegeneration. The major effects of the PPAR agonist treatments were to increase brain size, preserve insulin and IGF-II receptor bearing neurons in the CNS, and particularly with regard to the PPAR-δ agonist, preserve learning and memory performance to levels that were comparable to control. Since the ic-STZ-mediated losses of insulin and IGF-expressing cells were not prevented by the PPAR agonist treatments, the deficiency in local growth factor production per se was probably not sufficient to cause neurodegeneration or cognitive impairment. Instead, it appears that the preservation of insulin and IGF receptor positive (responsive) cells, was more critical. This concept is supported by the following observations: 1) genetic depletion of brain insulin receptors causes small brain size and impaired signaling with neuronal loss, increased levels of phospho-Tau, and GSK-3β activation as occur in AD; 2) although apoptosis was detected within the first week after ic-STZ treatment, brain atrophy, AD-type neurodegeneration, and cognitive impairment were not observed until 2 weeks after the ic-STZ treatment; 3) learning and memory deficits were observed in the ic-STZ and not the ic-STZ+PPAR-δ treated rats, which differed mainly with respect to the levels of insulin and IGF-II receptor expression and binding, and 4) the ChAT gene is regulated by insulin and IGF stimulation, expressed in insulin- and IGF-receptor bearing neurons (E. J. Rivera, A. Goldin, N. Fulmer, R. Tavares, J. R. Wands, S. M. de la Monte, J. Alzheimers Dis 8(3) (2005), 247-68) down-regulated in cells that have reduced levels of insulin and IGF-receptor expression, and reduced in brains with AD and experimental type 3 diabetes (ic-STZ model).

One unexpected finding was that in addition to preserving insulin-receptor bearing (responsive) cells, IGF-II receptor gene expression was also relatively preserved. This suggests that PPAR agonists may have broad stimulatory effects on insulin and IGF signaling, rather than function as selective insulin sensitizer agents. The fact that the AD-type morphological and molecular abnormalities in the ic-STZ model develop after the initial wave of neuronal apoptosis that corresponds with loss of insulin and IGF-II expressing cells, suggests that subsequent death of insulin and IGF-II receptor bearing neurons, i.e. the secondary targets of neurodegeneration, may mediate the neurobehavioral effects of ic-STZ treatment. Since PPAR agonists operate at the level of the nucleus to alter gene expression and function, their effectiveness in preserving viability of insulin receptor-bearing cells despite deficient local growth factor production, may be due to the activation of insulin-related survival signaling mechanisms. This concept is supported by the findings of reduced pro-apoptosis and oxidative stress-related (NOX) gene expression, decreased activation of GSK-3β, and lower levels of DNA damage (8-OHdG immunoreactivity) in brains treated with ic-STZ+PPAR-δ, who exhibited control-level performance on memory and learning tasks. The PPAR agonist mediated rescue of ic-STZ-induced neurodegeneration and neurobehavioral dysfunction was also associated with relative preservation of ChAT immunoreactivity in the basal forebrain, hypothalamus, cerebellar cortex, and temporal lobe. This observation is of interest because previous studies showed that the loss of insulin-receptor and IGF-receptor-bearing neurons overlapped with the reductions in ChAT expression in AD (E. J. Rivera, A. Goldin, N. Fulmer, R. Tavares, J. R. Wands, S. M. de la Monte, J. Alzheimers Dis 8(3) (2005), 247-68). Therefore, although the mechanisms by which the PPAR agonists rescued the brains from ic-STZ-induced neurodegeneration are complex, they appear to be mediated by improved survival and function of insulin and IGF-II receptor bearing cells.

STZ is nitrosamide methylnitrosourea (MNU) linked to the C2 position of D-glucose. The MNU functions as an alkylating agent that causes DNA damage, while the glucose moiety is taken up as glucose in insulin- (and possibly also IGF-) producing cells. Once metabolized, the N-nitrosoureido is liberated to cause DNA damage through generation of reactive oxygen species such as superoxide, hydrogen peroxide, and nitric oxide (A. D. Bolzan, M. S. Bianchi. Genotoxicity of streptozotocin. Mutat Res 512(2-3) (2002), 121-34., T. Szkudelski. The mechanism of alloxan and streptozotocin action in B cells of the rat pancreas. Physiol Res 50(6) (2001), 537-46). We demonstrated that ic-STZ results in increased microglial and astrocyte populations. The studies herein demonstrate that ic-STZ also causes increased CNS expression of p53, NOS2, NOS3, and NOX-1, and increased levels of HNE and 8-OHdG immunoreactivity as occur in AD. (W. R. Markesbery, J. M. Carney. Oxidative alterations in Alzheimer's disease. Brain Pathol 9(1) (1999), 133-46, L. M. Sayre, D. A. Zelasko, P. L. Harris, G. Perry, R. G. Salomon, M. A. Smith. 4-Hydroxynonenal-derived advanced lipid peroxidation end products are increased in Alzheimer's disease. J Neurochem 68(5) (1997), 2092-7). Therefore, the ic-STZ model has a neuro-inflammatory component marked by chronically increased levels of oxidative stress, lipid peroxidation, and DNA damage, which are now a well-recognized features of AD (P. Eikelenboom, W. A. van Gool. Neuroinflammatory perspectives on the two faces of Alzheimer's disease. J Neural Transm 111(3) (2004), 281-94, E. E. Tuppo, H. R. Arias. The role of inflammation in Alzheimer's disease. Int J Biochem Cell Biol 37(2) (2005), 289-305).

The ic-STZ mediated increases in APP gene expression confirm our previous observations correspond with the findings in AD brains (E. Steen, B. M. Terry, E. J. Rivera, J. L. Cannon, T. R. Neely, R. Tavares, et al. Impaired insulin and insulin-like growth factor expression and signaling mechanisms in Alzheimer's disease—is this type 3 diabetes? J Alzheimers Dis 7(1) (2005), 63-80, (E. J. Rivera, A. Goldin, N. Fulmer, R. Tavares, J. R. Wands, S. M. de la Monte, J. Alzheimers Dis 8(3) (2005), 247-68), and could account for the increased APP-β, accumulation in both AD and ic-STZ treated brains. Previous studies demonstrated that APP expression is increased with oxidative stress in cortical neurons (G. J. Chen, J. Xu, S. A. Lahousse, N. L. Caggiano, S. M. de la Monte. Transient hypoxia causes Alzheimer-type molecular and biochemical abnormalities in cortical neurons: potential strategies for neuroprotection. J Alzheimers Dis 5(3) (2003), 209-28). Therefore, the higher levels of APP mRNA detected in both AD and the ic-STZ-treated brains may be mediated by chronic oxidative stress produced by up-regulation of the p53 pro-apoptosis gene, increased expression of NOS and NOX genes, and impaired insulin/IGF signaling. Similarly, the increased GSK-3β activation and Tau phosphorylation observed in the ic-STZ-treated brains could be explained on the basis of chronic oxidative stress.

In conclusion, the PPAR agonist rescue of ic-STZ induced neurodegeneration was likely mediated by two separate mechanisms: 1) preservation of insulin and IGF-II receptor-bearing CNS cells; and 2) reduced indices of oxidative stress and the attendant molecular and biochemical lesions that typically correlate with AD-type neurodegeneration, i.e. APP over-expression, APP-Aβ accumulation, and Tau hyperphosphorylation. The findings herein provide evidence that systemic PPAR agonist treatment could be used to prevent or retard the AD neurodegeneration cascade in humans. Whether local administration of trophic factors such as insulin, IGF, or synthetic and natural homologs could also be therapeutically effective will likely depend on their pharmacokinetics. The effectiveness of systemic PPAR agonist treatment of ic-STZ induced neurodegeneration indicates that either the drugs were able to penetrate the blood-brain barrier, or the ic-STZ treatment disrupted the blood-brain barrier as occurs in AD. Thus PPAR agonists (particularly delta) that have selective penetration and action in the CNS may be of particular interest.

TABLE 8

PPAR GENE EXPRESSION LEVELS IN THE BRAIN

| PPAR Agonist | Control ($\times 10^{-3}$) | ic-STZ Treated ($\times 10^{-3}$) | P-value |
|---|---|---|---|
| PPAR-α | 0.035 ± 0.0015 | 0.036 ± 0.0021 | N.S. |
| PPAR-δ | 0.376 ± 0.051 | 0.258 ± 0.034 | 0.04 |
| PPAR-γ | 0.149 ± 0.008 | 0.182 ± 0.017 | N.S. |

PPAR mRNA levels were measured by real time quantitative RT-PCR with values normalized to 18S ribobomal RNA measured in the same samples. The calculated mean PPAR/18S ($\times 10^{-3}$) ratios (±S.E.M.) corresponding to relative levels of gene expression are listed for each class of PPAR. Inter-group comparisons were made using Student T-tests. PPAR=peroxisome-proliferator activated receptor; N.S.=Not significant

TABLE 9

PRIMER PAIRS FOR REAL TIME QUANTITATIVE RT-PCR*

| Primer | Direction | Sequence (5'→3') | Position (mRNA) | Amplicon Size (bp) |
|---|---|---|---|---|
| 18S | For | GGA CAC GGA CAG GAT TGA CA (SEQ ID NO: 43) | 1278 | 50 |
| 18S | Rev | ACC CAC GGA ATC GAG AAA GA (SEQ ID NO: 44) | 1327 | |
| Insulin | For | TTC TAC ACA CCC AAG TCC CGT C (SEQ ID NO: 31) | 145 | 135 |
| Insulin | Rev | ATC CAC AAT GCC ACG CTT CTG C (SEQ ID NO: 32) | 279 | |
| Insulin Receptor | For | TGA CAA TGA GGA ATG TGG GG C (SEQ ID NO: 45) | 875 | 129 |
| Insulin Receptor | Rev | GGG CAA ACT TTC TGA CAA TGA CTG (SEQ ID NO: 46) | 1003 | |
| IGF-I | For | GAC CAA GGG GCT TTT ACT TCA AC (SEQ ID NO: 47) | 65 | 127 |
| IGF-I | Rev | TTT GTA GGC TTC AGC GGA GCA C (SEQ ID NO: 48) | 191 | |
| IGF-I Receptor | For | GAA GTC TGC GGT GGT GAT AAA GG (SEQ ID NO: 49) | 2138 | 113 |
| IGF-I Receptor | Rev | TCT GGG CAC AAA GAT GGA GTT G (SEQ ID NO: 50) | 2250 | |

TABLE 9-continued

PRIMER PAIRS FOR REAL TIME QUANTITATIVE RT-PCR*

| Primer | Direction | Sequence (5'→3') | Position (mRNA) | Amplicon Size (bp) |
|---|---|---|---|---|
| IGF-II | For | CCA AGA AGA AAG GAA GGG GAC C (SEQ ID NO: 51) | 763 | 95 |
| IGF-II | Rev | GGC GGC TAT TGT TGT TCA CAG C (SEQ ID NO: 52) | 857 | |
| IGF-II Receptor | For | TTG CTA TTG ACC TTA GTC CCT TGG (SEQ ID NO: 53) | 1066 | 91 |
| IGF-II Receptor | Rev | AGA GTG AGA CCT TTG TGT CCC CAC (SEQ ID NO: 54) | 1156 | |
| Tau | For | CGC CAG GAG TTT GAC ACA ATG (SEQ ID NO: 61) | 244 | 65 |
| Tau | Rev | CCT TCT TGG TCT TGG AGC ATA GTG (SEQ ID NO: 62) | 308 | |
| APP | For | GCA GAA TGG AAA ATG GGA GTC AG (SEQ ID NO: 63) | 278 | 199 |
| APP | Rev | AAT CAC GAT GTG GGT GTG CGT C (SEQ ID NO: 64) | 476 | |
| AChE | For | TTC TCC CAC ACC TGT CCT CAT C (SEQ ID NO: 65) | 420 | 123 |
| AChE | Rev | TTC ATA GAT ACC AAC ACG GTT CCC (SEQ ID NO: 66) | 542 | |
| ChAT | For | TCA CAG ATG CGT TTC ACA ACT ACC (SEQ ID NO: 67) | 478 | 106 |
| ChAT | Rev | TGG GAC ACA ACA GCA ACC TTG (SEQ ID NO: 68) | 583 | |
| Hu | For | CAC TGT GTG AGG GTC CAT CTT CTG (SEQ ID NO: 69) | 271 | 50 |
| Hu | Rev | TCA AGC CAT TCC ACT CCA TCT G (SEQ ID NO: 70) | 320 | |
| GFAP | For | TGG TAA AGA CGG TGG AGA TGC G (SEQ ID NO: 71) | 1245 | 200 |
| GFAP | Rev | GGC ACT AAA ACA GAA GCA AGG GG (SEQ ID NO: 72) | 1444 | |
| MAG-1 | For | AAC CTT CTG TAT CAG TGC TCC TCG (SEQ ID NO: 73) | 18 | 63 |
| MAG-1 | Rev | CAG TCA ACC AAG TCT CTT CCG TG (SEQ ID NO: 74) | 80 | |

TABLE 9-continued

PRIMER PAIRS FOR REAL TIME QUANTITATIVE RT-PCR*

| Primer | Direction | Sequence (5'→3') | Position (mRNA) | Amplicon Size (bp) |
|---|---|---|---|---|
| AIF-1 | For | GGA TGG GAT CAA CAA GCA CT (SEQ ID NO: 75) | 168 | 158 |
| AIF-1 | Rev | GTT TCT CCA GCA TTC GCT TC (SEQ ID NO: 76) | 325 | |
| PPAR-α | For | CGT TGT CAT CAC AGA TTG GTG C (SEQ ID NO: 77) | 325 | 129 |
| PPAR-α | Rev | CTT CAG ATA AGG GAC TTT CCA GGT C (SEQ ID NO: 78) | 453 | |
| PPAR-δ | For | TGT CAA CAA AGA CGG ACT GCT G (SEQ ID NO: 79) | 1136 | 107 |
| PPAR-δ | Rev | CGA ACT TGG GCT CAA TGA TGT C (SEQ ID NO: 80) | 1242 | |
| PPAR-γ | For | TGG ACC TCT CTG TGA TGG ATG ACC (SEQ ID NO: 81) | 191 | 115 |
| PPAR-γ | Rev | GCT CTT GTG AAC GGG ATG TCT TC (SEQ ID NO: 82) | 305 | |
| NOS 1 | For | TGT CTT CCA CCA GGA GAT GCT C (SEQ ID NO: 83) | 2168 | 162 |
| NOS 1 | Rev | TTG GCT GAG AAC TTG ACG GC (SEQ ID NO: 84) | 2329 | |
| NOS 2 | For | TTT GCT TCT GTG CTA ATG CGG (SEQ ID NO: 85) | 1744 | 179 |
| NOS 2 | Rev | TCC TCT TCC AAG GTG TTT GCC (SEQ ID NO: 86) | 1924 | |
| NOS 3 | For | GCA GGT ATT TGA TGC TCG GGA C (SEQ ID NO: 87) | 582 | 109 |
| NOS 3 | Rev | CGT GAT GGC TGA ACG AAG ATT G (SEQ ID NO: 88) | 690 | |
| NOX 1 | For | GCA TCC CTT TAC TCT GAC CTC TGC (SEQ ID NO: 89) | 1135 | 81 |
| NOX 1 | Rev | TTT TCT GTC CAG TCC CCT GCT G (SEQ ID NO: 80) | 1215 | |
| p53 | For | CCA TCC TTA CCA TCA TCA CGC TG (SEQ ID NO: 91) | 766 | 80 |
| p53 | Rev | GGC ACA AAC ACG AAC CTC AAA G (SEQ ID NO: 92) | 845 | |

Table of forward (For) and reverse (Rev) primer pairs used to measure mRNA levels of specific genes expressed in rat brains using real time quantitative RT-PCR. The primer sequences are from 5' to 3'. The positions of primer binding from the most 5' nucleotide of the cDNA, and the amplicon (product) sizes are listed in Columns 4 and 5. RT-PCR=reverse transcriptase polymerase chain reaction; IGF-I=insulin-like growth factor, type I; APP=amyloid precursor protein; AChE=acetylcholinesterase; ChAT=choline acetyltransferase; GFAP=glial fibrillary acidic protein; MAG-1=myelin-associated glycoprotein; AIF-1=allograft inflammatory factor-1; NOS=nitric oxide synthase; NOX=NADPH oxidase; PPAR=peroxisome proliferator activated receptor

TABLE 10

ANALYSIS OF COMPETITIVE SATURATION BINDING TO INSULIN, IGF-I, AND IGF-II RECEPTORS IN THE BRAIN

| Best-fit values | Control | STZ | STZ + PPAR-α | STZ + PPAR-δ | STZ + PPAR-γ |
|---|---|---|---|---|---|
| INSULIN | | | | | |
| BMAX | 5.194 | 0.8421 | 1.172 | 2.186 | 1.127 |
| KD | 107.3 | 19.56 | 30.45 | 81.97 | 35.62 |
| Std. Error | | | | | |
| BMAX | 1.26E−07 | 5.70E−09 | 9.24E−09 | 3.99E−08 | 1.14E−08 |
| KD | 3.45E−06 | 3.23E−07 | 4.81E−07 | 2.12E−06 | 6.75E−07 |
| Goodness of Fit | | | | | |
| IGF-1 | | | | | |
| BMAX | 2.055 | 1.204 | 0.6361 | 0.7399 | 3.123 |
| KD | 19.35 | 8.249 | 4.613 | 8.667 | 52.7 |
| Std. Error | | | | | |
| BMAX | 1.30E−08 | 4.28E−09 | 2.22E−09 | 3.21E−09 | 4.16E−08 |
| KD | 3.02E−07 | 1.11E−07 | 8.33E−08 | 1.38E−07 | 1.14E−06 |

TABLE 10-continued

ANALYSIS OF COMPETITIVE SATURATION BINDING
TO INSULIN, IGF-I, AND IGF-II RECEPTORS IN THE BRAIN

| Best-fit values | Control | STZ | STZ + PPAR-α | STZ + PPAR-δ | STZ + PPAR-γ |
|---|---|---|---|---|---|
| Goodness of Fit | | | | | |
| | | | IGF-II | | |
| BMAX | 31.22 | 6.431 | 7.291 | 20.22 | 9.223 |
| KD | 445.7 | 66.03 | 77.7 | 373.3 | 91.92 |
| Std. Error | | | | | |
| BMAX | 2.95E–06 | 1.08E–07 | 1.35E–07 | 1.77E–06 | 1.85E–07 |
| KD | 4.56E–05 | 1.67E–06 | 2.07E–06 | 3.58E–05 | 2.53E–06 |
| Goodness of Fit | | | | | |

*Saturation binding studies were performed to determine maximum (BMAX) binding levels and the dissociation constants for insulin, IGF-I and IGF-II in brains from control, STZ, STZ + PPAR-α, STZ + PPAR-δ, and STZ + PPAR-γ treated rats. The data were fitted to a one-site binding model. The tabulated results list the calculated BMAX (fmol/mg protein) and KD (fmol) values, and the standard errors and 95% confidence intervals. The $R^2$ values reflect goodness of fit. *$P < 0.0001$ for STZ-associated reductions in BMAX (reduced top-level binding) and KD (increased affinity) by two-way ANOVA.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A method for reducing neurodegeneration in a human subject suffering from mild cognitive impairment or Alzheimer's Disease, said method comprising the steps of:
   a) assessing the level of cognitive impairment and determining the level of at least one factor in the insulin/insulin-like growth factor (IGF) signaling pathway in said subject;
   b) administering to said subject a therapeutically effective amount of a peroxisome proliferator-activated receptor (PPAR) δ receptor selective agonist, in an amount effective to increase the level of sensitivity to insulin in the brain of said subject; and
   c) re-assessing the level of cognitive impairment and the level of the at least one factor in the insulin/IGF signaling pathway in said subject; whereby a reduction in the level of cognitive impairment and an increase in the level of the factor in the insulin/IGF signaling pathway after administration of the PPAR δ receptor selective agonist is indicative of increased sensitivity to insulin and thereby reduced neurodegeneration.

2. The method of claim 1, further comprising administering to said subject an insulin/insulin-like growth factor (IGF) agonist.

3. The method of claim 2, wherein said PPAR δ receptor agonist and said IGF agonist are administered separately.

4. The method of claim 2, wherein said PPAR δ receptor agonist and said IGF agonist are administered together in a single composition.

5. The method of claim 1, wherein said PPAR δ receptor agonist is GW 501516.

6. The method of claim 1, wherein said PPAR δ receptor agonist is GW 0742.

7. The method of claim 1, wherein said PPAR δ receptor agonist is L-165041.

8. The method of claim 1, wherein said PPAR δ receptor agonist is carbaprostacyclin.

9. The method of claim 2, wherein said IGF agonist is selected from the group consisting of the D analog of IGF-I, long-Arg$^3$-IGF-I, Val$^{59}$-IGF-I, AlaGlu-IGF-I, Ala$^{63}$-IGF-I, Ser$^1$Ala$^{63}$Val$^{70}$-IGF-I, Leu$^{24,59,60}$Ala$^{31}$-IGF-II, Gln$^6$Ala$^7$Tyr$^{18}$Leu$^{19}$Leu$^{27}$-IGF-II, Gly$^1$-IGF-II, Leu$^{27}$-IGF-II and Gln$^{37}$Gln$^{38}$-IGF-II.

10. The method of claim 1, wherein the at least one factor in the insulin/IGF signaling pathway is selected from the group consisting of insulin, IGF-I, IGF-II, insulin receptor, IGF-I receptor, IGF-II receptor, tyrosine phosphorylated insulin receptor, tyrosine phosphorylated IGF-I receptor, tyrosine phosphorylated IGF-II receptor, insulin receptor substrate-1 (IRS-1), IRS-2, IRS-4, tyrosine phosphorylated IRS-1, tyrosine phosphorylated IRS-2, tyrosine phosphorylated IRS-4, phosphotidylinositol 3-kinase (PI3 kinase) the p85 subunit of PI3 kinase, Akt, phosphor-Akt, glycogen synthase kinase-3β (GSK-3β), and phospho-GSK-3β.

11. The method of claim 10, wherein the at least one factor in the insulin/IGF signaling pathway is insulin, IGF-I, IGF-II, insulin receptor, IGF-1 receptor or IGF-II receptor.

* * * * *

SEQUENCE LISTING

```
<160> NUMBER OF SEQ ID NOS: 92

<210> SEQ ID NO 1
<211> LENGTH: 22
<212> TYPE: DNA
<213> ORGANISM: Artificial
<220> FEATURE:
<223> OTHER INFORMATION: Human insulin PCR forward primer

<400> SEQUENCE: 1
ttctacacac ccaagtcccg tc                                            22

<210> SEQ ID NO 2
<211> LENGTH: 22
<212> TYPE: DNA
<213> ORGANISM: Artificial
<220> FEATURE:
<223> OTHER INFORMATION: Human insulin PCR reverse primer

<400> SEQUENCE: 2
atccacaatg ccacgcttct gc                                            22

<210> SEQ ID NO 3
<211> LENGTH: 25
<212> TYPE: DNA
<213> ORGANISM: Artificial
<220> FEATURE:
<223> OTHER INFORMATION: Human insulin receptor PCR forward primer

<400> SEQUENCE: 3
ggtagaaacc attactggct tcctc                                         25

<210> SEQ ID NO 4
<211> LENGTH: 25
<212> TYPE: DNA
<213> ORGANISM: Artificial
<220> FEATURE:
<223> OTHER INFORMATION: Human insulin receptor PCR reverse primer
```

```
<400> SEQUENCE: 4
cgtagagagt gtagttccca tccac                                          25

<210> SEQ ID NO 5
<211> LENGTH: 24
<212> TYPE: DNA
<213> ORGANISM: Artificial
<220> FEATURE:
<223> OTHER INFORMATION: Human IGF-I PCR forward primer

<400> SEQUENCE: 5
cacttctttc tacacaactc gggc                                           24

<210> SEQ ID NO 6
<211> LENGTH: 21
<212> TYPE: DNA
<213> ORGANISM: Artificial
<220> FEATURE:
<223> OTHER INFORMATION: Human IGF-I PCR reverse primer

<400> SEQUENCE: 6
cgacttgctg ctgcttttga g                                              21

<210> SEQ ID NO 7
<211> LENGTH: 25
<212> TYPE: DNA
<213> ORGANISM: Artificial
<220> FEATURE:
<223> OTHER INFORMATION: Human IGF-I receptor PCR forward primer

<400> SEQUENCE: 7
agggcgtagt tgtagaagag tttcc                                          25

<210> SEQ ID NO 8
<211> LENGTH: 22
<212> TYPE: DNA
<213> ORGANISM: Artificial
<220> FEATURE:
<223> OTHER INFORMATION: Human IGF-I receptor PCR reverse primer

<400> SEQUENCE: 8
tacttgctgc tgttccgagt gg                                             22

<210> SEQ ID NO 9
<211> LENGTH: 22
<212> TYPE: DNA
<213> ORGANISM: Artificial
<220> FEATURE:
<223> OTHER INFORMATION: Human IGF-II PCR forward primer

<400> SEQUENCE: 9
ctgattgctc tacccaccca ag                                             22

<210> SEQ ID NO 10
<211> LENGTH: 22
<212> TYPE: DNA
<213> ORGANISM: Artificial
<220> FEATURE:
<223> OTHER INFORMATION: Human IGF-II PCR reverse primer

<400> SEQUENCE: 10
ttgctcactt ccgattgctg gc                                             22

<210> SEQ ID NO 11
```

```
<211> LENGTH: 25
<212> TYPE: DNA
<213> ORGANISM: Artificial
<220> FEATURE:
<223> OTHER INFORMATION: Human IGF-II receptor PCR forward primer

<400> SEQUENCE: 11
cacgacttga agacacgcac ttatc                                              25

<210> SEQ ID NO 12
<211> LENGTH: 23
<212> TYPE: DNA
<213> ORGANISM: Artificial
<220> FEATURE:
<223> OTHER INFORMATION: Human IGF-II receptor PCR reverse primer

<400> SEQUENCE: 12
gctgctctgg actctgtgat ttg                                                23

<210> SEQ ID NO 13
<211> LENGTH: 20
<212> TYPE: DNA
<213> ORGANISM: Artificial
<220> FEATURE:
<223> OTHER INFORMATION: Human IRS-1 PCR forward primer

<400> SEQUENCE: 13
tgctgggggt ttggagaatg                                                    20

<210> SEQ ID NO 14
<211> LENGTH: 23
<212> TYPE: DNA
<213> ORGANISM: Artificial
<220> FEATURE:
<223> OTHER INFORMATION: Human IRS-1 PCR reverse primer

<400> SEQUENCE: 14
ggcactgttt gaagtccttg acc                                                23

<210> SEQ ID NO 15
<211> LENGTH: 19
<212> TYPE: DNA
<213> ORGANISM: Artificial
<220> FEATURE:
<223> OTHER INFORMATION: Human IRS-2 PCR forward primer

<400> SEQUENCE: 15
aaaattggcg gagcaaggc                                                     19

<210> SEQ ID NO 16
<211> LENGTH: 22
<212> TYPE: DNA
<213> ORGANISM: Artificial
<220> FEATURE:
<223> OTHER INFORMATION: Human IRS-2 PCR reverse primer

<400> SEQUENCE: 16
atgttcaggc agcagtcgag ag                                                 22

<210> SEQ ID NO 17
<211> LENGTH: 22
<212> TYPE: DNA
<213> ORGANISM: Artificial
<220> FEATURE:
<223> OTHER INFORMATION: Human IRS-4 PCR forward primer

<400> SEQUENCE: 17
```

-continued

```
ccgacacctc attgctcttt tc                                        22

<210> SEQ ID NO 18
<211> LENGTH: 22
<212> TYPE: DNA
<213> ORGANISM: Artificial
<220> FEATURE:
<223> OTHER INFORMATION: Human IRS-4 PCR reverse primer

<400> SEQUENCE: 18
tttcctgctc cgactcgttc tc                                        22

<210> SEQ ID NO 19
<211> LENGTH: 22
<212> TYPE: DNA
<213> ORGANISM: Artificial
<220> FEATURE:
<223> OTHER INFORMATION: Human tau PCR forward primer

<400> SEQUENCE: 19
agaagcaggc attggagaca cc                                        22

<210> SEQ ID NO 20
<211> LENGTH: 20
<212> TYPE: DNA
<213> ORGANISM: Artificial
<220> FEATURE:
<223> OTHER INFORMATION: Human tau PCR reverse primer

<400> SEQUENCE: 20
aagcagccac tttgggttcc                                           20

<210> SEQ ID NO 21
<211> LENGTH: 23
<212> TYPE: DNA
<213> ORGANISM: Artificial
<220> FEATURE:
<223> OTHER INFORMATION: Human APP PCR forward primer

<400> SEQUENCE: 21
caatccaggc acagaaagag tcc                                       23

<210> SEQ ID NO 22
<211> LENGTH: 22
<212> TYPE: DNA
<213> ORGANISM: Artificial
<220> FEATURE:
<223> OTHER INFORMATION: Human APP PCR reverse primer

<400> SEQUENCE: 22
ttccataacc aagagaggct gc                                        22

<210> SEQ ID NO 23
<211> LENGTH: 25
<212> TYPE: DNA
<213> ORGANISM: Artificial
<220> FEATURE:
<223> OTHER INFORMATION: Human Glut4 PCR forward primer

<400> SEQUENCE: 23
gtatcatctc tcagtggctt ggaag                                     25

<210> SEQ ID NO 24
<211> LENGTH: 20
<212> TYPE: DNA
```

```
<213> ORGANISM: Artificial
<220> FEATURE:
<223> OTHER INFORMATION: Human Glut4 PCR reverse primer

<400> SEQUENCE: 24
tttcatagga ggcagcagcg                                              20

<210> SEQ ID NO 25
<211> LENGTH: 23
<212> TYPE: DNA
<213> ORGANISM: Artificial
<220> FEATURE:
<223> OTHER INFORMATION: Human IDE PCR forward primer

<400> SEQUENCE: 25
tgatgaatga tgcctggaga ctc                                          23

<210> SEQ ID NO 26
<211> LENGTH: 22
<212> TYPE: DNA
<213> ORGANISM: Artificial
<220> FEATURE:
<223> OTHER INFORMATION: Human IDE PCR reverse primer

<400> SEQUENCE: 26
tcaatccctt cttggtttgg tc                                           22

<210> SEQ ID NO 27
<211> LENGTH: 20
<212> TYPE: DNA
<213> ORGANISM: Artificial
<220> FEATURE:
<223> OTHER INFORMATION: Human 18S PCR forward primer

<400> SEQUENCE: 27
ggacacggac aggattgaca                                              20

<210> SEQ ID NO 28
<211> LENGTH: 20
<212> TYPE: DNA
<213> ORGANISM: Artificial
<220> FEATURE:
<223> OTHER INFORMATION: Human 18S PCR reverse primer

<400> SEQUENCE: 28
acccacggaa tcgagaaaga                                              20

<210> SEQ ID NO 29
<211> LENGTH: 23
<212> TYPE: DNA
<213> ORGANISM: Artificial
<220> FEATURE:
<223> OTHER INFORMATION: Human 28S PCR forward primer

<400> SEQUENCE: 29
ggtaaacggc gggagtaact atg                                          23

<210> SEQ ID NO 30
<211> LENGTH: 24
<212> TYPE: DNA
<213> ORGANISM: Artificial
<220> FEATURE:
<223> OTHER INFORMATION: Human 28S PCR reverse primer

<400> SEQUENCE: 30
taggtaggga cagtgggaat ctcg                                         24
```

<210> SEQ ID NO 31
<211> LENGTH: 22
<212> TYPE: DNA
<213> ORGANISM: Artificial
<220> FEATURE:
<223> OTHER INFORMATION: Rat insulin PCR forward primer

<400> SEQUENCE: 31
ttctacacac ccaagtcccg tc                                              22

<210> SEQ ID NO 32
<211> LENGTH: 22
<212> TYPE: DNA
<213> ORGANISM: Artificial
<220> FEATURE:
<223> OTHER INFORMATION: Rat insulin PCR reverse primer

<400> SEQUENCE: 32
atccacaatg ccacgcttct gc                                              22

<210> SEQ ID NO 33
<211> LENGTH: 25
<212> TYPE: DNA
<213> ORGANISM: Artificial
<220> FEATURE:
<223> OTHER INFORMATION: Rat insulin receptor PCR forward primer

<400> SEQUENCE: 33
ggtagaaacc attactggct tcctc                                           25

<210> SEQ ID NO 34
<211> LENGTH: 25
<212> TYPE: DNA
<213> ORGANISM: Artificial
<220> FEATURE:
<223> OTHER INFORMATION: Rat insulin receptor PCR reverse primer

<400> SEQUENCE: 34
cgtagagagt gtagttccca tccac                                           25

<210> SEQ ID NO 35
<211> LENGTH: 24
<212> TYPE: DNA
<213> ORGANISM: Artificial
<220> FEATURE:
<223> OTHER INFORMATION: Rat IGF-I PCR forward primer

<400> SEQUENCE: 35
cacttctttc tacacaactc gggc                                            24

<210> SEQ ID NO 36
<211> LENGTH: 21
<212> TYPE: DNA
<213> ORGANISM: Artificial
<220> FEATURE:
<223> OTHER INFORMATION: Rat IGF-I PCR reverse primer

<400> SEQUENCE: 36
cgacttgctg ctgcttttga g                                               21

<210> SEQ ID NO 37
<211> LENGTH: 25
<212> TYPE: DNA
<213> ORGANISM: Artificial
<220> FEATURE:

```
<223> OTHER INFORMATION: Rat IGF-I receptor PCR forward primer

<400> SEQUENCE: 37
agggcgtagt tgtagaagag tttcc                                              25

<210> SEQ ID NO 38
<211> LENGTH: 22
<212> TYPE: DNA
<213> ORGANISM: Artificial
<220> FEATURE:
<223> OTHER INFORMATION: Rat IGF-I receptor PCR reverse primer

<400> SEQUENCE: 38
tacttgctgc tgttccgagt gg                                                 22

<210> SEQ ID NO 39
<211> LENGTH: 22
<212> TYPE: DNA
<213> ORGANISM: Artificial
<220> FEATURE:
<223> OTHER INFORMATION: Rat IGF-II PCR forward primer

<400> SEQUENCE: 39
ctgattgctc tacccaccca ag                                                 22

<210> SEQ ID NO 40
<211> LENGTH: 22
<212> TYPE: DNA
<213> ORGANISM: Artificial
<220> FEATURE:
<223> OTHER INFORMATION: Rat IGF-II PCR reverse primer

<400> SEQUENCE: 40
ttgctcactt ccgattgctg gc                                                 22

<210> SEQ ID NO 41
<211> LENGTH: 25
<212> TYPE: DNA
<213> ORGANISM: Artificial
<220> FEATURE:
<223> OTHER INFORMATION: Rat IGF-II receptor PCR forward primer

<400> SEQUENCE: 41
cacgacttga agacacgcac ttatc                                              25

<210> SEQ ID NO 42
<211> LENGTH: 23
<212> TYPE: DNA
<213> ORGANISM: Artificial
<220> FEATURE:
<223> OTHER INFORMATION: Rat IGF-II receptor PCR reverse primer

<400> SEQUENCE: 42
gctgctctgg actctgtgat ttg                                                23

<210> SEQ ID NO 43
<211> LENGTH: 20
<212> TYPE: DNA
<213> ORGANISM: Artificial
<220> FEATURE:
<223> OTHER INFORMATION: Rat 18S PCR forward primer

<400> SEQUENCE: 43
ggacacggac aggattgaca                                                    20
```

```
<210> SEQ ID NO 44
<211> LENGTH: 20
<212> TYPE: DNA
<213> ORGANISM: Artificial
<220> FEATURE:
<223> OTHER INFORMATION: Rat 18S PCR reverse primer

<400> SEQUENCE: 44
acccacggaa tcgagaaaga                                                    20

<210> SEQ ID NO 45
<211> LENGTH: 22
<212> TYPE: DNA
<213> ORGANISM: Artificial
<220> FEATURE:
<223> OTHER INFORMATION: Rat insulin receptor PCR forward primer

<400> SEQUENCE: 45
tgacaatgag gaatgtgggg ac                                                 22

<210> SEQ ID NO 46
<211> LENGTH: 24
<212> TYPE: DNA
<213> ORGANISM: Artificial
<220> FEATURE:
<223> OTHER INFORMATION: Rat insulin receptor PCR reverse primer

<400> SEQUENCE: 46
gggcaaactt tctgacaatg actg                                               24

<210> SEQ ID NO 47
<211> LENGTH: 23
<212> TYPE: DNA
<213> ORGANISM: Artificial
<220> FEATURE:
<223> OTHER INFORMATION: Rat IGF-I PCR forward primer

<400> SEQUENCE: 47
gaccaagggg cttttacttc aac                                                23

<210> SEQ ID NO 48
<211> LENGTH: 22
<212> TYPE: DNA
<213> ORGANISM: Artificial
<220> FEATURE:
<223> OTHER INFORMATION: Rat IGF-I PCR reverse primer

<400> SEQUENCE: 48
tttgtaggct tcagcggagc ac                                                 22

<210> SEQ ID NO 49
<211> LENGTH: 23
<212> TYPE: DNA
<213> ORGANISM: Artificial
<220> FEATURE:
<223> OTHER INFORMATION: Rat IGF-I receptor PCR forward primer

<400> SEQUENCE: 49
gaagtctgcg gtggtgataa agg                                                23

<210> SEQ ID NO 50
<211> LENGTH: 22
<212> TYPE: DNA
<213> ORGANISM: Artificial
<220> FEATURE:
<223> OTHER INFORMATION: Rat IGF-I receptor PCR reverse primer
```

```
<400> SEQUENCE: 50
tctgggcaca aagatggagt tg                                              22

<210> SEQ ID NO 51
<211> LENGTH: 22
<212> TYPE: DNA
<213> ORGANISM: Artificial
<220> FEATURE:
<223> OTHER INFORMATION: Rat IGF-II PCR forward primer

<400> SEQUENCE: 51
ccaagaagaa aggaagggga cc                                              22

<210> SEQ ID NO 52
<211> LENGTH: 22
<212> TYPE: DNA
<213> ORGANISM: Artificial
<220> FEATURE:
<223> OTHER INFORMATION: Rat IGF-II PCR reverse primer

<400> SEQUENCE: 52
ggcggctatt gttgttcaca gc                                              22

<210> SEQ ID NO 53
<211> LENGTH: 24
<212> TYPE: DNA
<213> ORGANISM: Artificial
<220> FEATURE:
<223> OTHER INFORMATION: Rat IGF-II receptor PCR forward primer

<400> SEQUENCE: 53
ttgctattga ccttagtccc ttgg                                            24

<210> SEQ ID NO 54
<211> LENGTH: 24
<212> TYPE: DNA
<213> ORGANISM: Artificial
<220> FEATURE:
<223> OTHER INFORMATION: Rat IGF-II receptor PCR reverse primer

<400> SEQUENCE: 54
agagtgagac ctttgtgtcc ccac                                            24

<210> SEQ ID NO 55
<211> LENGTH: 22
<212> TYPE: DNA
<213> ORGANISM: Artificial
<220> FEATURE:
<223> OTHER INFORMATION: Rat IRS-1 PCR forward primer

<400> SEQUENCE: 55
gataccgatg gcttctcaga cg                                              22

<210> SEQ ID NO 56
<211> LENGTH: 23
<212> TYPE: DNA
<213> ORGANISM: Artificial
<220> FEATURE:
<223> OTHER INFORMATION: Rat IRS-1 PCR reverse primer

<400> SEQUENCE: 56
tcgttctcat aatactccag gcg                                             23

<210> SEQ ID NO 57
<211> LENGTH: 23
```

```
<212> TYPE: DNA
<213> ORGANISM: Artificial
<220> FEATURE:
<223> OTHER INFORMATION: Rat IRS-2 PCR forward primer

<400> SEQUENCE: 57
caacattgac tttggtgaag ggg                                              23

<210> SEQ ID NO 58
<211> LENGTH: 24
<212> TYPE: DNA
<213> ORGANISM: Artificial
<220> FEATURE:
<223> OTHER INFORMATION: Rat IRS-2 PCR reverse primer

<400> SEQUENCE: 58
tgaagcagga ctactggctg agag                                             24

<210> SEQ ID NO 59
<211> LENGTH: 24
<212> TYPE: DNA
<213> ORGANISM: Artificial
<220> FEATURE:
<223> OTHER INFORMATION: Rat IRS-4 PCR forward primer

<400> SEQUENCE: 59
acctgaagat aagggtcgt ctgc                                              24

<210> SEQ ID NO 60
<211> LENGTH: 22
<212> TYPE: DNA
<213> ORGANISM: Artificial
<220> FEATURE:
<223> OTHER INFORMATION: Rat IRS-4 PCR reverse primer

<400> SEQUENCE: 60
tgtgtggggt ttagtggtct gg                                               22

<210> SEQ ID NO 61
<211> LENGTH: 21
<212> TYPE: DNA
<213> ORGANISM: Artificial
<220> FEATURE:
<223> OTHER INFORMATION: Rat tau PCR forward primer

<400> SEQUENCE: 61
cgccaggagt ttgacacaat g                                                21

<210> SEQ ID NO 62
<211> LENGTH: 24
<212> TYPE: DNA
<213> ORGANISM: Artificial
<220> FEATURE:
<223> OTHER INFORMATION: Rat tau PCR reverse primer

<400> SEQUENCE: 62
ccttcttggt cttggagcat agtg                                             24

<210> SEQ ID NO 63
<211> LENGTH: 23
<212> TYPE: DNA
<213> ORGANISM: Artificial
<220> FEATURE:
<223> OTHER INFORMATION: Rat APP PCR forward primer

<400> SEQUENCE: 63
```

-continued gcagaatgga aaatgggagt cag                                             23

<210> SEQ ID NO 64
<211> LENGTH: 22
<212> TYPE: DNA
<213> ORGANISM: Artificial
<220> FEATURE:
<223> OTHER INFORMATION: Rat APP PCR reverse primer

<400> SEQUENCE: 64
aatcacgatg tgggtgtgcg tc                                              22

<210> SEQ ID NO 65
<211> LENGTH: 22
<212> TYPE: DNA
<213> ORGANISM: Artificial
<220> FEATURE:
<223> OTHER INFORMATION: Rat AChE PCR forward primer

<400> SEQUENCE: 65
ttctcccaca cctgtcctca tc                                              22

<210> SEQ ID NO 66
<211> LENGTH: 24
<212> TYPE: DNA
<213> ORGANISM: Artificial
<220> FEATURE:
<223> OTHER INFORMATION: Rat AChE PCR reverse primer

<400> SEQUENCE: 66
ttcatagata ccaacacggt tccc                                            24

<210> SEQ ID NO 67
<211> LENGTH: 24
<212> TYPE: DNA
<213> ORGANISM: Artificial
<220> FEATURE:
<223> OTHER INFORMATION: Rat ChAT PCR forward primer

<400> SEQUENCE: 67
tcacagatgc gtttcacaac tacc                                            24

<210> SEQ ID NO 68
<211> LENGTH: 21
<212> TYPE: DNA
<213> ORGANISM: Artificial
<220> FEATURE:
<223> OTHER INFORMATION: Rat ChAT PCR reverse primer

<400> SEQUENCE: 68
tgggacacaa cagcaacctt g                                               21

<210> SEQ ID NO 69
<211> LENGTH: 24
<212> TYPE: DNA
<213> ORGANISM: Artificial
<220> FEATURE:
<223> OTHER INFORMATION: Rat Hu PCR forward primer

<400> SEQUENCE: 69
cactgtgtga gggtccatct tctg                                            24

<210> SEQ ID NO 70
<211> LENGTH: 22
<212> TYPE: DNA
<213> ORGANISM: Artificial

```
-continued

<220> FEATURE:
<223> OTHER INFORMATION: Rat Hu PCR reverse primer

<400> SEQUENCE: 70
tcaagccatt ccactccatc tg                                              22

<210> SEQ ID NO 71
<211> LENGTH: 22
<212> TYPE: DNA
<213> ORGANISM: Artificial
<220> FEATURE:
<223> OTHER INFORMATION: Rat GFAP PCR forward primer

<400> SEQUENCE: 71
tggtaaagac ggtggagatg cg                                              22

<210> SEQ ID NO 72
<211> LENGTH: 23
<212> TYPE: DNA
<213> ORGANISM: Artificial
<220> FEATURE:
<223> OTHER INFORMATION: Rat GFAP PCR reverse primer

<400> SEQUENCE: 72
ggcactaaaa cagaagcaag ggg                                             23

<210> SEQ ID NO 73
<211> LENGTH: 24
<212> TYPE: DNA
<213> ORGANISM: Artificial
<220> FEATURE:
<223> OTHER INFORMATION: Rat MAG-1 PCR forward primer

<400> SEQUENCE: 73
aaccttctgt atcagtgctc ctcg                                            24

<210> SEQ ID NO 74
<211> LENGTH: 23
<212> TYPE: DNA
<213> ORGANISM: Artificial
<220> FEATURE:
<223> OTHER INFORMATION: Rat MAG-1 PCR reverse primer

<400> SEQUENCE: 74
cagtcaacca agtctcttcc gtg                                             23

<210> SEQ ID NO 75
<211> LENGTH: 20
<212> TYPE: DNA
<213> ORGANISM: Artificial
<220> FEATURE:
<223> OTHER INFORMATION: Rat AIF-1 PCR forward primer

<400> SEQUENCE: 75
ggatgggatc aacaagcact                                                 20

<210> SEQ ID NO 76
<211> LENGTH: 20
<212> TYPE: DNA
<213> ORGANISM: Artificial
<220> FEATURE:
<223> OTHER INFORMATION: Rat AIF-1 PCR reverse primer

<400> SEQUENCE: 76
gtttctccag cattcgcttc                                                 20
```

<210> SEQ ID NO 77
<211> LENGTH: 22
<212> TYPE: DNA
<213> ORGANISM: Artificial
<220> FEATURE:
<223> OTHER INFORMATION: Rat PPAR-a PCR forward primer

<400> SEQUENCE: 77
cgttgtcatc acagattggt gc                                              22

<210> SEQ ID NO 78
<211> LENGTH: 25
<212> TYPE: DNA
<213> ORGANISM: Artificial
<220> FEATURE:
<223> OTHER INFORMATION: Rat PPAR-a PCR reverse primer

<400> SEQUENCE: 78
cttcagataa gggactttcc aggtc                                           25

<210> SEQ ID NO 79
<211> LENGTH: 22
<212> TYPE: DNA
<213> ORGANISM: Artificial
<220> FEATURE:
<223> OTHER INFORMATION: Rat PPAR-d PCR forward primer

<400> SEQUENCE: 79
tgtcaacaaa gacggactgc tg                                              22

<210> SEQ ID NO 80
<211> LENGTH: 22
<212> TYPE: DNA
<213> ORGANISM: Artificial
<220> FEATURE:
<223> OTHER INFORMATION: Rat PPAR-d PCR reverse primer

<400> SEQUENCE: 80
cgaacttggg ctcaatgatg tc                                              22

<210> SEQ ID NO 81
<211> LENGTH: 24
<212> TYPE: DNA
<213> ORGANISM: Artificial
<220> FEATURE:
<223> OTHER INFORMATION: Rat PPAR-? PCR forward primer

<400> SEQUENCE: 81
tggacctctc tgtgatggat gacc                                            24

<210> SEQ ID NO 82
<211> LENGTH: 23
<212> TYPE: DNA
<213> ORGANISM: Artificial
<220> FEATURE:
<223> OTHER INFORMATION: Rat PPAR-? PCR reverse primer

<400> SEQUENCE: 82
gctcttgtga acgggatgtc ttc                                             23

<210> SEQ ID NO 83
<211> LENGTH: 22
<212> TYPE: DNA
<213> ORGANISM: Artificial
<220> FEATURE:
<223> OTHER INFORMATION: Rat NOS1 PCR forward primer

<400> SEQUENCE: 83
tgtcttccac caggagatgc tc                                              22

<210> SEQ ID NO 84
<211> LENGTH: 20
<212> TYPE: DNA
<213> ORGANISM: Artificial
<220> FEATURE:
<223> OTHER INFORMATION: Rat NOS1 PCR reverse primer

<400> SEQUENCE: 84
ttggctgaga acttgacggc                                                 20

<210> SEQ ID NO 85
<211> LENGTH: 21
<212> TYPE: DNA
<213> ORGANISM: Artificial
<220> FEATURE:
<223> OTHER INFORMATION: Rat NOS2 PCR forward primer

<400> SEQUENCE: 85
tttgcttctg tgctaatgcg g                                               21

<210> SEQ ID NO 86
<211> LENGTH: 21
<212> TYPE: DNA
<213> ORGANISM: Artificial
<220> FEATURE:
<223> OTHER INFORMATION: Rat NOX2 PCR reverse primer

<400> SEQUENCE: 86
tcctcttcca aggtgtttgc c                                               21

<210> SEQ ID NO 87
<211> LENGTH: 22
<212> TYPE: DNA
<213> ORGANISM: Artificial
<220> FEATURE:
<223> OTHER INFORMATION: Rat NOS3 PCR forward primer

<400> SEQUENCE: 87
gcaggtattt gatgctcggg ac                                              22

<210> SEQ ID NO 88
<211> LENGTH: 22
<212> TYPE: DNA
<213> ORGANISM: Artificial
<220> FEATURE:
<223> OTHER INFORMATION: Rat NOS3 PCR reverse primer

<400> SEQUENCE: 88
cgtgatggct gaacgaagat tg                                              22

<210> SEQ ID NO 89
<211> LENGTH: 24
<212> TYPE: DNA
<213> ORGANISM: Artificial
<220> FEATURE:
<223> OTHER INFORMATION: Rat NOX1 PCR forward primer

<400> SEQUENCE: 89
gcatcccttt actctgacct ctgc                                            24

<210> SEQ ID NO 90

-continued

```
<211> LENGTH: 22
<212> TYPE: DNA
<213> ORGANISM: Artificial
<220> FEATURE:
<223> OTHER INFORMATION: Rat NOX1 PCR reverse primer

<400> SEQUENCE: 90
ttttctgtcc agtcccctgc tg                                                  22

<210> SEQ ID NO 91
<211> LENGTH: 23
<212> TYPE: DNA
<213> ORGANISM: Artificial
<220> FEATURE:
<223> OTHER INFORMATION: Rat p53 PCR forward primer

<400> SEQUENCE: 91
ccatccttac catcatcacg ctg                                                 23

<210> SEQ ID NO 92
<211> LENGTH: 22
<212> TYPE: DNA
<213> ORGANISM: Artificial
<220> FEATURE:
<223> OTHER INFORMATION: Rat p53 PCR reverse primer

<400> SEQUENCE: 92
ggcacaaaca cgaacctcaa ag                                                  22
```